(12) United States Patent
Schlom et al.

(10) Patent No.: US 6,969,609 B1
(45) Date of Patent: Nov. 29, 2005

(54) RECOMBINANT VECTOR EXPRESSING MULTIPLE COSTIMULATORY MOLECULES AND USES THEREOF

(75) Inventors: Jeffrey Schlom, Potomac, MD (US); James Hodge, Gaithersburg, MD (US); Dennis Panicali, Acton, MA (US)

(73) Assignee: The United States of America as represented by the Department of Health and Human Serivces, Washingtown, DC (US)

( * ) Notice: Subject to any disclaimer, the term of this patent is extended or adjusted under 35 U.S.C. 154(b) by 0 days.

(21) Appl. No.: 09/856,988

(22) PCT Filed: Nov. 12, 1999

(86) PCT No.: PCT/US99/26866

§ 371 (c)(1),
(2), (4) Date: Sep. 24, 2001

(87) PCT Pub. No.: WO00/34494

PCT Pub. Date: Jun. 15, 2000

Related U.S. Application Data

(60) Provisional application No. 60/111,582, filed on Dec. 9, 1998.

(51) Int. Cl.[7] .......................... C12N 5/10; C12N 5/16; C12N 5/22; C12N 15/85; A16K 48/00
(52) U.S. Cl. ................ 435/325; 435/365.1; 435/320.1; 435/360; 435/362; 435/372; 435/372.1; 435/374; 435/375; 435/377; 435/376; 435/366; 435/385; 435/386; 424/93.1; 424/9.1; 424/85.1
(58) Field of Search .................................. 435/325, 362, 435/365.1, 366, 372, 372.1, 375, 374, 377, 385, 386; 424/9.1

(56) References Cited

U.S. PATENT DOCUMENTS

| | | | |
|---|---|---|---|
| 5,185,146 A | 2/1993 | Altenburger | .................. 424/89 |
| 5,738,852 A | 4/1998 | Robinson et al. | |
| 6,045,802 A * | 4/2000 | Schlom et al. | ............ 424/199.1 |
| 6,440,422 B1 | 8/2002 | Sutter et al. | ............. 424/199.1 |
| 6,548,068 B1 * | 4/2003 | Schlom et al. | ........... 424/199.1 |

FOREIGN PATENT DOCUMENTS

| | | | |
|---|---|---|---|
| EP | 0 803 573 A1 * | 4/1996 | |
| EP | 0733 373 A * | 9/1996 | |
| WO | WO 9610419 | 4/1996 | |
| WO | WO097/00085 * | 1/1997 | |
| WO | WO 9804727 | 2/1998 | |

OTHER PUBLICATIONS

Zajac et al. Cancer Research, Oct. 1998, vol. 58, pp. 4567–4571.*
Oertli et al. J. Gene. Virol. vol. 77, pp. 3121–3125.*
Parra et al. Scand. J. Immunol. 1993, vol. 38, pp. 508–514.*
Goldbach–Mansky et al. Int J. Immunol. 1992, vol. 4, pp. 1315–1360.*
Young et al. J. Clin. Invest. 1992, vol. 90, pp. 229–237.*
Radmyr et al. Int. J. Cancer 1995, vol. 63, pp. 627–632.*
Delable et al. Leuk. Lymphoma 1995, vol. 18, pp. 35–40.*
Wyss–Coray et al. Eur. J. Immunol. 1993, vol. 23, pp. 3350–3357.*
Vyth–Dreese et al. Blood 1995, vol. 85, pp. 2802–2812.*
Cunningham et al. Journal of cell Science 1994, vol. 107, pp. 443–449.*
Hargreaves et al. International Immunology 1995, vol. 7, pp. 1505–1513.*
Hodge et al., "A Triad of Costimulatory Molecules Synergize to Amplify T–cell Activation", Cancer Research, vol. 59, Nov. 15, 1999, pp. 5800–5807.

* cited by examiner

*Primary Examiner*—James Housel
*Assistant Examiner*—Bao Qun Li
(74) *Attorney, Agent, or Firm*—Heller Ehram White and McAuliffe

(57) ABSTRACT

The present invention is a recombinant vector encoding and expressing at least three or more costimulatory molecules. The recombinant vector may additionally contain a gene encoding one or more target antigens or immunological epitope thereof. The synergistic effect of them costimulatory molecules on the enhanced activation of T cells is demonstrated. The degree of T-cell activation using recombinant vectors containing genes encoding three costimulatory molecules was far greater than the sum of recombinant vector constructs containing one costimulatory molecule and greater that the use of two costimulatory molecules. Results employing the triple costimulatory vectors were most dramatic under conditions of either low levels of first signal or low stimulator to T-cell ratios. This phenomenon was observed with both isolated $CD4^+$ and $CD8^+T$ cells. The recombinant vectors of the present invention are useful as immunogenes and vaccines against cancer and pathogenic micro-organisms, and in providing host cells, including dendritic cells and splenocytes with enhanced and antigen-presenting functions.

32 Claims, 55 Drawing Sheets

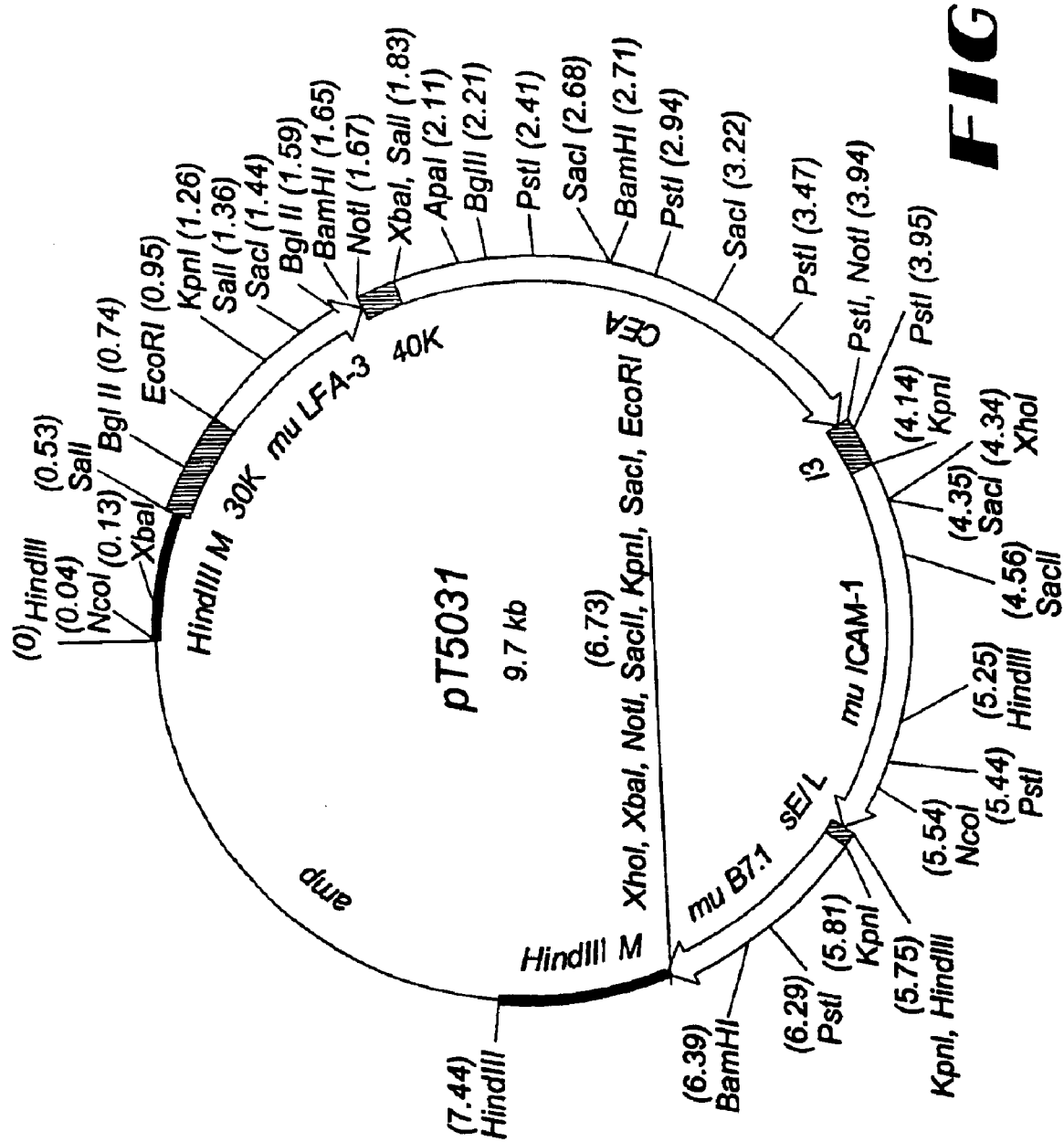

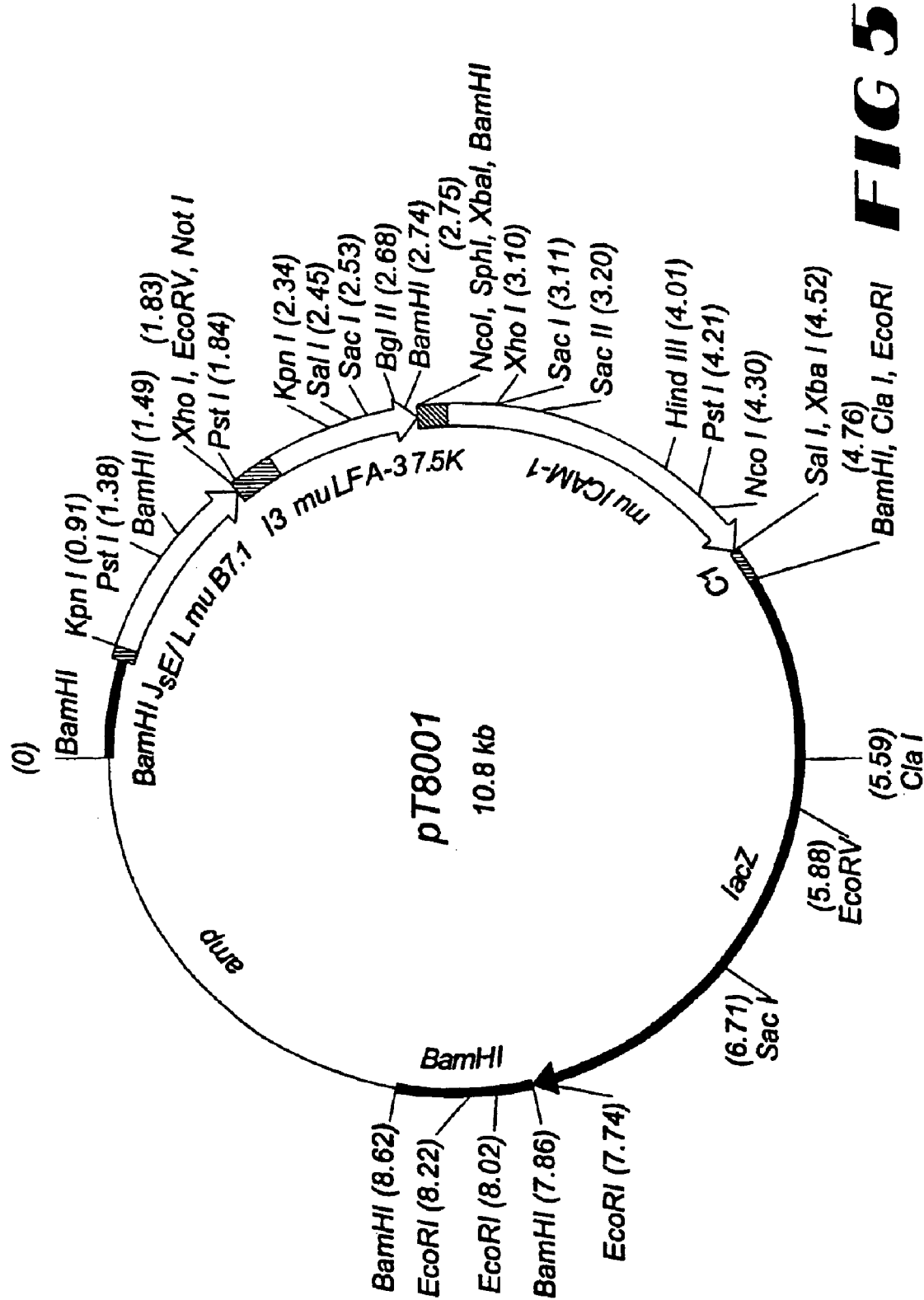

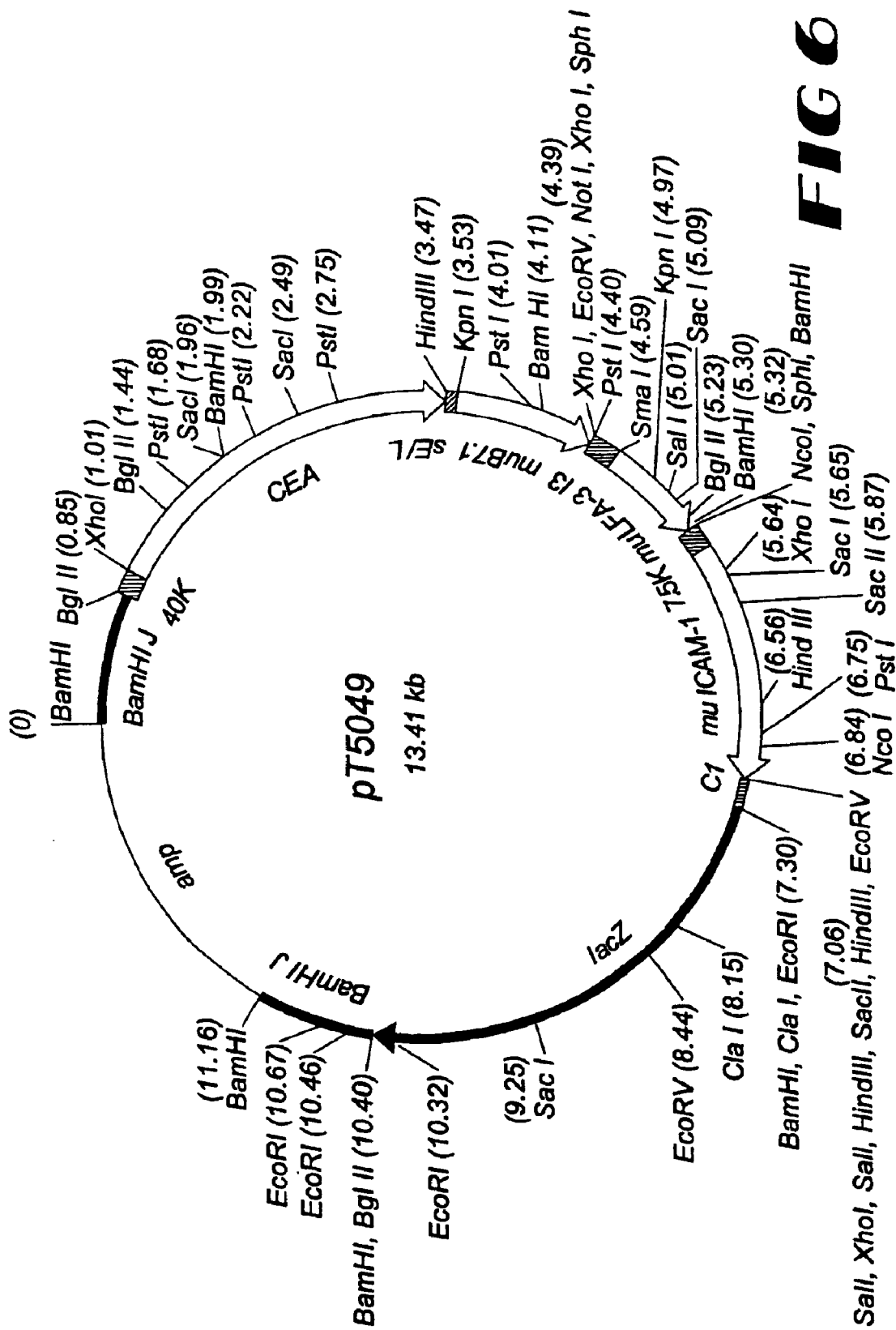

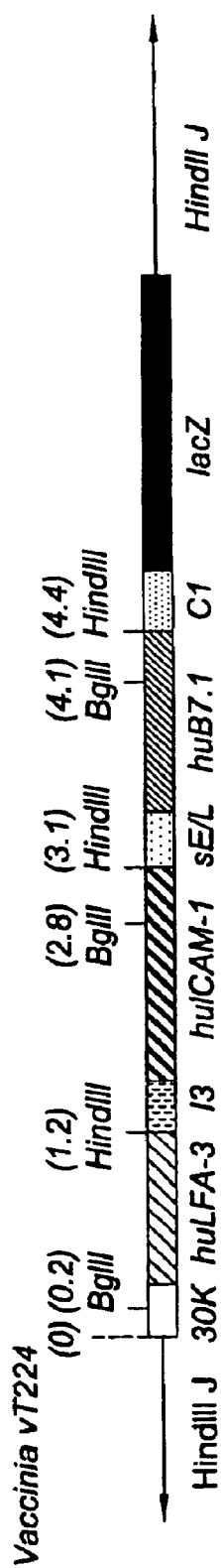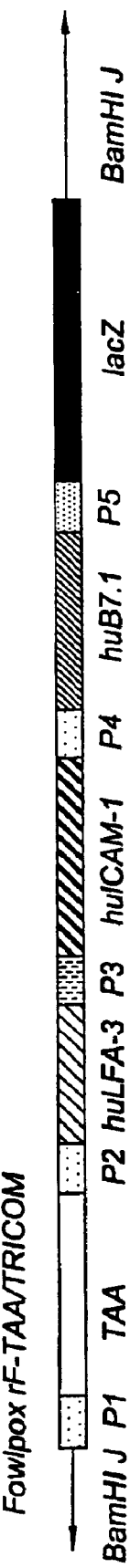

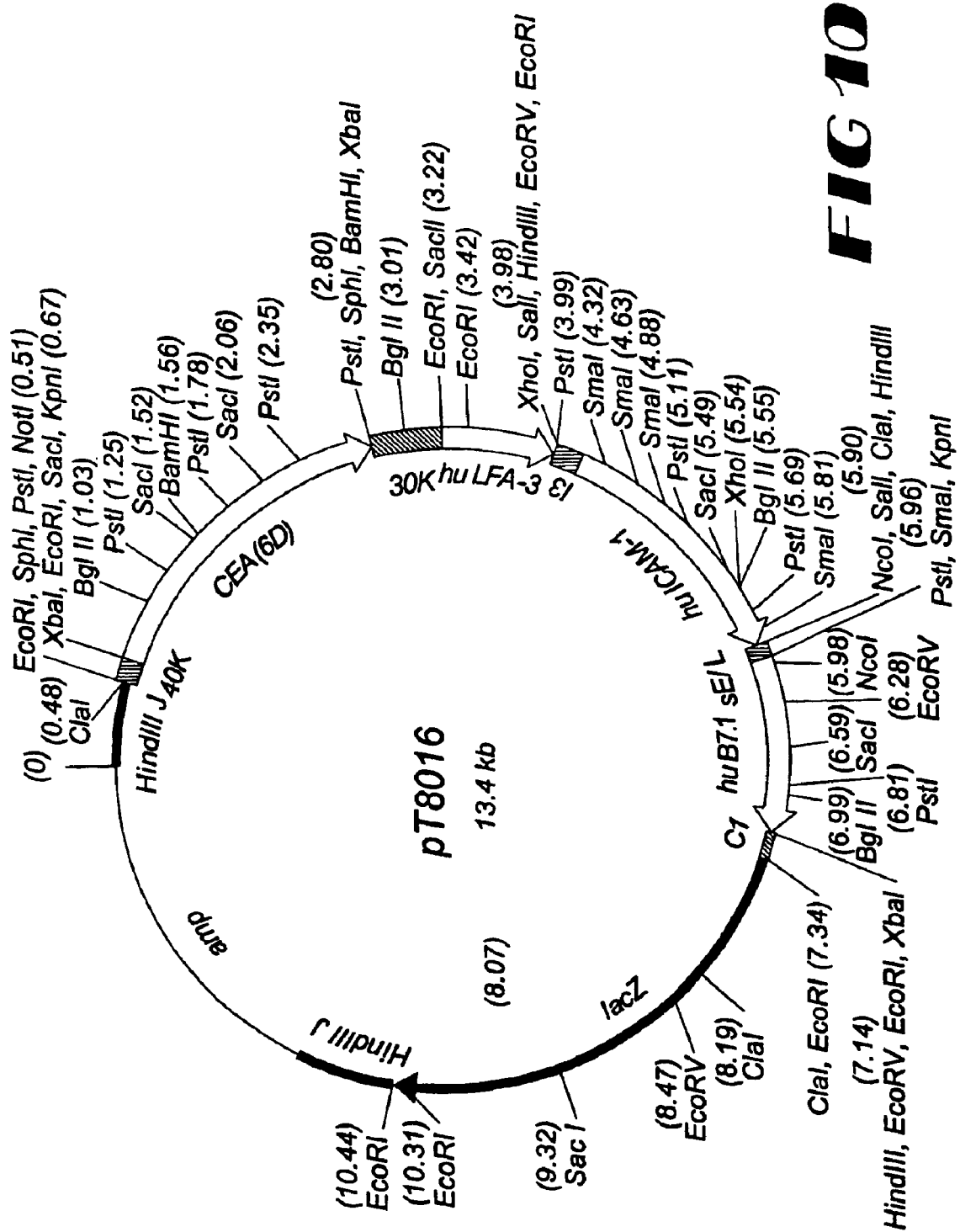

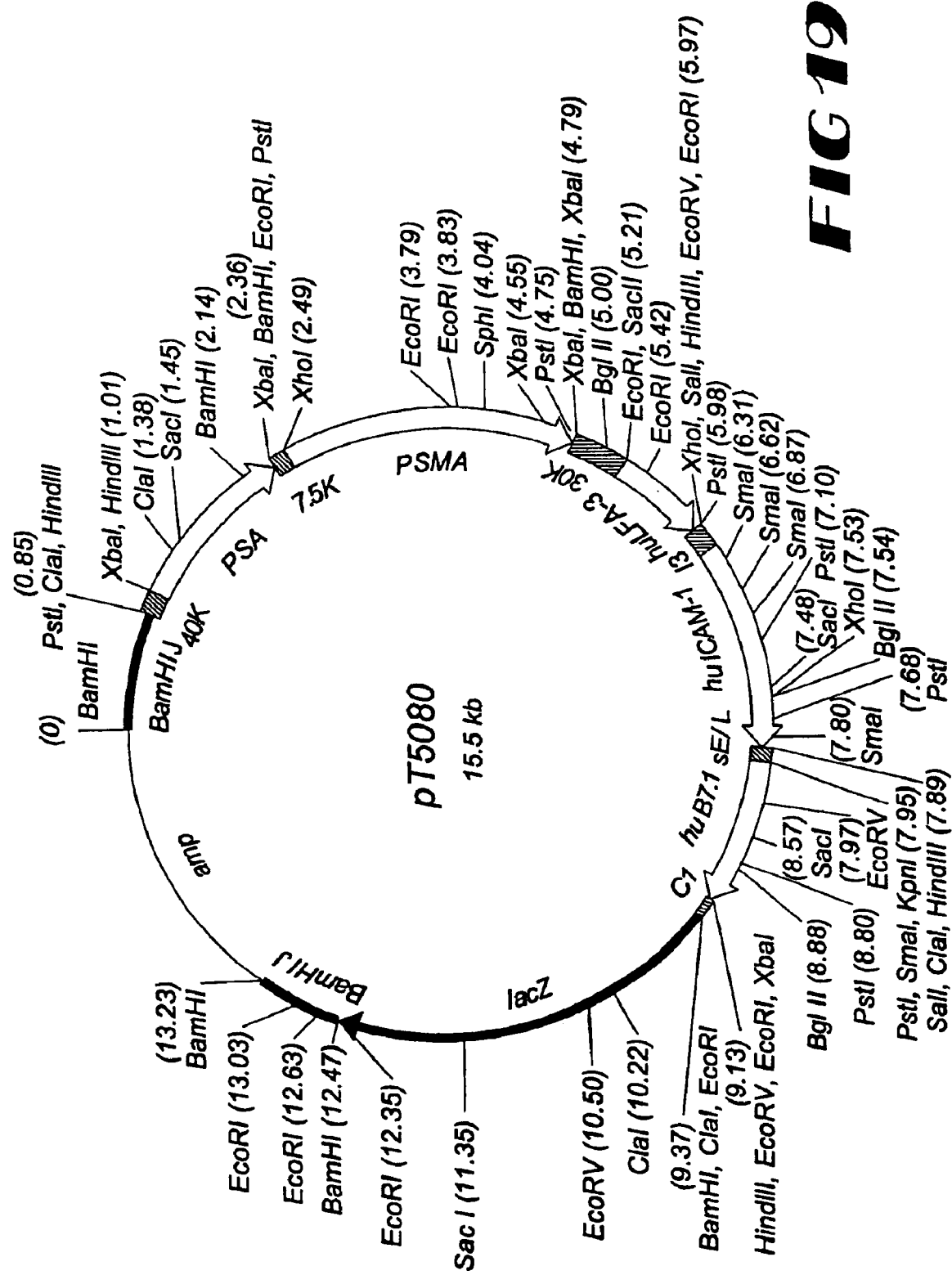

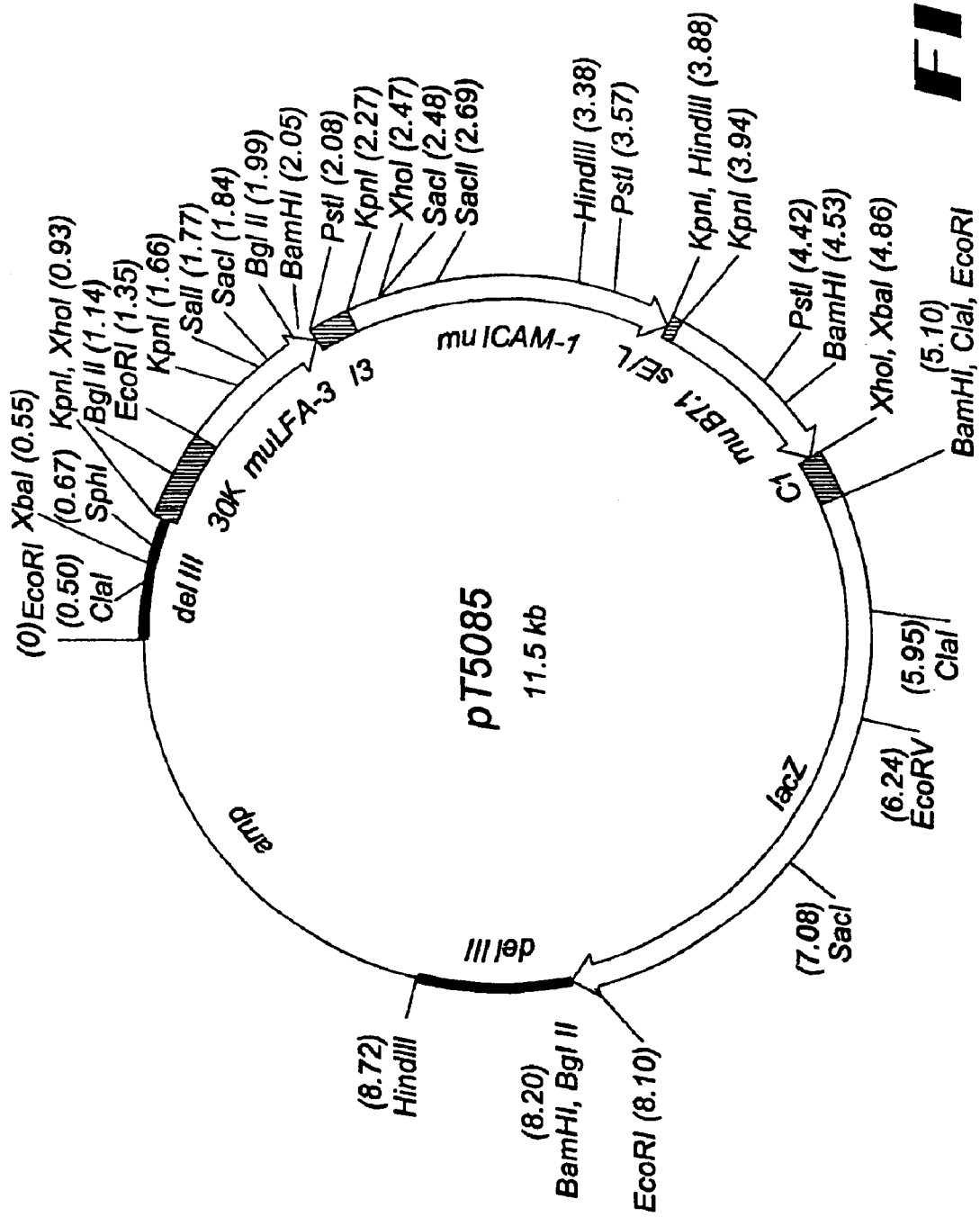

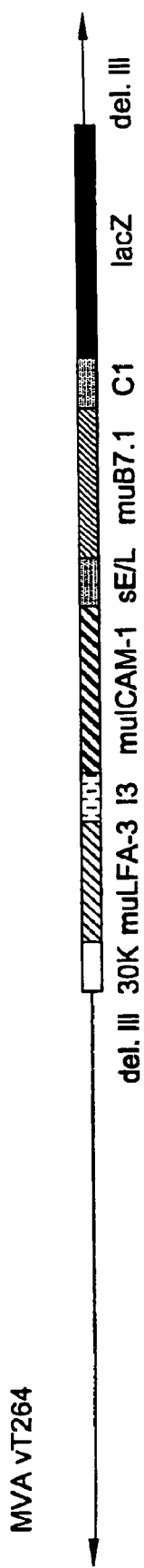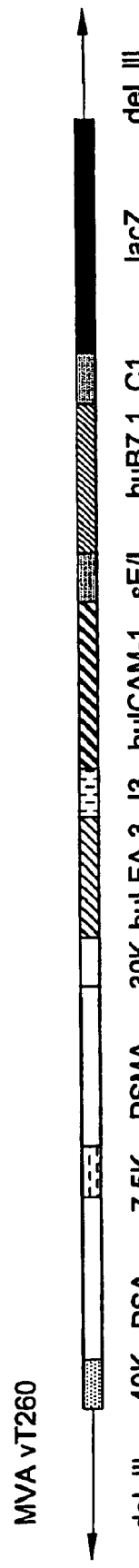

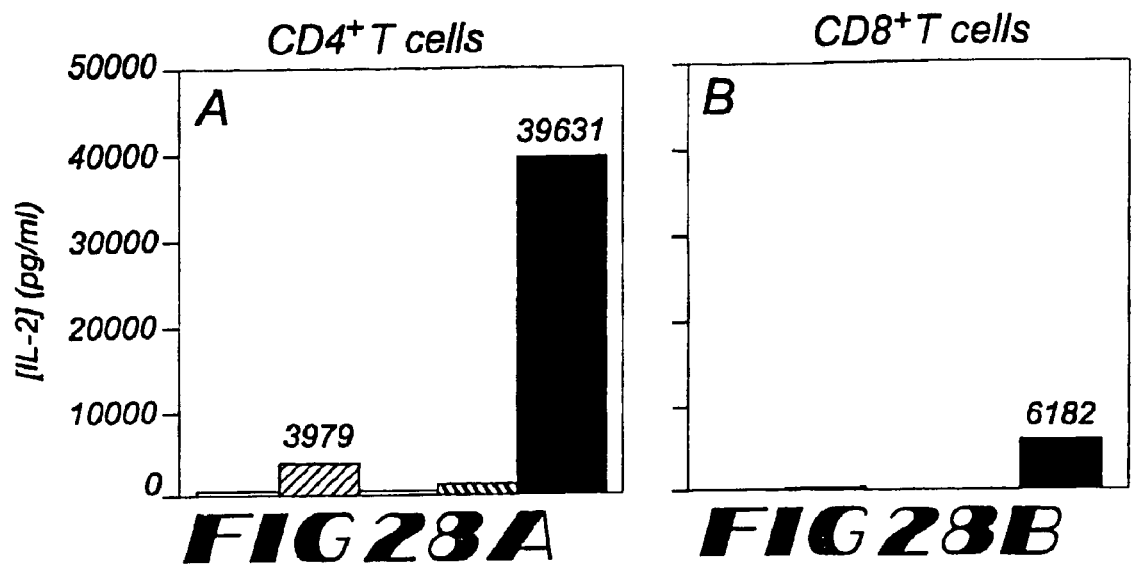
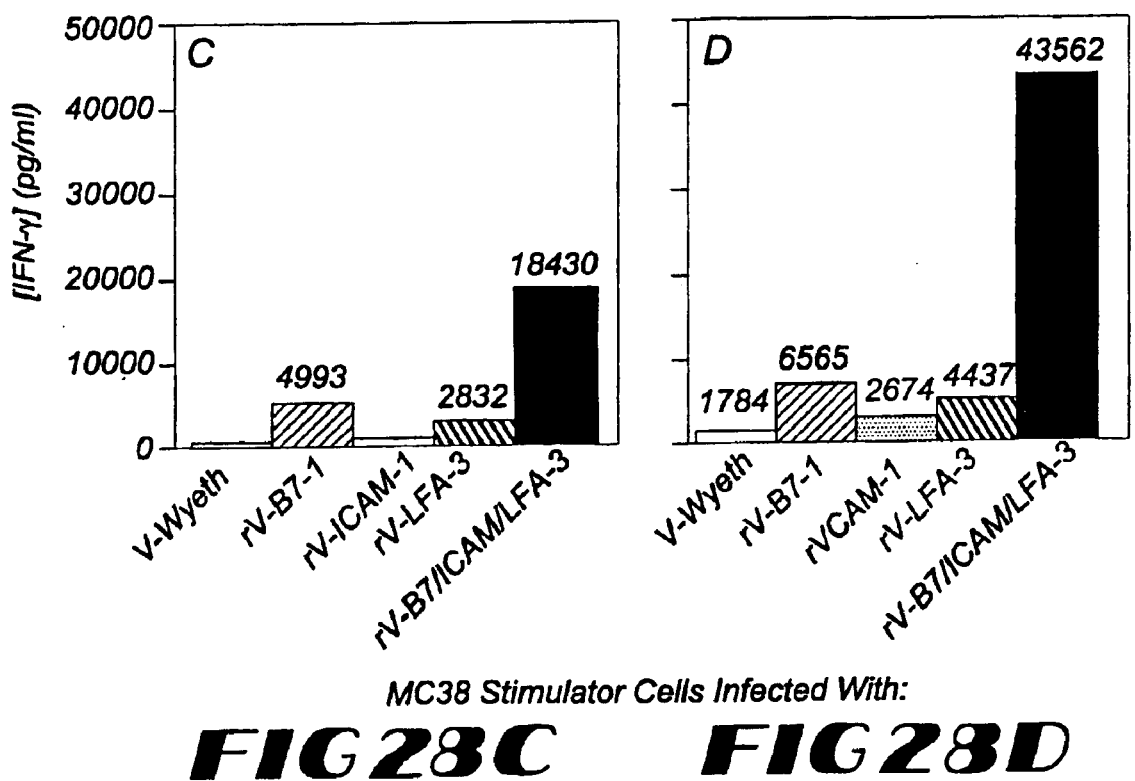
FIG 28A  FIG 28B  FIG 28C  FIG 28D

*In-Vitro Costimulation Assay:*
*Dendritic Cells*

Prepare Responder T-cells:
Mouse Spleen
CAP-M8 T-cell Line

↓

Unfractionated T-cells
Purified CD4$^+$ cells
Purified CD8$^+$ cells
CAP-M8 T-cell Line Prepare Stimulator cells:
CD34$^+$ BM Cells (Fresh)
or
DC [CD34$^+$ BM Cells
(cultured with
GMCSF and IL-4]

↓

5-18 Hours Infection
V-Wyeth
rV-B7
rV-CEA/B7/ICAM/LFA-3

↓

Irradiate Stimulator cells

Provide Signal 1:
← Con-A
CAP-M8 Peptide

Provide Signal 2:
← Costimulatory Molecule(s)

↓

Co-culture for 48 Hours at
10:1 Responder to Stimulator Ratio

↓

3H- Thymidine incorporation

FIG 31

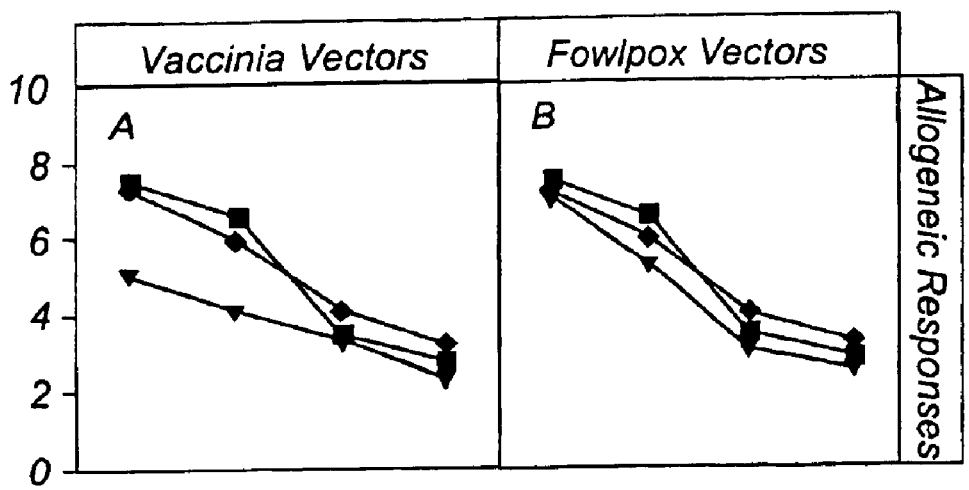
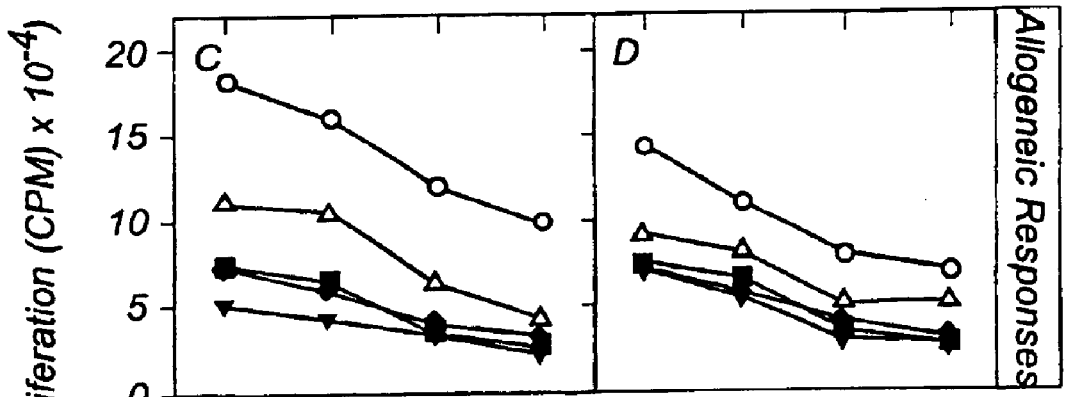
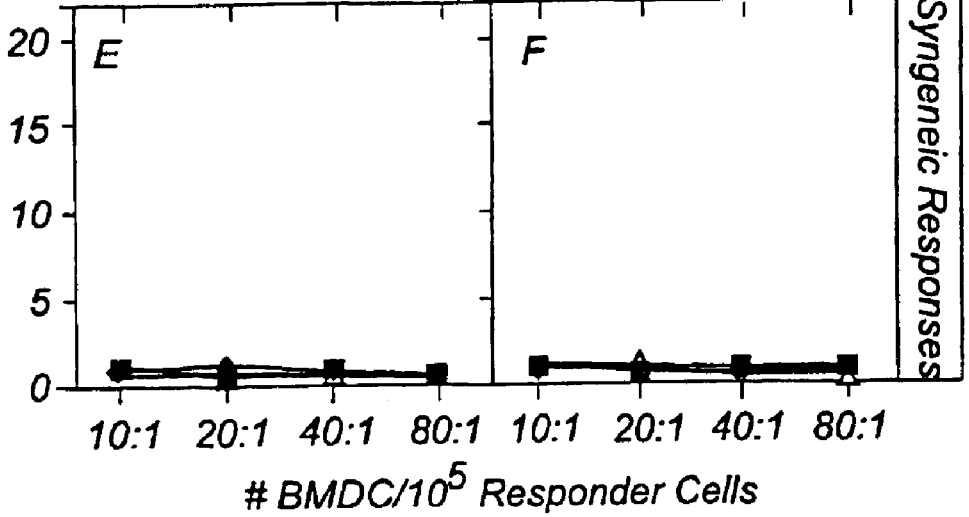
FIG 37A  FIG 37B
FIG 37C  FIG 37D
FIG 37E  FIG 37F

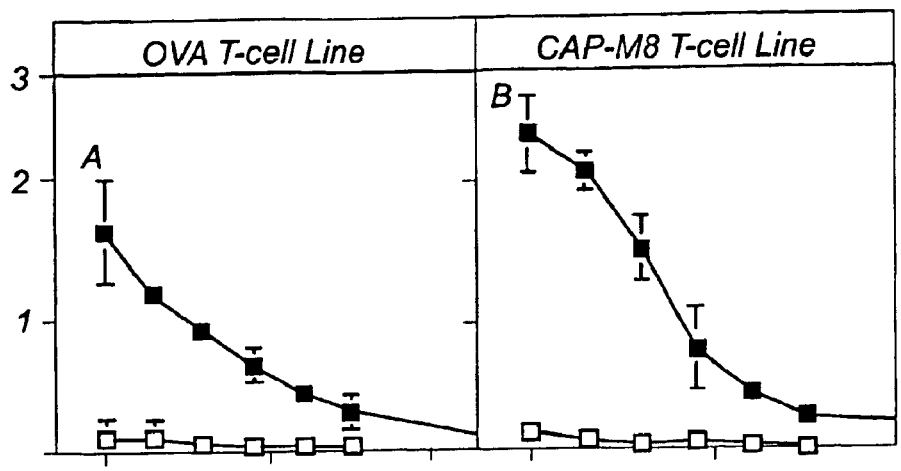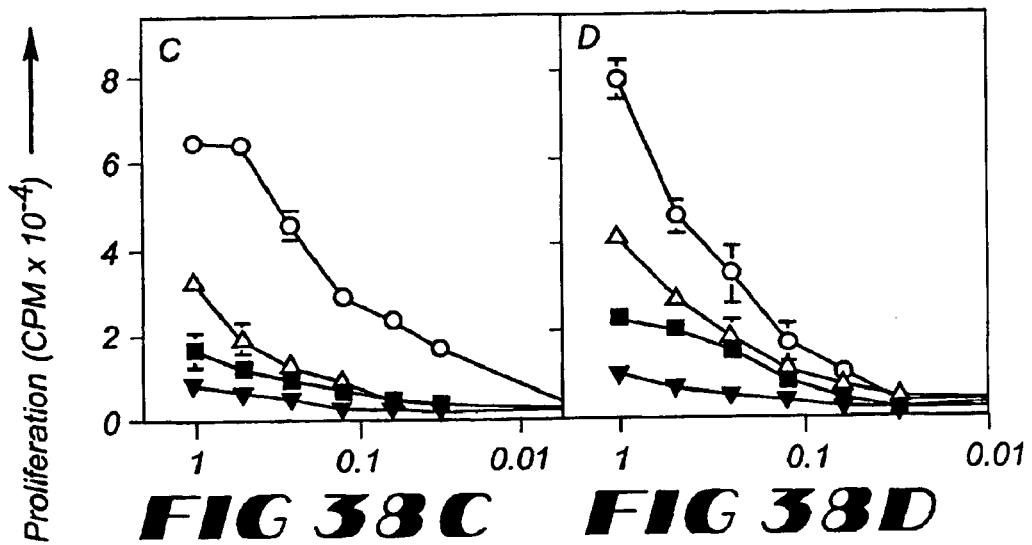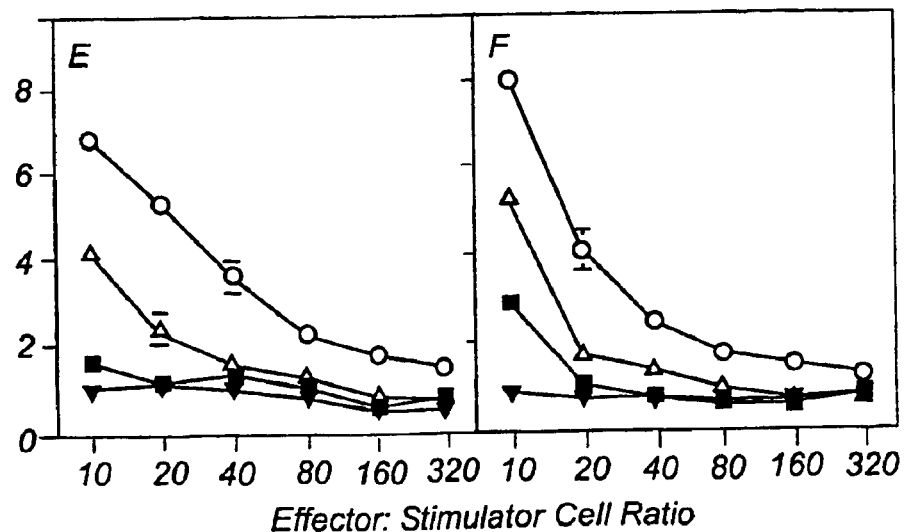
FIG 38A  FIG 38B
FIG 38C  FIG 38D
FIG 38F  FIG 38E

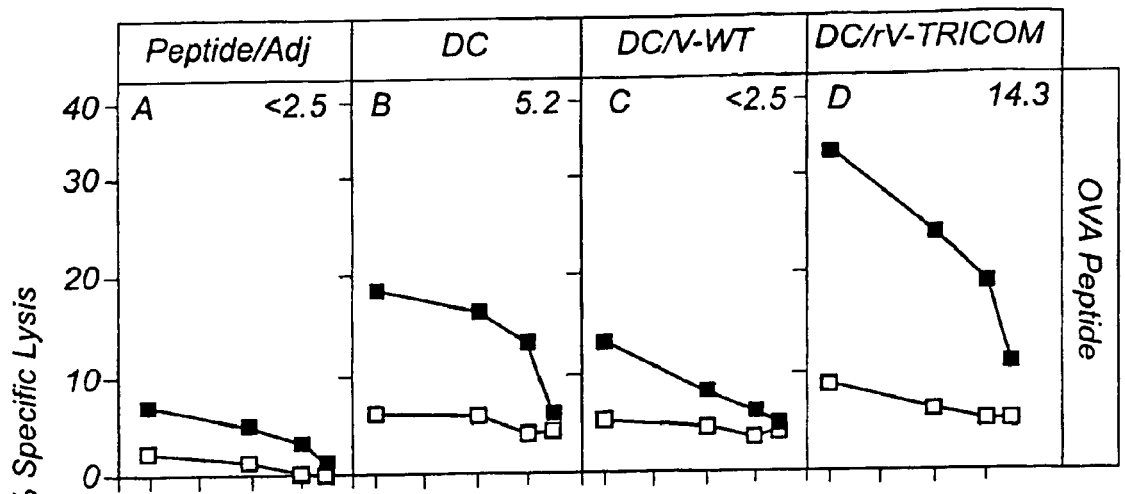
FIG 40A  FIG 40C
FIG 40B  FIG 40D
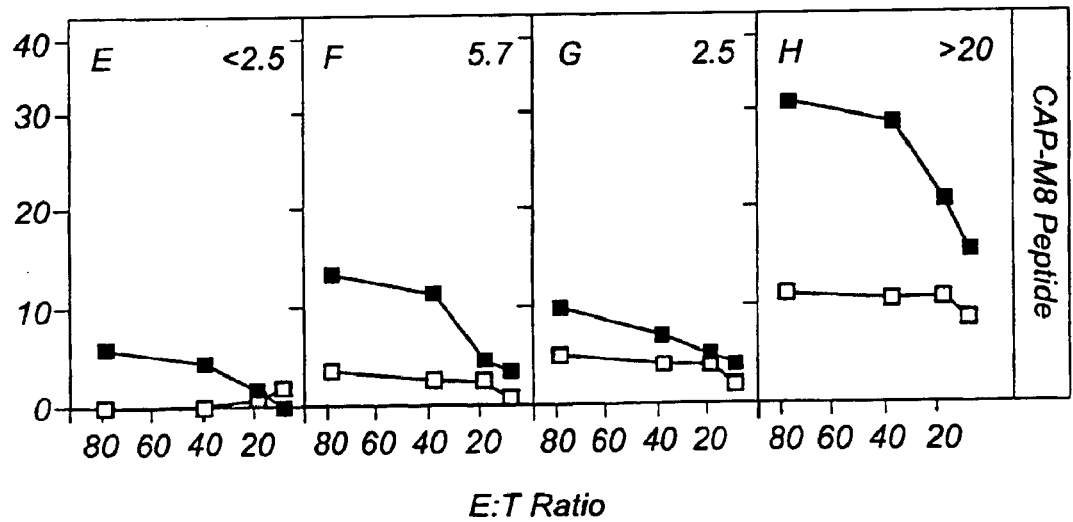
FIG 40E  FIG 40G
FIG 40F  FIG 40H

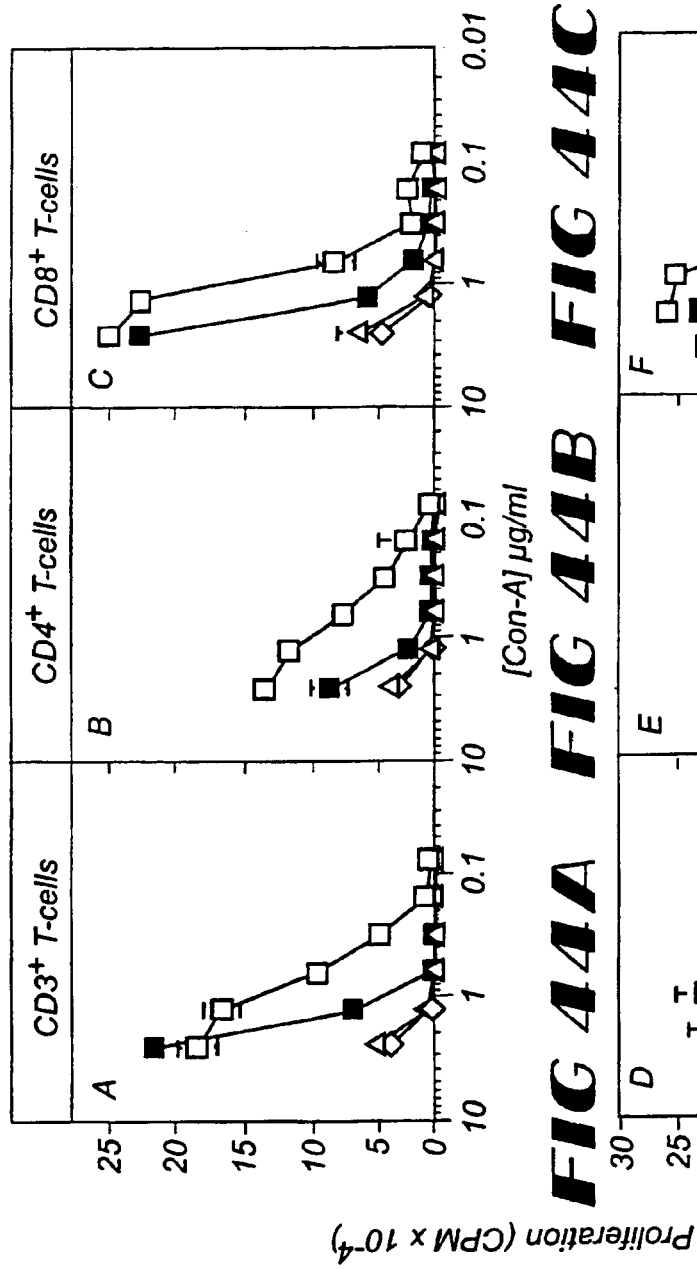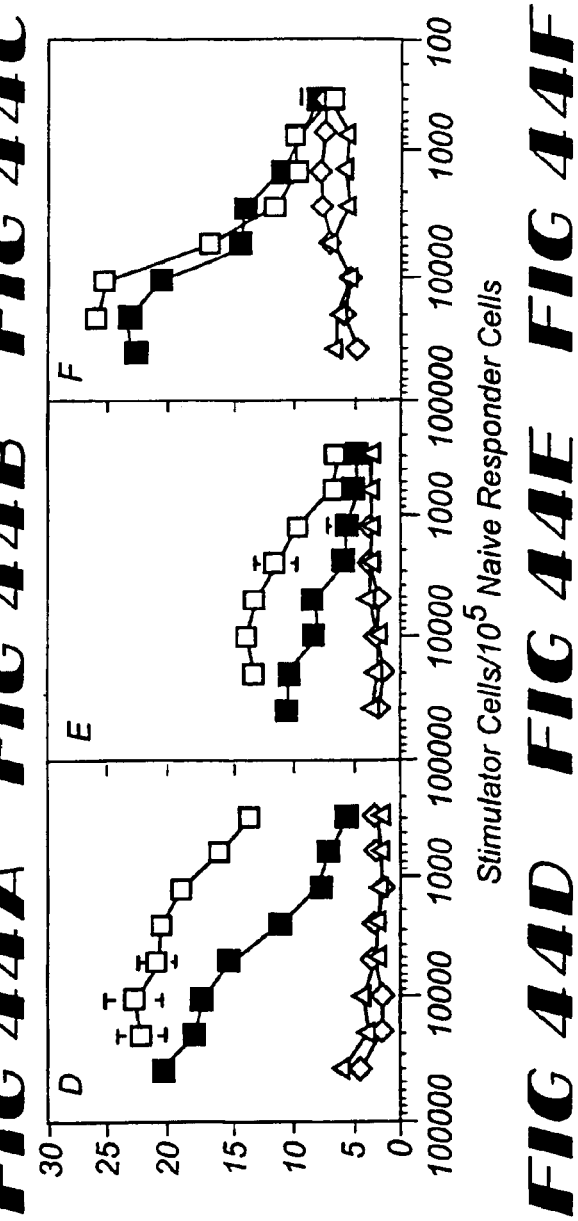
FIG. 44A  FIG. 44B  FIG. 44C
FIG. 44D  FIG. 44E  FIG. 44F

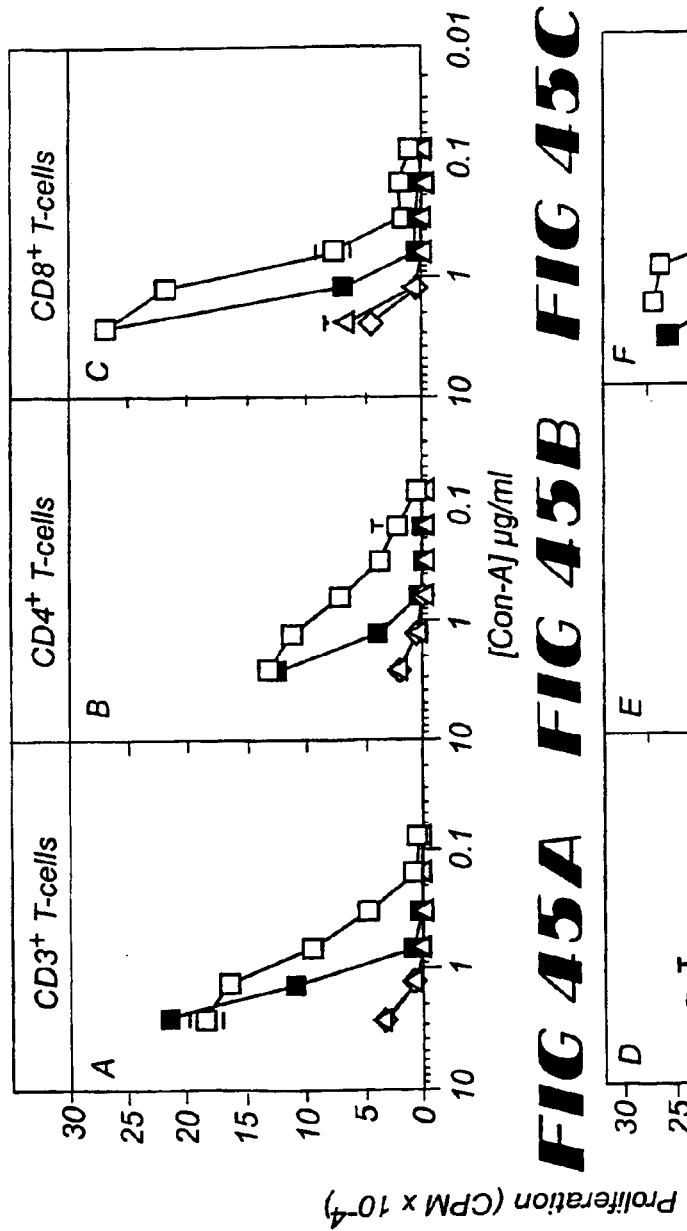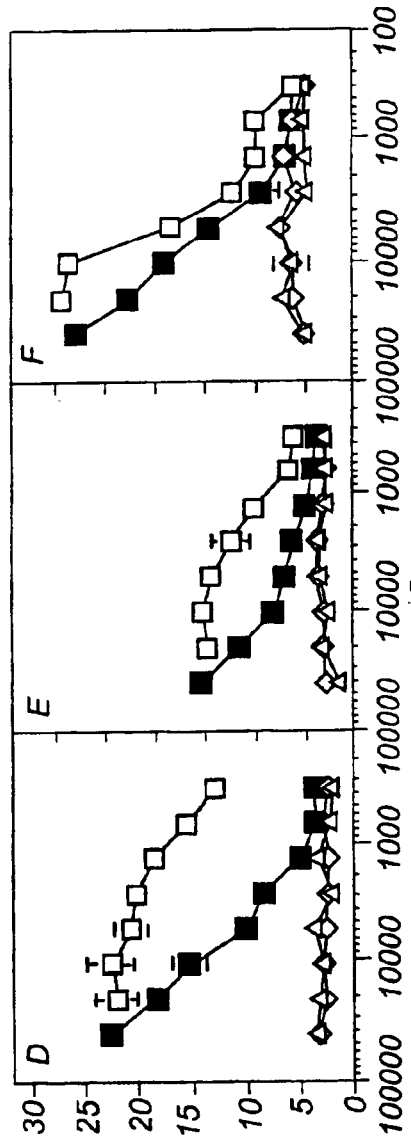
FIG 45A  FIG 45B  FIG 45C
FIG 45D  FIG 45E  FIG 45F

RECOMBINANT VECTOR EXPRESSING MULTIPLE COSTIMULATORY MOLECULES AND USES THEREOF

This application is a National Stage filing (371) of PCT/US99/26866, filed Nov. 12, 1999, which claims benefit of Provisional Appl. 60/111,582, filed Dec. 9, 1998.

FIELD OF THE INVENTION

The present invention relates to a recombinant vector comprising foreign genes encoding multiple costimulatory molecules and optionally a foreign gene encoding a target antigen. The invention further relates to a recombinant virus comprising foreign genes encoding at least three costimulatory molecules and optionally a foreign gene encoding at least one target antigen or immunological epitope thereof. More specifically, the present invention relates to a recombinant poxvirus comprising foreign genes encoding at least the costimulatory molecules: one molecule from the B7 family, LFA-3 and ICAM-1 and optionally a foreign gene encoding at least one target antigen or immunological epitope thereof and uses thereof as immunogens and vaccines. The invention further relates to antigen presenting cells transfected, infected or transduced by a recombinant vector comprising foreign genes encoding multiple costimulatory molecules and optionally a foreign gene encoding at least one target antigen or immunological epitope thereof.

BACKGROUND OF THE INVENTION

The extent of the primary response of T cells, which involves their activation, expansion, and differentiation, is paramount to a successful immune response to an antigen. The initiation of an immune response requires at least two signals for the activation of naïve T cells by antigen presenting cells (APC) (1–5). The first signal is antigen specific, delivered through the T-cell receptor via the peptide/major histocompatibility complex, and causes the T cell to enter the cell cycle. The second, or "costimulatory," signal is required for cytokine production and proliferation. At least three distinct molecules normally found on the surface of professional APC have been proposed as capable of providing the second signal critical for T-cell activation: B7.1 (CD80), Intercellular adhesion molecule-1 (ICAM-1; CD54), and Leukocyte function-associated antigen-3 (LFA-3; human CD58; murine CD48) (2, 6, 7). The T-cell ligands for these costimulatory molecules are distinct. B7-1 interacts with the CD28 and CTLA-4 molecules, ICAM-1 interacts with the CD11a/CD18 (LFA-1/2 integrin) complex, and LFA-3 interacts with the CD2 (LFA-2) molecules. It is not known whether these costimulatory molecules perform equivalent functions or carry out specialized functions at specific stages of an induced immune response (2). These molecules have been individually shown to costimulate T-cell proliferation in vitro (6). However, because they may be expressed simultaneously on APC, it has been difficult to examine relative potencies of individual costimulatory molecules during the induction of T-cell proliferation (2).

As it has been proposed that both antigen and costimulatory molecules must be expressed in proximity to each other to properly co-engage the T cell and costimulatory receptors (8, 9), the admixture of several recombinant viruses could be utilized to explore the potential cooperation of costimulatory molecules. The disadvantage of this approach, however, is that the admixture of three or more viruses has a statistically diminished probability of co-infecting the same cell, thereby making a multi-gene construct much more desirable for use with multiple costimulatory molecule genes.

WO 91/02805, published Mar. 7, 1991, discloses a recombinant retrovius vector construct which directs the expression of a target antigen, an MHC protein and other proteins involved in immune interactions which are missing or under-represented in a target cell.

Akagi, et al. 1997, *J. Immunotherapy* Vol. 20 (1):38–47 disclose an admixture of a recombinant vaccinia virus containing a modified MUC1 gene (rV-MUC1), and a recombinant vaccinia virus containing the gene for the murine costimulatory molecule B7 (rV-B7).

Cavallo, P. et al. 1995, *Eur. J. Immunol.* 25:1154–1162 disclose that transfection of B7-1 cDNA into three ICAM-1$^+$ tumor cell lines is sufficient to induce rejection in syngeneic mice.

Chen, L. et al. 1994, *J. Exp. Med.*, 179:523–532 disclose a recombinant retrovirus vector containing cDNA for murine B7 and the use of the vector in transducing various tumors.

Damle, N. K. et al 1992, *J. Immunol* Vol 148 (No. 7): 1985–1992 disclose the use of an antigen presenting cell (APC)-independent in vitro culture system consisting of immobilized combinations of monoclonal antibodies directed at the TCR/CD3 complex and soluble Ig chimeras (RG) of four distinct APC—associated costimulatory molecules to compare the abilities of these molecules to costimulate T cell proliferation.

Dubey, C. et al 1995, *J Immunol* 155: 45–57 disclose a study of the relative contribution of ICAM-1: LFA-1 and B7: CD28/CTLA-4 costimulatory pathways in naïve T cell activation, using either anti-CD28 antibody or fibroblast cell lines transfected with I-E$^k$, which express either no costimulatory molecules, ICAM-1 alone, B7-1 alone, or ICAM-1 and B7-1 together.

Fenton, R. G. et al, 1998 Vol. 21, No. 2, pp 95–108, disclose transfection of the costimulatory molecule B7-1 gene into three HLA-A2-expressing human melanoma cell lines, and their capacity to stimulate primary human T cells. The three melanoma lines also expressed detectable levels of the costimulatory molecules ICAM-1 (CD54) and LFA-3 (CD58).

Gjorloff Wingren, A. et al 1995, *Critical Reviews in Immunol* 15 (3 & 4): 235–253 disclose that with co-transfection of HLA-DR, B7 and LFA-3 into CHO cells, these molecules cooperate in activation of both naïve and memory T cells and allow responses at picomolar concentrations of the antigen, staphylococcal enterotoxin B (SEB).

Goldbach-Mansky, R. et al 1992, *International Immunol.* 4(No. 12): 1351–1360 disclose that CD4$^+$ T cells respond to staphylococcal enterotoxin B (SEB) in the presence of the LFA-3, ICAM-1 and B7 positive erythroleukemic cell line K562, murine L cells, and human B7 transfected L cells.

Hodge, J. W. et al 1994, *Cancer Research* 54:5552–5555 disclose the construction and characterization of recombinant vaccinia viruses containing the murine B7.1 and B72 genes.

Hodge, J. W. et al 1995, *Cancer Research* 55: 3598–3603 Cancer Research 55:3598–3603 disclose an admixture of recombinant vaccinia murine B7.1 (rV-B7) plus recombinant vaccinia expressing the human carcinoembryonic antigen gene (rV-CEA) and the use of this admixture for anti-tumor activity.

Parra, et al 1993, *Scand J. Immunol* 38: 508–514, Parra, E. et al 1994, L CHO cells transfected with the human HLA-DR4 molecule (CHO-DR4); HLA-DR4 and B7

(CHO-DR4/B7), HLA-DR4 and LFA-3 (CHO-DR4/LFA-3); HLA-DR4 and ICAM-1 (CHO-DR4/ICAM-1); or DR4, B7 and LFA-3 (CHO-DR4/B7/LFA-3) genes.

Thomas, R. et al. 1993 *J. Immunol.* 151:6840–6852 disclose that freshly obtained dendritic cells (DC) express similar densities of HLA-DR and the accessory molecules LFA-3, ICAM-1 and B7 as monocytes.

Uzendoski, K et al. May 1997, *Human Gene Therapy* 8:851–860 disclose the construction, characterization and immunological consequences of a recombinant vaccinia virus expressing the murine costimulatory molecule, ICAM-1.

WO 96/10419, published Apr. 11, 1996, of PCT/US95/12624 discloses subject matter relating to a single recombinant viral vector which has incorporated one or more genes or portion thereof encoding an immunostimulatory molecule and one or more genes or portion thereof encoding an antigen of a disease state.

Robinson et al U.S. Pat. No. 5,738,852 discloses a retroviral vector containing a polynucleotide sequence encoding a target antigen of an infectious agent and a polynucleotide sequence encoding a B7 costimulatory molecule.

The present invention is a vector containing foreign DNA encoding at least three costimulatory molecules, alone or in combination with foreign DNA encoding at least one target antigen or immunological epitope thereof which allows functional expression of each foreign DNA in an infected host cell.

SUMMARY OF THE INVENTION

The present invention provides a recombinant vector comprising foreign or exogenous genes or portions thereof encoding multiple costimulatory molecules.

Genes or functional portions thereof encoding costimulatory molecules having utility in the present invention include but are not limited to a B7 family member, ICAM-1, LFA-3,4-1BBL, CD59, CD40, CD70, VCAM-1, OX-40L, functional portions and homologs thereof. The vector of the invention may further provide a foreign gene encoding at least one target antigen or immunological epitope thereof in combination with the foreign genes encoding multiple costimulatory molecules. The foreign gene encoding at least one target antigen or immunological epitope thereof may be derived from cells, tissues or organisms such as viruses, bacteria, protozoans, parasites, yeast, tumor cells, preneoplastic cells, hyperplastic cells, tissue specific cells, or synthetic antigens. The vector may further provide a foreign gene encoding at least one or a combination of cytokines, chemokines and flt-3L.

The recombinant vector for use in the present invention group consisting of bacterial vectors, virus vectors, nucleic acid based vectors and the like. The recombinant virus vectors include but are not limited to poxvirus, adenovirus, herpes virus, alphavirus, retrovirus, picornavirus, iridovirus and the like. The poxvirus include but are not limited to the orthopox, avipox, suipox and capripox.

The present invention provides a recombinant virus comprising foreign genes or portions thereof encoding multiple costimulatory molecules for providing an enhanced immune response to a target cell, target antigen or immunological epitope thereof which is greater than a response provided by a recombinant virus comprising a foreign gene or genes encoding single or double costimulatory molecules. The recombinant virus of the invention may further provide a foreign gene encoding at least one target antigen or immunological epitope thereof in combination with the foreign genes encoding multiple costimulatory molecules. The recombinant virus may further provide a foreign gene encoding other classes of immunostimulatory molecules such as cytokines including but not limited to IL-2, IL-12, GM-CSF and the like, chemokines such as MIP1, MIP2, RANTES and the like, and Flt-3L which stimulates DC proliferation.

The present invention further provides a recombinant poxvirus comprising foreign genes or portions thereof encoding multiple costimulatory molecules for providing an enhanced immune response to a target cell, target antigen or immunological epitope thereof which is greater than a response provided by a recombinant poxvirus comprising a foreign gene or genes encoding single or double costimulatory molecules. The recombinant poxvirus of the invention may further provide a foreign gene encoding at least one target antigen or immunological epitope thereof in combination with the foreign genes encoding multiple costimulatory molecules.

The present invention also provides a recombinant poxvirus comprising a nucleic acid sequence encoding and expressing multiple costimulatory molecules, said nucleic acid sequence comprising a nucleic acid sequence encoding at least one molecule from the B7 family of costimulatory molecules, a nucleic acid sequence encoding an ICAM-1 costimulatory molecules, and a nucleic acid sequence encoding an LFA-3 costimulatory molecule. The recombinant virus farther provides a multiplicity of poxvirus promoters which regulate expression of each foreign gene.

The present invention provides a recombinant virus produced by allowing a plasmid vector comprising foreign DNA encoding multiple costimulatory molecules to undergo recombination with a parental virus genome to produce a recombinant virus having inserted into its genome the foreign DNA. The recombinant virus produced by recombination may further contain a foreign gene encoding at least one target antigen or immunological epitope thereof provided by the plasmid vector.

The present invention also provides a recombinant poxvirus produced by allowing a plasmid vector comprising foreign DNA encoding the costimulatory molecule, LFA-3, ICAM-1 and at least one molecule from the B7 family to undergo recombination with a parental poxvirus genome to produce a recombinant poxvirus having inserted into its genome the foreign DNA and a multiplicity of poxvirus promoters capable of controlling the expression of the foreign DNA. The recombinant poxvirus produced by recombination may further contain a foreign gene encoding at least one target antigen or immunological epitope thereof provided by the plasmid vector.

An object of the invention is to provide an immunogen for enhancement of immune responses against target cells, target antigens or immunological epitopes thereof comprising a recombinant vector having foreign nucleic acid sequences encoding multiple costimulatory molecules. The vector may further comprise a foreign nucleic acid sequence encoding at least one target antigen or immunological epitope thereof.

Another object of the invention is to provide an immunogen for enhancement of immune responses against target cells, target antigens or immunological epitopes thereof comprising a recombinant virus vector having foreign nucleic acid sequences encoding three or more costimulatory molecules. The recombinant virus vector may further comprise a foreign nucleic acid sequence encoding at least one or more target antigens or immunological epitopes thereof.

Yet another object of the invention is to provide an immunogen for enhancement of immune responses against target cells, target antigens or immunological epitopes thereof comprising a recombinant poxvirus vector comprising a foreign nucleic acid sequence encoding the costimulatory molecules LFA-3, ICAM-1 and at least one molecule from the B7 family and a foreign nucleic acid sequence encoding at least one target antigen or immunological epitope thereof.

The vector of the present invention provides a vaccine for eliciting and enhancing immune responses against target cells, target antigens or epitopes thereof for protection and/or treatment of disease states. The vector vaccine comprises foreign nucleic acid sequences encoding multiple costimulatory molecules. The vector vaccine may also comprise foreign nucleic acid sequences encoding one or more target antigens or immunological epitopes thereof for producing a monovalent or polyvalent vaccine against a disease.

The present invention provides pharmaceutical compositions comprising a vector having foreign nucleic acid sequences encoding multiple costimulatory molecules and a pharmaceutically acceptable carrier. The vector may further comprise a foreign nucleic acid sequence encoding at least one target antigen or immunological epitope thereof. The vector may additionally comprise a nucleic sequence encoding a cytokine, chemokine, flt-3L, or combination thereof.

The present invention provides a pharmaceutical composition comprising a recombinant virus vector which comprises foreign or exogenous genes or functional portions thereof encoding three or more costimulatory molecules, a foreign gene encoding at least one target antigen or immunological epitope thereof, and a pharmaceutically acceptable carrier.

The present invention also provides pharmaceutical compositions comprising a recombinant poxvirus comprising foreign genes or portions thereof encoding multiple costimulatory molecules and a pharmaceutically acceptable carrier. The recombinant poxvirus may further comprise a foreign nucleic acid sequence encoding at least one target antigen or immunological epitope thereof.

Another aspect of the invention is a pharmaceutical composition comprising a recombinant poxvirus comprising foreign genes or portions thereof encoding three or more costimulatory molecules, and may further comprise a foreign gene or portion thereof encoding at least one target antigen or immunological epitope thereof, and a pharmaceutically acceptable carrier or immunological epitope thereof.

The present invention also provides a pharmaceutical composition comprising a first vector comprising foreign genes or functional portions thereof encoding multiple costimulatory molecules and a second vector comprising foreign genes encoding at least one target antigen or immunological epitope thereof and a pharmaceutically acceptable carrier.

The present invention provides host cells infected, transfected or transduced with a first vector comprising foreign genes encoding multiple costimulatory molecules causing expression of the multiple costimulatory molecules in the host cells. The first vector or a second vector may further provide a foreign gene encoding at least one target antigen or immunological epitope thereof to the host cell.

The present invention provides antigen-presenting cells (APCs) or tumor cells infected, transfected or transduced with a first vector comprising foreign or exogenously provided genes encoding multiple costimulatory molecules causing expression or overexpression of the multiple costimulatory molecules. The first vector or a second vector may further provide a foreign gene encoding at least one target antigen or immunological epitope thereof to the host cell.

The present invention further provides host cells infected with a recombinant poxvirus causing expression of the multiple costimulatory molecules, and optionally causing expression of a target antigen or immunological epitope thereof.

Another aspect of the invention is a dendritic cell (DC) and precursor thereof infected, transfected or genetically engineered to overexpress genes encoding multiple exogenous costimulatory molecules. The DCs and precursors thereof may further be engineered to express foreign genes encoding at least one target antigen or immunological epitope thereof.

Yet another aspect of the invention is a DC and precursors thereof genetically engineered to overexpress genes encoding at least three exogenous costimulatory molecules. The DCs and precursor thereof may further be engineered to express foreign genes encoding at least one target antigen or immunological epitope thereof.

The present invention further provides a DC and precursors thereof genetically engineered to overexpress genes encoding at least one B7 molecule, ICAM-1 and LFA-3. The DCs and precursor thereof may further be engineered to express foreign genes encoding at least one target antigen or immunological epitope thereof.

The present invention provides methods and a plasmid vector for recombination with a parental virus designed to produce a recombinant virus capable of expressing foreign nucleic acid sequences encoding multiple costimulatory molecules comprising (a) a multiplicity of viral promoters, (b) the foreign nucleic acid sequences encoding the multiple costimulatory molecules, (c) DNA sequences flanking the constructs of elements (a) and (b), the flanking sequences at both the 5' and 3' ends being homologous to a region of a parental virus genome where elements (a) and (b) are to be inserted. The plasmid vector may further provide a foreign nucleic acid sequence encoding at least one target antigen or immunological epitope thereof. The plasmid vector may also provide a gene encoding a selectable marker.

The present invention also provides methods and a plasmid vector for recombination with a parental poxvirus designed to produce a recombinant poxvirus capable of expressing foreign nucleic acid sequences encoding the costimulatory molecules LFA-3, ICAM-1 and at least one B7 molecule which comprises (a) a multiplicity of poxviral promoters, (b) the foreign nucleic acid sequences encoding the LFA-3, ICAM-1 and at least one B7 molecule, (c) DNA sequences flanking the construct of elements (a) and (b), the flanking sequences at both 5' and 3' ends being homologous to a region of a parental poxvirus genome where elements (a) and (b) are to be inserted. The plasmid vector may further provide a foreign nucleic acid sequence encoding at least one target antigen or immunological epitope thereof. The plasmid vector may also provide a gene encoding a selectable marker.

One aspect of the invention is a method of enhancing immunological responses in a mammal to at least one target cell, target antigen or immunological epitope thereof comprising administration of a first vector comprising foreign nucleic acid sequences encoding multiple costimulatory molecules, each costimulatory molecule expressed in a cell in the mammal in an amount effective to enhance at least one immunological response in the mammal. Genes or functional portions thereof encoding costimulatory molecules having utility in the present invention include but are not limited to a B7 family member, ICAM-1, LFA-3,4-BBL, CD59, CD40, CD70, VCAM-1, OX-40L and homologs and portions thereof. A foreign nucleic acid sequence encoding at least one target antigen or immunological epitope thereof may further be provided in the method by the first vector or by a second vector.

In addition to genes or portion thereof encoding multiple costimulatory molecules, a foreign or exogenous nucleic acid sequence or functional portions thereof encoding at least one or a combination of other classes of immunostimulatory molecules may also be provided by the first vector, by the second vector, or by a third vector. Other classes of immunostimulatory molecules includes cytokines such as IL-2, IL-12, GM-CSF and the like, chemokines such as MIP1, MIP2, RANTES and the like and Flt-3L.

An aspect of the invention is a method of enhancing an antigen-specific T cell immune response in a mammal to a target cell, target antigen or immunological epitope thereof comprising administration of a foreign recombinant poxvirus comprising nucleic acid sequences encoding multiple costimulatory molecules LFA-3, ICAM-1 and at least one B7 molecule, each costimulatory molecule expressed in a cell in the mammal in an amount effective to enhance at least one T-cell immune response in which the enhancement is greater than the additive sum of enhancement provided by administration of single or double costimulatory molecules.

In another method of enhancing immunological responses, APCs or tumor cells expressing foreign or exogenously provided genes encoding multiple costimulatory molecules are provided to a mammal in an effective amount to enhance immunological responses. The APC or tumor cell may further express foreign genes encoding at least one target antigen or immunological epitope thereof for enhancement of immune responses. A target antigen or immunological epitope thereof may be administered to the mammal prior to, concurrently with or subsequent to the administration of the APC or tumor cell. In addition, or alternatively, APCs or tumor cells are pulsed with at least one target antigen or immunological epitope thereof prior to administration to the mammal.

The present invention provides methods of enhancing humoral responses in a mammal to a target cell, target antigen or immunological epitope thereof comprising administration of a recombinant vector comprising foreign nucleic acid sequences encoding multiple costimulatory molecules to a mammal in an amount effective to enhance an humoral response. The vector may further comprise nucleic acid sequences encoding at least one target antigen or immunological epitope thereof. The invention further provides an isolated antibody or functional portion thereof against a target cell, target antigen or immunological epitope thereof produced by the method.

The present invention also provides antibody specific for a target antigen or immunological epitope thereof produced in response to administration of a recombinant poxvirus comprising foreign genes encoding B7, ICAM-1 and LFA-3 and genes encoding one or more target antigens or epitopes thereof.

BRIEF DESCRIPTION OF THE DRAWINGS

These and other objects, features and many of the attendant advantages of the invention will be better understood upon a reading of the detailed description of the invention.

FIG. 3. Genomic structure of plasmid pT5031 comprising nucleic acid sequences encoding murine LFA-3, ICAM-1 and B7.1 and a nucleic acid sequence encoding CEA, flanked by portions of the Hind in M region of the vaccinia genome.

FIG. 4A shows the genomic structure of recombinant vaccinia, vT171. FIG. 4B shows the genomic structure of recombinant vaccinia vT199. FIG. 4C shows the genomic structure of recombinant vaccinia vT172. Hind III M and Hind III J are the sites of insertion in the poxvirus genomes of the foreign genes. Promoters 30K, I3, sE/L, 7.5K, 40K and C1 are poxviral promoters. Bam HI and Hind III restriction sites in the inserted sequences are shown, with the distance of each site (in kilobase pairs) from the 5' end of the insertion (0) listed above each site in parentheses (not drawn to scale).

FIG. 5. Genomic structure of plasmid pT8001 comprising nucleic acid sequences encoding murine B7.1, LFA-3, ICAM-1 and the lacZ gene, flanked by portions of the BamHI J region of the fowlpox genome.

FIG. 6. Genomic structure of plasmid pT5049 comprising a nucleic acid sequence encoding the tumor associated antigen, CEA, and murine B7.1, LFA-3, and ICAM-1, in combination with the lacZ gene, flanked by portions of the BamHI J region of the fowlpox genome.

FIG. 7A shows the genomic structure of recombinant fowlpox vT222. FIG. 7B shows the genomic structure of recombinant fowlpox vT194. FIG. 7C shows the genomic structure of recombinant fowlpox expressing MUC-1, B7.1, ICAM-1 and LFA-3. FIG. 7D shows the genomic structure of recombinant fowlpox expressing a tumor-associated antigen, B7.1, ICAM-1 and LFA-3. BamHI J is the site of insertion in the fowlpox virus genome of the foreign genes. sE/L, I3, 7.5K, C1, 40K and 30 K are poxviral promoters. P1–P5 denote five different poxvirus promoters. BamHI and HindIII restriction sites in the inserted sequences are shown, with the distance of each site (in kilobase pairs) from the 5' end of the insertion (0) listed above each site in parentheses (not drawn to scale).

FIGS. 9A through 9C Genomic structure of recombinant poxvirus expressing three human costimulatory molecules LFA-3, ICAM-1 and B7.1 along with the lacZ gene with (FIG. 9B, C) or without (FIG. 9A) a tumor associated antigen, HindIII J is the site of insertion in the vaccinia virus genome of the foreign genes. BamHI J is the site of insertion in the fowlpox virus genome. 30K, I3, sE/L, 40K and C1 are poxviral promoters. BglII and HindIII restriction sites in the inserted sequences are shown, with the distance of each site (in kilobase pairs) from the 5' end of the insertion (0) listed above each site in parentheses (not drawn to scale).

FIG. 10. Genomic structure of plasmid pT8016 comprising nucleic acid sequences encoding CEA (6D) and human LFA-3, ICAM-1, B7.1, and the E. coli lacZ gene, flanked by portions of the HindIII J region of the vaccinia genome.

FIG. 13A shows the genomic structure of recombinant fowlpox vT251. FIG. 13B shows the genomic structure of recombinant fowlpox vT232. BamHI J is the site of insertion in the poxvirus genome of the foreign genes. 30K, 13, sE/L and C1 are poxviral promoters.

FIG. 16A shows the genomic structure of recombinant fowlpox vT250. FIG. 16B shows the genomic structure of recombinant fowlpox vT742.

FIG. 16C shows the genomic structure of recombinant fowlpox vT236. FIG. 16D shows the genomic structure of recombinant fowlpox vT257. BamHI J is the site of insertion in the poxvirus genome of the foreign genes. 40K, 7.5K, 30K, 13, sE/L, and C1 are poxviral promoters.

FIG. 19. Genomic structure of plasmid pT5080 comprising nucleic acid sequences encoding PSA, PSMA, human LFA-3, ICAM-1, B7.1, and the E. coli lacZ gene, flanked by portions of the BamHI J region of the fowlpox genome.

FIG. 20. Genomic structure of plasmid pT5085 comprising nucleic acid sequences encoding murine LFA-3, ICAM-1, B7.1, and the E. coli !acZ gene, flanked by portions of the deletion III region of the MVA genome.

FIGS. 21A and 21B. Genomic structure of recombinant MVA viruses expressing murine or human costimulatory molecules with or without tumor-associated antigens. FIG. 21A shows the genomic structure of recombinant MVA vT264. FIG. 21B shows the genomic structure of recombinant MVA vT260. Deletion III is the site of insertion in the poxvirus genome of the foreign genes. 40K, 7.5K, 30K, 13, sE/L, and C1 are poxviral promoters.

FIGS. 27C and 27D show the proliferative responses of purified CD4$^+$ and CD8$^+$ cells, respectively, when co-cultured in the presence of vector-infected MC38 stimulator cells at a low Con A concentration (0.625 µg/ml).

FIGS. 28A through 28D. Effect of costimulation on cytokine production. Murine CD4+ (FIGS. 28A and 28C) or CD8+ (FIGS. 28B and 28D) T cells were purified as described in Materials and Methods and co-cultured with the indicated MC38 vector-infected stimulator cells for 24 hours in the presence of 2.5 µg/ml Con A. Supernatant fluids were analyzed for production of IL-2 (FIGS. 28A and 28B) and IFN-γ (FIGS. 28C and 28D) by capture ELISA.

FIG. 29A: murine CD4+ or CD8+ T cells were co-cultured with MC38 stimulator cells infected with V-Wyeth (lane A), rV-B7-1 (lane B), rV-ICAM-1 (lane C), rV-LFA-3 (lane D) or rV-B7-1/ICAM-1/LFA-3 (lane E) at a T-cell to stimulator cell ratio of 10:1 for 24 hours in the presence of 2.5 µg/ml Con A. Following culture, T-cell RNA was analyzed by multiprobe RNAse protection assay. The quantitative representation of results from the autoradiograph is normalized for expression of the housekeeping gene L32 in FIG. 29B (CD4+ cells) and FIG. 29C (CD8+ cells). Order of histogram bars (from left to right) is MC38N-Wyeth, MC38/B7-1, MC38/ICAM-1, MC38/LFA-3, and MC38/B7-1/ICAM-1/LFA-3.

FIG. 30: In a second experiment, C57BL/6 mice (5/group) were vaccinated with $10^7$ pfu rV-CEA, rV-CEA/B7.1, rV-CEA/TRICOM or HBSS buffer. Lymphoproliferative responses from pooled splenic T cells were analyzed 22 days following vaccination. Values represent the stimulation index of the mean cpm of triplicate sames vs. media. Standard deviation never exceeded 10%. Antigens used were Con A (5 µg/ml), CEA (100 µg/ml) and ovalbumin (100 µg/ml).

FIG. 31 shows a schematic of an in vitro costimulation assay of dendritic cells.

FIG. 36A: Uninfected DC (closed squares), mock-infected DC (closed diamonds), or DC infected with V-WT (closed inverse triangles), rV-B7.1 (open triangles) or rV-TRICOM (open circles). FIG. 36B: DC (closed squares), mock-infected DC (closed diamonds), or DC infected with WT-FP (closed inverse triangles), rF-B7.1 (open triangles) or rF-TRICOM (open circles).

FIGS. 37A through 37F. Enhanced allostimulatory activity by DC infected with vaccinia (FIGS. 37A, C, E) or fowlpox (FIGS. 37B, D, F) vectors. Uninfected DC (closed squares); mock-infected DC (closed diamonds); or DC infected with wild-type poxviral vectors (V-WT or F-WT, closed inverse triangles), rV-B7.2 or rF-B7.1 (open triangles), or rV-TRICOM or rF-TRICOM (open circles) were co-cultured with allogeneic (FIGS. 37A–D) or syngeneic T cells (FIGS. 37E–F) for 5 days. $^3$H-thymidine was added during the final 18 h.

FIGS. 38A through 38F. Effect of vaccinia infection of DC on peptide-specific T-cell proliferation. Uninfected DC (closed squares), or DC infected with V-WT (closed inverse triangles), rV-B7.1 (open triangles) or rV-TRICOM (open circles) were co-cultured with OVA peptide-specific T cells (FIGS. 38A, C, E) or CAP-M8 peptide-specific T cells (FIGS. 38B, D, F). Experimental conditions included a fixed effector: stimulator cell ration of 10:1 in the presence of various concentrations of the appropriate peptides (FIG. 38A-D), negative control peptides (open squares, either VSVN (FIG. 38A), or FLU-NP (FIG. 38B), or a fixed peptide concentration of 1 µM in the presence of various effector: stimulator cell ratios (FIGS. 38E and F).

FIGS. 40A through 40H: Effect of vaccinia infection of DC on induction of CTL activity. DC (FIG. 40B), or DC infected with V-WT (FIG. 40C), or rV-TRICOM (FIG. 40D) were pulsed with 10 µM OVA peptide for 2 h. DC populations were administered intravenously to mice ($1 \times 10^5$ cells/mouse). Control mice were immunized subcutaneously with 100 µg OVA peptide in Ribi/Detox adjuvant (FIG. 40A). Fourteen days later spleens were harvested, restimulated for 6 days with the corresponding peptide, and assessed for lytic ability against EL-4 cells pulsed with either OVA (closed squares) or VSVN peptides (open squares). Inset numbers depict CTL activity as expressed in lytic units. Also shown is the effect of vaccinia infection of DC on induction of CTL activity. DC (FIG. 40F), or DC infected with V-WT (FIG. 40G), or rV-TRICOM (FIG. 40H) were pulsed with 10 μM CAP-M8 peptide for 2 h. DC populations were administered intravenously to mice (1×10⁵ cells/mouse). Control mice were immunized subcutaneously with 100 μg CAP-MS peptide in Ribi/Detox adjuvant (FIG. 40E). Fourteen days later spleens were harvested, restimulated for 6 days with the corresponding peptide, and assessed for lytic ability against EL-4 cells pulsed with either CAP-M8 (closed squares) or FLU-NP peptides (open squares). Inset numbers depict CTL activity as expressed in lytic units.

FIGS. 44A through 44F. Effect of rV-TRICOM-infected splenocytes on specific T cell populations. Naïve murine T cells were fractionated with CD3', CD4⁺, and CD8⁺ subpopulations. T cells were co-cultured with either uninfected autologous BMDC or splenocytes infected with recombinant vaccinia vectors. Varying Con-A concentrations (FIGS. 44A–C) or varying number of stimulator cells (FIG. 44D-F) provided the first signal. T cell proliferation in response to mature BMDC is indicated by open squares, and to uninfected splenocytes by open triangles. Recombinant vectors were wild-type (V-WT, open diamonds) or rV-TRICOM (closed squares).

FIGS. 45A through 45F. Effect of rV-TRICOM-infected bone marrow cells on specific T cell populations. Naïve murine T cells were fractionated into CD3⁺, CD4', and CD8⁺ subpopulations. T cells were co-cultured with either uninfected autologous BMDC or splenocytes infected with recombinant vaccinia vectors. Varying Con-A concentrations FIG. 45A-C) or varying number of stimulator cells (FIG. 45D-F) provided the first signal. T cell proliferation in response to mature BMDC is indicated by open squares, and to uninfected splenocytes by open triangles. Recombinant vectors were wild-type (V-WT, open diamonds) or rV-TRICOM (closed squares).

DETAILED DESCRIPTION OF THE INVENTION

Figure 1:
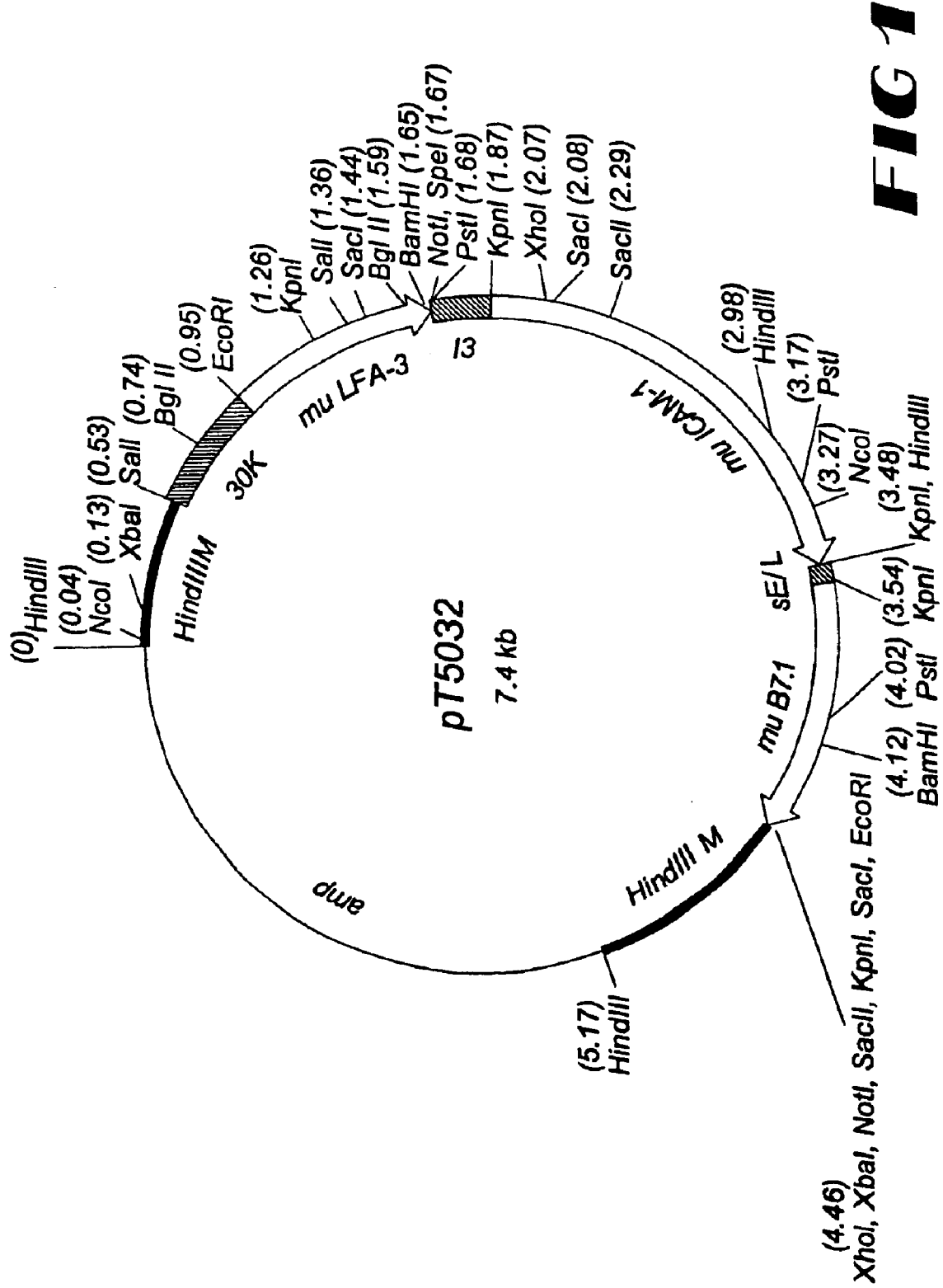
FIG. 1. Genomic structure of plasmid pT5032 comprising nucleic acid sequences encoding murine LFA-3, ICAM-1 and B7.1, flanked by portions of the Hind III M region of the vaccinia genome.

The present invention is a recombinant vector comprising foreign genes encoding multiple costimulatory molecules, in combination, or the functionally active portions of each costimulatory molecule. Multiple costimulatory molecules as used herein are at least three or more costimulatory molecules. As used herein a functionally active portion is that portion of the molecule responsible for binding to its respective ligand, triggering an appropriate costimulatory signal for immune-cell activation. One method of determining functional activity is to access the induction of naïve T-cell proliferation by delivering the costimulatory molecule to a target cell in vitro as described herein. A functional portion of a costimulatory molecule stimulates at least 20% increase in T cell proliferation.

The term foreign gene or foreign nucleic acid sequence or functional portion thereof as used herein is a gene, nucleic acid sequence or functional portion thereof that is exogenously provided by a recombinant vector to a host cell or organism. The exogenous gene or portion thereof which is provided to the host cell or host organism may be one which is not endogenously present in the host cell or organism or may be endogenously present and functional or non-functional. In the case in which a functional endogenous gene is present in the host cell or organism, the foreign or exogenously provided gene or functional portion thereof results in overexpression of the gene product.

The recombinant vectors of the present invention have utility in providing enhanced immunological response to cells of the immune system including but not limited to T lymphocytes, B lymphocytes, NK cells, antigen-presenting cells (APCs) and the like. The enhancement of the immunological response using the recombinant vectors expressing multiple costimulatory molecules is synergistic as compared to the use of a single costimulatory molecule or the use of two costimulatory molecules in enhancing immunological responses. The immunological response may be a cellular and/or humoral immune response and may be directed to a specific target antigen or epitope thereof or may be a generalized immune enhancing or upregulating effect as demonstrated by increased cytokine release, increase proliferation by immune cells, increased mitogen responsiveness and the like. The enhancement in an immune response preferably includes hyperstimulation or high intensity T cell stimulation (HITS) as a result of stimulation using the recombinant vectors of the present invention or cells transfected, transduced or induced by the recombinant vector of the present invention.

The foreign genes encoding the costimulatory molecules may be obtained from a variety of sources. The selection of the source of foreign genes encoding the costimulatory molecules may depend on the species to be immunized or treated using the recombinant vector.

The foreign genes encoding the costimulatory molecules may be murine-derived, human-derived, simian-derived, other mammalian homologs and may be chemically synthesized based on mammalian genes. The foreign genes encoding the costimulatory molecules may also be avian-derived or chemically synthesized based on avian costimulatory molecule genes. The recombinant vectors of the present invention are useful as immunogens and as vaccines in stimulating an enhancement of immunological responses to target cells, target antigens and immunological epitopes thereof. Such level of enhancement of a immune response using the present recombinant vectors comprising genes encoding multiple costimulatory molecules has not been obtainable using a single or double costimulatory molecule.

Genes or functional portions thereof encoding costimulatory molecules having utility in the present invention include but are not limited to B7.1, B7.2, ICAM-1, LFA-3, 4-1BBL, CD59, CD40, CD70, VCAM-1, OX-40L, mammalian homologs and the like. The recombinant vector of the present invention comprises genes encoding at least three costimulatory molecules for synergistic enhancement of immune responses which is not obtainable by the use of a single or a double costimulatory molecule. Genes encoding various combinations of costimulatory molecules are an ambit of the invention for use in the recombinant vector and may include such combinations as B7.1, B7.2, ICAM-1, LFA-3; B7.1, B7.2, ICAM-1, LFA-3; B7.1, B7.2, ICAM-1, 4-1BBL; B7.1, B7.2, ICAM-1, LFA-3,4-1BBL; CD59, VCAM-1; and B7.1, B7.2; CD59, CD40, 4-BBL, CD70 and VCAM-1, B7.1, B7.2; OX-40L, 4-1BBL; and the like depending on the desired immune response and the disease or condition to be treated. Based on the dramatic synergistic immune responses achieved using a recombinant vector encoding three costimulatory molecules as compared to the use of a recombinant vector encoding one or two costimulatory molecules, a recombinant vector encoding four, five or more costimulatory molecules will result in a synergistic immune response or immune response equal to/or greater than that using a recombinant vector encoding three costimulatory molecules.

B7 represents a family of costimulatory molecules which are members of the Ig gene superfamily. The members include murine B7.1 (CD80) and B7.2 (CD86). B7.1 and B7.2 are the natural ligands of CD28/CTLA-4 (CD152). The gene sequence of murine B7.1 is disclosed in Freeman et al (J. Immunol. 143:2714–2722, 1989) and in GENBANK under Accession No. X60958. The gene sequence of murine B7.2 is disclosed in Azuma et al (Nature 366:76–79, 1993) and in GENBANK under Accession No. L25606 and MUSB72X.

The human homologs of the murine B7 costimulatory molecules and functional portions thereof are an ambit of the present invention and have particular utility in recombinant vectors for human clinical use. The human homolog of the murine B7 costimulatory molecules include CD80, the homolog of murine B7.1, and CD86, the homolog of B7.2. The gene sequence of human B7.1 (CD80) is disclosed in GENBANK under Accession No. M27533, and the gene sequence of human B7.2 (CD86) is disclosed under Accession No. U04343 and AF099105. A license may be required to practice this invention.

For use in the present invention, a recombinant vector may contain a foreign nucleic acid sequence encoding at least one molecule from the B7 costimulatory molecule family, or a combination of B7 costimulatory molecules or functional portions thereof in addition to other costimulatory molecules. The combination of B7 costimulatory molecules includes but is not limited to two or more B7.1 molecules, two or more B7.2 molecules, B7.1 and B7.2 and the like. In one embodiment the recombinant vector contains a foreign nucleic acid sequence encoding the B7.1 molecule in combination with foreign nucleic acid sequences encoding LFA-3 and ICAM-1.

Intercellular adhesion molecule-1 (murine ICAM-1, CD54) and the human homolog, CD54, also acts as a costimulatory molecule. Its ligand is leukocyte function-associated antigen-1 (LFA-1, CD11a/CD18) which is expressed on the surface of lymphocytes and granulocytes. The gene for murine ICAM-1 is disclosed in GenBank under Accession No. X52264 and the gene for the human ICAM-1 homolog, (CD54), is disclosed in Accession No. J03132. In one embodiment, the recombinant vector of the present invention contains a foreign nucleic acid sequence encoding at least one murine ICAM-1 molecule, human homolog, other mammalian homolog or functional portion thereof in addition to foreign nucleic acid sequences encoding two or more additional costimulatory molecules.

The costimulatory molecule leukocyte function antigen 3, murine LFA-3 (CD48), and its human homolog LFA-3 (CD58), a glycosyl-phosphatidylinositol-linked glycoprotein, is a member of the CD2 family within the immunoglobulin gene superfamily. The natural ligand of LFA-3 is CD2 (LFA-2) which is expressed on thymocytes, T cells, B cells and NK cells. The gene for murine LFA-3 is disclosed in GenBank under Accession No. X53526 and the gene for the human homolog is disclosed in Accession No. Y00636.

The T cell antigen 4-1BBL is a costimulatory molecule that relays costimulatory signals in antigen-stimulated primary T cell cultures and in lectin-driven activation of thymocytes (Hurtado, J. C. et al *J. Immunol.* 158(6): 2600–2609, 1997). 4-1BBL belongs to the tumor necrosis factor receptor superfamily, a group of cysteine-rich cell surface molecules (Vinay, D. S. et al, *Seminars in Immunology*, 1998, Vol. 10, pp. 481–489). The gene for the murine 4-1BBL is disclosed in GenBank under Accession No. U02567. The gene for the human homolog, hu4-1BBL is disclosed in GenBank under Accession No. U03397.

OX-40L is a type II membrane protein with limited homology to TNF and is stimulatory to OX-40$^+$ T cells in vitro. The murine and human OX-40L cDNAs have 68% homology at the nucleotide level and 46% at the amino acid level. Human OX-40L stimulates human T cells exclusively, while murine OX-40L stimulates both human and mouse T cells. APC express OX-40L and can transmit the OX-40L: OX-40R signal during presentation of antigen to CD4$^+$ T cells. OX-40L signaling is important for differentiation of human dendritic cells and leads to increased production of IL-12, TNF-α, IL-1B, and IL-6. (Weinberg, A. D. et al 1998 *Seminars in Immunology*, Vol. 10:471480). OX-40L is a potent costimulatory molecule for sustaining primary CD4$^+$ T cell responses, used in combination with B7-1 (Gramaglia, I. et al 1998 *J. Immunology*, Vol. 161:6510–7.

Vectors having utility in the present invention are capable of causing expression of at least three or more foreign genes, preferably five or more foreign genes. Vectors having utility in the present invention include any vector capable of causing functional expression of at least three foreign costimulatory molecules gene products in a host cell. In addition to the genes encoding at least three costimulatory molecules, the vector is also capable of causing the expression of at least one foreign gene encoding at least one target antigen or immunological epitope thereof as well as a selectable marker.

Vectors of the present invention include but are not limited to bacterial vectors such as *Salmonella*, viral vectors, nucleic acid based vectors and the like. Viral vectors include but are not limited to poxvirus, Herpes virus, adenovirus, alphavims, retrovirus, picomavirus, iridovirus, and the like. Poxviruses having utility in the present invention include replicating and non-replicating vectors. Such poxviruses include but are not limited to orthopox such as vaccinia, raccoon pox, rabbit pox and the like, avipox, suipox, capripox and the like. Poxviruses may be selected from the group consisting of vaccinia-Copenhagen, vaccinia-Wyeth strain, vaccinia-MVA strain, NYVAC, fowlpox, TROVAC, canarypox, ALVAC, swinepox, and the like. In one embodiment, the recombinant vector is a vaccinia virus. In another embodiment, the recombinant vector is fowlpox.

A preferred vector of the present invention is a recombinant virus, preferably a poxvirus. The recombinant poxviruses having utility in the present invention have a number of attributes, including (i) efficient delivery of genes to multiple cell types, including APC and tumor cells; (ii) high levels of protein expression; (iii) optimal presentation of antigens to the immune system; (iv) the ability to elicit cell-mediated immune responses as well as antibody responses; (v) transient, rather than permanent, genetic modification of cells, and (vi) the ability to use combinations of poxviruses from different genera, as they are not immunologically cross-reactive. Parental poxviruses useful in constructing the recombinant poxvirus of the present invention include but are not limited to orthopox virus such as replicating vaccinia virus (Perkus et al *Science* 229:981–984, 1985; Kaufman et al *Int. J. Cancer* 48:900–907, 1991, Moss Science 252:1662, 1991), highly attenuated vaccinia viruses such as MVA, modified vaccinia Ankara (Sutter and Moss, *Proc. Nat'l Acad. Sci. U.S.A.* 89:10847–10851; Sutter et al *Virology* 1994), vaccinia-Copenhagen and NYVAC: avipoxviruses (15) such as fowlpox virus (15), canary poxviruses, such as ALVAC and the like (Baxby and Paoletti, *Vaccine* 10:8–9, 1992; Rinns, M. M. et al (Eds) *Recombinant Poxviruses* CRC Press, Inc, Boca Raton 1992; Paoletti, E. *Proc. Nat'l Acad. Sci. USA* 93:11349–11353, 1996), and suipoxvirus, capripoxvirus and the like.

In one embodiment, the parental poxvirus is a vaccinia virus. In a particular embodiment, the vaccinia virus is a Wyeth strain or derivative thereof A derivative of the Wyeth strain includes but is not limited to vTBC33 which lacks a functional K1L gene and the like. In yet another embodiment, the virus is Dry-Vax available as a smallpox vaccine from the Centers for Disease Control, Atlanta, Ga. In another embodiment, the parental poxvirus is a strain of fowlpox, for example POXVAC-TC (Schering-Plough Corporation), and the like.

The recombinant vector of the present invention is able to infect, transfect or transduce host cells in a host. The host includes but is not limited to mammals, birds, fish and the like. The host cells are any cell amenable to infection, transfection or transduction by the recombinant vector and capable of expressing the foreign genes from the recombinant vector at functional levels. The host cells include but are not limited to professional APC and antigen presenting precursor cells such as monocytes, macrophages, DC, Langerhans cells and the like. The recombinant vector of the present invention may also infect tumor cells or other cell types such as fibroblasts or muscle cells. Infection of the host cells allows expression of each foreign, exogenous costimulatory molecule and expression of the foreign nucleic acid sequence encoding target antigen(s) if present in the recombinant vector. The host cells express, or are engineered to express, the appropriate MHC (HLA) Class I or II molecules for appropriate antigenic presentation to CD4$^+$ and/or CD8$^+$ T cells. As such virtually any mammalian cell may be engineered to become an appropriate antigen presenting cell expressing multiple costimulatory molecules.

The recombinant vector of the present invention comprises at least one expression control element operably linked to the nucleic acid sequence. The expression control elements are inserted in the vector to control and regulate the expression of the nucleic acid sequence (Ausubel et al, 1987, in "Current Protocols in Molecular Biology, John Wiley and Sons, New York, N.Y.). Expression control elements are known in the art and include promoters. Promoters useful in the present invention are poxviral promoters as are known in the art which include but are not limited to 30K, 13, sE/L, 7.5K, 40K, C1 and the like. The nucleic acid sequence of the 30K promoter is disclosed in GenBank Accession No. M35027 at base numbers 28,012 through 28,423 (antisense). The nucleic acid sequence of 13 is disclosed in GenBank Accession No. J03399 at base numbers 1100 through 1301 (antisense). The nucleic acid sequence of the 7.5K promoter is disclosed in GenBank Accession No. M35027 at base numbers 186550 through 186680. The nucleic acid sequence of the 40K promoter is disclosed in GenBank Accession No. M13209 at base numbers 9700 through 9858 (antisense). The nucleic acid sequence of the C1 promoter is disclosed in GenBank Accession No. M59027 at base numbers 1 through 242 and in U.S. Pat. No. 5,093,258. The sequence of the sE/L promoter is disclosed in Reference 16. Other poxvirus promoters may be used, such as, those described by Davison and Moss (*J. Mol. Biol.* 210:749–769, (1989). Any of these promoters can be synthesized by using standard methods in the art. The selection of an appropriate promoter is based on its timing and level of expression. Early or early/late promoters are preferred. In a preferred embodiment, the promoter or combination of promoters utilized allow for optimal expression of each costimulatory molecule in an infected host to provide a synergistic immune response. In a preferred embodiment, each foreign gene encoding a costimulatory molecule is controlled by a separate and distinct promoter.

In the case of nucleic acid-based vectors, the constructs may be either nucleic acid (DNA or RNA) or associated with/or encapsulated in a lipid carrier. Optionally, the lipid carrier molecule and/or construct may provide targeting and/or expression in a particular target cell type or types. Naked DNA vectors may be prepared by methods described in U.S. Pat. No. 5,827,703. For the transcriptional initiation region, or promoter element, any region may be used with the proviso that it provides the desired level of transcription of the DNA sequence of interest. The transcriptional initiation region may be native to or homologous to the host cell and/or to the DNA to be transcribed, or foreign or heterologous to the host cell and/or the DNA sequence to be transcribed. Efficient promoter elements for transcription initiation of naked DNA include but are not limited to the SV40 (simian virus 40) early promoter, the RSV (Rous sarcoma virus) promoter, the adenovirus major late promoter, the human CMV (cytomegalovirus) immediate early I promoter, and the like. Nucleic acid-based vectors may be delivered to a host using a syringe, a catheter, or a needle-free injection device such as a gene gun.

In an embodiment of the invention, a recombinant vector is provided comprising a foreign nucleic acid sequence encoding a first costimulatory molecule or functional portion thereof under control of a first promoter, a foreign nucleic acid sequence encoding a second costimulatory molecule or functional portion thereof under control of a second promoter, and a foreign nucleic acid sequence encoding a third costimulatory molecule or functional portion thereof under control of a third promoter. The recombinant vector may further provide a foreign nucleic acid sequence encoding a target antigen or immunological portion thereof under control of a fourth promoter.

Figure 4A:
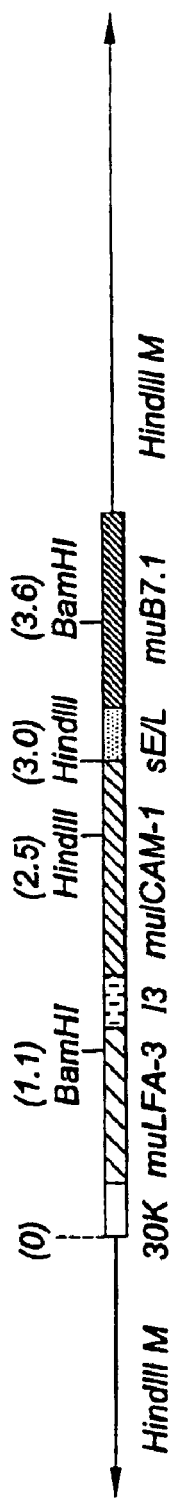
FIGS. 4A through 4C. Genomic structure of recombinant vaccinia viruses expressing three murine costimulatory molecules with (FIG. 4C) or without (FIGS. 4A and B) a tumor-associated antigen.
Figure 4B:
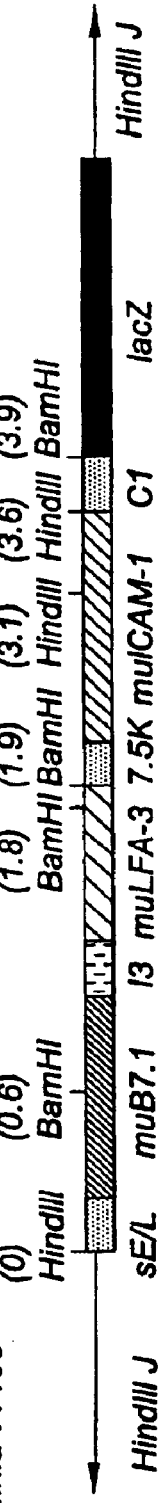
Figure 4C:

In one embodiment of the present invention, a recombinant poxvirus is provided comprising a nucleic acid sequence encoding LFA-3 or functional portion thereof under control of a 30K poxviral promoter, a nucleic acid sequence encoding ICAM-1 or portion thereof under control of an 13 poxviral promoter, and a nucleic acid sequence encoding B7.1 or portion thereof under control of an sE/L poxviral promoter. One example of such a recombinant poxvirus construct is vaccinia vT171 as depicted in FIG. 11A. The recombinant poxvirus may further provide a nucleic acid sequence encoding a tumor associated antigen or immunological portion thereof. One embodiment of the invention is recombinant vaccinia vT172 as depicted in FIG. 4C.

In another embodiment of the present invention, a recombinant poxvirus is provided comprising a nucleic acid sequence encoding B7.1 under control of a sE/L poxviral promoter, a nucleic acid sequence encoding LFA-3 or portion thereof under control of the 13 poxviral promoter, and a nucleic acid sequence encoding ICAM-1 or portion thereof under control of the 7.5K poxvirus promoter. Optionally the construct further comprises a nucleic acid sequence encoding at least one target antigen or immunological epitope thereof and/or a nucleic acid sequence encoding a selectable marker. One embodiment of such a recombinant poxvirus construct is vaccinia vT199 as depicted in FIG. 4B containing a lacZ gene as the selectable marker.

In an embodiment of the invention a recombinant fowlpox virus comprises a nucleic acid sequence encoding B7.1 or portion thereof under control of the sE/L poxviral promoter, a nucleic acid sequence encoding LFA-3 or portion thereof under control of the 13 poxviral promoter, and a nucleic acid sequence encoding ICAM-1 or portion thereof under control of the 7.5K poxviral promoter. An example of this embodiment is fowlpox vT222 as depicted in FIG. 4A. A recombinant fowlpox virus may further comprise a nucleic acid sequence encoding a target antigen, CEA, under control of the 40K poxviral promoter and a nucleic acid sequence encoding the selectable marker, lacZ under control of the C1 poxviral promoter. An example of this embodiment is fowlpox vT194 as depicted in FIG. 4B.

Figure 14:
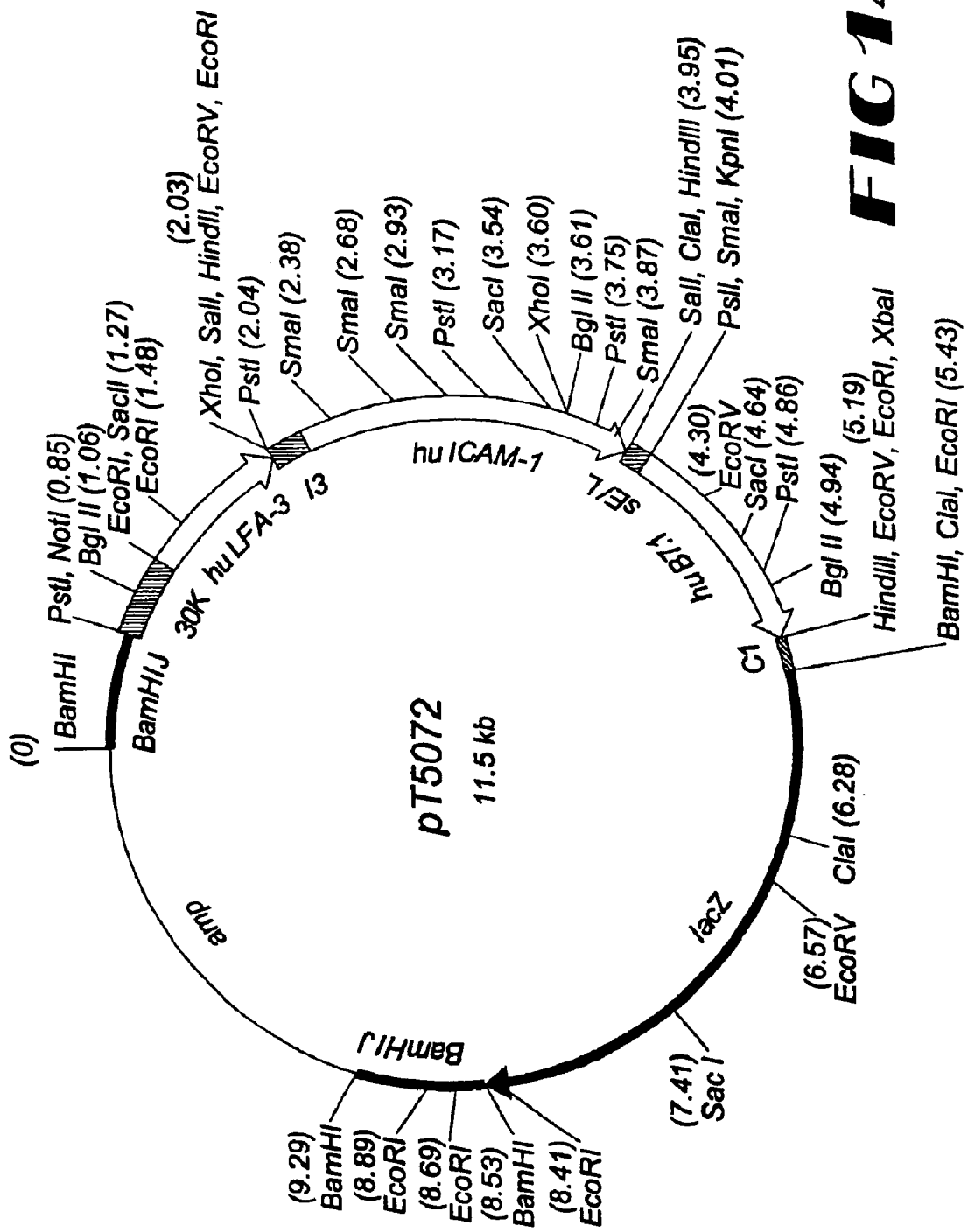
FIG. 14. Genomic structure of plasmid pT5072 comprising nucleic acid sequences encoding human LFA-3, ICAM-1, B7.1, and the E. coli lacZ gene, flanked by portions of the BamHI J region of the fowlpox genome.

In another embodiment, a recombinant fowlpox virus comprises a nucleic acid sequence encoding the tumor-associated antigen MUC-1 or portion thereof under the control of the 40K promoter, a nucleic acid sequence encoding LFA-3 or portion thereof under the control of the 30K promoter, a nucleic acid sequence encoding ICAM-1 or portion thereof under the control of the 13 promoter, and a nucleic acid sequence encoding B7.1 or portion thereof under the control of the sE/L promoter, as depicted in FIG. 14C. The recombinant fowlpox virus may comprise a nucleic acid sequence encoding any tumor-associated antigen or portion thereof and nucleic acid sequences encoding LFA-3, ICAM-1 and B7.1, under the control of a multiplicity of promoters, as depicted in FIG. 4D.

Another embodiment of the present invention is a recombinant vector comprising nucleic acid sequences encoding the human homologs of the costimulatory molecules LFA-3, B7 and ICAM-1. The recombinant vector may further provide the appropriate promoters to allow expression of each sequence in an infected host cell. One embodiment of the recombinant vector is vT224 depicted in FIG. 9.

The present invention provides plasmid vectors comprising a foreign nucleic acid sequence encoding multiple costimulatory molecules. In one embodiment, foreign nucleic acid sequences are selected that encode at least three or more costimulatory molecules selected from the group consisting of B7, ICAM-1, LFA-3,4-1BBL, CD59, CD40, CD70, VCAM-1, OX-40L and the like. In one embodiment of the present invention, plasmid vectors comprising a foreign nucleic acid sequence encoding at least one B7 costimulatory molecule, a foreign nucleic acid sequence encoding an ICAM-1 costimulatory molecule and a foreign nucleic acid sequence encoding a LFA-3 costimulatory molecule are provided. The plasmid vectors of the present invention further provide at least one promoter sequence for controlling the expression of the costimulatory molecules. In a preferred embodiment each nucleic acid sequence encoding a costimulatory molecule is controlled by a separate discrete promoter sequence. For use in making a recombinant poxvirus, the plasmid vectors of the present invention further provide flanking viral nucleic acid sequences from a non-essential region of a poxvirus genome. The flanking viral nucleic acid sequences direct insertion of the foreign sequences into a parental poxviral genome via homologous recombination. The plasmid vectors of the present invention may further comprise one or more selectable markers for selection and identification of recombinant progeny containing the inserted foreign DNA as are known in the art including but not limited to the vaccinia KI L host range gene, the *E. coli* lacZ gene, antibiotic resistance genes, the gene encoding β-glucuronidase and the like.

In an embodiment, a plasmid vector of the present invention comprises a nucleic acid sequence encoding LFA-3 under control of the 30K promoter, a nucleic acid sequence encoding ICAM-1 under control of the I3 promoter and a nucleic acid sequence encoding B7 under control of the sE/L promoter, flanked by portions of the Hind III M region of the vaccinia genome. In one embodiment, the plasmid vector is as depicted in FIG. 1 as pT5032.

Figure 2:
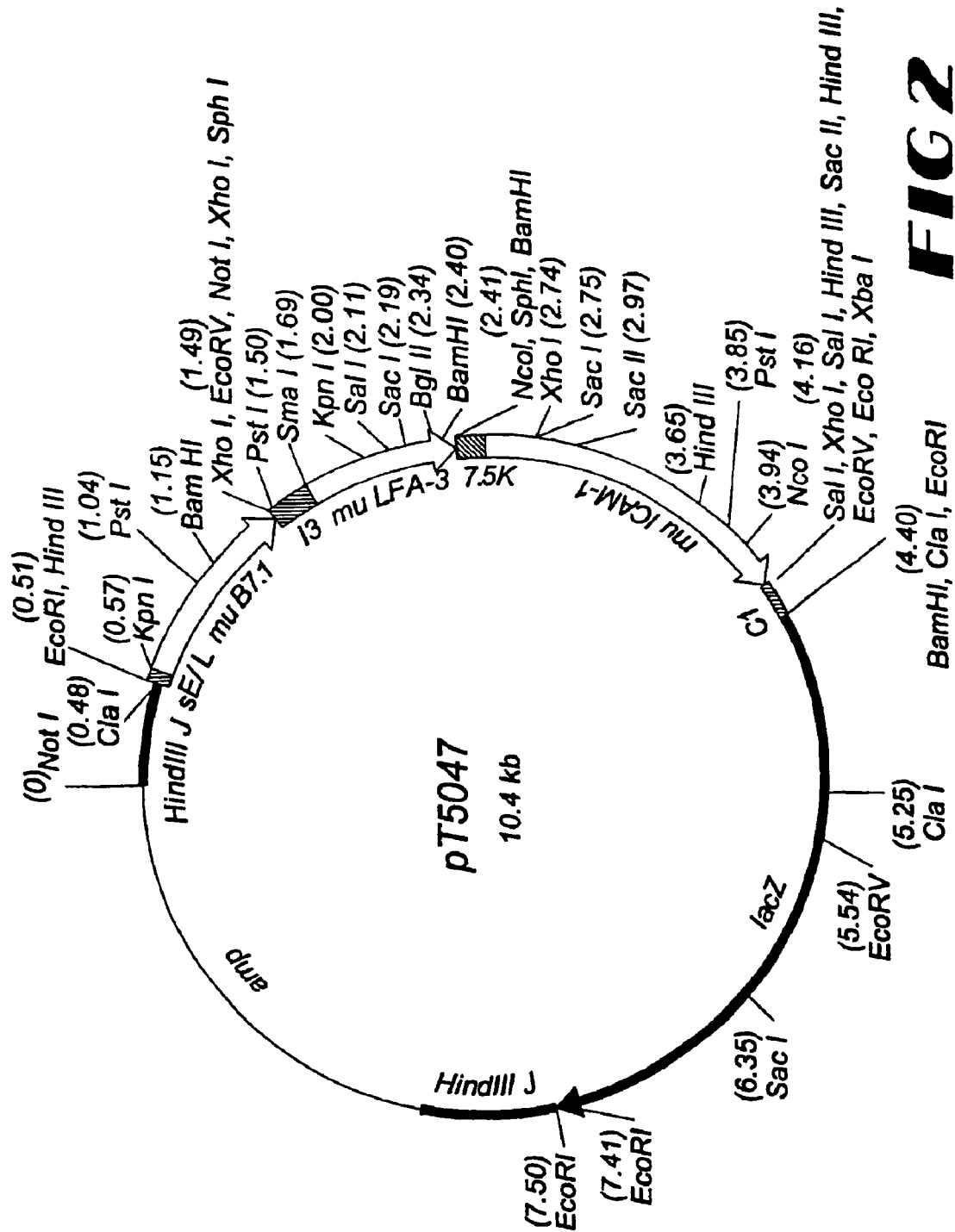
FIG. 2. Genomic structure of plasmid pT5047 comprising nucleic acid sequences encoding murine LFA-3, ICAM-1, B7.1, and the lacZ gene, flanked by portions of the Hind III J region of the vaccinia genome.

Another embodiment of the plasmid vector of the present invention comprises a nucleic acid sequence encoding B7 under control of the sE/L promoter, a nucleic acid sequence encoding LFA-3 under control of the 13 promoter and a nucleic acid sequence encoding ICAM-1 under control of the 7.5K promoter. The plasmid vector may further comprise a lacZ gene or portion thereof driven by a distinct promoter sequence. These sequences are flanked by portions of the Hind III J region of the vaccinia genome. A particular embodiment of the plasmid vector is depicted as pT5047 in FIG. 2.

In another embodiment of the plasmid vector comprises in combination with the nucleic acid sequences encoding B7, ICAM-1, and LFA-3, a nucleic acid sequence encoding at least one target antigen or immunological epitope thereof. A promoter is provided for controlling the expression of the target antigen. A particular embodiment of the plasmid vector is depicted as pT5031 in FIG. 3 and comprises a nucleic acid sequence encoding the target antigen, CEA.

In another particular embodiment the plasmid vector comprises a nucleic acid sequence encoding the tumor associated antigen, CEA, under control of the 40K promoter, a nucleic acid sequence encoding B7 under control of the sE/L promoter, a nucleic acid sequence encoding LFA-3 under control of a 13 promoter and a nucleic acid sequence encoding ICAM-1. The plasmid vector may further comprise a lacZ gene under control of a C1 promoter as depicted in FIG. 6 as pT5049. Plasmid pT5049, was deposited with the American Type Culture Collection, 10801 University Boulevard, Manassas, Va. 20110 on Nov. 13, 1998 as ATCC Accession No. 203481 under the terms of the Budapest Treaty.

Figure 8:
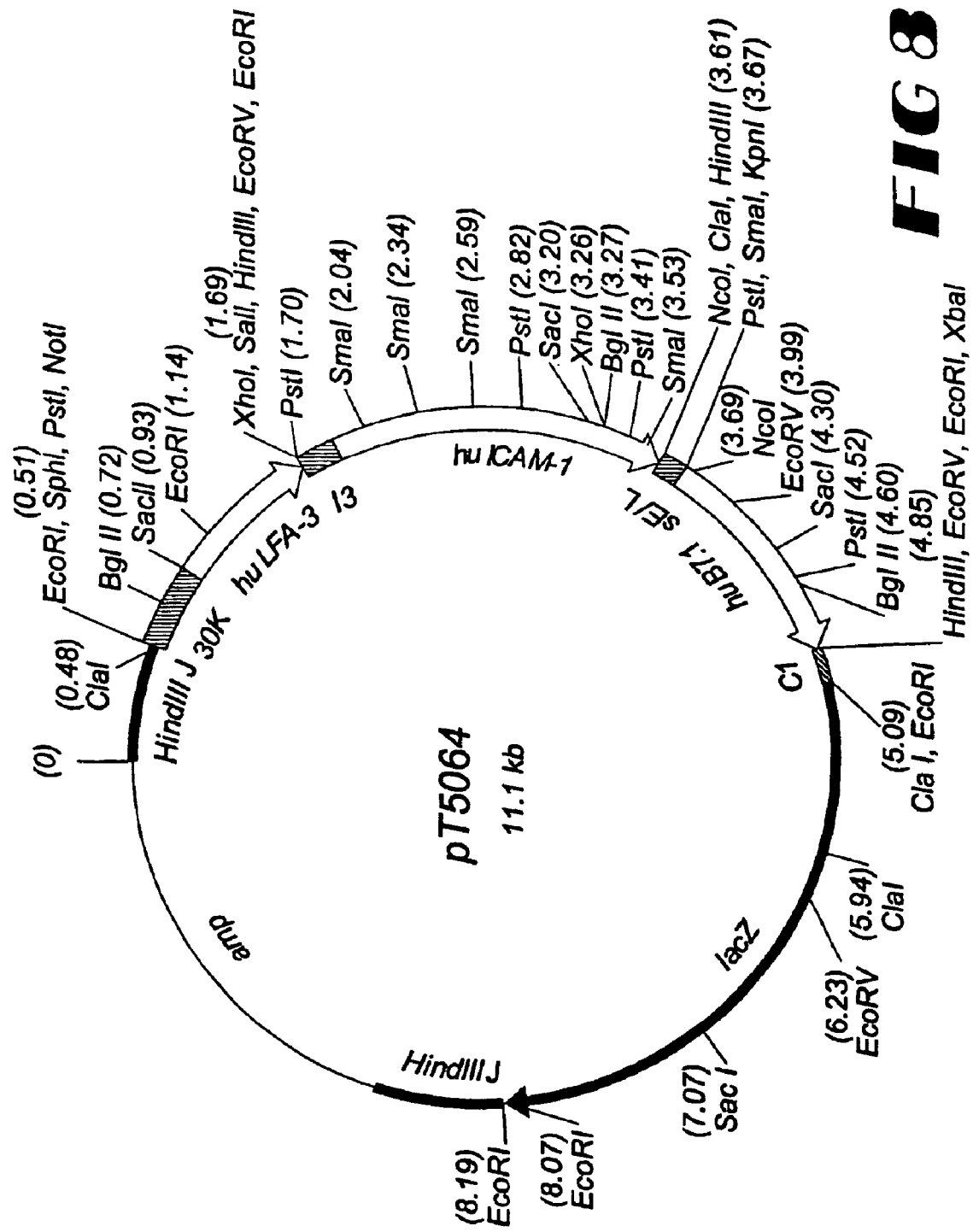
FIG. 8. Genomic structure of plasmid pT5064 comprising nucleic acid sequences encoding human LFA-3, human ICAM-1, human B7.1 and the lacZ gene, flanked by portions of the HindIII J region of the vaccinia genome.

In yet another embodiment of the plasmid vector, the vector comprises a nucleic acid sequence encoding huLFA-3 under control of the 30K promoter, a nucleic acid sequence encoding huICAM-1 under control of an 13 promoter and huB7.1 under control of the sE/L promoter. A particular embodiment of the plasmid vector is depicted as pT5064 in FIG. 8, which was deposited with the ATCC on Nov. 13, 1998 as ATCC Accession No. 203482 under the terms of the Budapest Treaty.

The plasmid vector of the present invention may be provided in kit form for use in methods of generating recombinant vectors. The kit may further provide a parental virus, and other reagents used in the recombination process.

The present invention further provides methods of generating recombinant poxviruses comprising nucleic acid sequences encoding multiple costimulatory molecules. One method of generation of recombinant poxviruses is accomplished via homologous recombination in vivo between parental poxvirus genomic DNA and a plasmid vector that carries the heterologous sequences to be inserted as disclosed in U.S. Pat. No. 5,093,258. Plasmid vectors for the insertion of foreign sequences into poxviruses are constructed by standard methods of recombinant DNA technology (36). The plasmid vectors contain one or more chimeric foreign genes, each comprising a poxvirus promoter linked to a protein coding sequence, flanked by viral sequences from a non-essential region of the poxvirus genome. The plasmid is transfected into cells infected with the parental poxvirus using art accepted transfection methods, and recombination between poxvirus sequences on the plasmid and the corresponding DNA in the parental viral genome results in the insertion into the viral genome of the chimeric foreign genes from the plasmid. Recombinant viruses are selected and purified using any of a variety of selection or screening systems as are known in the art (14). Insertion of the foreign genes into the vaccinia genome is confirmed by polymerase chain reaction (PCR) analysis. Expression of the foreign genes is demonstrated by Western blot analysis. An alternative method of generation of recombinant poxviruses is accomplished by direct ligation (Pleiderer et al *J. Gen. Virol.* 76:2957–2962, 1995; Merchlinsky et al *Virol.* 238:444451, 1997).

Use of the recombinant vector comprising nucleic acid sequences encoding multiple costimulatory molecules in combination with a nucleic acid sequence encoding at least one target antigen or epitope thereof is useful in enhancing an immune response against the target antigen or epitope thereof, and enhance the immune response against cells expressing the target antigen or epitope thereof. The magnitude of the immune response against the target antigen, epitope, or cells expressing target antigen obtained using the recombinant vector of the present invention is significantly greater than that achieved using systems employing a single or a double costimulatory molecule.

The recombinant vector encodes at least three or more costimulatory molecules in combination with a nucleic acid sequence encoding a target antigen or immunological epitope thereof for providing a synergistic immunological response to the target antigen or epitope thereof. In one embodiment, a recombinant poxvirus provides a nucleic acid sequence encoding B7, ICAM-1 and LFA-3, along with a nucleic acid sequence encoding at least one target antigen or immunological epitope thereof. In some instances it may be beneficial to provide more than one nucleic acid sequence to provide multiple target antigens or immunological epitopes thereof for the purpose of having a multivalent vaccine.

The target antigen, as used herein, is an antigen or immunological epitope on the antigen which is crucial in immune recognition and ultimate elimination or control of the disease-causing agent or disease state in a mammal. The immune recognition may be cellular and/or humoral. In the case of intracellular pathogens and cancer, immune recognition is preferably a T lymphocyte response.

The target antigen may be derived or isolated from a pathogenic microorganism such as viruses including HIV, (Korber et al, eds HIV Molecular Immunology Database, Los Alamos National Laboratory, Los Alamos, N. Mex. 1977) influenza, Herpes simplex, human papilloma virus (U.S. Pat. No. 5,719,054), Hepatitis B (U.S. Pat. No. 5,780, 036), Hepatitis C (U.S. Pat. No. 5,709,995), EBV, Cytomegalovirus (CMV) and the like. Target antigen may be derived or isolated from pathogenic bacteria such as from *Chlamydia* (U.S. Pat. No. 5,869,608), *Mycobacteria, Legionella, Meningiococcus*, Group A *Streptococcus, Salmonella, Listeria, Hemophilus influenzae* (U.S. Pat. No. 5,955,596) and the like.

Target antigen may be derived or isolated from pathogenic yeast including *Aspergillus*, invasive *Candida* (U.S. Pat. No. 5,645,992), *Nocardia, Histoplasmosis, Cryptosporidia* and the like.

Target antigen may be derived or isolated from a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589,343) and *Toxoplasma gondii*.

Target antigen includes an antigen associated with a preneoplastic or hyperplastic state. Target antigen may also be associated with, or causative of cancer. Such target antigen may be tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-I, CAP-1-6D (46) and the like (GenBank Accession No. M29540), MART-1 (Kawakami et al, *J. Exp. Med.* 180:347–352, 1994), MAGE-1 (U.S. Pat. No. 5,750,395), MAGE-3, GAGE (U.S. Pat. No. 5,648,226), GP-100 (Kawakami et al *Proc. Nat'l Acad. Sci. USA* 91:6458–6462, 1992), MUC-1, MUC-2, point mutated ras oncogene, normal and point mutated p53 oncogenes (Hollstein et al *Nucleic Acids Res.* 22:3551–3555, 1994), PSMA (Israeli et al *Cancer Res.* 53:227–230, 1993), tyrosinase (Kwon et al *PNAS* 84:7473–7477, 1987, TRP-1 (gp75) (Cohen et al *Nucleic Acid Res.* 18:2807–2808, 1990; U.S. Pat. No. 5,840,839), NY-ESO-1 (Chen et al *PAS* 94: 1914–1918, 1997), TRP-2 (Jackson et al *EMBOJ*, 11:527–535, 1992), TAG72, KSA, CA-125, PSA, HER-2/neu/c-erb/B2, (U.S. Pat. No. 5,550,214), BRC-I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each.

Possible human tumor antigens and tissue specific antigens as well as immunological epitopes thereof for targeting using the present invention include but are not limited to those exemplified in Table 1.

TABLE 1

Antigens and Epitopes Recognized by T Cells

| Target antigens | Restriction element | Immunological Peptide epitope | SEQ. ID No. |
|---|---|---|---|
| Human target tumor antigens recognized by T cells | | | |
| gp 100 | HLA-A2 | KTWGQYWZY | 1 |
|  | HLA-A2 | ITDQVPPSV | 2 |
|  | HLA-A2 | YLEPGPVTA | 3 |
|  | HLA-A2 | LLDGTATLRL | 4 |
|  | HLA-A2 | VLYRYGSFSV | 5 |
| MART-/Melan A | HLA-A2 | AAGIGILTV | 6 |
|  | HLA-A2 | ILTVILGVL | 7 |
| TRP-1 (GP75) | HLA-A31 | MSLQRQFLR | 8 |
|  | HLA-A2 | MLLAVLYCL | 9 |
| Tyrosinase | HLA-A2 | YMNGTMSQV | 10 |
|  | HLA-B44 | SEIWRDIDF | 11 |
|  | HLA-A24 | AFLPWHRLF | 12 |
|  | HLA-DR4 | QNILLSNAPLGPQFP | 13 |
|  | HLA-DR4 | SYLQDSDPDSFQD | 14 |
| MAGE-1 | HLA-A1 | EADPTGHSY | 15 |
|  | HLA-Cw16 | SAYGEPRKL | 16 |
| MAGE-3 | HLA-A1 | EVDPIGHLY | 17 |
|  | HLA-A2 | FLWGPRALV | 18 |
| BAGE | HLA-Cw16 | AARAVFLAL | 19 |
| GAGE-1,2 | HLA-Cw6 | YRPRPRRY | 20 |
| N-acetyl-glucos-aminyl-transferase-V | HLA-A2 | VLPDVFIRC | 21 |

TABLE 1-continued

Antigens and Epitopes Recognized by T Cells

| Target antigens | Restriction element | Immunological Peptide epitope | SEQ. ID No. |
|---|---|---|---|
| p15 | HLA-A24 | AYGLDFYIL | 22 |
| CEA |  | YLSGANLNL(CAP1) | 23 |
|  |  | YLSGADLNL (CAP1-6D) | 24 |
|  |  |  | 37 |
| β-catenin | HLA-A24 | SYLDSGIHF | 25 |
| MUM-1 | HLA-B44 | EEKLIVVLF | 26 |
| CDK4 | HLA-A2 | ACDPHSGHFV | 27 |
| HER-2/neu (Breast and ovarian carcinoma) | HLA-A2 | IISAVVGIL | 28 |
|  | HLA-A2 | KIFGSLAFL | 29 |
| Human papilloma-virus-E6,E7 (cervical carcinoma) | HLA-A2 | YMLDLQPETT | 30 |
| MUC-1 (Breast, ovarian and pancreatic carcinoma) | Non-MHC restricted MHC restricted | PDTRPAPGSTAPPAHGVTSA (and portions thereof) | 31 |
| PSA | A2, A3 | FLTPKKLQCVDLHVISNDVCA-QVHPQKVTK | 32 |
|  |  | FLTPKKLQCV | 33 |
|  |  | KLQCVDLHV | 34 |
|  |  | VISNDVCAQV | 35 |
|  |  | QVHPQKVTK | 36 |

For organisms which contain a DNA genome, a gene encoding a target antigen or immunological epitope thereof of interest is isolated from the genomic DNA For organisms with RNA genomes, the desired gene may be isolated from cDNA copies of the genome. If restriction maps of the genome are available, the DNA fragment that contains the gene of interest is cleaved by restriction endonuclease digestion by methods routine in the art. In instances where the desired gene has been previously cloned, the genes may be readily obtained from the available clones. Alternatively, if the DNA sequence of the gene is known, the gene can be synthesized by any of the conventional techniques for synthesis of deoxyribonucleic acids.

Genes encoding an antigen of interest can be amplified by cloning the gene into a bacterial host. For this purpose, various prokaryotic cloning vectors can be used. Examples are plasmids pBR322, pUC and pEMBL.

The genes encoding at least one target antigen or immunological epitope thereof can be prepared for insertion into the plasmid vectors designed for recombination with a virus by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with a virus, then purified prior to insertion into the vectors at restriction endonuclease cleavage sites (cloning sites) as described herein.

Diseases may be treated or prevented by use of the present invention and include diseases caused by viruses, bacteria, yeast, parasites, protozoans, cancer cells and the like. The recombinant vector comprising multiple costimulatory molecules may be used as a generalized immune enhancer and as such has utility in treating diseases of no known etiological cause.

Preneoplastic or hyperplastic states which may be treated or prevented using a recombinant vector of the present invention include but are not limited to preneoplastic or hyperplastic states such as colon polyps, Crohn's disease, ulcerative colitis, breast lesions and the like.

Cancers which may be treated using the recombinant vector of the present invention include but are not limited to primary or metastatic melanoma, adenocarcinoma, squamous cell carcinoma, adenosquamous cell carcinoma, thymoma, lymphoma, sarcoma, lung cancer, liver cancer, non-Hodgkins lymphoma, Hodgkins lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

The present invention provides a pharmaceutical composition comprising a recombinant vector comprising foreign genes encoding multiple costimulatory molecules in a pharmaceutically acceptable carrier. At least three genes encoding a costimulatory molecule form part of the recombinant vector and may be selected from the group of genes encoding B7, ICAM-1, LFA-3,4-1BBL, CD59, CD40, CD70, VCAM-1, OX-40L and the like. The recombinant vector may further comprise a nucleic acid sequence encoding at least one target antigen or immunological epitope thereof. In another embodiment, the pharmaceutical composition comprises a first recombinant vector comprising foreign genes encoding multiple costimulatory molecules, a second recombinant vector comprising nucleic acid sequences encoding at least one target antigen or immunological epitope thereof and a pharmaceutically acceptable carrier. Administration of the pharmaceutical composition provides host cells with the foreign genes encoding multiple costimulatory molecules.

In one embodiment, a pharmaceutical composition comprises a recombinant poxvirus containing foreign genes encoding multiple costimulatory molecules in a pharmaceutically acceptable carrier. The recombinant poxvirus may further comprise a nucleic acid sequence encoding at least one target antigen or immunological epitope thereof or alternatively, a second recombinant poxvirus may be provided encoding at least one target antigen or immunological epitope thereof.

The present invention provides a pharmaceutical composition comprising a recombinant poxvirus comprising a nucleic acid sequence encoding B7.1 to B7.2, a nucleic acid sequence encoding ICAM-1, and a nucleic acid sequence encoding LFA-3 and a pharmaceutically acceptable carrier. In addition to the B7, ICAM-1, LFA-3 construct, the recombinant poxvirus of the pharmaceutical composition may additionally comprise a nucleic acid sequence encoding at least one target antigen or immunological epitope thereof or the nucleic acid sequence encoding at least one target antigen or immunological epitope thereof may be provided in the composition by a second recombinant poxvirus.

The pharmaceutical composition may also comprise exogenously added immunostimulatory molecules as are known in the art including the costimulatory molecules B7, ICAM-1, LFA-3,4-1BBL, CD59, CD40, CD70, VCAM-1, OX-40L and the like and/or cytokines and chemokines including but not limited to IL2, GM-CSF, TNFα, IFNγ IL-12, RANTES, MIP-1α, Flt-3L (U.S. Pat. No. 5,554,512; 5,843,423) and the like for additional synergy or enhancement of an immune response. The cytokines and chemokines themselves may be provided in the composition or, alternatively, the cytokines and chemokines may be provided by a recombinant viral vector encoding the cytokine or chemokine.

The present invention also encompasses methods of treatment or prevention of a disease caused by pathogenic microorganisms or by cancer disclosed herein.

In the method of treatment, the administration of the recombinant vector of the invention may be for either "prophylactic" or "therapeutic" purpose. When provided prophylactically, the recombinant vector of the present invention is provided in advance of any symptom. The prophylactic administration of the recombinant vector serves to prevent or ameliorate any subsequent infection or disease. When provided therapeutically, the recombinant vector is provided at or after the onset of a symptom of infection or disease. Thus the present invention may be provided either prior to the anticipated exposure to a disease-causing agent or disease state or after the initiation of the infection or disease.

The term "unit dose" as it pertains to the inoculum refers to physically discrete units suitable as unitary dosages for mammals, each unit containing a predetermined quantity of recombinant vector calculated to produce the desired immunogenic effect in association with the required diluent. The specifications for the novel unit dose of an inoculum of this invention are dictated by and are dependent upon the unique characteristics of the recombinant virus and the particular immunologic effect to be achieved.

The inoculum is typically prepared as a solution in tolerable (acceptable) diluent such as saline, phosphate-buffered saline or other physiologically tolerable diluent and the like to form an aqueous pharmaceutical composition.

The route of inoculation may be scarification, intravenous (I.V.), intramuscular (I.M.), subcutaneous (S.C.), intradermal (I.D.), intraperitoneal (I.P.), intratumor and the like, which results in eliciting a protective response against the disease causing agent. The dose is administered at least once. Subsequent doses may be administered as indicated.

In one embodiment, heterologous prime-boost regimens are employed. In one example, the host is immunized at least once with a first vector such as a nucleic acid-based vector. Subsequent immunizations are performed with a poxvirus vector. In another example, the host is first immunized with a first poxvirus vector and then with a second poxvirus vector of a different genus.

In providing a mammal with the recombinant vector of the present invention, preferably a human, the dosage of administered recombinant vector will vary depending upon such factors as the mammal's age, weight, height, sex, general medical condition, previous medical history, disease progression, tumor burden and the like.

In general, it is desirable to provide the recipient with a dosage of recombinant virus in the range of about $10^5$ to about $10^{10}$ plaque forming units, although a lower or higher dose may be administered.

The genetic definition of tumor-associated and tumor-specific antigens allows for the development of targeted antigen-specific vaccines for cancer therapy. Insertion of a tumor antigen gene in the genome of recombinant pox viruses in combination with genes encoding multiple costimulatory molecules is a powerful system to elicit a specific immune response in terms of prevention in individuals with an increased risk of cancer development (preventive immunization), to shrink tumors prior to surgery, to prevent disease recurrence after primary surgery (anti-metastatic vaccination), or to expand the number of cytotoxic lymphocytes (CTL) in vivo, thus improving their effectiveness in eradication of diffuse tumors (treatment of established disease). Recombinant viruses of the present invention can elicit an immune response ex vivo in autologous lymphocytes (CD8$^+$), either cytotoxic T lymphocytes and/or CD4$^+$ helper T cells or NK cells prior to being transferred back to the tumor bearing patient (adoptive immunotherapy).

In cancer treatments, the recombinant vectors can be introduced into a mammal either prior to any evidence of cancers such as an adenocarcinoma or to mediate regression of the disease in a mammal afflicted with a cancer such as adenocarcinoma.

Depending on the disease or condition to be treated and the method of treatment, the recombinant vector may or may not comprise a nucleic acid sequence encoding a target antigen or immunological epitope thereof in addition to the genes encoding multiple costimulatory molecules. The target antigen or immunological epitope thereof may be provided endogenously by the host cell infected with the recombinant vector as, for instance, a tumor cell may endogenously express a tumor associated antigen or epitope thereof and may not require the addition of a foreign gene encoding an exogenous tumor associated antigen. In the case in which a tumor associated antigen is absent, not expressed or expressed at low levels in a host cell, a foreign gene encoding an exogenous tumor associated antigen may be provided. Further, genes encoding several different tumor associated antigens may be provided. The foreign gene encoding an exogenous tumor associated antigen may be provided by the same recombinant vector comprising genes encoding multiple costimulatory molecules or may be provided by a second recombinant vector in an admixture with the first recombinant vector.

Examples of methods for administering the recombinant vector into mammals include, but are not limited to, exposure of tumor cells to the recombinant virus ex vivo, or injection of the recombinant vector into the affected host by intravenous, S.C., I.D. or I.M. administration of the virus. Alternatively the recombinant vector or combination of recombinant vectors may be administered locally by direct injection into the cancerous lesion or tumor or topical application in a pharmaceutically acceptable carrier. The quantity of recombinant vector carrying the nucleic acid sequence of one or more tumor associated antigens (TAAs) in combination with nucleic acid sequences encoding multiple costimulatory molecules to be administered is based on the titer of virus particles. A preferred range of the immunogen to be administered is $10^5$ to $10^{10}$ virus particles per mammal, preferably a human. If the mammal to be immunized is already afflicted with cancer or metastatic cancer, the vaccine can be administered in conjunction with other therapeutic treatments.

In one method of treatment, autologous cytotoxic lymphocytes or tumor infiltrating lymphocytes may be obtained from blood, lymph nodes, tumor and the like from a patient with cancer. The lymphocytes are grown in culture and target antigen-specific lymphocytes are expanded by culturing in the presence of specific target antigen and either antigen presenting cells expressing multiple foreign costimulatory molecules or target antigen pulsed APCs of the present invention. The target antigen-specific lymphocytes are then reinfused back into the patient.

After immunization the efficacy of the vaccine can be assessed by production of antibodies or immune cells that recognize the antigen, as assessed by specific lytic activity or specific cytokine production or by tumor regression. One skilled in the art would know the conventional methods to assess the aforementioned parameters.

The present invention encompasses methods of enhancing antigen-specific T-cell responses by administration of an effective amount of a recombinant vector encoding multiple foreign costimulatory molecules and a target antigen into a mammal alone, or infecting a target cell with the vector, target antigen or immunological epitope thereof. In one embodiment of the method, a recombinant vector encoding at least one molecule from the B7 family, ICAM-1 and LFA-3 is administered alone, or admixed with a target cell, target antigen or immunological epitope thereof. This immunization approach augments or enhances immune responses generated by the target antigen, providing a synergistic response compared to the use of single or double costimulatory molecules. The method of administering a recombinant vector containing genes encoding multiple costimulatory molecules results in increased target antigen-specific lymphoproliferation, enhanced cytolytic activity, enhanced cytokine secretion and longer lasting immunity to the target antigen as compared to the use of recombinant vector encoding a single or double costimulatory molecule. The recombinant vector may further comprise a nucleic acid sequence encoding at least one target antigen or immunological epitope thereof for synergistic enhancement of target-antigen-specific immune responses. Alternatively, the nucleic acid sequence encoding at least one target antigen or immunological epitope thereof is provided by a second recombinant vector, distinct from the vector encoding the multiple costimulatory molecules. In one embodiment of the method of enhancing antigen-specific T-cell responses, mammals, preferably humans, are immunized with an rV-HIV-1 epitope/37-1/ICAM-1/LFA-3 construct. The efficacy of the treatment may be monitored in vitro and/or in vivo by determining target antigen-specific lymphoproliferation, target antigen-specific cytolytic response, clinical responses and the like.

The method of enhancing antigen-specific T-cell responses may be used for any target antigen or immunological epitope thereof. Of particular interest are tumor associated antigens, tissue specific antigens and antigens of infectious agents.

In addition to administration of the recombinant vector to the patient, other exogenous immunomodulators or immunostimulatory molecules, chemotherapeutic drugs, antibiotics, antifungal drugs, antiviral drugs and the like alone or in combination thereof may be administered depending on the condition to be treated. Examples of other exogenously added agents include exogenous IL-2, IL-6, alpha-, beta- or gamma-interferon, GM-CSF, tumor necrosis factor, Flt-3L, cyclophosphamide, cisplatinum, gancyclovir, amphotericin B, 5 fluorouracil and the like.

The present invention provides for host cells expressing multiple, exogenous foreign costimulatory molecules in which the molecules are provided by a recombinant vector having foreign nucleic acid sequences encoding multiple costimulatory molecules. The host cells may also express one or more endogenous target antigens or immunological epitopes thereof or may be engineered to express one or more exogenous, foreign target antigens or immunological epitopes thereof which may also be provided by the recombinant vector encoding multiple costimulatory molecules or by a second recombinant vector.

The host cells of the present invention, with utility in stimulating an antigen-specific immune response may be any cell capable of infection using the recombinant virus of the present invention and capable of expressing multiple, exogenous costimulatory molecules and may further be genetically engineered to express one or more exogenous target antigens or immunological epitopes thereof. Such host cells included but are not limited to tumor cells, antigen presenting cells, such as PBMC, dendritic cells, cells of the skin or muscle, and the like. Antigen presenting cells include, but are not limited to, monocytes, macrophages, dendritic cells, progenitor dendritic cells, Langerhans cells, splenocytes, B-cells, tumor cells, muscle cells, epithelial cells and the like.

In one embodiment, the host cells are tumor cells in which the tumor cells are exposed to the recombinant vector in situ or in vitro to cause expression of multiple foreign or exogenous costimulatory molecules on the tumor cells. The tumor cells may express an endogenous target antigen or the tumor cells may be further genetically engineered to express a target antigen such as TAA or immunological epitope thereof. Tumor cells expressing both the TAA along with multiple immunostimulatory molecules are administered to a mammal in an effective amount to result in tumor reduction or elimination in the mammal afflicted with a cancer.

The present invention also provides progenitor dendritic cells, dendritic cells (DC), DC subpopulations, and derivatives thereof overexpressing multiple costimulatory molecules in which multiple costimulatory molecules are exogenously provided by a recombinant vector having nucleic acid sequences encoding multiple costimulatory molecules. The progenitor DC and DC of the present invention express higher levels of costimulatory molecules, than levels endogenously expressed by a nontreated progenitor DC or DC. The APCs such as progenitor dendritic cells and dendritic cells may also express one or more endogenous target antigens or immunological epitopes thereof or exogenous target antigen may also be provided by the recombinant vector encoding multiple costimulatory molecules or by a second recombinant vector. The present invention further provides methods of using the multiple costimulatory molecule-overexpressing APCs, such as multiple costimulatory molecule-overexpressing progenitor dendritic cells and multiple costimulatory molecule-overexpressing dendritic cells in activating T cells in vivo or in vitro for vaccination and immunotherapeutic responses against one or more target cells, target antigens and immunological epitopes thereof.

The APCs such as progenitor dendritic cells, dendritic cells, DC subpopulations and derivatives thereof isolated from a source are infected, transfected or transduced with a recombinant vector comprising exogenous genes encoding at least three costimulatory molecules for a time period sufficient to allow functional overexpression of the multiple costimulatory molecules. Such multiple costimulatory molecule-overexpressing antigen presenting progenitor dendritic cells and dendritic cells may also be pulsed or incubated with at least one target cell, target cell lysate, target cell membrane, target antigen, or immunological epitope thereof, or with RNA or DNA of at least one target cell and administered to a species in an amount sufficient to activate the relevant T cell responses in vivo. In another embodiment, the antigen presenting progenitor dendritic cells and dendritic cells additionally express at least one foreign target antigen or immunological epitope thereof.

Host cells expressing multiple, exogenous costimulatory molecules may be provided in a dose of $10^3$ to $10^9$ cells. Routes of administration that may be used include intravenous, subcutaneous, intralymphatic, intratumoral, intradermal, intramuscular, intraperitoneal, intrarectal, intravaginal, intranasal, oral, via bladder instillation, via scarification, and the like.

In one embodiment, the multiple costimulatory molecule-overexpressing antigen presenting progenitor dendritic cells or dendritic cells are exposed to a target cell, target cell lysates, target cell membranes, target antigen or immunological epitope thereof or with DNA or RNA from at least one target cell in vitro and incubated with primed or unprimed T cells to activate the relevant T cell responses in vitro. The activated T cells alone or in combination with the progenitor DC or DC are then administered to a species such as a human for vaccination or immunotherapy against a target cell, target antigen or immunological epitope thereof. In one method of use, the progenitor dendritic cells or dendritic cells are advantageously used to elicit an immunotherapeutic growth inhibiting response against cancer cells.

In another embodiment, the multiple costimulatory molecule-overexpressing antigen-presenting cell, preferably a precursor DC or DC is fused with a target cell expressing a relevant target antigen or immunological epitope thereof to form a heterokaryon of APC and target cell by methods known in the art (Gong, J. et al *Proc. Natl. Acad. Sci. USA* 95:6279–6283, 1998). Such a fusion cell or chimeric APC/target antigen cell expresses both multiple costimulatory molecules and target antigen or immunological epitopes thereof. In a preferred embodiment the target cell is a hyperplastic cell, premalignant or malignant cell. The chimeric APC/target antigen cell may be used both in vivo and in vitro to enhance immune responses of T and B lymphocytes.

Progenitor dendritic cells are obtained from bone marrow, peripheral blood and lymph nodes from a patient. The patient may have been previously vaccinated, or treated with a compound such as Flt-3L to enhance the number of antigen-presenting cells. Dendritic cells are obtained from any tissue such as the epidermis of the skin (Langerhans cells) and lymphoid tissues such as found in the spleen, bone marrow, lymph nodes, and thymus as well as the circulatory system including blood and lymph (veiled cells). Cord blood is another source of dendritic cells.

Dendritic cells may be enriched or isolated for use in the present invention using methods known in the art such as those described in U.S. Pat. No. 5,788,963. Once the progenitor dendritic cells, dendritic cells and derivatives thereof are obtained, they are cultured under appropriate culture conditions to expand the cell population and/or maintain the cells in a state for optimal infection, transfection or transduction by a recombinant vector and for optimal target antigen uptake, processing and presentation. Particularly advantageous for maintenance of the proper state of maturity of dendritic cells in in vitro culture is the presence of both the granulocyte/macrophage colony stimulating factor (GM-CSF) and interleukin 4 (IL-4). Subpopulations of dendritic cells may be isolated based in adherence and/or degree of maturity based on cell surface markers. The phenotype of the progenitor DC, DC and subpopulations thereof are disclosed in Banchereau and Steinman *Nature* 392:245–252, 1998.

In one embodiment GM-CSF and IL4 are each provided in a concentration of about 500 units/ml for a period of about 6 days (41,42). In another embodiment, TNFα and/or CD40 is used to cause precursor DC or DC to mature.

The progenitor dendritic cells or dendritic cells may be obtained from the individual to be treated and as such are autologous in terms of relevant HLA antigens or the cells may be obtained from an individual whose relevant HLA antigens (both class I and II, e.g. HLA-A, B, C and DR) match the individual that is to be treated. Alternatively, the progenitor dendritic cell is engineered to express the appropriate, relevant HLA antigens of the individual receiving treatment.

The progenitor dendritic cells and dendritic cells may be further genetically modified to extend their lifespan by such methods as EBV-transformation as disclosed in U.S. Pat. No. 5,788,963.

The dendritic cells and precursors thereof may be provided in the form of a pharmaceutical composition in a physiologically acceptable medium. The composition may further comprise a target cell, target cell lysate, target cell membrane, target antigen or immunological epitope thereof. The composition may additionally comprise cytokines and/or chemokines such as IL4 and GM-CSF for additional synergistic enhancement of an immune response.

In another embodiment, the APC of the present invention overexpressing multiple costimulatory molecules is useful in methods of evaluating efficacy of a vaccine by determination of antigen-specific lymphocyte proliferation and function. In such a method, lymphocytes are recovered from an individual who has been vaccinated with a target cell lysate, target cell membrane, target antigen or immunological epitope thereof. The lymphocytes are cultured in vitro with an APC of the present invention in the presence of the target cell, target cell lysate, target cell membrane, target antigen or immunological epitope thereof and an enhancement of antigen-specific lymphocyte numbers and functions determined by methods known in the art. An enhancement in numbers and/or functions is indicative of efficacy of the vaccine. The method is particularly useful in determining efficacy of peptide vaccines in stimulating an appropriate immune response.

In another embodiment, the APCs of the present invention expressing exogenous multiple costimulatory molecules are useful in a method of screening for novel immunogenic peptides from a multiplicity of peptides. In the method of screening, antigen presenting cells infected with a recombinant vector encoding multiple costimulatory molecules or functional portions thereof are pulsed with a multiplicity of peptides to form a peptide-pulsed antigen presenting cell. The peptide-pulsed antigen presenting cell is incubated with lymphoid cells and the immunoreactivity of the lymphoid cells measured. An enhancement of immunoreactivity of the lymphoid cells in the presence of the peptide-pulsed APC is indicative of an antigen specific response to the peptide. The peptide eliciting the enhanced response can be identified by eluting from tumor, by analysis of HLA binding, etc. The source of the multiplicity of peptides may be a combinatorial library which expresses a multiplicity of random peptides. The enhanced immunoreactivity may be a humoral or cell-mediated immune response and may be measured using standard techniques known in the art such as antigen-induced proliferation, cytotoxicity, antibody secretion, signal transduction, and the like. The novel peptides identified may be used as immunogens, vaccines or diagnostic agents. The proteins that contain the peptides may be identified by subtraction libraries and differential display gene technologies.

The recombinant vectors of the present invention as well as host cells infected, transfected or induced by the recombinant vector of the present invention are useful in methods of stimulating an enhanced humoral response both in vivo and in vitro. Such an enhanced humoral response may be monoclonal or polyclonal in nature. The enhancement of humoral responses using multiple costimulatory molecules is synergistic as compared to a humoral response using a single or double costimulatory molecule. The synergistic enhancement of a humoral response may be determined by increased proliferation and/or cytokine secretion by CD4$^+$ T cells, increased proliferation or antibody production by B cells, increased antibody dependent cellular toxicity (ADCC), increased complement-mediated lysis, and the like. Antibody elicited using the recombinant vectors of the present invention or using host cells infected, transfected or induced by the recombinant vector of the present invention are expected to be higher affinity and/or avidity and higher titer than antibody elicited by standard methods. The antibody elicited by methods using the recombinant vector may recognize immunodominant target epitopes or nondominant target epitopes.

This invention further comprises an antibody or antibodies elicited by immunization with the recombinant vector of the present invention. The antibody has specificity for and reacts or binds with the target antigen or immunological epitope thereof of interest. In this embodiment of the invention the antibodies are monoclonal or polyclonal in origin.

Exemplary antibody molecules are intact immunoglobulin molecules, substantially intact immunoglobulin molecules or those portions of an immunoglobulin molecule that contain the antigen binding site, including those portions of immunoglobulin molecules known in the art as F(ab), F(ab'), F(ab')$_2$ and F(v). Polyclonal or monoclonal antibodies may be produced by methods known in the art. (Kohler and Milstein (1975) Nature 256, 495–497; Campbell "Monoclonal Antibody Technology, the Production and Characterization of Rodent and Human Hybridomas" in Burdon et al. (eds.) (I 985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in E. coli is the subject of the PCT patent applications: publication number WO 901443, WO 901443 and WO 9014424 and in Huse et al. (1989) Science 246:1275–1281.

In one embodiment the antibodies of this invention are used in immunoassays to detect the novel antigen of interest in biological samples.

In one embodiment, the antibodies of this invention generated by immunization with a recombinant vaccinia virus expressing a TAA and expressing B7-1, ICAM-1 and LFA-3 are used to assess the presence of the a TAA from a tissue biopsy of a mammal afflicted with a cancer expressing TAA using immunocytochemistry. Such assessment of the delineation of the a TAA antigen in diseased tissue can be used to prognose the progression of the disease in a mammal afflicted with the disease or the efficacy of immunotherapy. In this embodiment, examples of TAAs include but are not limited to CEA, PSA, and MUC-1. Conventional methods for immunohistochemistry are described in (Harlow and Lane (eds) (1988) In "Antibodies A Laboratory Manual", Cold Spinning Harbor Press, Cold Spring Harbor, N.Y.; Ausubel et al. (eds) (1987). In Current Protocols In Molecular Biology, John Wiley and Sons (New York, N.Y.).

In another embodiment the antibodies of the present invention are used for immunotherapy. The antibodies of the present invention may be used in passive immunotherapy.

In providing a patient with the antibodies or antigen binding fragments to a recipient mammal, preferably a human, the dosage of administered antibodies or antigen binding fragments will vary depending upon such factors as the mammal's age, weight, height, sex, general medical condition, previous medical condition and the like.

The antibodies or antigen-binding fragments of the present invention are intended to be provided to the recipient subject in an amount sufficient to prevent, lessen or attenuate the severity, extent or duration of the disease or infection.

Anti-idiotypic antibodies arise normally during the course of immune responses, and a portion of the anti-idiotype antibody resembles the epitope that induced the original immune response. In the present invention, the immunoglobulin gene or portion thereof of an antibody whose binding site reflects a target antigen of a disease state, is incorporated into the genome or portion thereof of a virus genome, alone or in combination with a gene or portion thereof of multiple immunostimulatory molecules, the resulting recombinant virus is able to elicit cellular and humoral immune response to the antigen.

The description of the specific embodiments will so fully reveal the general nature of the invention that others can readily modify and/or adopt for various purposes such specific embodiments without departing from the generic concept, and therefor such adaptations and modifications are intended to be comprehended within the meaning and range of equivalents of the disclosed embodiments.

All references and patents referred to are incorporated herein by reference.

EXAMPLE 1

Generation of Recombinant Vaccinia, rV-TRICOM (mu1) No. vT171

The origin of vaccinia parental virus is the New York City Board of Health strain and was obtained by Wyeth from the New York City Board of Health and passaged in calves to create the Smallpox Vaccine Seed. Flow Laboratories received a lyophilized vial of the Smallpox Vaccine Seed, Lot 3197, Passage 28 from Drs. Chanock and Moss (National Institutes of Health). This seed virus was ether-treated and plaque-purified three times.

For the generation of rV-TRICOM(mu1), a plasmid vector, designated pT5032 was constructed to direct insertion of the foreign sequences into the M2L (30K) gene, which is located in the Hind III M region of the vaccinia genome. The murine LFA-3 gene is under the transcriptional control of the vaccinia 30K (M2L) promoter (34), the murine ICAM-1 gene is under the control of the vaccinia 13 promoter (18), and the murine B7.1 gene is under the control of the synthetic early/late (sE/L) promoter (32). These foreign sequences are flanked by DNA sequences from the Hind III M region of the vaccinia genome (see FIG. 1). These flanking sequences include the vaccinia K1L host range gene (33). A derivative of the Wyeth strain of vaccinia was used as the parental virus in the construction of recombinant vaccinia virus. This parental virus, designated vTBC33, lacks a functional K1L gene and thus cannot efficiently replicate on rabbit kidney $RK_{13}$ cells (38). The generation of recombinant vaccinia virus was accomplished via homologous recombination between vaccinia sequences in the vTBC33 vaccinia genome and the corresponding sequences in pT5032 in vaccinia-infected $RK_{13}$ cells transfected with pT5032. Recombinant virus, designated vT171, was selected by growth on $RK_{13}$ cells (ATCC, CCL 37). Plaques were picked from the cell monolayer and their progeny were further propagated. Two rounds of plaque isolation and replating on $RK_{13}$ cells resulted in the purification of the desired recombinant. The genomic structure of recombinant vT171 is depicted in FIG. 4A.

EXAMPLE 2

Generation of Recombinant Vaccinia, rV-TRICOM (mu2) No. vT199

For the generation of rV-TRICOM(mu2), a plasmid vector, designated pT5047, was constructed to direct insertion of the foreign sequences into the thymidine kinase (TK) gene, which is located in the Hind III J region of the vaccinia genome. The murine B7.1 gene is under the control of the sE/L promoter, the murine LFA-3 gene is under the transcriptional control of the 13 promoter, and the murine ICAM-1 gene is under the control of the vaccinia 7.5K promoter (39). In addition, the *E. coli* lacZ gene, under the control of the fowlpox virus C1 promoter (15) is included as a screen for recombinant progeny. These foreign sequences are flanked by DNA sequences from the Hind III J region of the vaccinia genome (see FIG. 2). A plaque-purified isolate from the Wyeth (New York City Board of Health) strain of vaccinia was used as the parental virus for this recombinant vaccine. The generation of recombinant vaccinia virus was accomplished via homologous recombination between vaccinia sequences in the Wyeth vaccinia genome and the corresponding sequences in pT5047 in vaccinia-infected Hu143TK cells (Bacchetti and Graham 1977) transfected with pT5047. Recombinant virus was identified using selection for TK virus in the presence of bromodeoxyuridine (BudR) in combination with a chromogenic assay, performed on viral plaques in situ, that detects expression of the lacZ gene product in the presence of halogenated indolyl-beta-D-galactoside (Bluo-gal), as described previously (31). Viral plaques expressing lacZ appeared blue against a clear background. Positive plaques, designated vT199, were picked from the cell monolayer and their progeny were replated under the selective conditions described above. In other recombinant viruses selected and purified in this manner, the only plaques that appeared under these selective conditions were blue, and these blue plaques were readily isolated and purified. However, in the case of vT199, only white plaques were observed at the second round of plaque-purification; no blue plaques were apparent. A new set of blue plaques were picked and replated; again, only white plaques were observed at the second round of plaque-purification. A final attempt, using yet another set of blue plaques, yielded both blue and white plaques after the second round of plaque-purification. Blue plaques were selected and replated. Two additional rounds of plaque-purification (a total of four rounds) yielded recombinant viruses that were 100% blue. The genomic structure of recombinant vT199 is depicted in FIG. 4B.

EXAMPLE 3

Generation of Recombinant Vaccinia rV-TAA/ TRICOM(mu)

For the generation of rV-TAA/TRICOM(mu), a plasmid vector is constructed to direct insertion of the foreign sequences into the vaccinia genome. The TAA gene, the murine LFA-3 gene, the murine ICAM-1 gene, and the murine B7.1 gene are under the control of a multiplicity of promoters. These foreign sequences are flanked by DNA sequences from the vaccinia genome, into which the foreign sequences are to be inserted. The generation of recombinant vaccinia virus is accomplished via homologous recombination between vaccinia sequences in the vaccinia genome and the corresponding sequences in the plasmid vector in vaccinia-infected cells transfected with the plasmid vector. Recombinant plaques are picked from the cell monolayer under selective conditions and their progeny are further propagated. Additional rounds of plaque isolation and replating result in the purification of the desired recombinant virus.

EXAMPLE 4

Generation of Recombinant Vaccinia rV-MUC-1/TRICOM(mu)

For the generation of rV-MUC-1/TRICOM(mu), a plasmid vector is constructed to direct insertion of the foreign sequences into the vaccinia genome. The MUC-1 gene, the murine LFA-3 gene, the murine ICAM-1 gene, and the murine B7.1 gene are under the control of a multiplicity of promoters. These foreign sequences are flanked by DNA sequences from the vaccinia genome into which the foreign sequences are to be inserted. The generation of recombinant vaccinia virus is accomplished via homologous recombination between vaccinia sequences in the vaccinia genome and the corresponding sequences in the plasmid vector in vaccinia-infected cells transfected with the plasmid vector. Recombinant plaques are picked from the cell monolayer under selective conditions and their progeny are further propagated. Additional rounds of plaque isolation and replating result in the purification of the desired recombinant virus.

EXAMPLE 5

Generation of Recombinant Vaccinia rV-CEA/TRICOM(mu) No. vT172

For the generation of rV-CEA/TRICOM(mu), a plasmid vector, designated pT5031, was constructed to direct insertion of the foreign sequences into the M2L (30K) gene, which is located in the Hind III M region of the vaccinia genome (see FIG. 3). The CEA gene is under the control of the 40K promoter (13), the murine LFA-3 gene is under the control of the 30K promoter, the murine ICAM-1 gene is under the control of the 13 promoter, and the murine B7.1 gene is under the control of the sE/L promoter. These foreign sequences are flanked by DNA sequences from the Hind III M region of the vaccinia genome, including the vaccinia K1L host range gene. vTBC33, described above, was used as the parental virus in the construction of the recombinant vaccinia virus. The generation of recombinant vaccinia virus was accomplished via homologous recombination between vaccinia sequences in the vTBC33 vaccinia genome and the corresponding sequences in pT5031 in vaccinia-infected $RK_{13}$ cells transfected with pT5031. Recombinant virus, designated vT172, was selected by growth on $RK_{13}$ cells as described above. Plaques were picked from the cell monolayer and their progeny were further propagated. Two rounds of plaque isolation and replating on RK13 cells resulted in the purification of the desired recombinant. The genomic structure of recombinant vT172 is depicted in FIG. 4C.

EXAMPLE 6

Generation of Recombinant Fowlpox, rF-TRICOM (mu) No. vT222

The origin of parental fowlpox virus used for the generation of recombinants was plaque-purified from a vial of a USDA-licensed poultry vaccine, POXVAC-TC, which is manufactured by Schering-Plough Corporation. The starting material for the production of POXVAC-TC was a vial of Vineland Laboratories' chicken embryo origin Fowlpox vaccine, obtained by Schering-Plough. The virus was passaged twice on the chorioallantoic membrane of chicken eggs to produce a master seed virus. The master seed virus was passaged 27 additional times in chicken embryo fibroblasts to prepare the POXVAC-TC master seed. To prepare virus stocks for the generation of POXVAC-TC product lots, the POXVAC-TC master seed was passaged twice on chicken embryo fibroblasts. One vial of POXVAC-TC, Serial # 96125, was plaque-purified three times on primary chick embryo dermal cells.

Figure 7A:
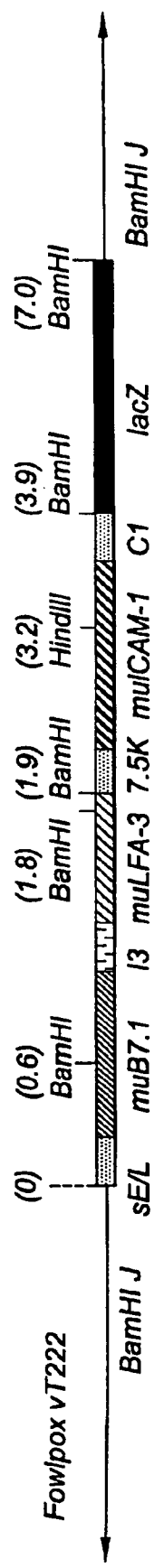
FIGS. 7A through 7D. Genomic structure of recombinant fowlpox viruses expressing three murine costimulatory molecules with (FIGS. 7B, 7C and 7D) or without (FIG. 7A) a tumor-associated antigen (TAA).

For the generation of rF-TRICOM(mu), a plasmid vector, designated pT8001, was constructed to direct insertion of the foreign sequences into the BamHI J region of the fowlpox genome. The murine B7.1 gene is under the control of the sE/L promoter, the murine LFA-3 gene is under the control of the 13 promoter, the murine ICAM-1 gene is under the control of the 7.5K promoter, and the lacZ gene is under the control of the C1 promoter. These foreign sequences are flanked by DNA sequences from the BamHI J region of the fowlpox genome (see FIG. 5). A plaque-purified isolate from the POXVAC-TC (Schering-Plough Corporation) strain of fowlpox was used as the parental virus for this recombinant vaccine. The generation of recombinant fowlpox virus was accomplished via homologous recombination between fowlpox sequences in the fowlpox genome and the corresponding sequences in pT8001 in fowlpox-infected primary chick embryo dermal cells transfected with pT8001. Recombinant virus was identified using the chromogenic assay for the lacZ gene product described above. Viral plaques expressing lacZ appeared blue against a clear background. Positive plaques, designated vT222, were picked from the cell monolayer and their progeny were replated. Six rounds of plaque isolation and replating in the presence of Bluo-Gal resulted in the purification of the desired recombinant. The genomic structure of recombinant vT222 is depicted in FIG. 7A.

EXAMPLE 7

Generation of Recombinant Fowlpox rF-TAA/TRICOM(mu)

For the generation of rF-TAA/TRICOM(mu), a plasmid vector is constructed to direct insertion of the foreign sequences into the BamHI J region of the fowlpox genome. The TAA gene, the murine LFA-3 gene, the murine ICAM-1 gene, and the murine B7.1 gene are under the control of a multiplicity of promoters. In addition, the lacZ gene is under the control of the C1 promoter. These foreign sequences are flanked by DNA sequences from the BamHI J region of the fowlpox genome. A plaque-purified isolate from the POXVAC-TC (Schering-Plough Corporation) strain of fowlpox is used as the parental virus for this recombinant vaccine. The generation of recombinant fowlpox virus is accomplished via homologous recombination between fowlpox sequences in the fowlpox genome and the corresponding sequences in the plasmid vector in fowlpox-infected primary chick embryo dermal cells transfected with the plasmid vector. Recombinant virus is identified using the chromogenic assay for the lacZ gene product described above. Viral plaques expressing lacZ appear blue against a clear background. Positive plaques are picked from the cell monolayer and their progeny are replated. Additional rounds of plaque isolation and replating in the presence of Bluo-Gal result in the purification of the desired virus.

37

EXAMPLE 8

Generation of Recombinant Fowlpox rF-MUC-1/TRICOM(mu)

For the generation of rF-MUC-1/TRICOM(mu), a plasmid vector is constructed to direct insertion of the foreign sequences into the BamHI J region of the fowlpox genome. The MUC-1 gene, the murine LFA-3 gene, the murine ICAM-1 gene, and the murine B7.1 gene are under the control of a multiplicity of promoters. In addition, the lacZ gene is under the control of C1 promoter. These foreign sequences are flanked by DNA sequences from the BamHI J region of the fowlpox genome. A plaque-purified isolate from the POXVAC-TC (Schering-Plough Corporation) strain of fowlpox is used as the parental virus for this recombinant vaccine. The generation of recombinant fowlpox virus is accomplished via homologous recombination between fowlpox sequences in the fowlpox genome and the corresponding sequences in the plasmid vector in fowlpox-infected primary chick embryo dermal cells transfected with the plasmid vector. Recombinant virus is identified using the chromogenic assay for the lacZ gene product described above. Viral plaques expressing lacZ appear blue against a clear background. Positive plaques are picked from the cell monolayer and their progeny are replated. Additional rounds of plaque isolation and replating in the presence of Bluo-Gal result in the purification of the desired recombinant virus.

EXAMPLE 9

Generation of Recombinant Fowlpox, rF-CEA/TRICOM(mu) No. vT194

Figure 7B:
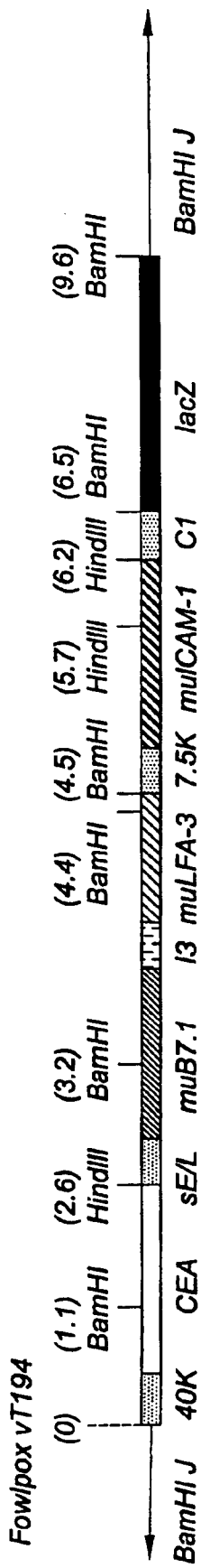
Figure 7C:
Figure 7D:

For the generation of rF-CEA/TRICOM(mu), a plasmid vector, designated pT5049, was constructed to direct insertion of the foreign sequences into the BamHI J region of the fowlpox genome. The CEA gene is under the control of the vaccinia 40K promoter, the murine B7-1 gene is under the control of the sE/L promoter, the murine LFA-3 gene is under the transcriptional control of the 13 promoter, the murine ICAM-1 gene is under the transcriptional control of the vaccinia 7.5K promoter, and the lacZ gene is under the control of the C1 promoter. These foreign sequences are flanked by DNA sequences from the BamHI J region of the fowlpox genome (see FIG. 6). A plaque-purified isolate from the POXVAC-TC (Schering Corporation) strain of fowlpox was used as the parental virus for this recombinant vaccine. The generation of recombinant fowlpox virus was accomplished via homologous recombination between fowlpox sequences in the fowlpox genome and the corresponding sequences in pT5049 in fowlpox-infected primary chick embryo dermal cells transfected with pT5049. Recombinant virus was identified using the chromogenic assay for the lacZ gene product described above. Viral plaques expressing lacZ appeared blue against a clear background. Positive plaques, designated vT194, were picked from the cell monolayer and their progeny were replated. Five rounds of plaque isolation and replating in the presence of Bluo-Gal resulted in the purification of the desired recombinant. The genomic structure of recombinant fowlpox vT194 is depicted in FIG. 7B.

EXAMPLE 10

Generation of Recombinant Vaccinia, rV-TRICOM (hu) No. vT224

For the generation of rV-TRICOM(hu), a plasmid vector, designated pT5064, was constructed to direct insertion of the foreign sequences into the thymidine kinase (TK) gene, which is located in the Hind III J region of the vaccinia genome. The human LFA-3 gene is under the control of the 30K promoter, the human ICAM-1 gene is under the control of the 13 promoter, and the human B7.1 gene is under the control of the sE/L promoter. In addition, the E. coli lacZ gene, under the control of the C1 promoter, is included as a screen for recombinant progeny. These foreign sequences are flanked by DNA sequences from the Hind III J region of the vaccinia genome (see FIG. 8). A plaque-purified isolate from the Wyeth (New York City Board of Health) strain of vaccinia was used as the parental virus for this recombinant vaccine. The generation of recombinant vaccinia virus was accomplished via homologous recombination between vaccinia sequences in the Wyeth vaccinia genome and the corresponding sequences in pT5064 in vaccinia-infected CV-1 cells (ATTC, CCL 70) transfected with pT5064. Recombinant virus was identified using the chromogenic assay for the lacZ gene product described above. Viral plaques expressing lacZ appeared blue against a clear background. Positive plaques, designated vT224, were picked from the cell monolayer and their progeny were replated. Five rounds of plaque isolation and replating in the presence of Bluo-Gal resulted in the purification of the desired recombinant. The genomic structure of recombinant vT224 is depicted in FIG. 9A.

EXAMPLE 11

Generation of Recombinant Vaccinia rV-TAA/TRICOM(hu)

For the generation of rV-TAA/TRICOM(hu), a plasmid vector is constructed to direct insertion of the foreign sequences into the thymidine kinase (TK) gene, which is located in the Hind III J region of the vaccinia genome. The TAA gene, the human LFA-3 gene, the human ICAM-1 gene, the human B7.1 gene, and the E. coli lacZ gene are under the control of a multiplicity of poxvirus promoters. These foreign sequences are flanked by DNA sequences from the Hind III J region of the vaccinia genome. A plaque-purified isolate from the Wyeth (New York City Board of Health) strain of vaccinia is used as the parental virus for this recombinant vaccine. The generation of recombinant vaccinia virus is accomplished via homologous recombination between vaccinia sequences in the Wyeth vaccinia genome and the corresponding sequences in the plasmid vector in vaccinia-infected CV-1 cells (ATTC, CCL 70) transfected with the plasmid. Recombinant virus is identified using the chromogenic assay for the lacZ gene product described above. Viral plaques expressing lacZ appear blue against a clear background. Positive plaques are picked from the cell monolayer and their progeny are replated. Additional rounds of plaque isolation and replating in the presence of Bluo-Gal result in the purification of the desired recombinant.

EXAMPLE 12

Generation of Recombinant Fowlpox rF-TAA/TRICOM(hu)

For the generation of rF-TAA/TRICOM(hu), a plasmid vector is constructed to direct insertion of the foreign sequences into the BamHI J region of the fowlpox genome. The TAA gene, the human LFA-3 gene, the human ICAM-1 gene, the human B7.1 gene, and the E. coli lacZ gene are under the control of a multiplicity of poxvirus promoters. These foreign sequences are flanked by DNA sequences from the BamHI J region of the fowlpox genome. A plaque-purified isolate from the POXVAC-TC (Schering-Plough Corporation) strain of fowlpox is used as the parental virus for this recombinant vaccine. The generation of recombinant fowlpox virus is accomplished via homologous recombination between fowlpox sequences in the fowlpox genome and the corresponding sequences in the plasmid vector in fowlpox-infected primary chick embryo dermal cells transfected with the plasmid vector. Recombinant virus is identified using the chromogenic assay for the lacZ gene product described above. Viral plaques expressing lacZ appear blue against a clear background. Positive plaques are picked from the cell monolayer and their progeny are replated. Additional rounds of plaque isolation and replating in the presence of Bluo-Gal result in the purification of the desired recombinant virus.

EXAMPLE 13

Generation of Recombinant Vaccinia Virus, rV-CEA (6D)/TRICOM(hu) No. vT238

Figure 11:
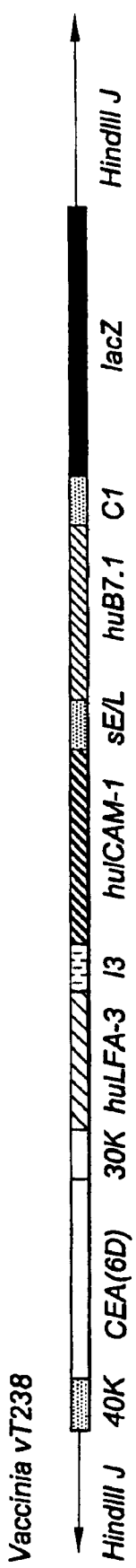
FIG. 11. Genomic structure of recombinant vaccinia virus vT238 expressing CEA (6D) and three human costimulatory molecules. HindIII J is the site of insertion in the poxvirus genome of the foreign genes. 40K, 30K, 13, sE/L, and C1 are poxviral promoters.

For the generation of rV-CEA(6D)/TRICOM(hu), a plasmid vector, designated pT8016, was constructed to direct insertion of the foreign sequences into the thymidine kinase (TK) gene, which is located in the Hind III J region of the vaccinia genome. The CEA gene was altered by in vitro mutagenesis to express full-length protein containing one modified epitope. This mutation changed the encoded amino acid at position 576 from asparagine to aspartic acid. The modified gene, designated CEA(6D), was designed to enhance the immunogenicity of CEA (Zaremba et al, 1997, *Cancer Res.* 57:4570–4577). The CEA(6D) gene is under the control of the 40K promoter. The human LFA-3 gene is under the control of the 30K promoter, the human ICAM-1 gene is under the control of the 13 promoter, and the human B7.1 gene is under the control of the sE/L promoter. In addition, the *E. coli* lacZ gene, under the control of the C1 promoter, is included as a screen for recombinant progeny. These foreign sequences are flanked by DNA sequences from the Hind III J region of the vaccinia genome (see FIG. 10). A plaque-purified isolate from the Wyeth (New York City Board of Health) strain of vaccinia was used as the parental virus for this recombinant vaccine. The generation of recombinant vaccinia virus was accomplished via homologous recombination between vaccinia sequences in the Wyeth vaccinia genome and the corresponding sequences in pT8016 in vaccinia-infected CV-1 cells (American Type Culture Collection (ATCC), Rockville, Md., CCL 70) transfected with pT8016. Recombinant virus was identified using the chromogenic assay for the lacZ gene product described above. Viral plaques expressing lacZ appeared blue against a clear background. Positive plaques, designated vT238, were picked from the cell monolayer and their progeny were replated. Six rounds of plaque isolation and replating in the presence of Bluo-Gal resulted in the purification of the desired recombinant. The genomic structure of recombinant vaccinia virus vT238 is shown in FIG. 11.

EXAMPLE 14

Generation of Recombinant Fowlpox Virus, rF-TRICOM(mu) No. vT251

Figure 12:
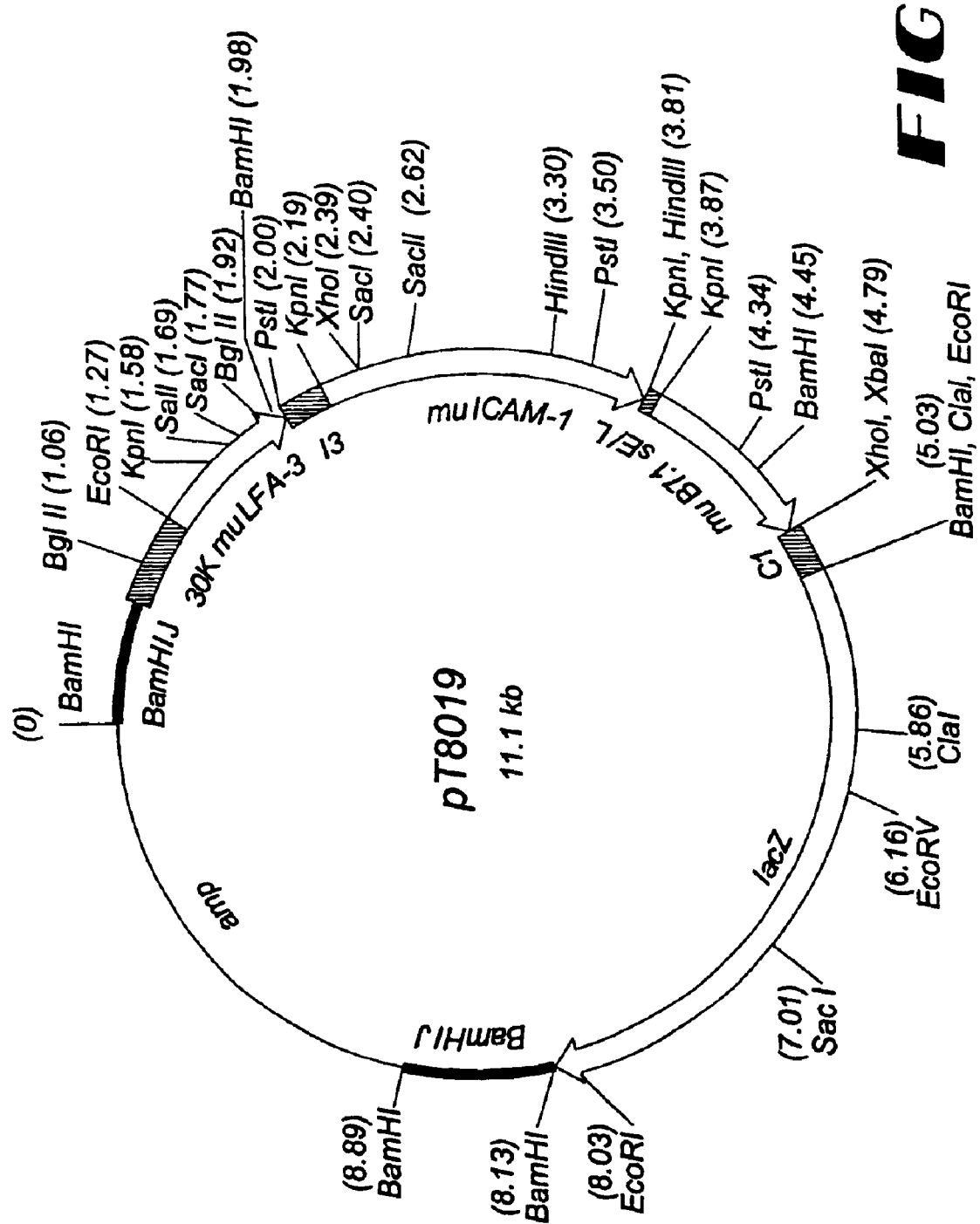
FIG. 12. Genomic structure of plasmid pT8019 comprising nucleic acid sequences encoding murine LFA-3, ICAM-1, B7.1, and the E. coli lacZ gene, flanked by portions of the BamHI J region of the fowlpox genome.
Figure 13:
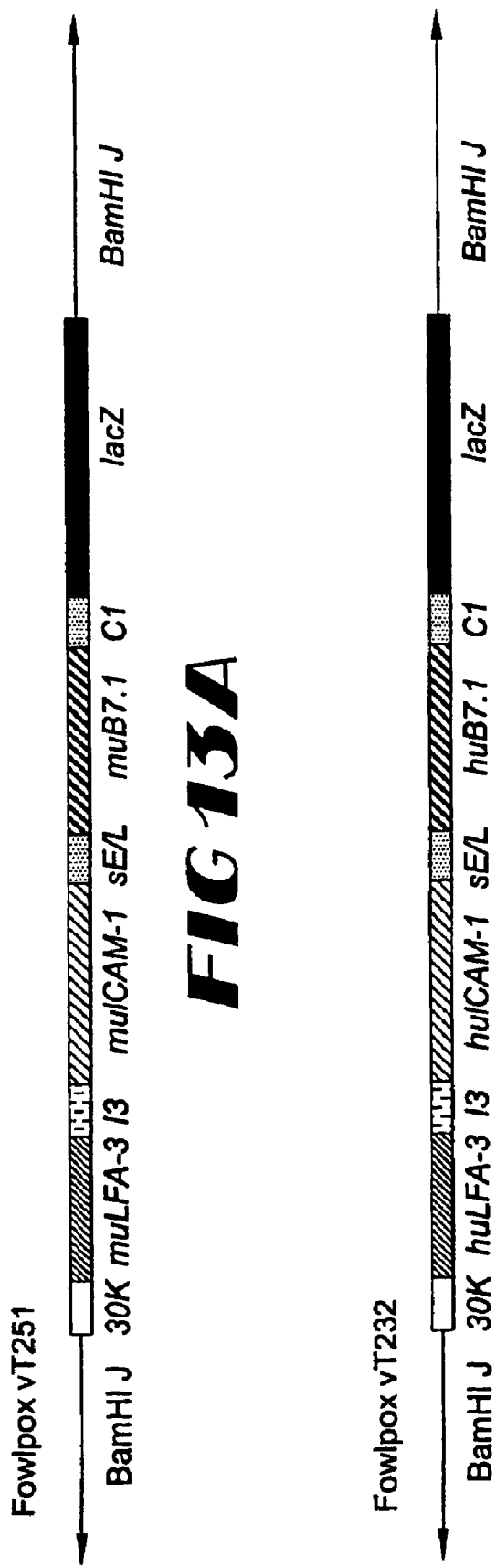
FIGS. 13A and 13B. Genomic structure of recombinant fowlpox viruses expressing murine or human costimulatory molecules.

For the generation of rF-TRICOM(mu), a plasmid vector, designated pT8019, was constructed to direct insertion of the foreign sequences into the BamHI J region of the fowlpox genome. The murine LFA-3 gene is under the control of the 30K promoter, the murine ICAM-1 gene is under the control of the B3 promoter, the murine B7.1 gene is under the control of the sE/L promoter, and the lacZ gene is under the control of the C1 promoter. These foreign sequences are flanked by DNA sequences from the BamHI J region of the fowlpox genome (see FIG. 12). A plaque-purified isolate form the POXVAC-TC (Schering-Plough Corporation) strain of fowlpox was used as the parental virus for this recombinant vaccine. The generation of recombinant fowlpox virus was accomplished via homologous recombination between fowlpox sequences in the fowlpox genome and the corresponding sequences in pT8019 in fowlpox-infected primary chick embryo dermal cells transfected with pT8019. Recombinant virus was identified using the chromogenic assay for the lacZ gene product described above. Viral plaques expressing lacZ appeared blue against a clear background. Positive plaques, designated vT251, were picked from the cell monolayer and their progeny were replated. Three rounds of plaque isolation and replating in the presence of Bluo-Gal resulted in the purification of the desired recombinant. The genomic structure of recombinant vaccinia virus vT251 is shown in FIG. 13A.

EXAMPLE 15

Generation of Recombinant Fowlpox Virus, rF-TRICOM(hu) No. vT232

For the generation of rF-TRICOM(hu), a plasmid vector, designated pT5072, was constructed to direct insertion of the foreign sequences into the BamHI J region of the fowlpox genome. The human LFA-3 gene is under the control of the 30K promoter, the human ICAM-1 gene is under the control of the 13 promoter, the human B7.1 gene is under the control of the sE/L promoter, and the lacZ gene is under the control of the C1 promoter. These foreign sequences are flanked by DNA sequences from the BamHI J region of the fowlpox genome (see FIG. 14). A plaque-purified isolate from the POXVAC-TC (Schering-Plough Corporation) strain of fowlpox was used as the parental virus for this recombinant vaccine. The generation of recombinant fowlpox virus was accomplished via homologous recombination between fowlpox sequences in the fowlpox genome and the corresponding sequences in pT5072 in fowlpox-infected primary chick embryo dermal cells transfected with pT5072. Recombinant virus was identified using the chromogenic assay for the lacZ gene product described above. Viral plaques expressing lacZ appeared blue against a clear background. Positive plaques, designated vT232 were picked from the cell monolayer and their progeny were replated. Four rounds of plaque isolation and replating in the presence of Bluo-Gal resulted in the purification of the desired recombinant. The genomic structure of recombinant vaccinia virus vT232 is shown in FIG. 13B.

EXAMPLE 16

Generation of Recombinant Fowlpox Virus, rF-MUC-I/TRICOM(mu) No. vT250

Figure 15:
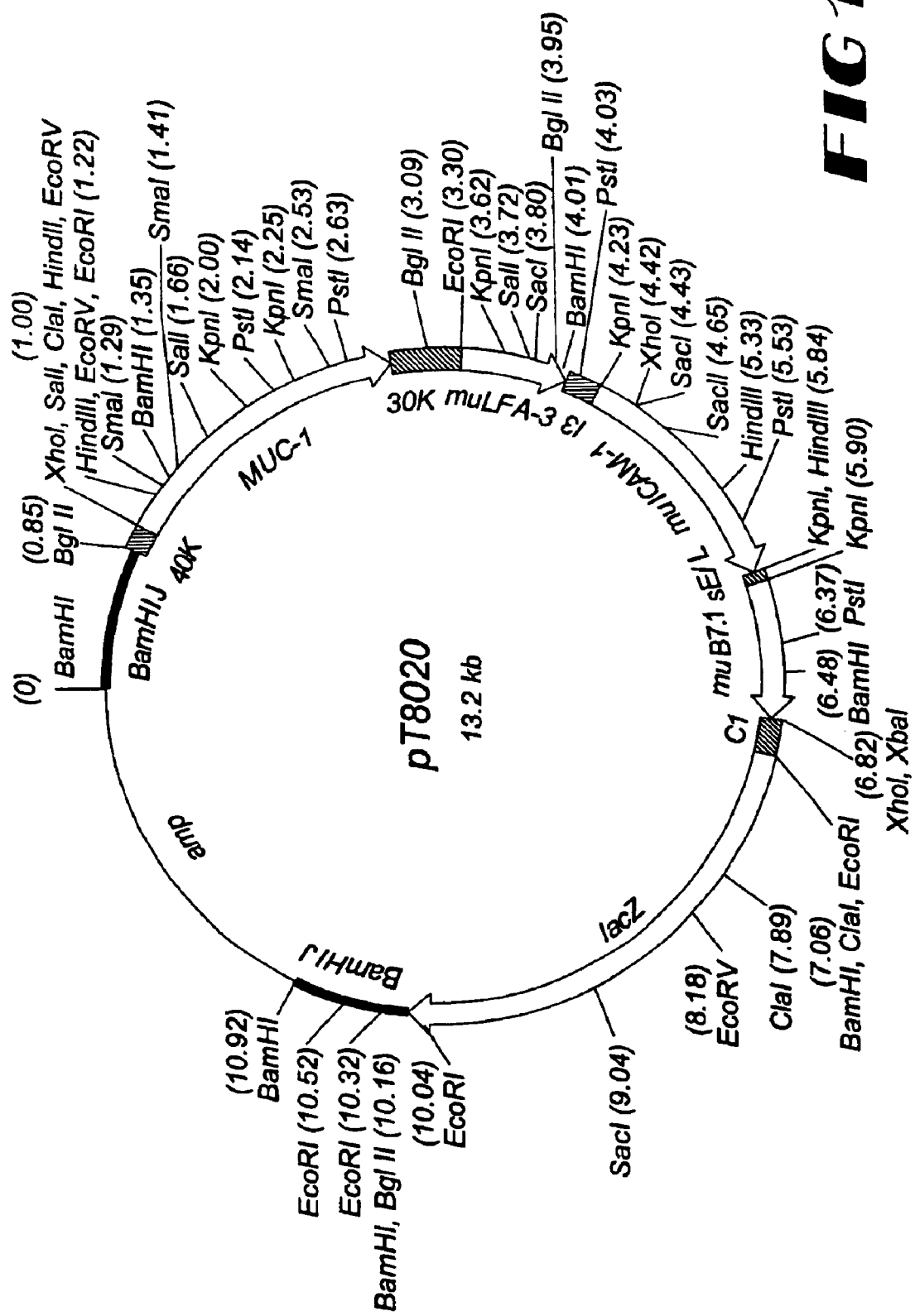
FIG. 15. Genomic structure of plasmid pT8020 comprising nucleic acid sequences encoding MUC-I, murine LFA-3, ICAM-1, B7.1, and the E. coli lacZ gene, flanked by portions of the BamHI J region of the fowlpox genome.
Figure 16A:
FIG. 16A through 16D. Genomic structure of recombinant fowlpox viruses expressing murine or human costimulatory molecules with at least one tumor-associated antigen.

For the generation of rF-MUC-1/TRICOM(mu), a plasmid vector, designated pT8020, was constructed to direct insertion of the foreign sequences into the BamHI J region of the fowlpox genome. A truncated version of the MUC-1 gene was used, consisting of the signal sequence, ten copies of the tandem repeat sequence, and the 3' unique coding sequence. (SEQ ID NO:41). The nucleotide sequence of the tandem repeat region was altered to minimize homology between the repeats without changing the amino acid sequence. The gene was contained on an 1881 bp fragment which includes the truncated coding sequence, 6 nucleotides of the 5' untranslated region, and 186 nucleotides of the 3' untranslated region (Gendler et al, 1990, *J. Biol. Chem.* 265:15286–15293). The murine LFA-3 gene is under the control of the 30K promoter, the murine ICAM-1 gene is under the control of the 13 promoter, the murine B7.1 gene is under the control of the sE/L promoter, and the lacZ gene is under the control of the C1 promoter. These foreign sequences are flanked by DNA sequences from the BamHI J region of the fowlpox genome (see FIG. 15). A plaque-purified isolate from the POXVAC-TC (Schering-Plough Corporation) strain of fowlpox was used as the parental virus for this recombinant vaccine. The generation of recombinant fowlpox virus was accomplished via homologous recombination between fowlpox sequences in the fowlpox genome and the corresponding sequences in pT8020 in fowlpox-infected primary chick embryo dermal cells transfected with pT8020. Recombinant virus was identified using the chromogenic assay for the lacZ gene product described above. Viral plaques expressing lacZ appeared blue against a clear background. Positive plaques, designated vT250, were picked from the cell monolayer and their progeny were replated. Four rounds of plaque isolation and replating in the presence of Bluo-Gal resulted in the purification of the desired recombinant. The genomic structure of recombinant vaccinia virus vT250 is shown in FIG. 16A.

EXAMPLE 17

Generation of Recombinant Fowlpox Virus, rF-MUC-1/TRICOM(hu) No. vT242

Figure 16B:
Figure 17:
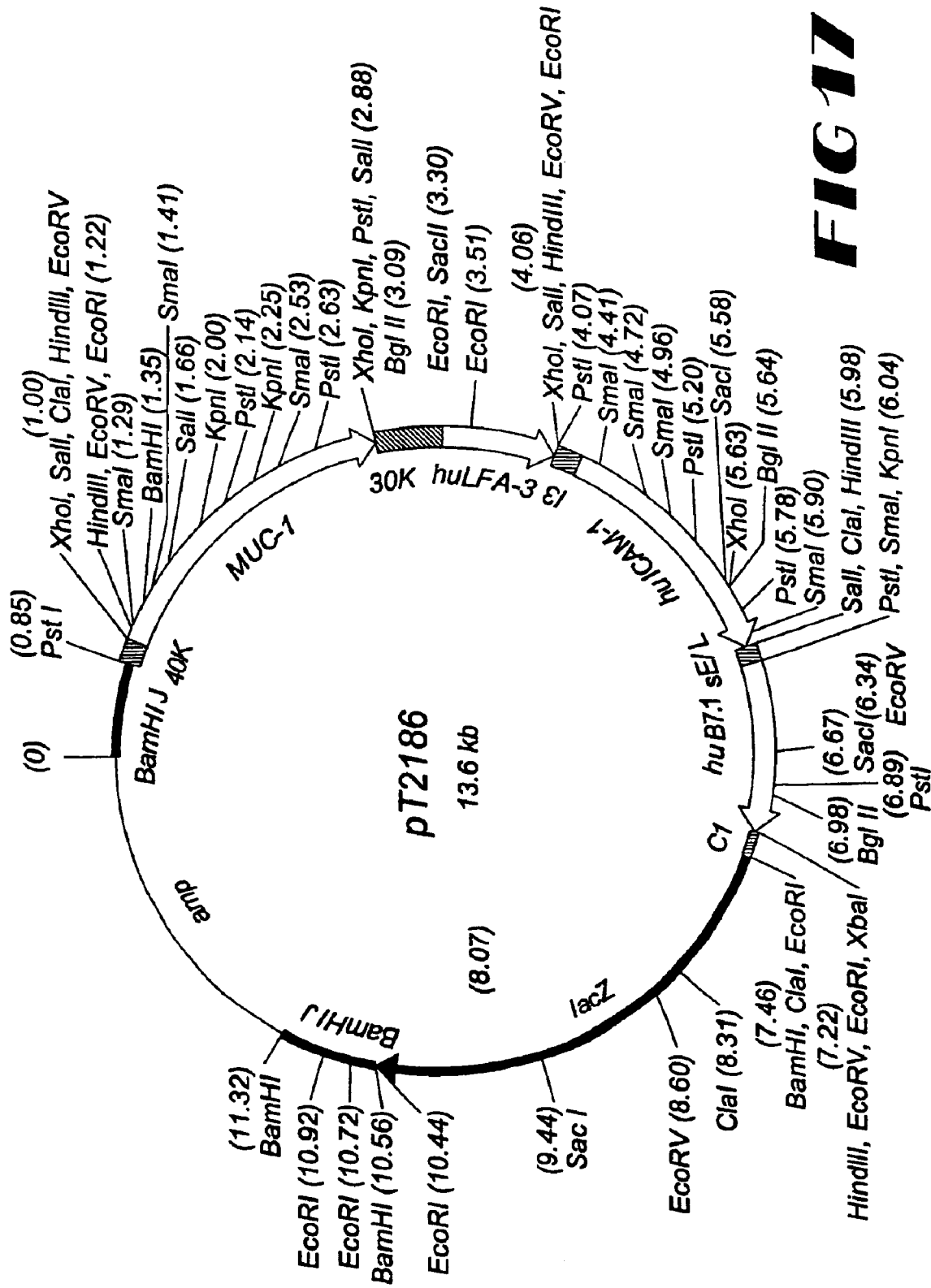
FIG. 17. Genomic structure of plasmid pT2186 comprising nucleic acid sequences encoding MUC-1, human LFA-3, ICAM-1, B7.1, and the E. coli lacZ gene, flanked by portions of the BamHI J region of the fowlpox genome.

For the generation of rF-MUC-1/TRICOM(hu), a plasmid vector, designated pT2186 was constructed to direct insertion of the foreign sequences into the BamHI J region of the fowlpox genome. A truncated version of the MUC-1 gene was used, as described in Example 16 above. The MUC-1 gene is under the control of the 40K promoter. The human LFA-3 gene is under the control of the 30K promoter, the human ICAM-1 gene is under the control of the 13 promoter, the human B7.1 gene is under the control of the sE/L promoter, and the lacZ gene is under the control of the C1 promoter. These foreign sequences are flanked by DNA sequences from the BamHI J region of the fowlpox genome (see FIG. 17). A plaque-purified isolate from the POXVAC-TC (Schering-Plough Corporation) strain of fowlpox was used as the parental virus for this recombinant vaccine. The generation of recombinant fowlpox virus was accomplished via homologous recombinant between fowlpox sequences in the fowlpox genome and the corresponding sequences in pT2186 in fowlpox-infected primary chick embryo dermal cells transfected with pT2186. Recombinant virus was identified using the chromogenic assay for the lacZ gene product described above. Viral plaques expressing lacZ appeared blue against a clear background. Positive plaques, designated vT242, were picked from the cell monolayer and their progeny were replated. Four rounds of plaque isolation and replating in the presence of Bluo-Gal resulted in the purification of the desired recombinant. The genomic structure of recombinant vaccinia virus vT242 is shown in FIG. 16B.

EXAMPLE 18

Generation of Recombinant Fowlpox Virus, rF-CEA(6D)/TRICOM(hu) No. vT236

Figure 16C:
Figure 18:
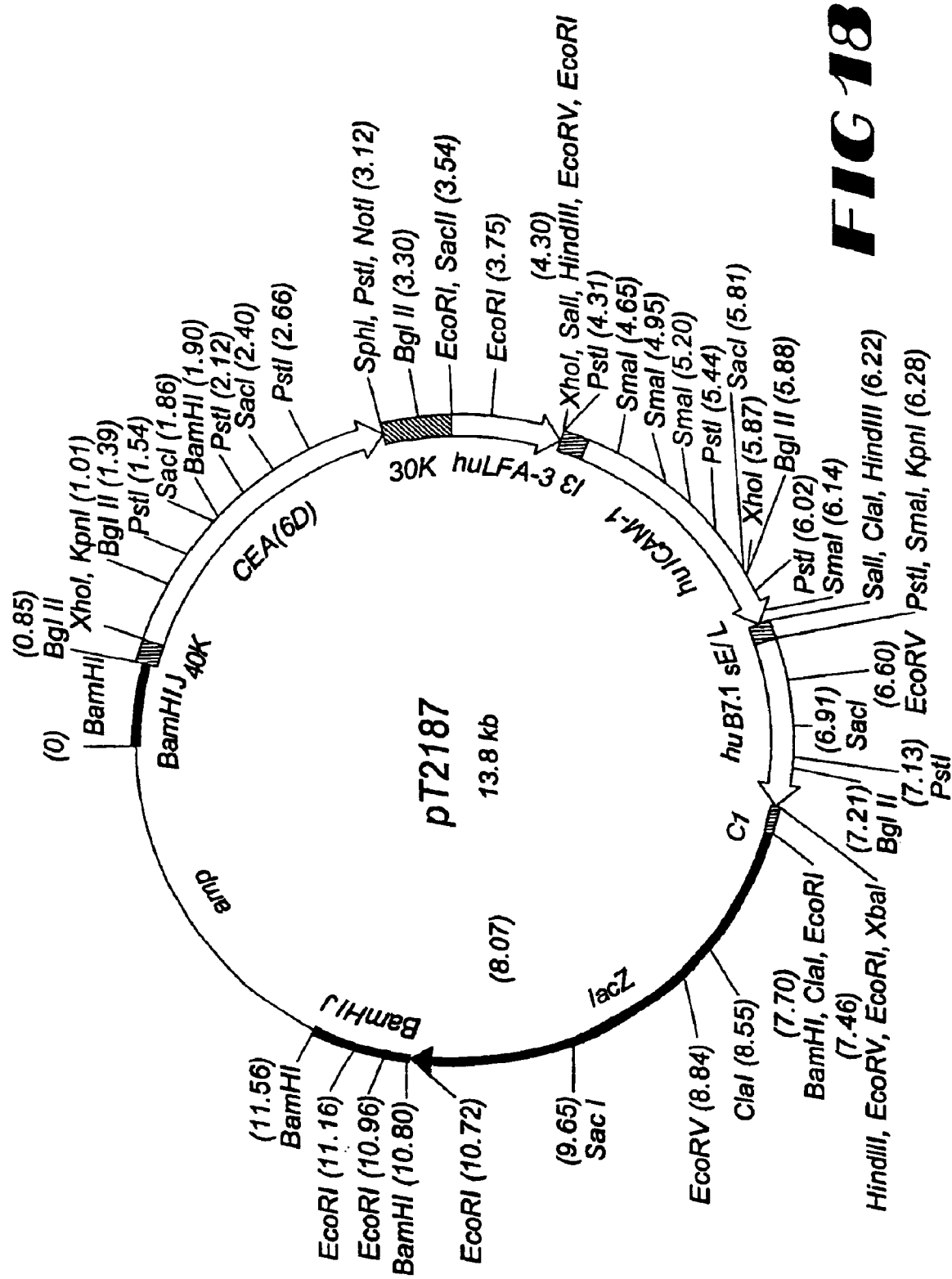
FIG. 18. Genomic structure of plasmid pT2187 comprising nucleic acid sequences encoding CEA (6D), human LFA-3, ICAM-1, B7.1, and the E. coli lacZ gene, flanked by portions of the BamHI J region of the fowlpox genome.

For the generation of rF-CEA(6D)/TRICOM(hu), a plasmid vector, designated pT2187, was constructed to direct insertion of the foreign sequences into the BamHI J region of the fowlpox genome. The CEA(6D) gene is under the control of the 40K promoter. The human LFA-3 gene is under the control of the 30K promoter, the human ICAM-1 gene is under the control of the 13 promoter, the human B7.1 gene is under the control of the sE/L promoter, and the lacZ gene is under the control of the C1 promote. These foreign sequences are flanked by DNA sequences from the BamHI J region of the fowlpox genome (see FIG. 18). A plaque-purified isolate from the POXVAC-TC (Schering-Plough Corporation) strain of fowlpox was used as the parental virus for this recombinant vaccine. The generation of recombinant fowlpox virus was accomplished via homologous recombination between fowlpox sequences in the fowlpox genome and the corresponding sequences in pT2187 in fowlpox-infected primary chick embryo dermal cells transfected with pT2187. Recombinant virus was identified using the chromogenic assay for the lacZ gene product described above. Viral plaques expressing lacZ appeared blue against a clear background. Positive plaques, designated vT236, were picked from the cell monolayer and their progeny were replated. Eight rounds of plaque isolation and replating in the presence of Bluo-Gal resulted in the purification of the desired recombinant. The genomic structure of recombinant vaccinia virus vT236 is shown in FIG. 16C.

EXAMPLE 19

Generation of Recombinant Fowlpox Virus, rF-PSA/PSMA/TRICOM(hu) No. vT257

Figure 16D:

For the generation of rF-PSA/PSMA/TRICOM(bu), a plasmid vector, designated pT5080, was constructed to direct insertion of the foreign sequences into the BamHI J region of the fowlpox genome. The gene encoding PSA was isolated by polymerase chain reaction amplification of cDNA derived from RNA from the human LNCaP cell line (CRL 1740, American Type Culture Collection (ATCC), Rockville, Md.). The gene was contained on a 1346 bp fragment which includes the entire coding sequence for PSA, 41 nucleotides of the 5' untranslated region, and 552 nucleotides of the 3' untranslated region (Lundwall and Lilja, 1987, *FEBS Lett.* 214:317–322). The gene encoding PSMA was isolated by polymerase chain reaction amplification of cDNA derived from RNA from the human LNCaP cell line. The gene was contained on a 2298 bp fragment which includes the entire coding sequence for PSMA, 26 nucleotides of the 5' untranslated region, and 19 nucleotides of the 3' untranslated region (Israeli et al, 1993 *Cancer Res.* 53:227–230). The PSA gene is under the control of the 40K promoter and the PSMA gene is under the control of the 7.5K promoter. The human LFA-3 gene is under the control of the 30K promoter, the human ICAM-1 gene is under the control of the 13 promoter, the human B7.1 gene is under the control of the sE/L promoter, and the lacZ is under the control of the C1 promoter. These foreign sequences are flanked by DNA sequences from the BamHI J region of the fowlpox genome (see FIG. 19). A plaque-purified isolate from the POXVAC-TC (Schering-Plough Corporation) strain of fowlpox was used as the parental virus for this recombinant vaccine. The generation of recombinant fowlpox virus was accomplished via homologous recombination between fowlpox sequences in the fowlpox genome and the corresponding sequences in pT5080 in fowlpox-infected primary chick embryo dermal cells transfected with pT5080. Recombinant virus was identified using the chromogenic assay for the lacZ gene product described above. Viral plaques expressing lacZ appeared blue against a clear background. Positive plaques, designated vT257, were picked from the cell monolayer and their progeny were replated. Five rounds of plaque isolation and replating in the presence of Bluo-Gal resulted in the purification of the desired recombinant. The genomic structure of recombinant vaccinia virus vT257 is shown in FIG. 16D.

EXAMPLE 20

Generation of Recombinant MVA Virus, rMVA-TRICOM(mu) No. vT264

Modified Vaccinia Ankara (MVA) is an attenuated derivative of the Ankara strain of vaccinia virus (Meyer et al, 1991, J. Gen. Virol. 72:1031–1038). The seed stock from the MVA vaccine used as smallpox vaccine in humans was obtained from Dr. Anton Mayr (institute for Medical Microbiology, Munich). The seed stock was plaque-purified two times on primary chick embryo dermal cells.

For the generation of rMVA-TRICOM(mu), a plasmid vector, designated pT5085, was constructed to direct insertion of the foreign sequences into the deletion III region of the MVA genome (Meyer et al, 1991, J. Gen. Virol. 72:1031–1038). The murine LFA-3 gene is under the control of the 30K promoter, the murine ICAM-1 gene is under the control of the I3 promoter, the murine B7.1 gene is under the control of the sE/L promoter, and the lacZ gene is under the control of the C1 promoter. These foreign sequences are flanked by DNA sequences from the deletion III region of the MVA genome (see FIG. 20). A plaque-purified isolate from the MVA vaccine seed stock was used as the parental virus for this recombinant vaccine. The generation of recombinant MVA was accomplished via homologous recombinant between MVA sequences in the MVA genome and the corresponding sequences in pT5085 in MVA-infected primary chick embryo dermal cells transfected with pT5085. Recombinant virus was identified using the chromogenic assay for the lacZ gene product described above. Viral plaques expressing lacZ appeared blue against a clear background. Positive plaques, designated vT264 were picked from the cell monolayer and their progeny were replated. Four rounds of plaque isolation and replating in the presence of Bluo-Gal resulted in the purification of the desired recombinant. The genomic structure of recombinant MVA vT264 is shown in FIG. 21A.

EXAMPLE 21

Generation of Recombinant MVA Virus, rMVA-PSA/PSMA/TRICOM(hu) No. vT260

Figure 22:
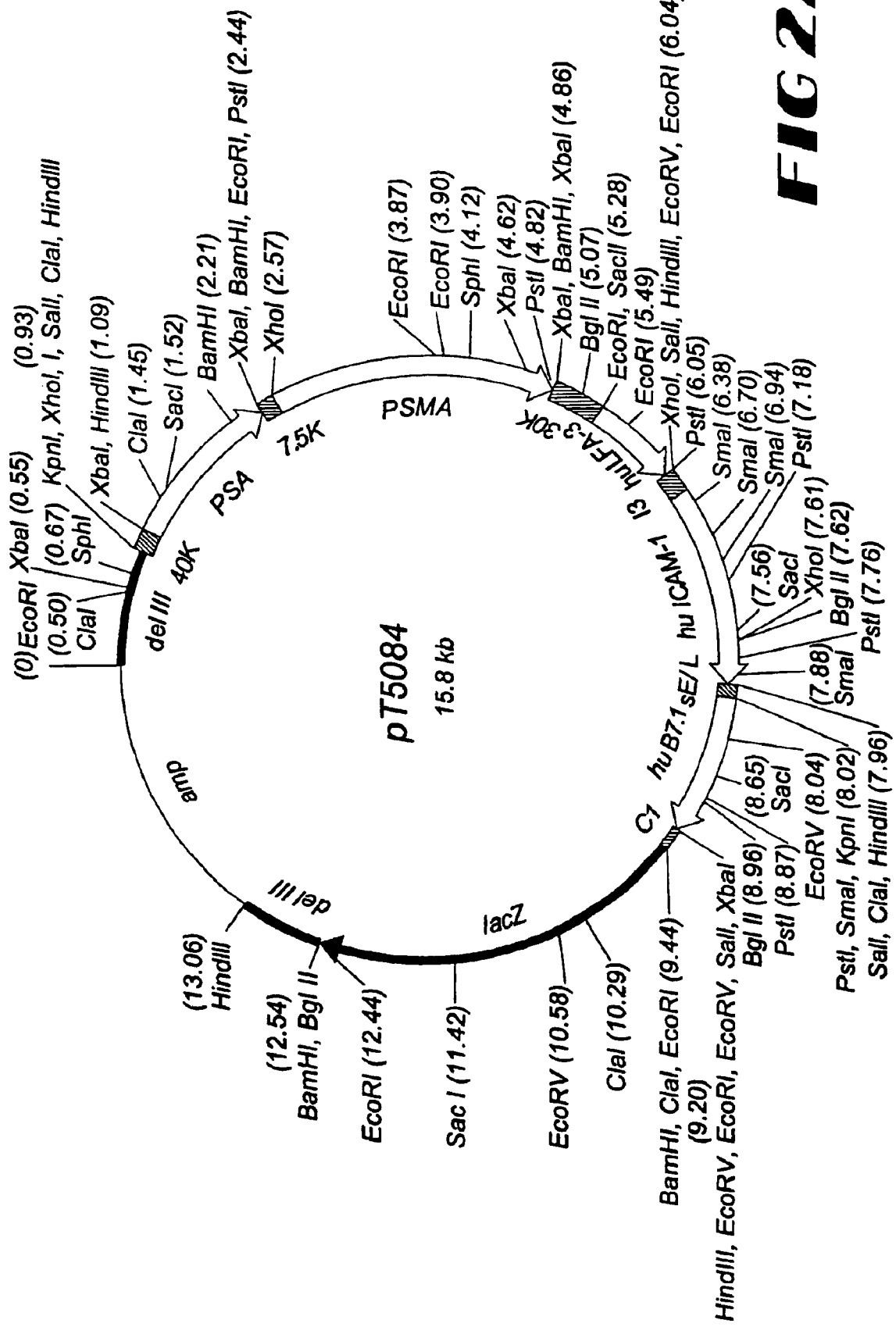
FIG. 22. Genomic structure of plasmid pT5084 comprising nucleic acid sequences encoding PSA, PSMA, human LFA-3, ICAM-1, B7.1, and the E. coli lacZ gene, flanked by portions of the deletion III region of the MVA genome.

For the generation of rMVA-PSA/PSMA/TRICOM(hu), a plasmid vector, designated pT5094, was constructed to direct insertion of the foreign sequences into the deletion III region of the MVA genome. The PSA gene is under the control of the 40K promoter and the PSMA gene is under the control of the 7.5K promoter. The human LFA-3 gene is under the control of the 30K promoter, the human ICAM-1 gene is under the control of the I3 promoter, the human B7.1 gene is under the control of the sE/L promoter, and the lacZ gene is under the control of the C1 promoter. These foreign sequences are flanked by DNA sequences from the deletion III region of the MVA genome (see FIG. 22). A plaque-purified isolate from the MVA vaccine seed stock was used as the parental virus for this recombinant vaccine. The generation of recombinant MVA was accomplished via homologous recombination between MVA sequences in the MVA genome and the corresponding sequences in pT5084 in MVA-infected primary chick embryo dermal cells transfected with pT5084. Recombinant virus was identified using the chromogenic assay for the lacZ gene product described above. Viral plaques expressing lacZ appeared blue against a clear background. Positive plaques, designated vT260, were picked from the cell monolayer and their progeny were replated. Four rounds of plaque isolation and replating in the presence of Bluo-Gal resulted in the purification of the desired recombinant. The genomic structure of recombinant MVA vT260 is shown in FIG. 21B.

EXAMPLE 22

Recombinant Poxviruses

The individual recombinant vaccinia viruses containing either the gene encoding murine costimulatory molecule B7-1 (designated rV-B7-1) or the gene encoding murine Intercellular adhesion molecule-1 (designated rV-ICAM-1) have been described (10, 11). The recombinant vaccinia virus containing the gene for murine CD48 [designated rV-LFA-3; murine CD48 is the homologue of human LFA-3 (CD58) (6)] was constructed in a similar fashion to rV-B7-1 and rV-ICAM-1, and has been described (12). In each of these single recombinant vaccinia viruses, the gene encoding the costimulatory molecule was put under the control of the vaccinia virus early/late 40K promoter (15), and the transgene was inserted into the HindIII M region of the genome of the Wyeth strain of vaccinia virus as described (13). Recombinant fowlpox viruses were constructed by the insertion of foreign sequences into the BamHI J region of the genome of the POXVAC-TC (Scherng Corporation) strain of fowlpox virus as described (14). In recombinant viruses containing a single foreign gene, the gene is under control of the vaccinia 40K promoter. rV-B7-1/ICAM-1 is a recombinant vaccinia virus that contains the murine B7-1 gene under control of the synthetic early/late (sE/L) promoter (16) and the murine ICAM-1 gene under control of the 40K promoter. rV-B7-1/ICAM-1/LFA-3 is a recombinant vaccinia virus that contains the murine LFA-3 gene under control of the vaccinia 30K (M2L) promoter (17), the murine ICAM-1 gene under control of the vaccinia I3 promoter (18), and the murine B7-1 gene under control of the synthetic early/late (sE/L) promoter. rF-CEA/B7-1/ICAM-1/LFA-3 is a recombinant fowlpox virus that contains the human carcinoembryonic antigen (CEA) gene under control of the 40K promoter, the murine B7-1 gene under control of the sE/L promoter, the murine LFA-3 gene under control of the I3 promoter, and the murine ICAM-1 gene under control of the vaccinia 7.5K promoter (19). Non-recombinant vaccinia virus was designated V-Wyeth, while non-recombinant fowlpox virus was designated WT-FP.

EXAMPLE 23

Expression of Recombinant Costimulatory Molecules

Figure 23:
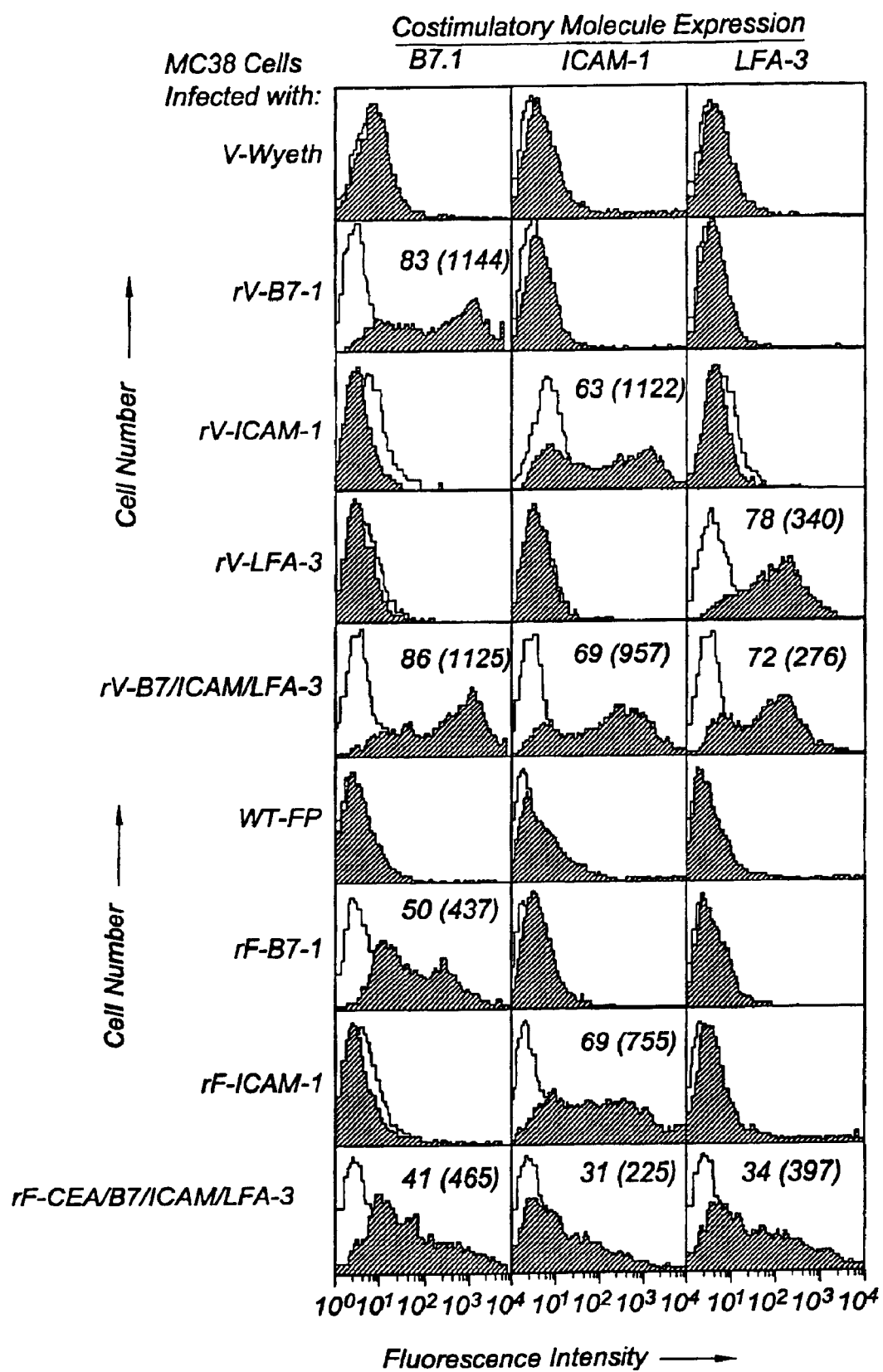
FIG. 23. Costimulatory molecule surface expression following infection with recombinant viruses. MC38 tumor cells were infected for 5 hours at 5 MOI (multiplicity of infection; pfu/cell) with the indicated virus. After infection, cells were immunostained with FITC-labeled monoclonal antibodies (MAb) specific for the costimulatory molecule. Shaded areas are fluorescence intensity of the specific MAb while unshaded areas are the fluorescence intensity of the appropriate isotype control antibody (see Materials and Methods).

To confirm that each of the recombinant vectors could express the appropriate transgene(s), the murine adenocarcinoma cell line MC38 was infected with the various recombinant vaccinia or fowlpox constructs, and cell-surface expression of the transgene(s) was demonstrated by flow cytometry (FIG. 23). Uninfected cells (data not shown) and cells infected with wild-type vaccinia failed to express any of the three costimulatory molecules. This observation was confirmed by PCR (data not shown). In contrast, cells infected with rV-B7-1 became strongly positive for B7-1 protein; cells infected with rV-ICAM-1 became positive for ICAM-1; and cells infected with rV-LFA-3 became positive for LFA-3 protein. Similar analysis of a construct containing two costimulatory molecules (rV-B7-1/ICAM-1) showed expression of B7-1 (78% positive with a mean fluorescent intensity (MFI) of 1012) and ICAM-1 (70% positive with a MFI of 690). Moreover, cells infected with the vaccinia multiple-gene construct rV-B7-1/ICAM-1/LFA-3 co-expressed all three costimulatory molecules. To determine if the recombinant fowlpox viruses expressed their recombinant proteins, MC38 cells were infected with the fowlpox constructs in a similar manner (FIG. 23).

Again, cells infected with wild-type fowlpox virus WT-FP failed to express any costimulatory molecule. Cells infected with rF-B7-l became positive for B7-l protein, and cells infected with rF-ICAM-1 became positive for ICAM-1 protein. A rF-LFA-3 vector was not constructed. However, cells infected with the fowlpox multiple-gene construct rF-CEA/B7-1/ICAM-1/LFA-3 co-expressed all three costimulatory molecules.

Characterization of Recombinant Viruses: Fluorescent Analysis of Protein Surface Expression The MC38 murine colonic adenocarcinoma cell line has been described (20).

Confluent MC38 cells were infected with vaccinia constructs (V-Wyeth, rV-B7-1, rV-ICAM-1, rV-LFA-3, rV-B7-1/ICAM-1/LFA-3) or fowlpox constructs (WT-FP, rF-B7-1, rF-ICAM-1, rF-CEA/B7-1/ICAM-1/LFA-3) at 5 MOI (multiplicity of infection; PFU/cell) for 5 hours. CEA was used in one rF construct as a marker gene only. After infection, cells were harvested and immunostained with FITC conjugated monoclonal antibodies (MAb) specific for murine CD80 (B7-1), CD54 (ICAM-1), or CD48 (LFA-3; PharMingen, San Diego, Calif.). Cell fluorescence was analyzed with a FACSCAN cytometer (Becton Dickinson, Mountain View, Calif.) with the Lysis II software.

In vitro Costimulation Analysis

Female C57BL/6 mice (6–8 weeks old) were obtained from Taconic Farms (Germantown, N.Y.). Naïve T cells were isolated from spleens mechanically dispersed through 70 m cell strainers (Falcon, Becton Dickinson, Franklin Lakes, N.J.) to isolate single cell suspensions, and erythrocytes and dead cells were removed by centrifugation over Ficoll-Hypaque gradients (density=1.119 g/ml) (Sigma, St. Louis, Mo.). Populations consisting of approximately 95% T cells were obtained by passage of splenic mononuclear cells over two nylon wool columns sequentially (Robbins Scientific Corp., Sunnyvale, Calif.). For certain experiments, T cells were further fractionated into $CD4^+$ and $CD8^+$ populations by negative selection utilizing anti-CD4 or anti-CD8 paramagnetic beads (MiniMACS, Miltenyi Biotec, Auburn, Calif.). T cells were added at $10^5$/well in 96-well flat-bottomed plates (Costar, Cambridge, Mass.). Stimulator cells consisted of uninfected MC38 cells or cells infected for 5 hours with 5 MOI of vaccinia constructs (V-Wyeth, rV-B7-1, rV-ICAM-1, rV-LFA-3, rV-B7-1/ICAM-1/LFA-3) or fowlpox constructs (WT-FP, rF-B7-1, rF-ICAM-1, rF-CEA/B7-1/ICAM-1/LFA-3) fixed with 2% paraformaldehyde and added at $1^{04}$/well. Cells in all wells were cultured in a total volume of 200 μl of complete media (CM) [RPMI 1640 with fetal calf serum (10%), glutamine (2 mM), sodium pyruvate (1 mM), Hepes (7 mM), gentamicin (50 μg/ml), 2-mercaptoethanol (50 μM), and non-essential amino acids (0.1 mM), (Biofluids, Rockville, Md.)] in the presence of several dilutions (5 to 0.625 μg/ml for 2 days) of Concanavalin-A (Con A, Sigma). Control wells received T cells, stimulator cells and media only. For indicated experiments, plate-bound anti-CD3 (1.5 μg/well-0.012 μg/well) was substituted for Con A. Cells were labeled for the final 12–18 h of the incubation with 1 Ci/well $^3$H-Thymidine (New England Nuclear, Wilmington, Del.) and harvested with a Tomtec cell harvester (Wallac Incorporated, Gaithersburg, Md.). The incorporated radioactivity was measured by liquid scintillation counting (Wallac 1205 Betaplate, Wallac, Inc.) The results from triplicate wells were averaged and are reported as mean CPM±SEM. For indicated experiments, the in vitro costimulation analysis was performed in the presence of either a MAb specific for the expressed costimulatory molecule or the matching isotype control antibody (Armenian hamster IgG, polyclonal). Antibodies used to block T-cell proliferation were Hamster anti-murine CD80 (B7-1; clone 16-10A1), Hamster anti-murine CD54 (ICAM-1; clone 3E2), or Hamster anti-murine CD48 (BCM-1; clone HM48-1), all from PharMingen. All antibodies were used at 25 μg/ml final concentration.

Determination of Costimulatory Molecule Capacity

T cells and stimulator cells were prepared as described above. Fixed stimulator cells expressing one or more costimulatory molecules were added to wells in various ratios in combination with V-Wyeth-infected/fixed stimulator cells to a total of $10^4$/well. T cells ($10^5$/well) were then added, and cells were cultured in a total volume of 200 μl of CM in the presence of 2.5 μg/ml Con A for 2 days and labeled for the final 12–18 h of the incubation with 1 μCi/well $^3$H-Thymidine. The incorporated radioactivity was measured by liquid scintillation counting as before.

Cytokine Analysis $CD4^+$ and $CD8^+$ T-cell populations were prepared as described above and added at $2.5 \times 10^6$/well in a Swell plate (Costar). Stimulator cell populations were prepared as above and added at $2.5 \times 10^5$/well. Cells were cultured in a total volume of 5 ml of CM in the presence of 2.5 μg/ml Con A for 24 hours. Supernatant fluids were collected and analyzed for murine IL-2, IFNγ, TNF-α, GM-CSF, and IL-4 by capture ELISA as described previously (21). Sensitivity of detection was 30, 100, 20, 20, and 20 pg/ml, respectively.

RNA populations from stimulated cells were also analyzed by multiprobe RNAse protection assay (mpRPA). Defined riboprobes for murine cytokines were purchased from PharMingen. Assays were performed as described previously (22). Protected probe-tagged duplexes were separated by electrophoresis on 6% polyacrylamide gels. Dried gels were exposed to Biomax film (Kodak) at −70° C. for 24–72 hours. Radioactivity contained in the bands was quantified using a Storm system phosphoimager (Molecular Dynamics, Sunnyvale, Calif.). The net CPM for a given band was calculated by the following formula [cpm of cytokine gene minus cpm of background] and was expressed as a percent of the housekeeping gene transcript L32.

EXAMPLE 24

Figure 24A:
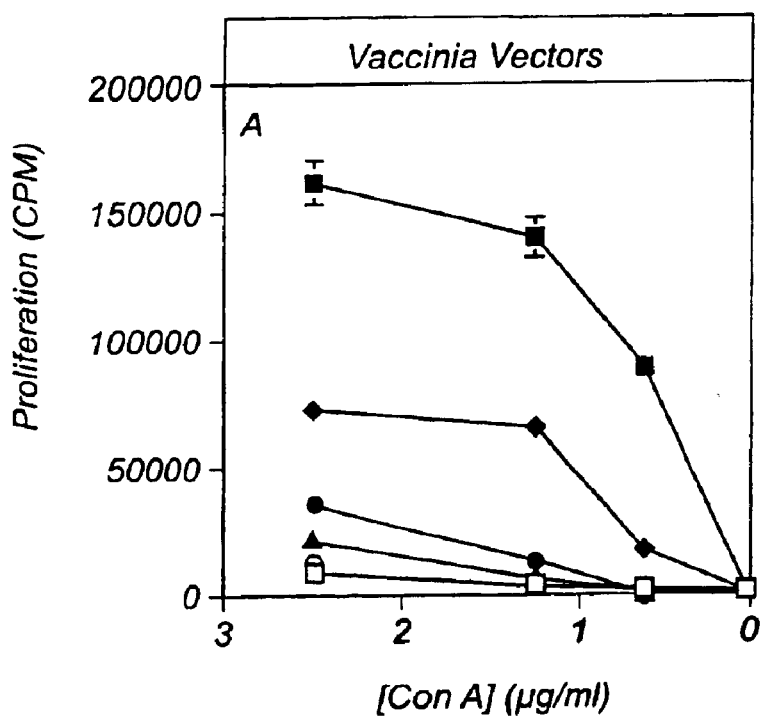
FIGS. 24A and 24B. Effect of multiple costimulatory molecules on T-cell proliferation. Naïve murine T cells, in the presence of varying concentrations of Con A to provide the first signal, were co-cultured with MC38 stimulator cells infected with either recombinant vaccinia (FIG. 24A) or recombinant fowlpox (FIG. 24B) vectors. Recombinant vectors were wild-type (i.e., V-Wyeth or WT-FP [open squares]), rV-LFA-3 (closed triangle), rV-ICAM-1 or rF-ICAM-1 (closed circles), rV-B7-1 or rF-B7-1 (closed diamonds), and rV-B7-1/ICAM-1/LFA-3 or rF-CEA/B7-1/ICAM-1/LFA-3 (closed squares). Uninfected MC38 cells are open circles. Proliferation assay is as described in Materials and Methods.

B7-1, ICAM-1, and LFA-3 Cooperate Synergistically to Enhance T-cell 110 Proliferation The B7-1, ICAM-1, and LFA-3 molecules have been shown individually to costimulate T-cell proliferation. However, because they may be expressed simultaneously on APC, it has been difficult to examine relative roles of individual costimulatory molecules during the induction of T-cell proliferation (2). To analyze the contribution of B7-1, ICAM-1 and/or LFA-3 molecules to the induction of naïve T-cell proliferation, a modified in vitro model (23, 24) was employed where the first signal for T-cell activation was delivered via a pharmacological reagent (Con A). A panel of stimulator cells that differed only in costimulatory molecules was created using the MC38 cell line infected with various recombinant vaccinia (FIG. 24A) or fowlpox (FIG. 24B) viruses engineered to express costimulatory molecules. The second, or "costimulatory," signal was delivered to the T cell via one or more costimulatory molecules expressed on the surface of these "stimulator" MC38 cells. As shown in FIG. 24A, both uninfected MC38 cells and MC38/V-Wyeth induced marginal proliferation of T cells at all levels of Con A examined. MC38/LFA-3 induced a small (2.1-fold) but significant (P<0.05) increase in T-cell proliferation. Delivery of signal-2 via MC38/ICAM-1 induced a 3.5-fold increase in T-cell proliferation at 2.5 µg/ml Con A. MC38/B7-1 induced a 7.8-fold and a 16-fold increase in proliferation at 2.5 and 1.25 µg/ml Con A respectively. However, MC38/B7-1/ICAM-1/LFA-3 (MC38 cells co-expressing all three costimulatory molecules) induced a 17.5-fold increase in T-cell proliferation at 2.5 µg/ml Con A, and a 34-fold increase at 1.25 µg/ml Con A. Moreover, at low Con A levels (0.625 µg/ml), expression of ICAM-1 and LFA-3 did not induce T-cell proliferation. While B7-1 induced measurable proliferation (20,000 CPM) at 0.625 µg/ml Con A, the co-expression of all three costimulatory molecules induced an even greater level of proliferation (100,000 CPM) (FIG. 24A). These experiments were repeated four times with similar results.

Figure 24B:
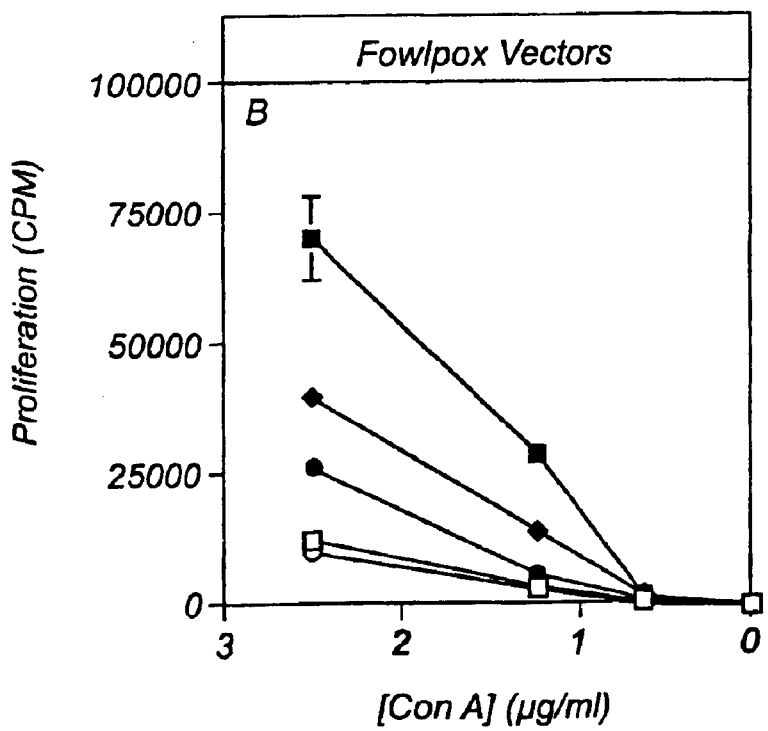

MC38 stimulator cells were also prepared by infection with recombinant fowlpox vectors (FIG. 24B). Again, uninfected MC38 or MC38/WT-FP induced marginal proliferation of T cells at all levels of Con A examined. MC38/rF-ICAM-1 supported a 2-fold increase, MC38/rF-B7-1 supported a 3.2-fold increase, and MC38/rF-B7-1/ICAM-1/LFA-3 supported a 6-fold increase in T-cell proliferation at 2.5 µg/ml Con A. Similar results were obtained when this experiment was repeated two additional times. Similar results were also observed when the first signal was delivered via immobilized anti-CD3 (data not shown). The differences noted in proliferation supported by MC38/rV-B7-1/ICAM-1/LFA-3 and MC38/rF-CEA/B7-1/ICAM-1/LFA-3 (17.5-fold vs. 6-fold) are most likely due to the levels of expressed recombinant protein(s) following a 5-hour infection period (FIG. 23). Specifically, approximately 70% of the cells infected with rV-B7-1/ICAM-1/LFA-3 express the costimulatory molecules, while approximately 40% of cells infected with rF-CEA/B7-1/ICAM-1/LFA-3 are positive. Those positive cells infected with the rF vectors express recombinant B7-1 and ICAM-1 at levels of 50% of those cells infected with rV-B7-1/ICAM-1/LFA-3 with the conditions used.

EXAMPLE 25

Specificity of Costimulatory Molecule Contribution on T-cell Proliferation

Figure 25A:
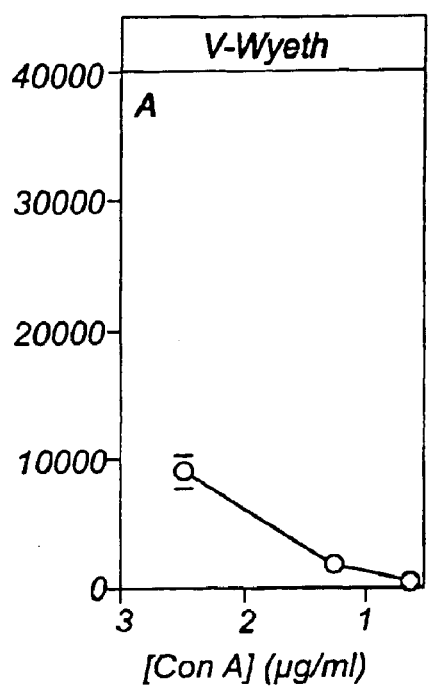
FIGS. 25A through 25D. Specificity of costimulation delivered via recombinant vaccinia viruses. T cells, in the presence of Con A, were co-cultured with MC38 stimulator cells infected with V-Wyeth (FIG. 25A), rV-B7-1 (FIG. 25B), rV-ICAM-1 (FIG. 25C), and rV-LFA-3 (FIG. 25D), as denoted by open circles. Infected stimulator cells in the presence of costimulatory molecule-specific MAb are denoted by closed circles, and isotype control antibody is denoted by closed triangles.
Figure 25B:
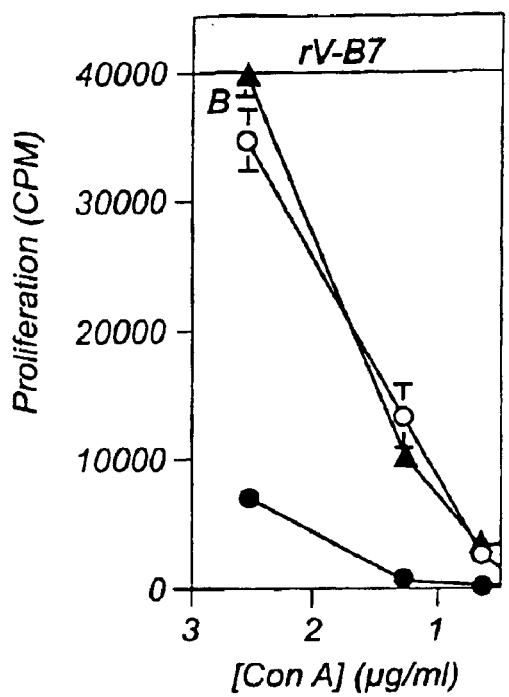
Figure 25C:
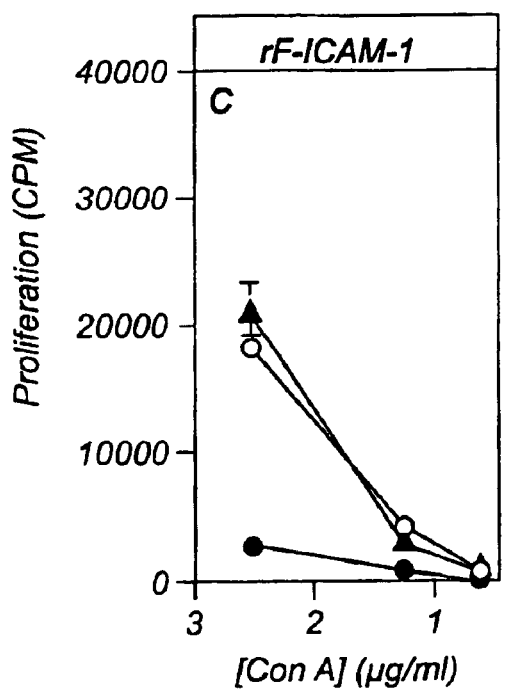
Figure 25D:
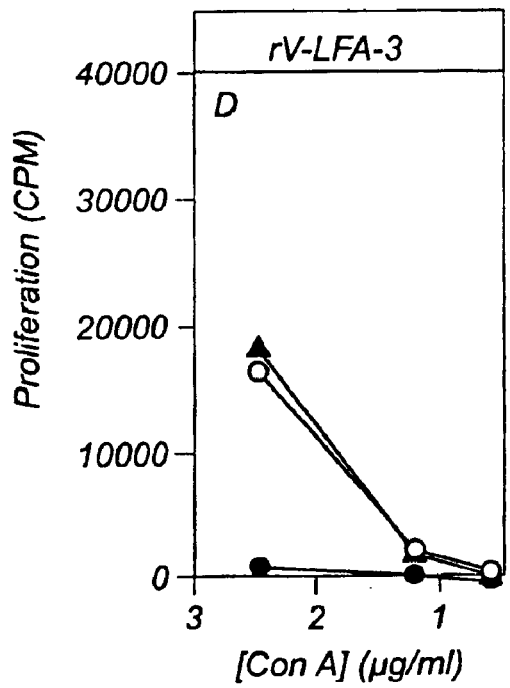

To further confirm the specificity of the proliferative contribution of B7-1, ICAM-1, or LFA-3, MC38 stimulator cells were again prepared by infection with V-Wyeth, rV-B7-1, rV-ICAM-1, or rV-LFA-3 and co-cultured with naïve murine T cells and Con A in the presence or absence of MAb specific for the given costimulatory molecule. As shown in FIG. 3B, MC38/B7-1 enhanced Tell proliferation 4.5-fold more than that of MC38N-Wyeth (FIG. 25A). This increased proliferation was inhibited 83% by the addition of a blocking MAb for murine B7-1. Similarly, MC38/ICAM-1 (FIG. 25C) increased proliferation 2.25-fold, which was then reduced by 88% in the presence of anti-murine ICAM-1 MAb. Finally, MC38/LFA-3 (FIG. 25D) increased proliferation 2.1-fold, which was then reduced by 98% in the presence of anti-murine CD48 MAb. For each group, incubation with the appropriate isotype control antibody (as specified in Materials and Methods) failed to block the noted proliferation. This experiment was repeated two additional times with similar results.

EXAMPLE 26

Determination of Costimulatory Molecule Capacity

Figure 26:
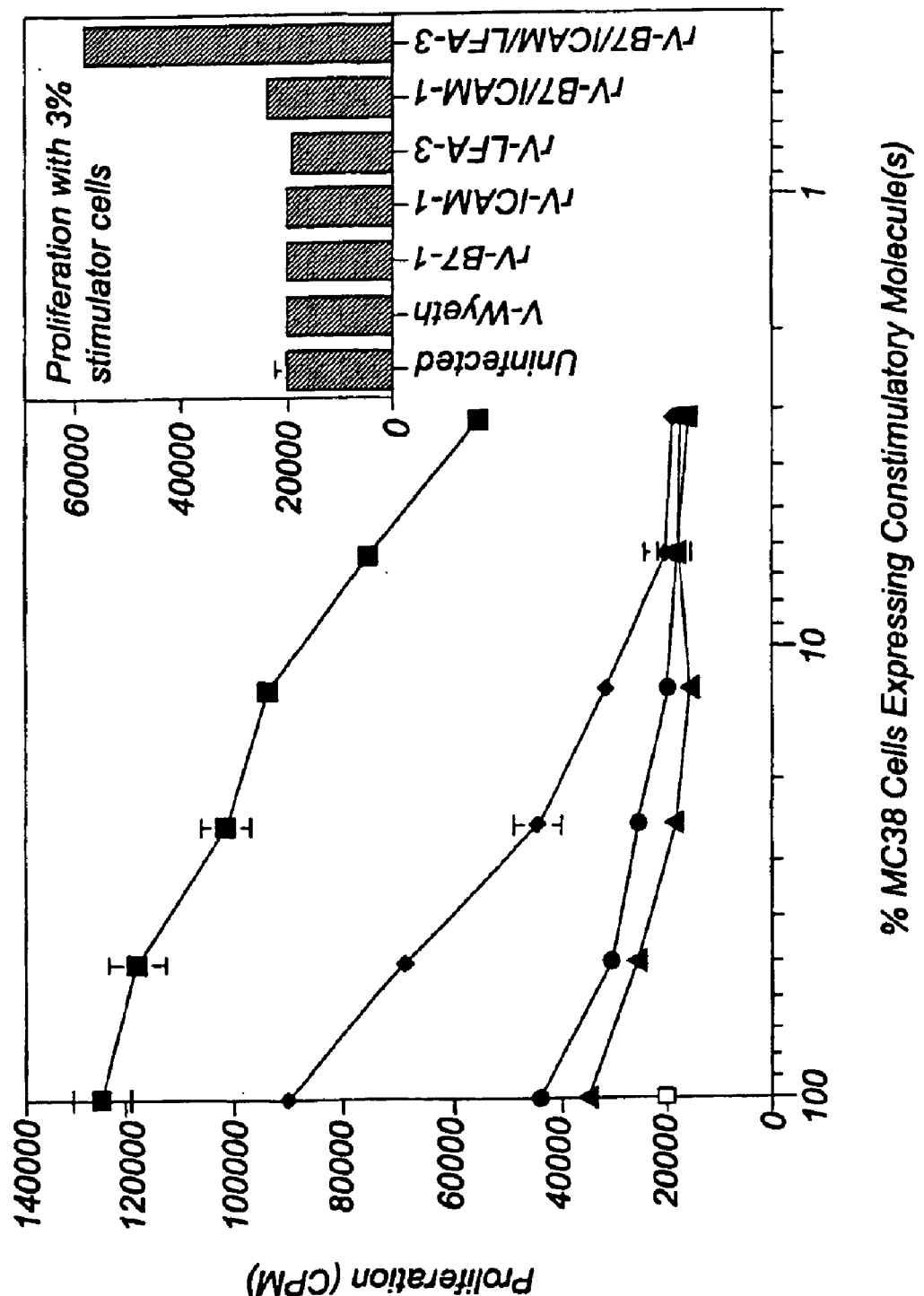
FIG. 26; Relative capacity of B7-1, ICAM-1, LFA-3 and the coexpression of all three costimulatory molecules to deliver the second signal for T-cell proliferation. In the presence of Con A (2.5 µg/ml), 100,000 T cells were co-cultured with 10,000 MC38 cells. The stimulator MC38 cells expressing one or all of the costimulatory molecules were added to the wells in various ratios in combination with V-Wyeth-infected stimulator cells to a total of $10^4$ MC38 cells/well. MC38 cells were infected with V-Wyeth (open square), rV-LFA-3 (closed triangles), rV-ICAM-1 (closed circles), rV-B7-1 (closed diamonds), or rV-B7-1-ICAM-1-LFA-3 (closed squares). Cells were co-cultured for 48 hours. During the final 18 hours, 3H-Thymidine was added to measure T-cell proliferation. Inset panel depicts proliferation values obtained from a culture in which 3% of the MC38 stimulator cells were infected with the vectors shown. Thus, in this experiment, the final ratio of stimulator cells to T cells was 0.003. Note the relatively poor effect of rVB7.1/ICAM under these conditions as compared to rV-B7/ICAM/LFA-3.

Modification of the in vitro costimulation assay allowed a quantitative estimation of the relative capacity of B7-1, ICAM-1, and/or LFA-3 to deliver the second signal for T-cell proliferation. To that end, stimulator cells (MC38 cells infected with the various recombinant vaccinia viruses) were titered out by dilution with varying amounts of MC38 cells infected with V-Wyeth and co-cultured with a constant number of T cells in the presence of 2.5 µg/ml Con A. The MC38 to T-cell ratio in these experiments remained constant at 1:10. As seen in FIG. 4, MC38/LFA-3 (closed triangles) enhanced proliferation of T cells over that of MC38/V-Wyeth (open square) out to a concentration of 40% (i.e., of the stimulator cells in the well, 40% were infected with rV-LFA-3 and the remaining 60% were infected with V-Wyeth). MC38/ICAM-1 (closed circles) or MC38/B7-1 (closed diamonds) supported increased proliferation out to a concentration of 13% and 6%, respectively. In contrast, MC38/B7-1/ICAM-1/LFA-3 enhanced proliferation when less than 3% of stimulator cells contained the triad vector (extrapolated to less than 1% via linear least squares analysis). Given the titration curves of these individual costimulatory molecules, it appeared that the extent of T-cell proliferation mediated by ICAM-1 and B7-1 is 3-fold and 6-fold, respectively, more potent than that mediated by LFA-3 alone. Clearly the strongest proliferation, however, is mediated by B7-1/ICAM-1/LFA-3. It should be noted (FIG. 26) that at relatively low stimulator cell concentrations (i.e., when 3%–6% of the MC38 cells are acting as stimulator cells), expression of LFA-3, ICAM-1, and even B7-1 alone does not enhance T-cell activation, while the three costimulatory molecules expressing stimulator cells substantially enhance T-cell activation. The data in FIG. 26 (insert) shows proliferation results obtained when 3% of the MC38 stimulator cells were infected with the vectors denoted. Since each well contained 10⁴ total MC38 cells and 10⁵ naïve T cells, the actual stimulator to T-cell ratio in these cultures was 0.003. Note that the MC38 cells infected with the two-gene construct (rV-B7-1/ICAM-1) induced little, if any, proliferation of T cells under these conditions, while MC38/B7-1/ICAM-1/LFA-3 increased proliferation substantially (p<0.0001).

EXAMPLE 27

Costimulation of CD4⁺ and CD8⁺ T cells

Figure 27A:
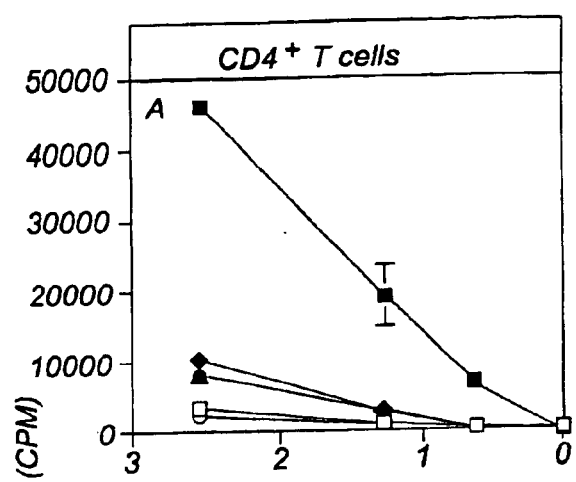
FIGS. 27A through 27D. Effect of costimulation on specific T-cell populations. Murine CD4$^+$ (FIG. 27A) or CD8$^+$ T cells (FIG. 27B) were co-cultured with uninfected MC38 cells (open circle), or cells infected with V-Wyeth (open squares), rV-LFA-3 (closed triangles), rV-ICAM-1 (closed circles), rV-B7-1 (closed diamonds) or rV-B7-l/ICAM-1/LFA-3 (closed squares) at a 10:1 ratio for 48 hours in the presence of various concentrations of Con A. During the final 18 hours, $^3$H-Thymidine was added to measure T-cell proliferation.
Figure 27B:
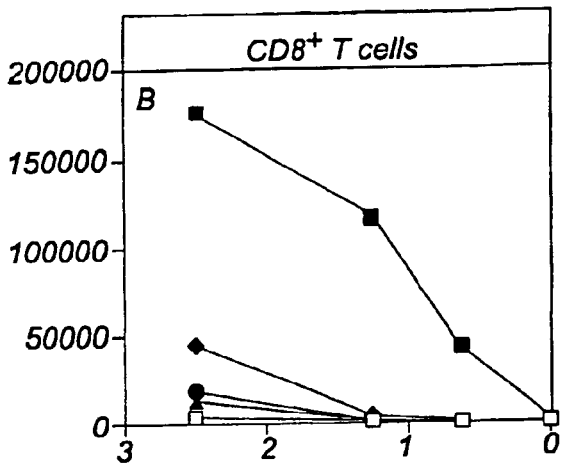
Figure 27C:
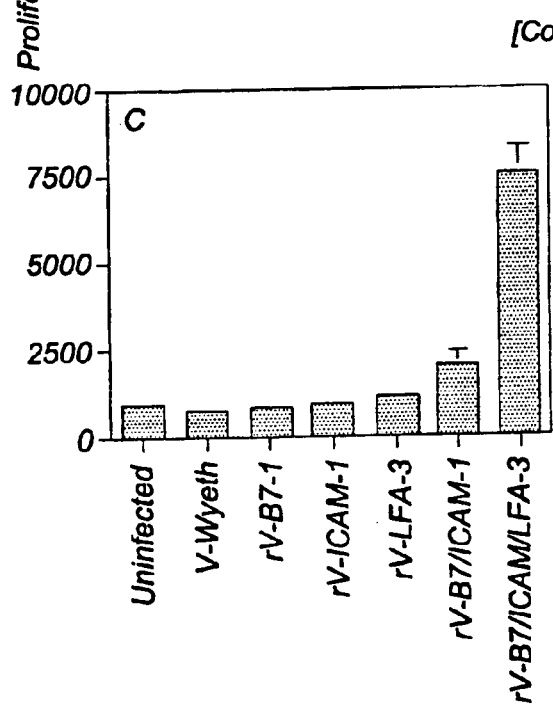
Figure 27D:
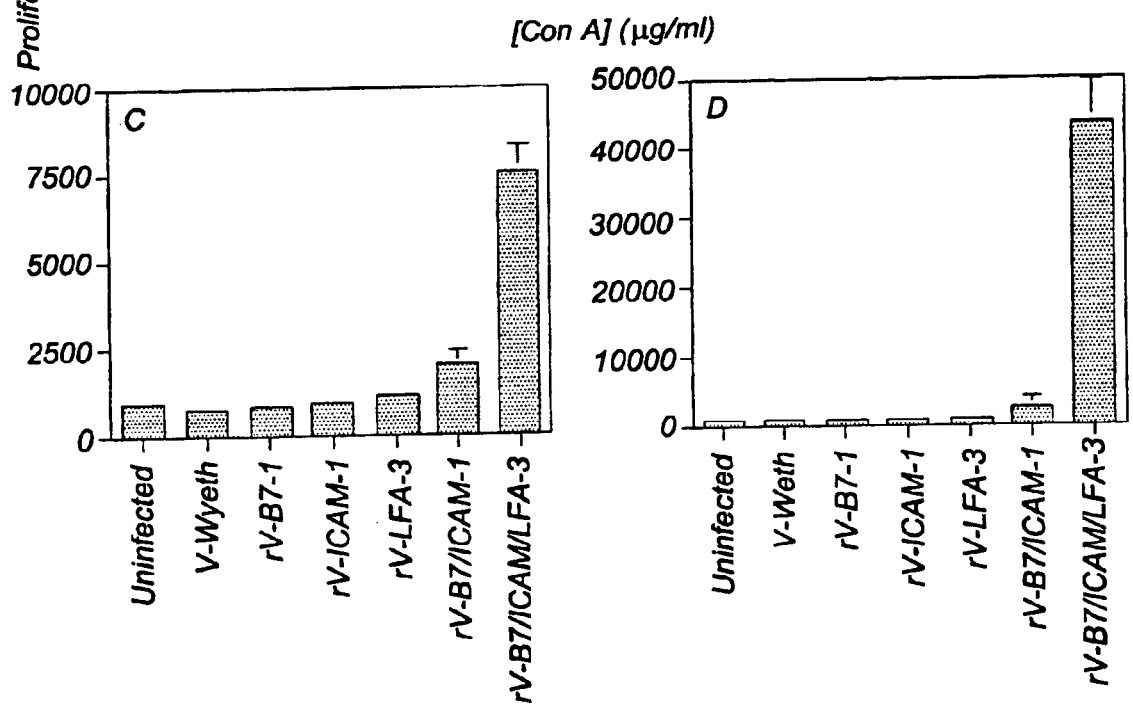

To further characterize the T-cell response to costimulatory molecules expressed singly or in combination, the ability of B7-1, ICAM-1, and LFA-3 to costimulate purified CD4⁺ and CD8⁺ T cells was tested. FIG. 5 shows the proliferation of purified CD4⁺ (FIG. 27A) and CD8⁺ (FIG. 27B) cells activated with suboptimal concentrations of Con A. The stratification of stimulator cell effects on proliferation was similar for both CD4⁺ and CD8⁺ cells: MC38/LFA-3 stimulated the weakest proliferation, followed by MC38/ICAM-1 and MC38/B7-1. MC38/B7-1/ICAM-1/LFA-3 were the most potent stimulator cells for CD4⁺ and CD8⁺ T cells. These experiments were repeated three additional times with similar results. It should be noted that at very low concentrations of Con A (0.625 µg/ml, FIG. 5, panels C and D), there was no significant enhancement in activation of CD4⁺ or CD8⁺ T cells when either ICAM-1, LFA-3, B7-1, or the B7-1/ICAM-1 combination was used to provide the second signal. However, substantial activation of both T-cell subsets was observed when the vaccinia virus coexpressing the triad of costimulatory molecules was employed. Similar results were noted when the first signal was delivered via immobilized anti-CD3 (data not shown).

It has been reported that B7-1 costimulation prolongs IL-2 mRNA half life and upregulation of IL-2 transcription, resulting in production of considerable amounts of secreted IL-2 (4, 25). Additionally, T-cell costimulation with LFA-3 has been reported to have an effect on a variety of cytokines, notably IL-2 and IFN-γ (6). To determine qualitative and quantitative effects of costimulation by single or multiple costimulatory molecules on cytokine production, purified CD4+ and CD8+ T cells were again co-cultured with various stimulator cells expressing B7-1, ICAM-1, and LFA-3 alone or in combination in the presence of 2.5 μg/ml Con A. Supernatant fluids were analyzed for IL-2, IFN-γ, TNF-α, GM-CSF, and IL-4 after 24 hours. Uninfected MC38 (data not shown) and MC381V-Wyeth induced a marginal quantity of IL-2 from CD4+ cells (FIG. 28A), while MC38/B7-1 induced 3,979 μg/ml. However, T-cell stimulation with MC38/B7-1/ICAM-1/LFA-3 induced a 10-fold greater amount of IL-2. Similarly, MC38/B7-1 induced a marginal quantity of IL-2 from CD8+ cells (FIG. 28B), while MC38/B7-1/ICAM-1/LFA-3 induced a 20-fold greater amount (6,182 μg/ml). IFN-γ production by stimulated T cells was also examined. MC38/B7-1 and MC38/LFA-3 induced only moderate amounts of IFN-γ from CD4+ cells (FIG. 28C). In contrast, stimulation of CD4+ cells with MC38/B7-1/ICAM-1/LFA-3 induced 4-fold more IFN-γ than stimulation with any other construct. Stimulation of CD8+ cells with MC38/B7-1/ICAM-1/LFA-3 induced the greatest amount of IFN-γ greater than 6-fold more than CD8+ cells stimulated with any of the other constructs (FIG. 28D). Stimulation of either cell type with any construct failed to mediate significant changes (p>0.05) in the levels of secreted TNF GM-CSF, or IL4 (data not shown). It appears that the predominant culmination of stimulation via the triad construct (rV-B7-1/ICAM-1/LFA-3) was IL-2 secretion from CD4 cells and IFN-γ secretion from CD8+ T cells. These experiments were repeated three additional times with similar results. Studies were also carried out comparing stimulator cells infected with the two-gene construct (rV-B7-1/ICAM-1) vs. the multi-gene construct (rV-B7-1/ICAM-1/LFA-3) for their ability to enhance cytokine production by T cells. Only small differences were observed between the two in IFN-γ production by either CD4+ or CD8+ cells, or in IL-2 production by CD8+ cells. But a substantial difference was seen in the stimulation of IL-2 production by CD4+ cells (5000 μg/ml employing MC38/B7-1/ICAM-1 vs. 39,600 μg/ml employing MC38/B7-1/ICAM-1/LFA-3).

Figure 29:
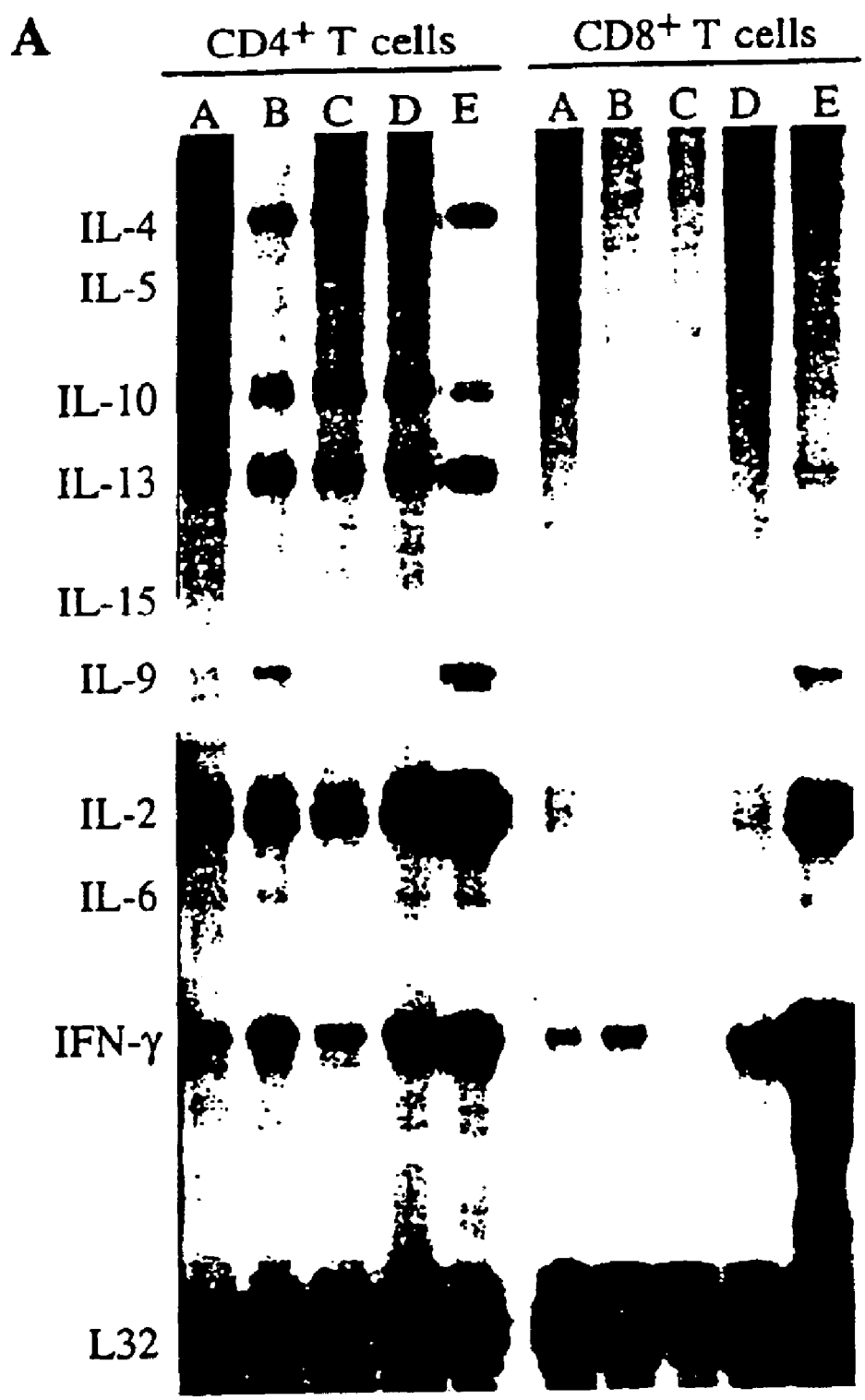
FIGS. 29A through 29C. Effect of costimulation on cytokine RNA expression.
Figure 29B:
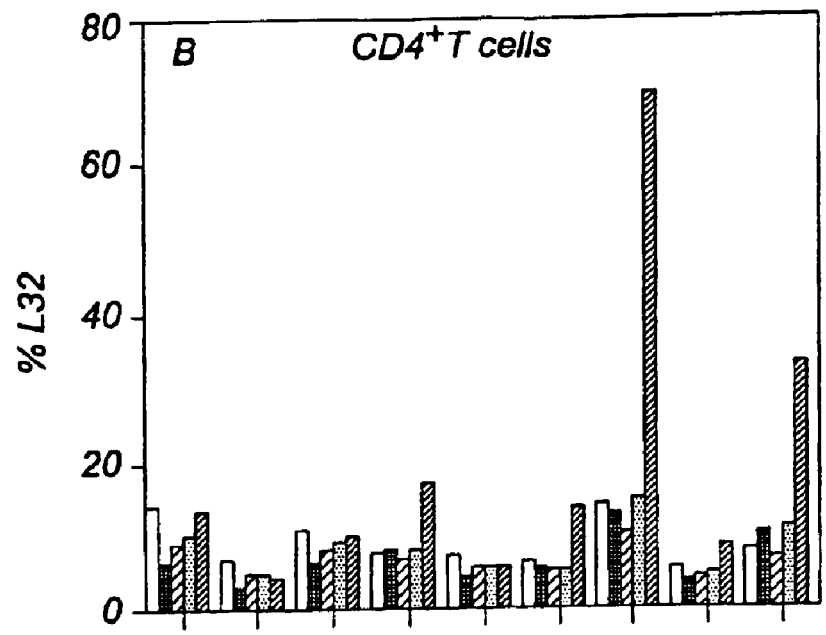
Figure 29C:
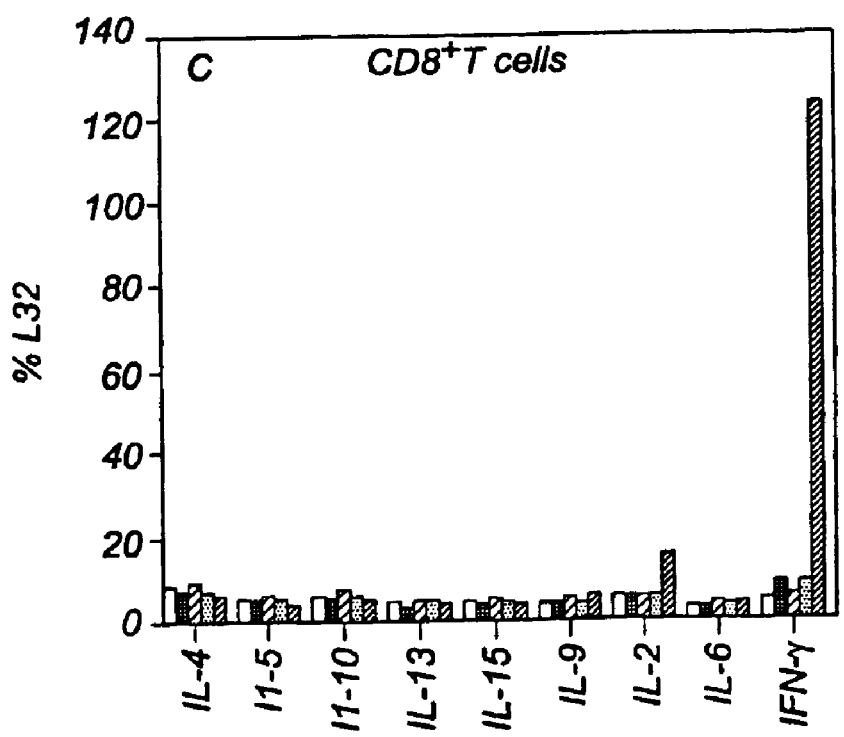

Cytokine expression from CD4+ and CD8+ T cells stimulated with single or multiple costimulatory molecules was also analyzed at the RNA level utilizing the multiprobe RNAse protection assay (mRPA). A representative radiographic profile and quantitative analysis from two independent experiments are depicted (FIG. 29). Levels of IL4, IL-5, IL-10, IL-15, and IL-6 were similar in CD4+ T cells stimulated with MC38N-Wyeth, MC38/B7-1, MC38/ICAM-1, MC38/LFA-3, or MC38/B7-1/ICAM-1/LFA-3 (FIG. 29, panel B histogram). IL-2 and IFN-γ expression levels were highest in CD4+ T cells stimulated with MC38/B7-1/ICAM-1/LFA-3 when compared with CD4+ cells stimulated with MC38 cells expressing any single costimulatory molecule (FIG. 29B). Slightly higher levels of IL-13, IL-9, and IL-6 were also noted in CD4+ cells stimulated with MC38/B7-1/ICAM-1/LFA-3. Expression of cytokine genes was also analyzed in stimulated CD8+ T cells. Of the cytokine RNAs analyzed, IL2 and particularly IFN-γ levels were significantly higher when these cells were stimulated with MC38/B7-1/ICAM-1/LFA-3, compared to T cells stimulated with MC38 cells expressing any single costimulatory molecule. Thus, the predominant synergistic effect of the triad of costimulatory molecules in cytokine production was IL-2 in CD4+ cells and IFN-γ in CD8+T cells.

EXAMPLE 28

Effect of TRICOM Costimulation on Apoptosis of Stimulated T cells

Apoplosis Studies

To determine if stimulation of T cells with signal 1 and rV-TRICOM would lead to cell survival or programmed cell death (PCD), CD8+ T cells were activated with Con A for signal 1, cultured with either V-WT, rV-B7-1 or rV-TRICOM-infected MC38 cells for 48 hr, and replated for 24 hr in medium to measure apoptosis. Apoptosis was assessed using the TUNEL assay, as described by Gavrieli, Y et al. *J Cell Biol* 119: 493–501, 1992. T cells activated by the combination of MC38 and Con A or MC38N-WT and Con A in the absence of costimulatory signals exhibited high levels of spontaneous apoptosis (82.9±1, respectively). T cells activated by Con A and MC38/B7-1 or Con A and MC38/TRICOM exhibited substantially less spontaneous apoptosis (31.3+3.8 and 30.7 A 1, respectively).

The results clearly demonstrate apoptosis in T cells stimulated with MC38 cells in the presence of Con A with or without V-WT infection (i.e., in the absence of signal 2). While Con A with MC38/TRICOM clearly stimulated CD8[4] cells to far greater levels than Con A with MC38/B7-1 and resulted in the production of higher levels of IFN-γ and IL-2, this did not result in any greater degree of apoptosis.

EXAMPLE 29

Anti-tumor Effect of rV-CEA/TRICOM In vivo

Studies were conducted to determine if an antigen-specific immune response could be enhanced using a TRICOM vector. A four-gene vaccinia recombinant was constructed that contained the human CEA gene and the B7-1, ICAM-1 and LFA-3 genes, designated rV-CEA/TRICOM, as disclosed herein. Six to eight-week-old female C57 BL/6 mice (Taconic Farms) or C57BL/6 mice transgenic for human CEA (Kass, E et al *Cancer Res.* 59: 676683, 1999) were vaccinated by tail scarification with either Hank's Balanced Salt Solution (HBSS) or one time with 107 pfu rV-CEA, rV-CEA/B7-1 or rV-CEA/TRICOM, and spleens were harvested 22 days later. Lymphoproliferative activity of splenocytes was analyzed as described previously (5).

Figure 30:
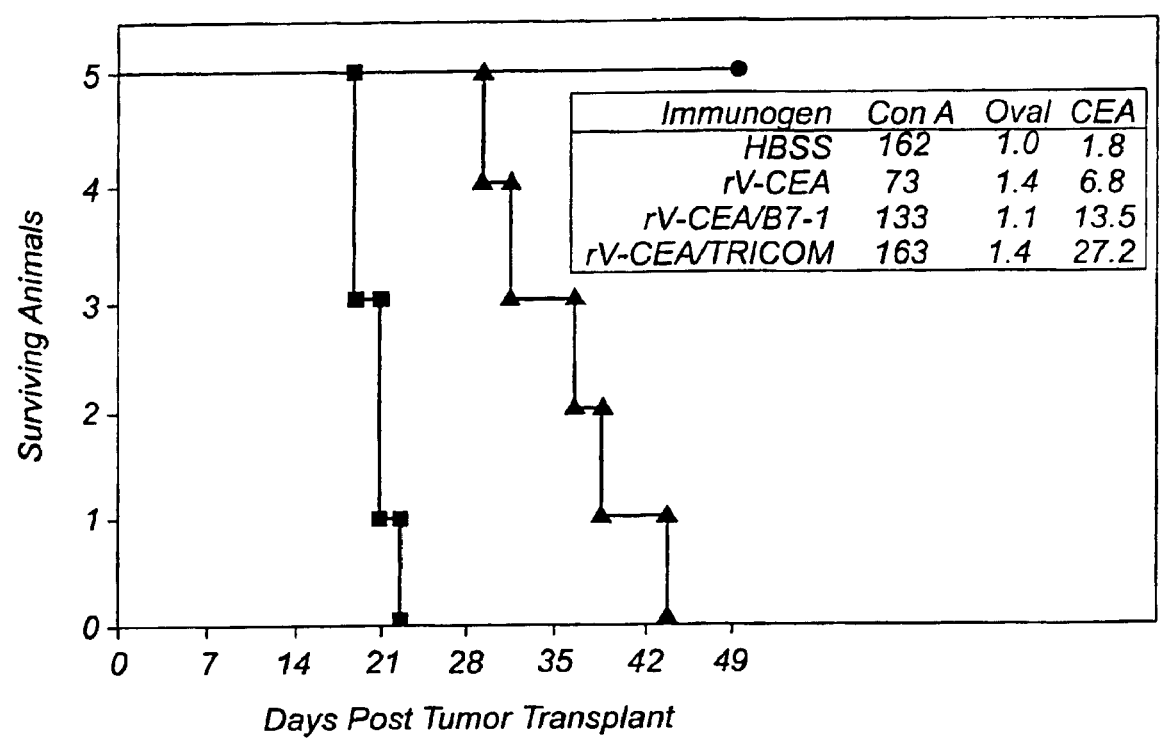
FIG. 30. C57BL/6 mice (5/group) were administered HBSS (closed squares) or vaccinated with 107 pfu rV-CEA (closed triangles) or rV-CEA/TRICOM (closed circle). One hundred days later, mice were inoculated with $1 \times 10^6$ MC38 carcinoma cells expressing CEA and survival was monitored. All mice other than the rV-CEA/TRICOM group developed tumors and were sacrificed when tumors exceeded 20 mm in length or width, or when the mice were moribund.

As seen in FIG. 30 (insert), splenic T cells of mice vaccinated with rV-TRICOM showed higher levels of CEA-specific stimulation compared with T cells obtained from mice vaccinated with rV-CEA; Ovalbumin and Con A were used as controls. An experiment was then conducted to determine if rV-CEA/TRICOM could induce long-term immunity. Mice (5/group) were vaccinated one time with either V-WT, rV-CEA, or rV-CEA/TRICOM. One hundred days later, mice were challenged with a high dose (1×10$^6$) of MC38 colon carcinoma cells expressing CEA (5). All mice receiving V-WT and rV-CEA succumbed to tumors, while all mice vaccinated with rV-TRICOM were alive 50 days post-challenge (FIG. 30).

CEA-transgenic mice (Kass 1999, ibid; Thompson, J. A. et al. *J. Clin. Lab. Anal* 5:344366, 1999) in which the human CEA gene is expressed in normal adult gastrointestinal tissue, and whose serum is CEA-positive, were employed to determine if the rV-CEA/TRICOM vector could enhance T-cell responses to a self-antigen. CEA transgenic mice were separated into 5 mice/group. Two mice were vaccinated once with 107 pfu rV-CEA, rV-CEA/B7-1, rV-CEA/TRICOM or buffer and were euthanized on day 30 to analyze CEA-specific T-cell responses. T-cell responses obtained after vaccination with rV-CEA/TRICOM were substantially greater than those obtained with rV-CEA (Table 2). Responses to ovalbumin and Con A were used as controls. The remaining 3 CEA-transgenic mice in each group were used to determine if anti-tumor responses to a CEA-expressing tumor could be enhanced employing a TRICOM vector. These mice were first inoculated s.c. with $4\times10^5$ MC38 carcinoma cells expressing the CEA gene (5). Four days later, mice were vaccinated one time at a distal site with $10^7$ pfu viral recombinant or buffer. No tumors grew in mice vaccinated with rV-CEA/TRICOM, whereas tumors continued to grow in mice vaccinated with buffer, rV-CEA and rV-CEA/B7-1 (Table 2). These results support the in vivo activity of TRICOM vectors.

TABLE 2

Enhanced Immune Response and Anti-Tumor Response of rV-CEA/TRICOM in CEA Transgenic Mice

| Immunogen | Stimulation Index (SI) | | | | Tumor Value | |
|---|---|---|---|---|---|---|
| | Con A (5 µg/ml) | Oval (100 µg/ml) | CEA (100 µg/ml) | CEA (25 µg/ml) | Day 14 | Day 35 |
| HBSS | 109 | 1.0 | 1.3 | 2.0 | 698 ± 928 | 3,674 ± 3,107 |
| rV-CEA | 123 | 0.9 | 4.9 | 4.0 | 259 ± 0 | 1,112 ± 1,685 |
| rV-CEA/B7-1 | 93 | 1.3 | 7.1 | 4.3 | 150 ± 236 | 2,696 ± 1,936 |
| rV-CEA/TRICOM | 111 | 1.1 | 19.2 | 15.9 | 0 ± 0 | 0 ± 0 |

C57B/L6 CEA-transgenic mice (5 per group) were vaccinated via skin scarification with buffer or vaccinia recombinant ($10^7$ pfu) one time on Day 0. On Day 30, 2 mice were killed and splenic T cells were analyzed for T-cell proliferative responses. Each value represents the SI of the mean CPM of triplicate samples versus media.
Standard deviation never exceeded 10%. On Day 4, 3 mice per group were given $4 \times 10^5$ MC38 colon carcinoma cells expressing CEA. Tumor volume is given at Days 14 and 35 post-vaccination.

EXAMPLE 30

Costimulation of CD4$^+$ and CD8$^+$ T cells by Progenitor Dendritic Cells and Dendritic Cells Infected with rV-B7/ICAM-1/LFA-3

Fresh CD34$^+$ bone marrow cells (dendritic cell precursors) were obtained from C57BL/6 mice by the method of Inaba et al (41). These precursor cells were either used immediately or cultured for 6 days in GM-CSF and IL4 (42) to generate mature dendritic cells (DC). CD34$^+$ precursor cells and DC were infected for 18 hours with the recombinant vaccinia virus encoding multiple costimulatory molecules rV-B7/ICAM-1/LFA-3 (rV-Tricom), 10 MOI. After 5 hours of infection, a sample of cells were harvested and a phenotypic analysis was performed. Dendritic cells are though of in the art as the 'ultimate' APC, expressing a large array of costimulatory molecules at high levels. Table 3 shows that murine DC indeed express the costimulatory molecules B7-1, B7-2, ICAM-1, and LFA-3 at relatively high levels (mean fluorescent intensity, MFI; depicted in parenthesis). However, when DC were infected with rV-B7/ICAM-1/LFA-3, there was a significant increase in both the level of costimulatory molecule expression as well as the percentage of cell expressing the multiple costimulatory molecules. The percentage of cells expressing B7-1 increased from 65% to 86%, while the MFI increased 4-fold; the percentage of cells expressing ICAM-1 increased from 32% to 68%, while the MFI increased 2.5 fold; the percentage of cells expressing LFA-3 increased from 44% to 75%.

TABLE 3

Phenotypic Analysis of Progenitor DC Pre and Post Infection[1] with rV-COS[2]

| Infection | Marker | | | | | | | |
|---|---|---|---|---|---|---|---|---|
| | H2-K$^b$ | I-A$^b$ | CD11b | CD11c | B7-2 | B7-1 | ICAM-1 | LFA-3 |
| None | 90[3] | 64 | 63 | 29 | 38 | 65 | 32 | 44 |
| | (994)[4] | (621) | (397) | (223) | (319) | (300) | (336) | (378) |
| V-Wyeth | 75 | 60 | 59 | 27 | 36 | 65 | 33 | 43 |
| | (554) | (633) | (398) | (218) | (317) | (311) | (296) | (322) |
| rV-B7 | 76 | 67 | 70 | 34 | 41 | 83 | 43 | 51 |
| | (516) | (755) | (419) | (213) | (320) | (661) | (363) | (333) |
| rV-B7/ICAM/LFA-3 | 79 | 63 | 63 | 30 | 42 | 86 | 68 | 75 |
| | (579) | (696) | (408) | (203) | (360) | (1253) | (810) | (484) |

[1] 5 hour infection at 10 MOI
[2] rV-COS = recombinant vaccinia encoding a foreign costimulatory molecule.
[3] = % cells expressing marker
[4] = mean fluorescent intensity For use as stimulator cells, the infected CD34+ precursor cells and DC were irradiated (2000 rad) and used to stimulate naïve CD4+ and CD8+ T-cells in the presence of Con A as outlined in FIG. 31.

Figures 32A, 32B:
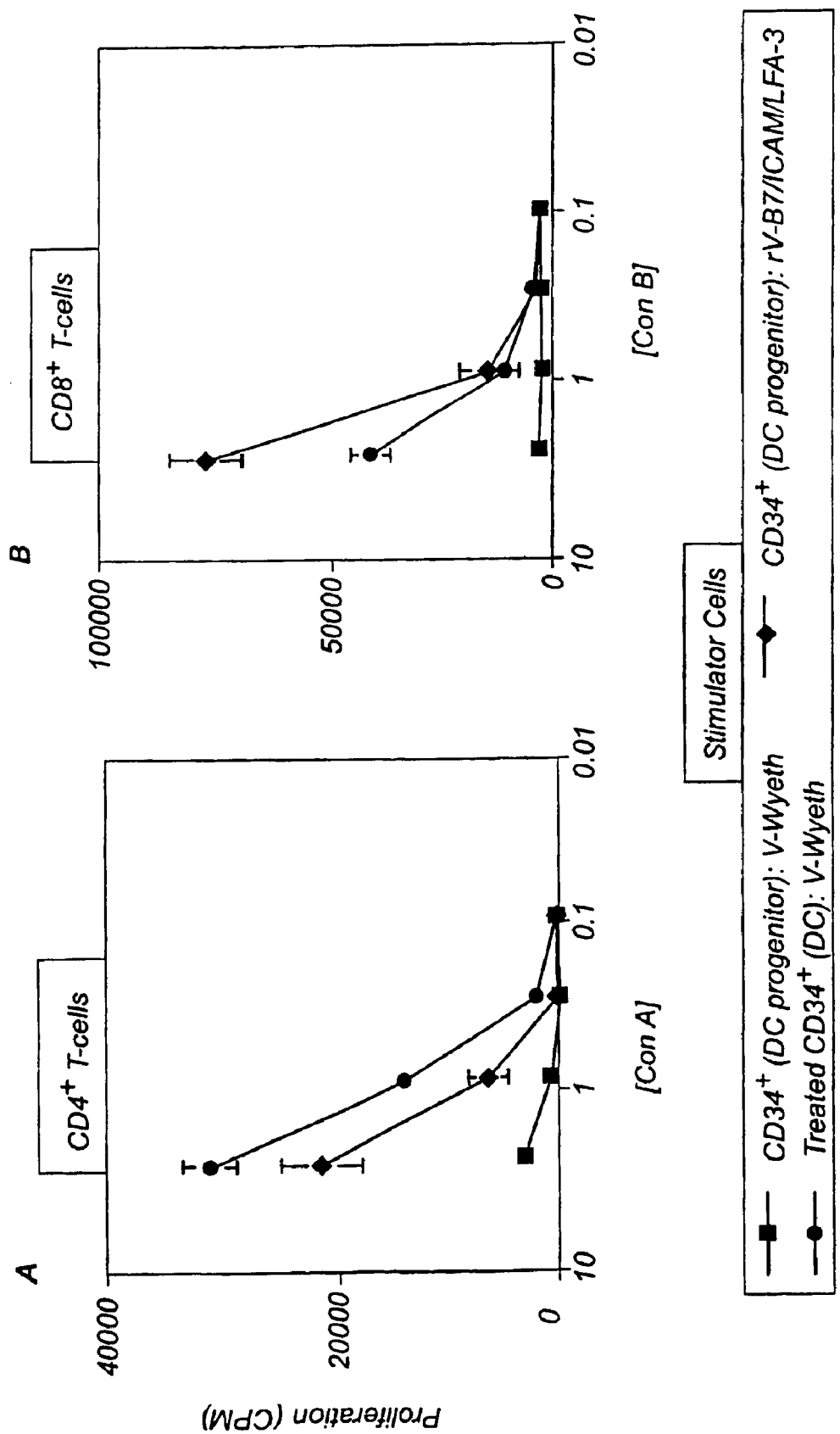
FIGS. 32A and 32B show the proliferative response of naïve CD4 (FIG. 32A) or naïve CD8+ (FIG. 32B) T cells stimulated with progenitor DCs infected with rV-B7/ICAM-1/LFA-3 or DCs (noninfected, ie, CD 34+ cells treated with GM-CSF+IL-4 for 6 days) in the presence of Con A
Figures 33A, 33B:
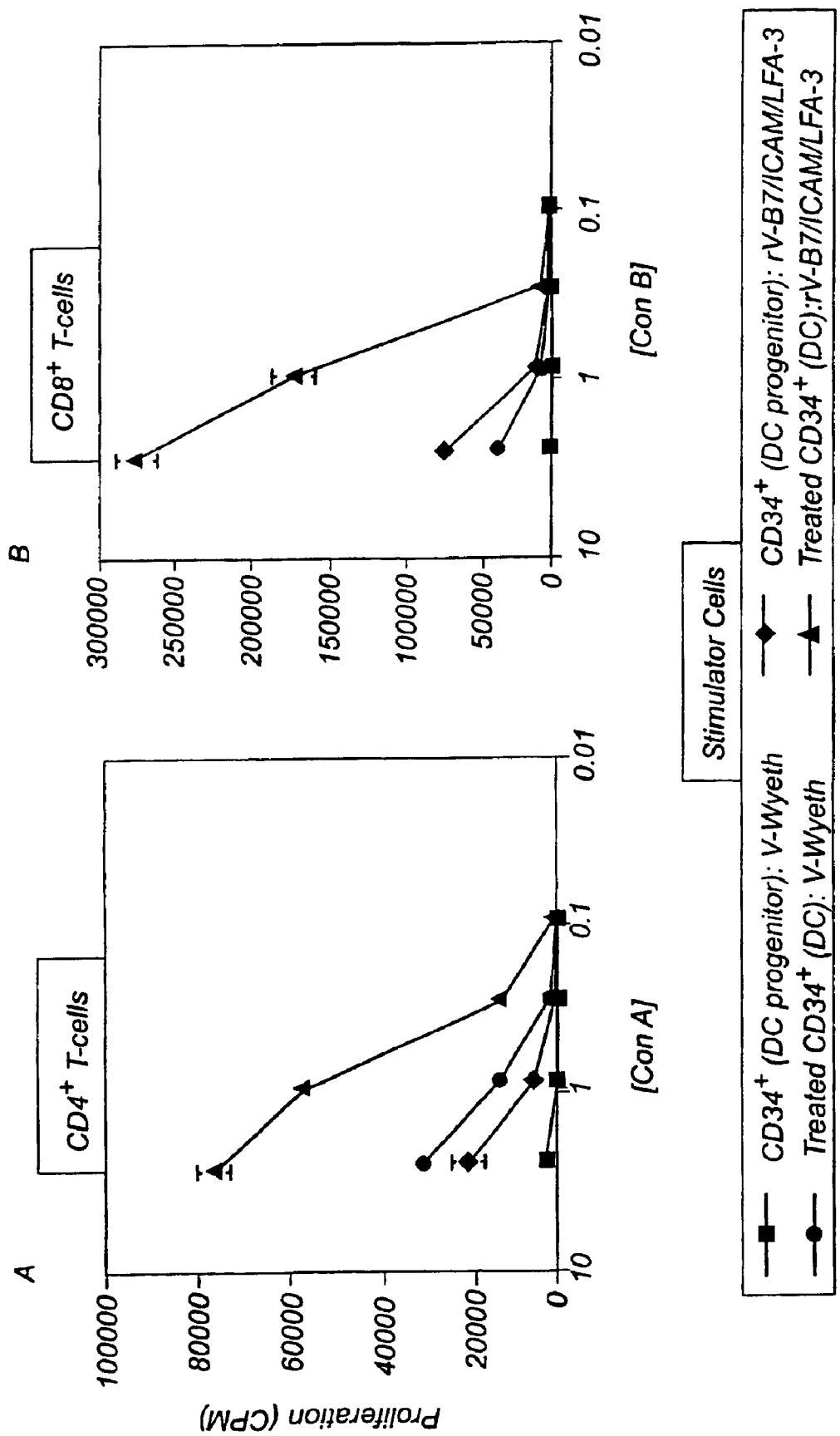
FIGS. 33A and 33B show the proliferative response of naïve CD4+ (FIG. 33A) or naïve CD8+ (FIG. 33B) T cells stimulated with progenitor DCs infected with rV-B7/ICAM-1/LFA-3 or DCs infected with rV-B7/ICAM-I/LFA-3 or V-Wyeth (control).

Progenitor dendritic cells infected with recombinant poxvirus encoding B7.1, ICAM-1, and LFA-3 were able to stimulate both CD4+ and CD8+ T cells. The stimulation of CD8+ T cells by the B7.1, ICAM-1, LFA-3 expressing progenitor dendritic cells was greater than that achieved using non-infected mature CD34+dendritic cell (FIG. 32). Moreover, infection and expression of the three costimulatory molecules in mature CD34+ dendritic cells (pretreated with IL-4 and GM-CSF) resulted in a dramatic increase in stimulation of both CD4+ and CD8+ T cells (FIG. 33).

Figure 34:
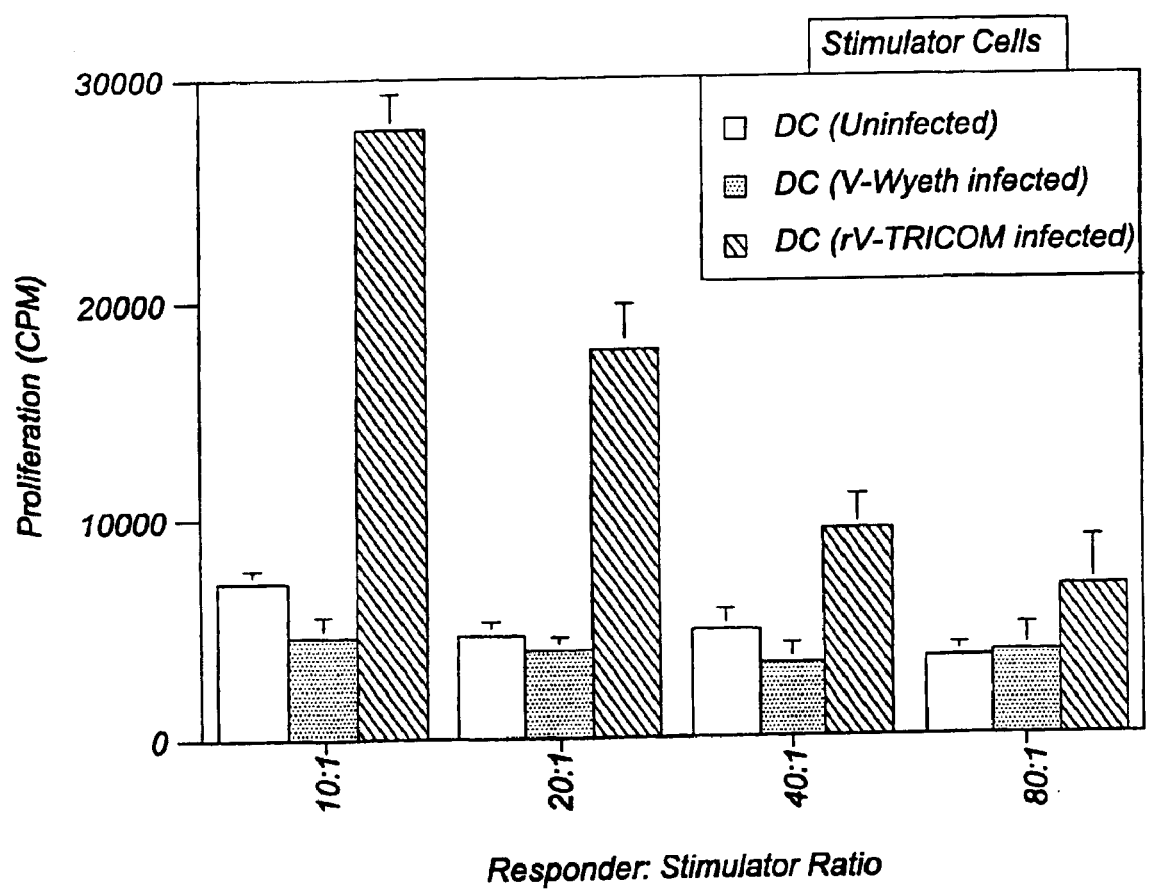
FIG. 34 shows the mixed lymphocyte reaction (MLR) of Balb/C splenocytes vs. irradiated C57b1/6 dendritic cells infected with 25 MOI of V-Wyeth or rV-TRICOM. $^3$H-thymidine pulsed on day 3, harvest on day 4, 0 DC (uninfected), ■DC (V-Wyeth infected), □DC (rV-TRICOM infected).

One skilled in the art can also measure the quality of a dendritic cell population by its ability to support an alloreactive response (mixed lymphocyte reaction, MLR) (43). FIG. 34 shows the results of a mixed lymphocyte culture using dendritic cells infected with rV-TRICOM. The mixed lymphocyte reaction uses DCs from C57BL/6 mice which are stimulating T lymphocytes from Balb/c, (i.e. an anti-allotype reaction).

These data show that the degree of proliferation in a mixed lymphocyte reaction is dramatically higher using DCs infected with rV-TRICOM as compared to uninfected DCs or DCs infected with wild-type vaccinia.

Figure 35:
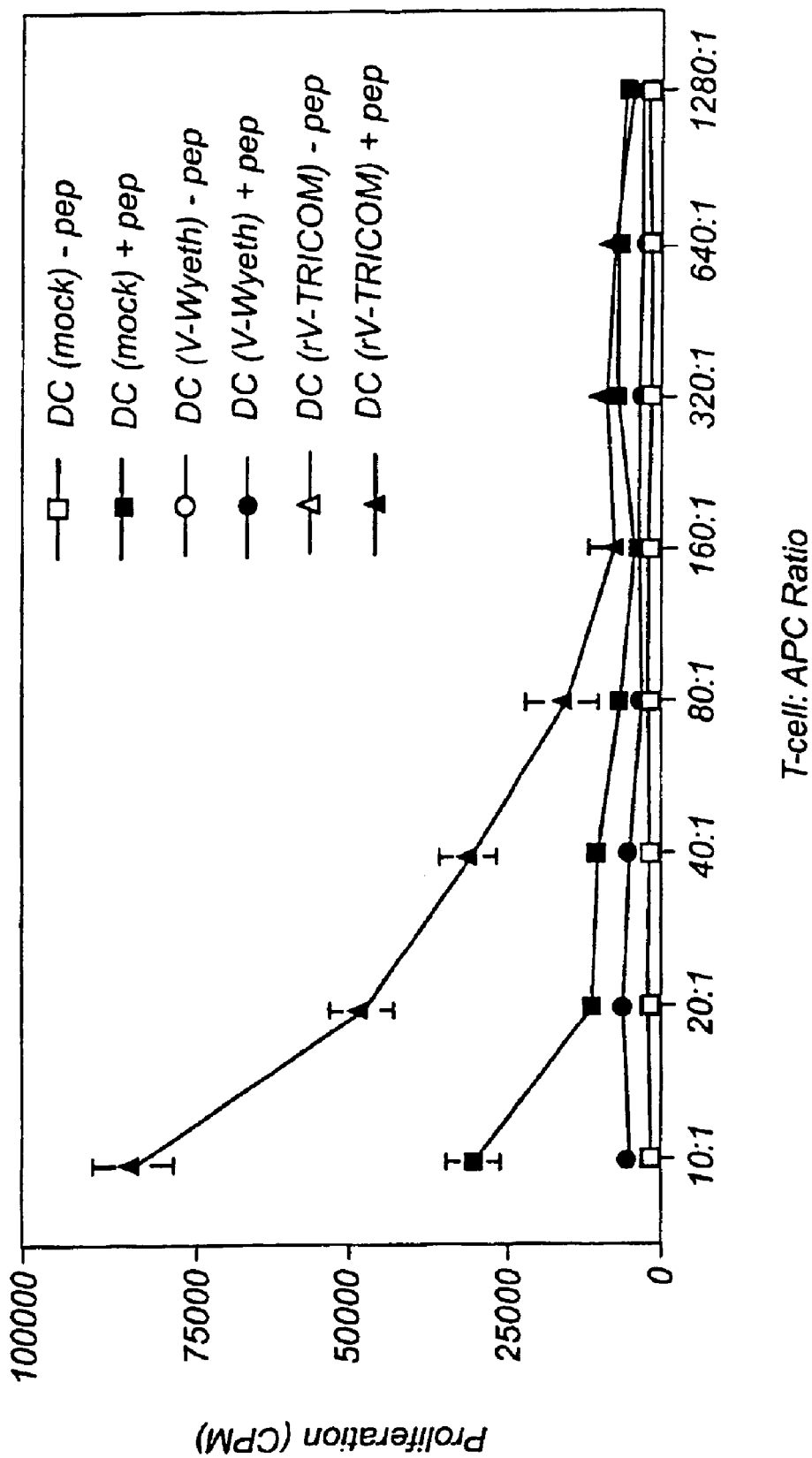
FIG. 35 shows the proliferative response of responder T cells (CAP-M8 T-cell line specific for CEA peptide 8) at various APC ratios harvested on day 5 after stimulation with peptide-pulsed DCs infected with rV-TRICOM and rested 2 days with 10 u/ml IL-2 (no APC or peptide). Peptide 8-(EAQNTTYL) (SEQ ID NO: 37) in assay at 1 ug/ml final concentration. $^3$H-thymidine added on day 2, T cells harvested on day 3. 0=DC(v-Wyeth)—pep and Δ=DC (rV-TRICOM)—pep results are at baseline.

FIG. 35 demonstrates that DCs infected with rV-TRICOM are far superior than standard DCs in stimulating a CEA peptide-specific murine T cell line. This T-cell line is CD8+ and is specific for the CEA $D^b$ Class-I restricted epitope EAQNTTYL (SEQ ID NO: 37) (CAP-M8). The combination of DCs pulsed with the CEA peptide (1 μg/ml) and previously infected with rV-TRICOM is clearly superior in stimulating CEA-specific T cell responses, especially at low T-cell to DC ratios.

EXAMPLE 31

Murine T Cell Stimulation In Vitro and In Vivo Using rV- or rF-TRICOM Infected Murine Bone Marrow-Derived Dendritic Cells Experimental Protocol
Peptides The H-2k$^b$-restricted peptides OVA (ovalbumin$_{257-264}$, SIINFEKL)[41] (SEQ ID NO: 38) and VSVN (vesicular stomatitis virus N$_{52-59}$, RGYVYQGL)[42] (SEQ ID NO: 39) and the H-2 D$^b$ restricted peptides CAP-M8 (CEA$_{526-533}$, EAQNTTYL) (SEQ ID NO: 37) and FLU-NP(NP$_{366-374}$, ASNENMDAM)$_{43}$ (SEQ ID NO: 40) were either purchased (Multiple Peptide Systems, San Diego, Calif.) or synthesized in-house (Applied Biosystems 432A Synergy Peptide Synthesizer, Foster City, Calif.).

Cell Lines and Cell Cultures

The OVA and Cap-M8 CD8+ cytotoxic T-cell lines were generated in-house from C57BL/6 mice and recognize the OVA and Cap-M8 peptides, respectively. The CTL lines were maintained by weekly in vitro stimulation cycles with irradiated naïve splenocytes in complete medium (CM) [RPMI 1640 with fetal calf serum (10%); glutamine (2 mM), sodium pyruvate (1 mM), Hepes (7 mM), gentamicin (50 μg/ml), 2-mercaptoethanol (50 μM), and non-essential amino acids (0.1 mM), (Biofluids, Rockville, Md.)], supplemented with 1 μg/ml specific peptide and 10 U/ml murine IL-2 (Boehringer Mannheim, Indianapolis, Ind.). Twenty-four hours prior to using these cells as responders in antigen-specific proliferation assays, the cells were purified by centrifugation over a Ficoll-Hypaque gradient (density= 1.119 g/ml, Sigma Chemical Co., St. Louis, Mo.) and replated in six-well culture plates ($10^6$ cells/ml, 5 ml/well) in CM supplemented with 10 U/ml murine IL-2 only. For cytotoxicity assays, the target tumor-cell line used was EL-4 (C57BL/6, H-2$^b$, thymoma, ATCC TIB-39).

DC Preparation

Bone marrow was derived from six- to eight-week-old female C57BL/6 mice (Taconic Farms, Germantown, N.Y.). The procedure used in this study was a slightly modified version of that described by Inaba et al.[41]. Briefly, bone marrow was flushed from the long bones of the limbs and passed over a Ficoll-Hypaque gradient. Bone-marrow cells were depleted of lymphocytes and Ia+cells using a cocktail of magnetic beads specific for CD4, CD8, and anti-MHC Class-I (MiniMACS, Miltenyi Biotec, Auburn, Calif.). Cells were plated in six-well culture plates ($10^7$ cells/ml, 5 ml/well) in CM supplemented with 10 ng/ml GM-CSF and 10 ng/ml 14 (R&D Systems, Minneapolis, Minn.). Cells were replated in fresh cytokine-supplemented media on days 2 and 4. At 6 days of culture, cells were harvested for infection, analysis and immunizations. For specified experiments, DC were treated with murine TNF-α (100 ng/ml, Boehringer Mannheim, Indianapolis, Ind.) or CD40 mAb (5 μg/ml, PharMingen, San Diego, Calif.) during the final 24 h of culture.

Recombinant Poxviruses

The rV virus containing the gene that encodes the murine costimulatory molecule B7-1 (CD80) under control of the synthetic early/late (sE/L) promoter (designated rV-B7-1) has been described herein. The rV virus containing the murine LFA-3 gene (CD48) under control of the vaccinia 30K (M2L) promoter, the murine ICAM-1 (CD54) gene under control of the vaccinia 13 promoter, and the murine B7-1 gene under control of the synthetic early/late (sE/L) promoter has been designated rV-TRICOM. The vectors rF-B7-1 and rF-B7-1/ICAM-1/LFA-3 (designated rF-TRICOM) are rF viruses that were constructed similarly to rV-B7-1 and rV-TRICOM, respectively. A fowlpox-TRICOM construct containing a reporter gene, human CEA, was used in certain experiments. Non-recombinant wild-type vaccinia virus (Wyeth strain) was designated V-WT, while wild-type fowlpox virus was designated FP-WT.

Infection of DC

DC were harvested on day 6 and washed with Opti-Mem (Gibco-BRL, Gaithersburg, Md.). The cells were then either mock-infected with HBSS; infected with V-WT, rV-B7, or rV-TRICOM at 25 MOI (multiplicity of infection; PFU/cell); or infected with FP-WT, rF-B7-1, or rF-TRICOM at 50 MOI in Opti-Mem for 5 h. Warm CM was added after infection, and the cells were incubated at 37° C. overnight. After infection, the cells were harvested for immunostaining, in vitro costimulation analysis, and in vivo administration.

Flow Cytometric Analysis

Cell-surface staining utilized three-color immunofluorescence. Staining was performed with primary FITC-labeled antibodies CD11c, CD11b, H-2 Kb, H 2 Db, CD19, Pan-NK; primary PE-labeled antibodies IA$^b$, CD48 (mLFA-3), CD86 (B7-2), CD3, CD14; and the biotin-labeled antibodies CD80 (B7-1), CD57 (ICAM-1), CD40. Biotin-labeled antibodies were subsequently labeled with Cychrome-streptavidin. All antibodies were purchased from PharMingen. Cell fluorescence was analyzed and compared with the appropriate isotype matched controls (PharMingen) with a FACSCAN cytometer (Becton Dickinson, Mountain View, Calif.) using the Lysis II software.

In vitro Costimulation Analysis: Pharmacological Signal-1

Female, six- to eight-week-old C57BL/6 mice were obtained (Taconic Farms, Germantown, N.Y.), and naïve T cells were isolated as previously described. T cells were added at $10^5$/well in 96-well, flat-bottomed plates (Costar, Cambridge, Mass.). Stimulator cells consisted of either uninfected DC, mock-infected DC, or DC infected with vaccinia vectors (V-WT, rV-B7-1, rV-TRICOM) or fowlpox vectors (FP-WT, rF-B7-1 or rF-TRICOM) irradiated (20 Gy) and added at $10^4$/well. Cells in all wells were cultured in a total volume of 200 µl of CM in the presence of several concentrations (2.5 to 0.9 µg/ml) of Con A (Sigma) for 2 days. Cells were labeled for the final 12–18 hr of the incubation with 1 µCi/well $^3$H-Thymidine (New England Nuclear, Wilmington, Del.) and harvested with a Tomtec cell harvester (Wallac Incorporated, Gaithersburg, Md.). The incorporated radioactivity was measured by liquid scintillation counting (Wallac 1205 Betaplate, Wallac, Inc.). The results from triplicate wells were averaged and are reported as mean CPM+SEM.

Mixed-Lymphocyte Reaction

MLR was used to assess the stimulatory function of DC for allogeneic and syngeneic naïve T cells. T cells were isolated from Balb/C or C57BL/6 mice as before. Stimulator cells consisted of DC that were either uninfected; mock infected; or infected with V-WT, rV-137-1, rV-TRICOM, FP-WT, rF-B7-1 or rF-TRICOM and irradiated (20 Gy). T cells ($5 \times 10^4$/well) were co-cultured with graded numbers of stimulator cells in CM in flat-bottom 96-well culture plates and incubated at 37° C., 5% $CO_2$ for 4 days, labeled for the final 12–18 hr of the incubation with 1 µCi/well $^3$H-Thymidine, harvested, and analyzed as before.

In vitro Costimulation Analysis: Peptide-Specific Signal

Rested OVA or CAP-M8 T cells (responders) were added at $5 \times 10^4$/well in 96-well, flat-bottomed plates. Stimulator cells consisted of DC that were either uninfected, or infected with V-WT, rV-137-1, or rV-TRICOM and irradiated (20 Gy). Cells in all wells were cultured in a total volume of 200 µl of CM. The costimulation assay was carried out using two sets of conditions: (1) a 10:1 fixed ratio of responder: stimulator cells that were cultured in the presence of several concentrations of specific peptide or appropriate control peptide or (2) a fixed concentration of specific peptide or control peptide cultured at various responder: stimulator cell ratios. Cells were cultured for 72 h, labeled for the final 12–18 h of incubation with 1 µCi/well $^3$H-Thymidine, harvested, and analyzed as before.

CTL Induction In Vivo and Cyototoxic Analysis

DC ($1 \times 10^6$) that were either uninfected or infected with V-WT or rV-TRICOM were washed twice in Opti-Mem and resuspended in 1 ml of the same medium containing 10 µM of either OVA or CAP-M8 peptides. After 2 h incubation at 37° C., cells were washed twice in HBSS and resuspended in HBSS for injections. Peptide-pulsed DC ($1 \times 10^5$ cell/mouse) were injected 1–3 times intravenously at 7-day intervals. Control mice were immunized subcutaneously with 100 µg indicated peptide in Ribi/Detox adjuvant (Ribi ImmunoChem Research, Hamilton, Mont.). Fourteen days following the final inoculation, spleens from two animals per group were removed, dispersed into single-cell suspensions, pooled, and co-incubated with 10 µg/ml of appropriate peptide for six days. Bulk lymphocytes were recovered by centrifugation through a density gradient (LSM, Organon Teklika, West Chester, Pa.). EL-4 cells were prepared for use as targets in a standard cytolytic assay using $^{111}$In, as previously[45]. Target cells were pulsed with 10 µM specific peptide for 1 hour at 37° C., while a second group of target cells was pulsed with control peptide. Lymphocytes and peptide-pulsed targets ($5 \times 10^3$ cells/well) were suspended in CM, combined at effector: target ratios of 80:1 to 10:1 in 96-well U-bottomed plates (Costar) and incubated for 5 h at 37° C. with 5% $CO_2$. After incubation, supernatants were collected using a Supernatant Collection System (Skantron, Sterling, Va.), and radioactivity was quantified using a gamma counter (Cobra Autogamma, Packard, Downers Grove, Ill.). The percentage of specific release of $^{111}$In was determined by the standard equation: % specific lysis=[(experimental-spontaneous)/(maximum-spontaneous)]×100. Where indicated, CTL activity was converted to lytic units (LU) as described by Wunderlich et al, 1994.

Anti-Vaccinia Antibody Analysis

V-WT was added at $5 \times I^5$/well to polyvinyl chloride plates (Dynatech, Chantilly, Va.), dried overnight at 37° C. and blocked with 5% BSA. Graded dilutions of sera from immunized mice was added in triplicate and incubated for 1 h at 37° C. Plates were washed and incubated with peroxidase labeled goat anti-mouse IgG (Kirkegaard and Perry Laboratories, Gaithersburg, Md.) for an additional hour. Wells were developed with o-phenylenediamine dihydrochloride (Sigma, St. Louis, Mo.) and $H_2O_2$. Reactions were stopped with $H_2SO_4$. The absorbance of each well was read at 405 nm using a Bio-Tek EL312e microplate ELISA reader (Winooski, Vt.).

Results

Increased Expression of Costimulatory Molecules on DC

To determine the efficiency of poxvirus infection of DC, these cells were infected with either a rV virus encoding B7-1, ICAM-1, and LFA-3 (designated rV-TRICOM) or a rF virus encoding B7-, ICAM-1, LFA-3 and human capcinoembryonic antigen (CEA) (designated rF-CEA/TRICOM). In the latter case, CEA was used as a reporter gene since fowlpox structural proteins are not expressed in infected cells. After 18 h, c ells were analyzed for the expression of cell-surface markers associated with the particular viral infection. Uninfected control DC expressed CD11b (97%) and were negative for the expression of vaccinia proteins. After infection with rV-TRICOM, 94% of DC co-expressed both CD11b and vaccinia proteins. DC infected with rF-CEA/TRICOM co-expressed both CD11b and CEA (87%). These DC failed to express fowlpox proteins as detected by polyclonal rabbit anti-fowlpox sera (data not shown), which is in agreement with reports stating that fowlpox does not replicate in mammalian cells. Taken together, these data indicate that DC are efficiently infected by both rV and rF vectors.

The cardinal characteristics of DC are high expression levels of both histocompatibility antigens and costimulatory molecules. To further characterize the phenotype of DC after virus infection, cells were infected with wild-type vaccinia virus (V-WT), rV-B7-1, rV-TRICOM, wild-type fowlpox (FP-WT) or rF-TRICOM and analyzed for the expression of cell-surface markers associated with the DC phenotype (Table 4). As expected, uninfected and mock-infected DC expressed high levels of MHC Class I and IL CD11b, B7-2 and CD40 molecules, as well as high levels of B7-1, ICAM-1, and LFA-3. DC infected with V-WT expressed lower cell-surface densities (as determined by MFI) of several molecules, while DC infected with rV-B7-1 expressed 5-fold more B7-1 than uninfected DC (MFI from 329 to 1689). Infection of DC with rV-TRICOM substantially increased MFI and the percentage of cells positive for B7-1, ICAM-1, and LFA-3. DC infected with FP-WT had a similar phenotypic profile to that of uninfected DC. Infection of DC with rF-TRICOM also substantially increased MFI and the percentage of cells positive for B7-1, ICAM-1, and LFA-3. All DC populations remained negative for T-cell (CD3), B-cell (CD19), monocyte/neutrophil (CD14), and NK-cell (Pan NK) markers both before and after infection with rF or N vectors (Table 4).

allogeneic T cells (FIG. 37A, B). The stimulatory capacity of DC was increased after infection with rV-B7-1 (FIG. 37C). Infection of DC with rV-TRICOM increased the stimulatory capacity over DC and DC/rV-B7-1 at all DC/responder ratios (FIG. 37C). Importantly, DC populations infected with rV-TRICOM vectors failed to stimulate

TABLE 4

Infection of BMDC with rV-TRICOM or FP-TRICOM Increases the Expression Level of B7-1, ICAM-1, and LFA-3

| Infection | DC Panel [% positive cells (MFI)] | | | | | | | | | Non-DC Markers | | | |
| --- | --- | --- | --- | --- | --- | --- | --- | --- | --- | --- | --- | --- | --- |
|  | 1-$A^b$ | H-2$K^b$/$D^b$ | CD11b | CD11c | B7-2 | CD40 | B7-1 | ICAM-1 | LFA-3 | CD14 | CD19 | CD3 | Pan NK |
| None | 88 | 89 | 93 | 20 | 68 | 68 | 91 | 96 | 88 | 2 | 2 | 0.3 | 2 |
|  | (1124) | (125) | (935) | (74) | (490) | (82) | (329) | (595) | (153) | (20) | (26) | (33) | (56) |
| Mock | 87 | 88 | 90 | 25 | 77 | 71 | 85 | 97 | 86 | 1 | 4 | 0.6 | 2 |
|  | (989) | (125) | (1129) | (49) | (432) | (99) | (330) | (519) | (189) | (42) | (30) | (37) | (29) |
| V-WT | 87 | 86 | 86 | 29 | 61 | 79 | 90 | 95 | 70 | 3 | 3 | 1 | 5 |
|  | (890) | (83) | (588) | (54) | (274) | (98) | (197) | (241) | (196) | (20) | (45) | (59) | (50) |
| rV-B7-1 | 85 | 85 | 81 | 25 | 73 | 73 | 94 | 97 | 72 | 3 | 3 | 0.8 | 4 |
|  | (856) | (104) | (693) | (62) | (304) | (103) | (1689) | (364) | (131) | (42) | (40) | (67) | (37) |
| rV-TRICOM | 87 | 78 | 77 | 22 | 66 | 71 | 96 | 94 | 92 | 3 | 4 | 0.9 | 4 |
|  | (901) | (103) | (558) | (54) | (298) | (81) | (1442) | (1528) | (304) | (32) | (29) | (70) | (31) |
| FP-WT | 91 | 98 | 89 | 24 | 65 | 71 | 94 | 97 | 91 | 2 | 2 | 1 | 2 |
|  | (985) | (126) | (889) | (69) | (487) | (90) | (382) | (464) | (130) | (18) | (10) | (60) | (31) |
| rF-B7-1 | 88 | 99 | 86 | 28 | 74 | 68 | 95 | 98 | 90 | 2 | 2 | 1 | 2 |
|  | (987) | (114) | (793) | (72) | (404) | (90) | (1559) | (437) | (180) | (30) | (29) | (45) | (54) |
| rF-TRICOM | 90 | 99 | 84 | 27 | 76 | 73 | 99 | 98 | 95 | 3 | 3 | 1 | 3 |
|  | (900) | (115) | (789) | (66) | (499) | (93) | (1824) | (1697) | (530) | (22) | (13) | (50) | (33) |

DC were uninfected, mock infected, or infected with 25 MOI of either V-WT, rV-B7, or rV-TRICOM or 50 MOI of either WT-FP or FP-TRICOM for 5h.
After 18h incubation, cells were phenotyped by 3-color flow cytometric analysis.
Bold numbers indicate a >100% change in cell-surface expression (MFI).

Figures 36A, 36B:
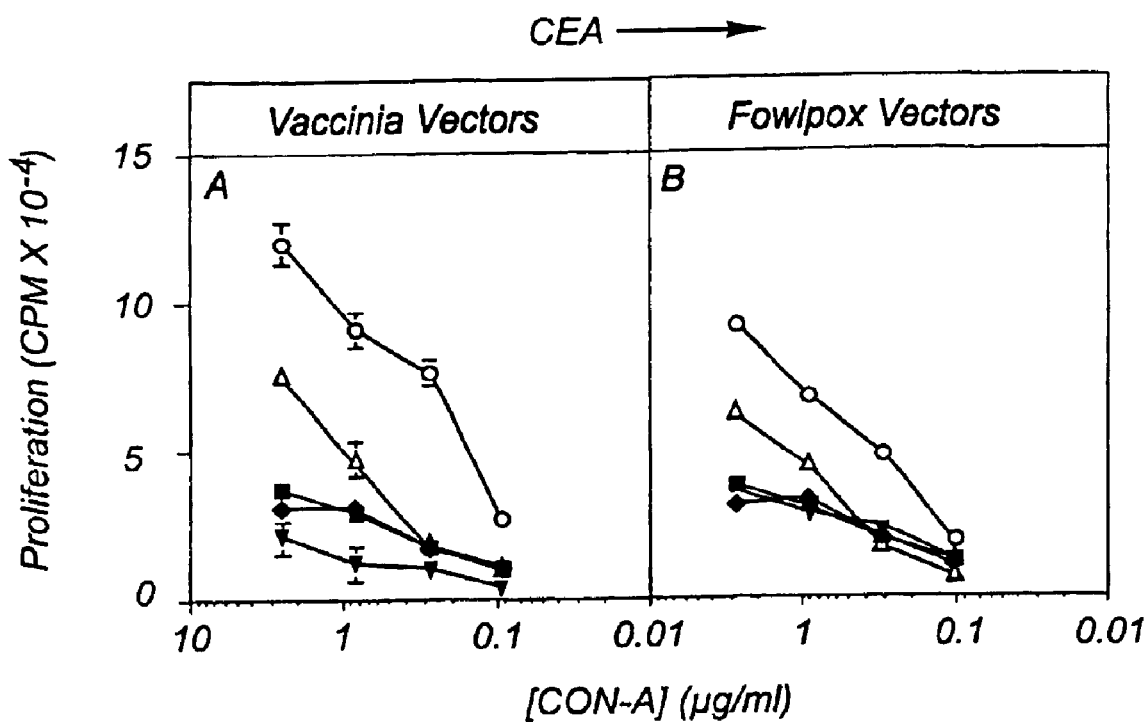
FIGS. 36A and 36B. Efficiency of poxviral infection of murine dendritic cells (DC). DC were infected with 25 MOI rV-TRICOM or 50 MOI rF CEA/TRICOM for 5 h. DC infected with TRICOM vectors exhibit enhanced capacity to stimulate naïve T-cells. All DC populations were co-cultured for 48 h with T-cells at a ratio of 10:1 in the presence of different concentrations of Con A to provide signal-1. $^3$H-thymidine was added during the final 18 h.

DC Infected with TRICOM Vectors Exhibit Enhanced Capacity to Stimulate Naïve T cells An in vitro model was used to analyze how increased levels of B7-l, ICAM-1 and LFA-3 expression help induce naïve T-cell proliferation. In this model, the first signal for T-cell activation was delivered via a pharmacological reagent (Con A) and the additional, or costimulatory, signal was delivered to the T-cell via DC or DC expressing higher levels of TRICOM as a consequence of recombinant poxvirus infection. In these and all subsequent studies reported here, V-WT and FP-WT were also used to rule out effects due to the vector alone. As shown in FIG. 36A, both uninfected and mock-infected DC induced proliferation of T-cells. DC infected with V-WT (designated DC/V-TRICOM) induced less T-cell proliferation than uninfected DC. Delivery of additional costimulatory signals via DC infected with rV-B7-1 (designated DC/rV-B7-1) increased proliferation compared with uninfected DC. However, DC infected with rV-TRICOM (designated DC/rV-TRICOM) induced further increases in T-cell proliferation at all concentrations of Con A. In addition, when T-cells were stimulated with DC/rV-TRICOM, 28-fold less Con A was needed to induce proliferation to levels comparable to that of uninfected DC. When these experiments were repeated using fowlpox vectors, DC/rF-TRICOM induced increases in T-cell proliferation at all Con A concentrations, unlike DC or DC/rF-B7-l (FIG. 36B). These experiments were repeated 4 times with similar results.

Enhanced Allostimulatory Activity by DC Infected with TRICOM Vectors

The effect of rV-TRICOM (FIG. 37A, C, E) or rF-TRICOM (FIG. 37B, D, E) infection on DC stimulatory capacity was assessed in an allospecific mixed-lymphocyte reaction. Both uninfected DC and mock-infected DC populations induced a strong proliferation (78,000 CPM) of syngeneic T cells (FIG. 37E). When these experiments were repeated using fowlpox vectors (FIG. 37B, D), DC/rF-TRICOM induced larger increases in allogeneic T-cell proliferation than DC and DC/rF-B7-1, DC/rF-TRICOM, however, failed to stimulate syngeneic T cells (FIG. 37F). These experiments were repeated 3 times with similar results.

In vitro Costimulation Analysis: Presentation of Peptides to Effector T Cells

Studies were undertaken to determine if the stimulatory capacity of peptide-pulsed DC could be enhanced by infecting DC with rV-TRICOM. To that end, the H-2 Kb-restricted OVA (ovalbumin$_{257}$–264, SIINFEKL) (SEQ ID NO: 38) peptide and an OVA-specific CD8$^+$ effector T-cell line were used. DC were exposed to different concentrations of OVA peptide and incubated in the presence of the OVA T-cell line (FIG. 38A-38F). The conventional (i.e., uninfected) DC induced a strong proliferation of OVA-specific T cells when incubated with the OVA peptide (FIG. 38A). These DC did not induce proliferation of OVA-specific T cells when incubated with the control peptide VSVN (vesicular stomatitis virus N$_{52-59}$ RGYVYQGL) (SEQ ID NO: 39) (FIG. 38A, open squares). DC/rV-B7-1 increased the overall peptide-specific proliferation of these cells 1.8-fold (FIG. 38C). In addition, DC/rV-B7-1 induced similar proliferation to that of uninfected or mock-infected DC in the presence of 4-fold less peptide. In contrast, DC/rV-TRICOM increased the overall proliferation of these T-cells several-fold, and in the presence of 32-fold less OVA peptide, induced proliferation comparable to that of uninfected DC (FIG. 38C). To further evaluate the capacity of vaccinia-infected DC to present peptide, DC were pulsed with a single concentration of OVA peptide (1 PM) and incubated in the presence of several ratios of T cells (FIG. 38E). On a per-cell basis, 4-fold fewer DC/rV-B7-1 were required to induce proliferation levels comparable to that of DC (open triangles vs. closed squares). The greatest stimulatory effect was that of DC/rV-TRICOM, which induced proliferation levels comparable to that of DC with 32-fold less cells (open circles vs. closed squares).

A second peptide system employing peptide-pulsed DC and an established T-cell line were employed to determine if results similar to those obtained with the OVA peptide could be noted. These experiments were conducted using the H-2 $D^b$-restricted peptide CAP-M8 (CEA$_{526-533}$, EAQNTTYL) (SEQ ID NO: 37) and a CAP-M8-specific CD8$^+$effector T-cell line; similar results were noted (FIG. 38B, D, F). These experiments were repeated 5 additional times with the same results.

Effect of rV-TRICOM Infection on TNFα or CD40-Matured DC

Figures 39A, 39B:
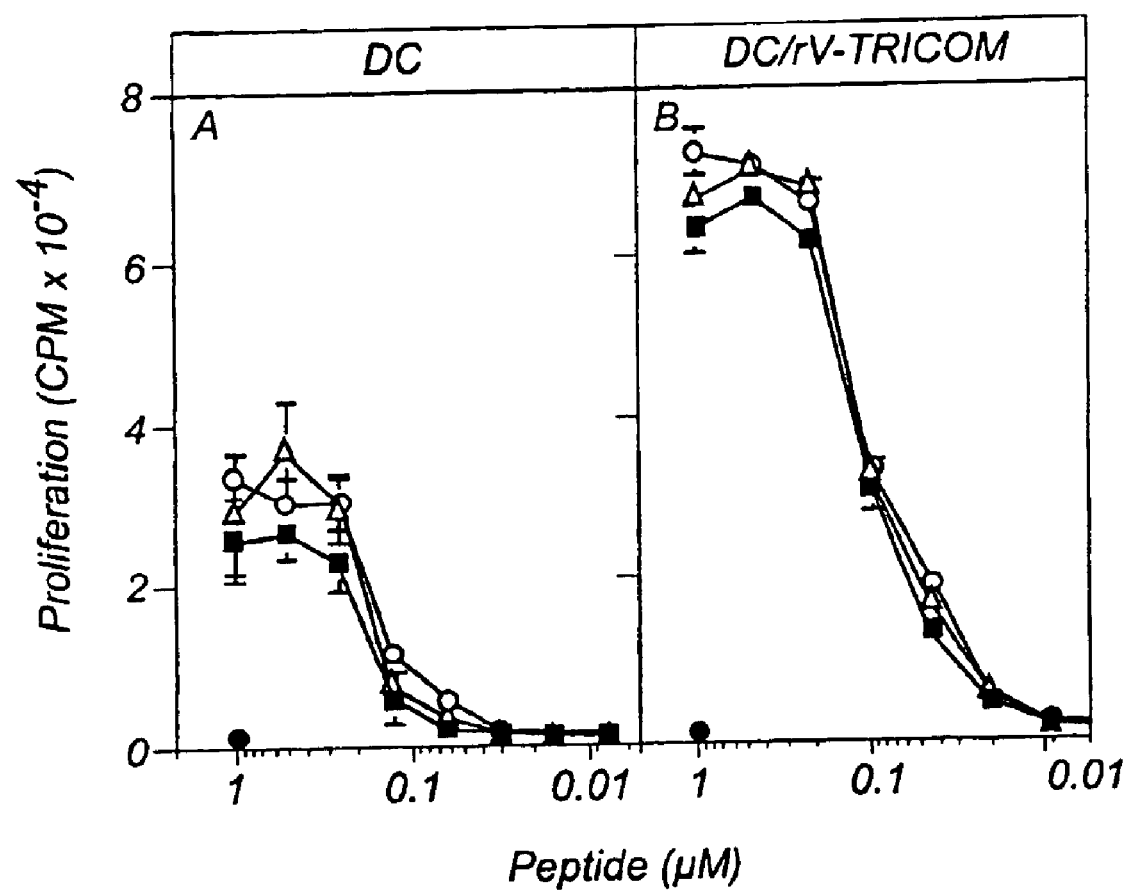
FIGS. 39A and 39B. Effect of rV-TRICOM infection with DC matured with TNF-α or CD40. DC (closed squares), or DC cultured with either 100 ng/ml TNF-α (open triangles), or 5 µg/ml CD40 mAb (open circles) for the final 24 h of culture were used to stimulate CAP-M8-specific effector T cells (FIG. 39A). The proliferation of CAP-Mg T cells in response to these DC populations after infection with 25 MOI rV-TRICOM (FIG. 39B). For all panels, the T-cell: DC ratio was 10:1, while the CAP-M8 peptide concentration was 1 µg/ml. Closed circles denote proliferation of CAP-M8 T cells stimulated with all DC populations in the presence of 1 µg/ml VSVN peptide.

Since the functional maturation of DC is believed to correlate with the upregulation of T-cell costimulatory molecules, experiments were conducted to examine the effect of rV-TRICOM infection on DC that had been matured by co-culture with either TNF or CD40 mAb. Treatment of DC with TNF during the final 24 h of culture resulted in some upregulation of MHC-II, B7-2, and ICAM-1 as determined by flow cytometric analysis (Table 5), while treatment of DC with CD40 mAb resulted in the upregulation of ICAM-1 expression and a slight upregulation of MHC-II. Functionally, treatment of DC with TNF-a or CD40 mAb culminated in a 28% and 16% increase, respectively, in peptide-specific proliferation over that of unmanipulated DC (FIG. 39A). Similar data were also obtained after treating DC with lipopolysaccharide (LPS). Infection of untreated DC with rV-TRICOM resulted in a substantial increase in T-cell proliferation (FIG. 39A vs. 39B). Pretreatment with TNF-α or CD40 mAb followed by infection with rV-TRICOM, however, conferred only a slight stimulatory capacity in excess of that seen with rV-TRICOM infection alone (FIG. 39B). These experiments were repeated 3 additional times with similar results.

TRICOM were pulsed with 10 μM OVA peptide and administered intravenously to C57BL/6 mice. Control mice were immunized with OVA peptide in Ribi/Detox adjuvant subcutaneously. Splenocytes were harvested 14 days following vaccination, restimulated in vitro for 6 days, and assessed for their peptide-specific lytic ability against OVA-pulsed EL-4 cells. EL-4 cells pulsed with VSVN peptide were used as control target cells. As seen in FIG. 40A, CTL generated from mice immunized with peptide/adjuvant exhibited modest levels of CTL activity (FIG. 40A). Mice immunized with peptide-pulsed DC exhibited a greater peptide-specific CTL response (FIG. 40B). The induced CTL response was somewhat blunted in mice immunized with DC/v-WT (FIG. 40C, <2.5 lytic units (LU) vs. 5.2 LU). In contrast, mice immunized with peptide-pulsed DC/rV-TRICOM (FIG. 40D) exhibited a CTL response that was significantly stronger than that of DC (LU=14.3, p=0.001). Similar experiments were then conducted using a second model peptide, CEA peptide CAP-M8 (FIG. 40E-H). Again, peptide-pulsed DC elicited much greater CTL activity than that educed by peptide/adjuvant (5.7 LU vs. <2.5 LU). In addition, mice immunized with peptide-pulsed DC/rV-TRICOM (FIG. 40H) exhibited a strong CTL response (>20 LU) compared with that induced by peptide-pulsed DC (5.7 LU, p=<0.001; FIG. 40F).

Efficacy of Multiple Vector-Infected DC Vaccinations

Figures 41A, 41B, 41C:
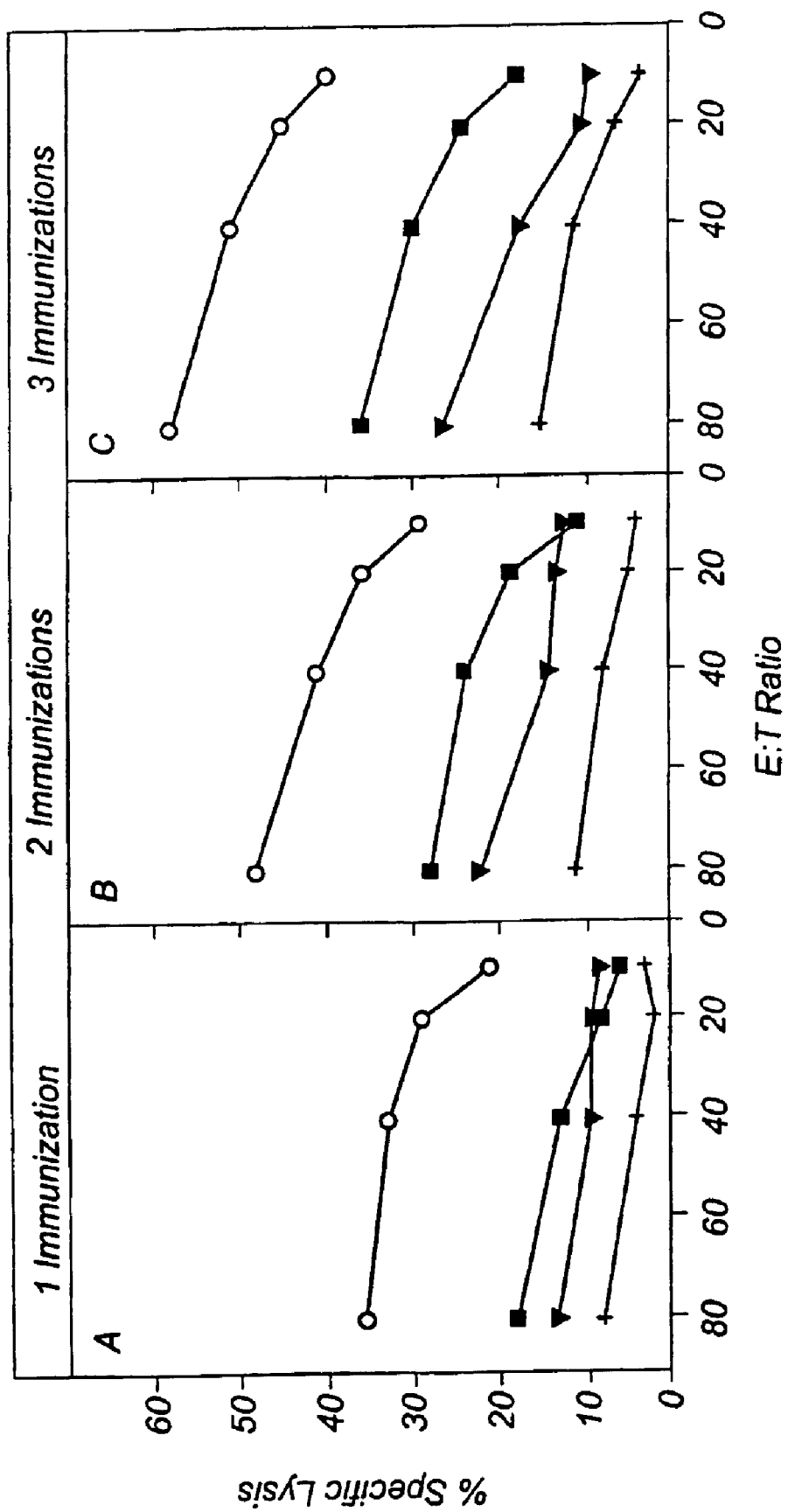
FIGS. 41A through 41C: Effect of multiple immunizations with vaccinia-infected DC on induction of CTL activity. DC (closed squares), or DC infected with V-WT (closed inverse triangles) or rV-TRICOM (open circles) were pulsed with 10 μM CAP-M8 peptide for 2 h. DC populations were administered intravenously to mice (1×10⁵ cells/mouse) 1, 2 or 3 times at 7 day intervals. Control mice were immunized subcutaneously with 100 μg CAP-M8 peptide in Ribi/Detxo adjuvant (crosses). Fourteen days after the final immunization, spleens were harvested, restimulated for 6 days with CAP-M8, and assessed for lytic ability against EL-4 cells pulsed with CAP-M8 or control peptide VSVN (not shown).
Figures 42A, 42B:
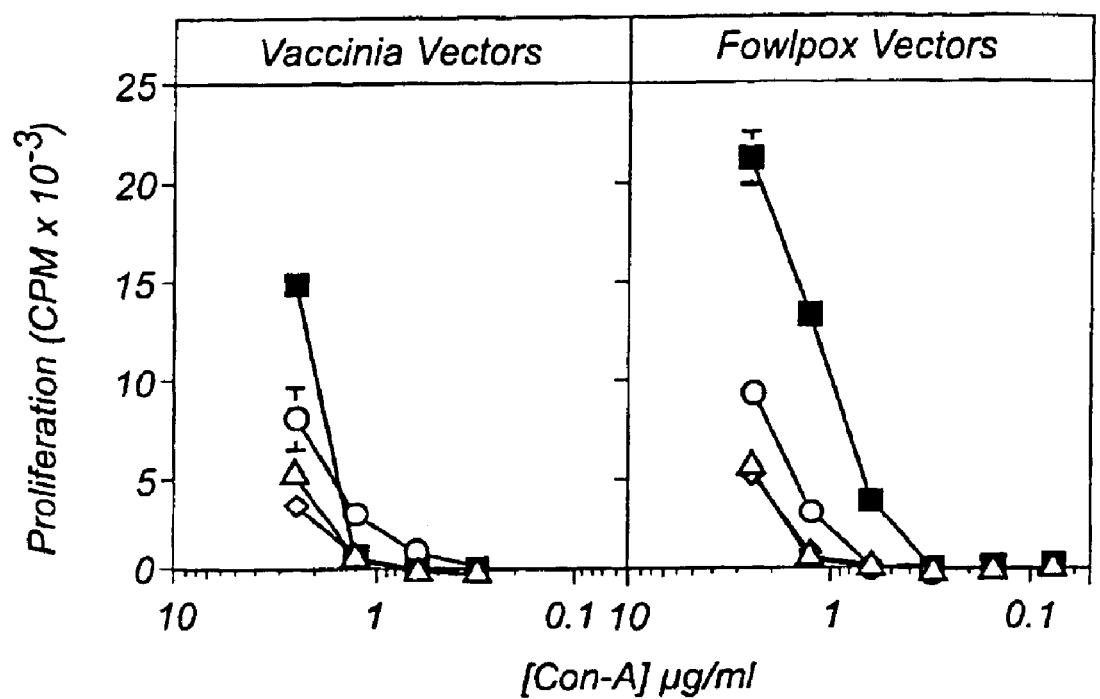
FIGS. 42A and 42B. Effect of vaccinia and fowlpox TRICOM-infected splenocytes on T cell proliferation. Naïve murine T cells were co-cultured with autologous splenocytes infected with either recombinant vaccinia or fowlpox vectors. Co-culture was performed in varying concentrations of Con-A as Signal-1. Recombinant vectors were wild type (i.e. V-WT, FP-WT, open diamond), rV-B7-1 or rF-B7-1, (open circles) or rV-TRICOM or rF-TRICOM (closed squares). Uninfected splenocytes are shown as open triangles.
Figures 43A, 43B:
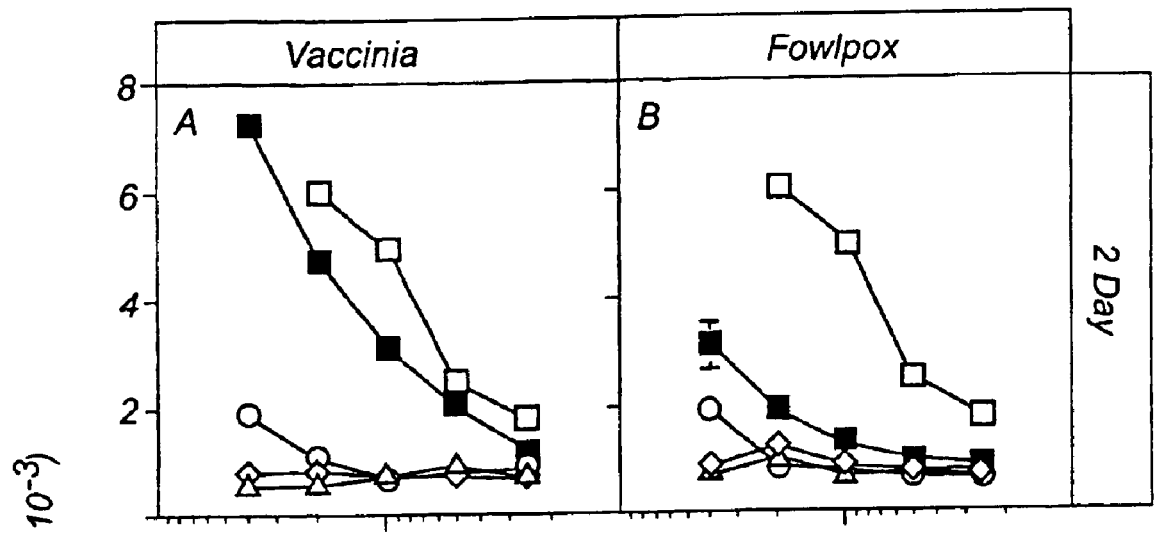
FIGS. 43A through 43D. Effect of TRICOM vector infected splenocytes on allogeneic T cells. Naïve Balb/C T cells were co-cultured with C57B 1/6 splenocytes infected with recombinant vaccinia (FIGS. 43A and C) or fowlpox (FIGS. 43B and D) vectors for either 2 days (FIGS. 43A and B) or 5 days (FIGS. 43C and 43D). Recombinant vectors were V-WT or FP-WT, open diamonds, rV-B7-1 or rF-B7-1 (open circles), or rV-TRICOM or rF-TRICOM (closed squares). Uninfected splenocytes are indicated as open triangles. Proliferation induced by DC is indicated as closed squares.
Figures 43C, 43D:
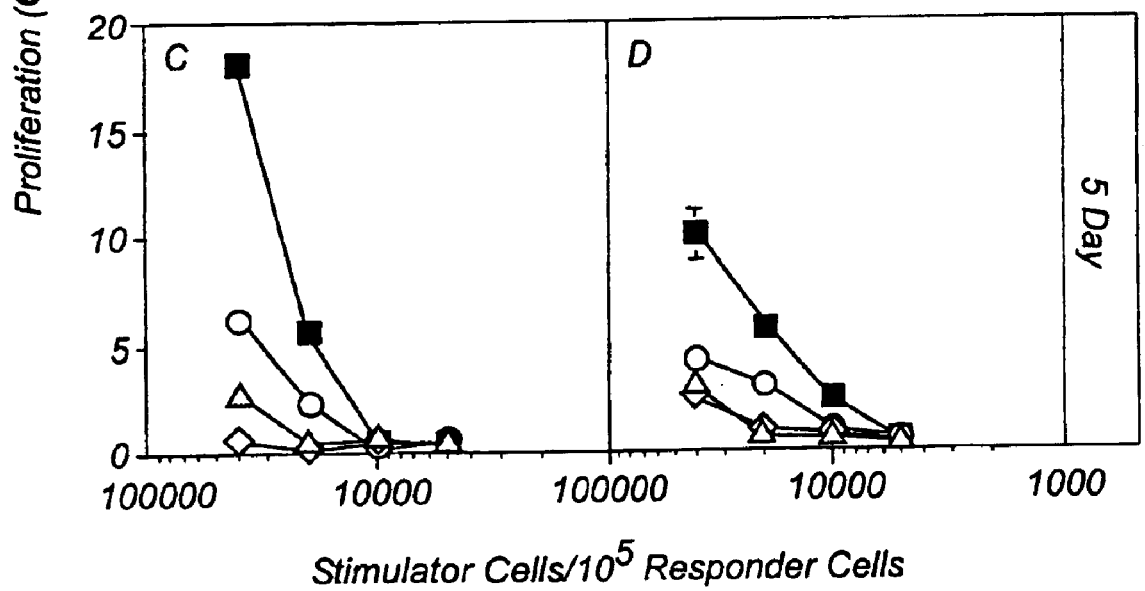
Figures 46A, 46B, 46C, 46D:
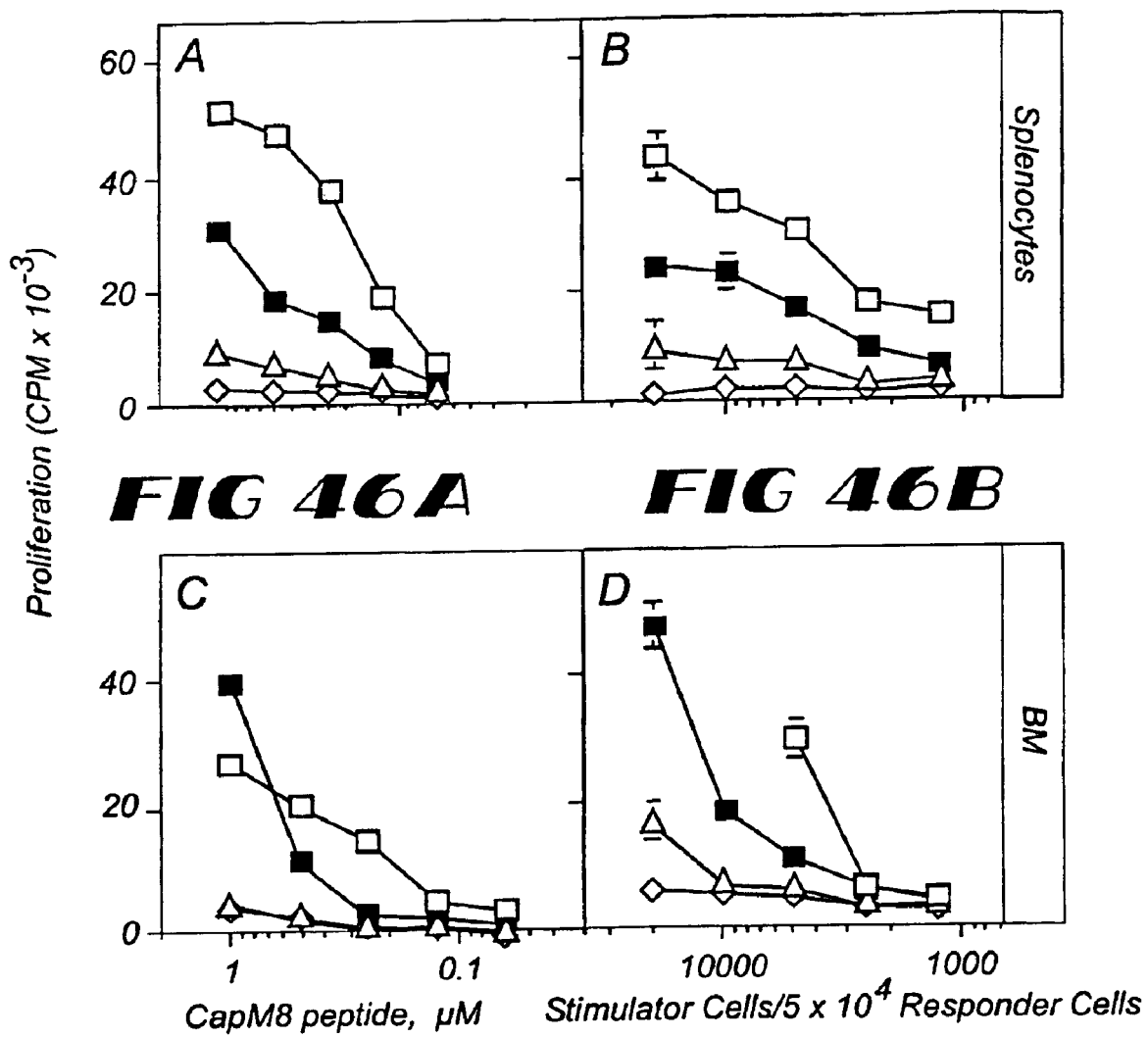
FIGS. 46A through 46D. Effect or rV-TRICOM-infected splenocytes or bone marrow (BM) cells on peptide-specific memory CD8⁺ T cells. CAP-M8-specific T cells were co-cultured with autologous splenocytes (FIGS. 46A and B) or bone marrow cells (FIGS. 46C and D) infected with recombinant vaccinia vectors. The analysis was carried out using two sets of conditions: a) a 10:1 fixed ratio of responder: stimulator cells that were cultured in the presence of several concentrations of CAP-M8 peptide (FIGS. 46A and 46C), or b) a fixed concentration of peptide (1 uM) at various responder: stimulator ratios (FIGS. 46B and 46D). Recombinant vectors were wild type (open diamonds), and rV-TRICOM (closed squares). Uninfected splenocytes are shown as open triangles. BM are shown as open squares.
Figure 47:
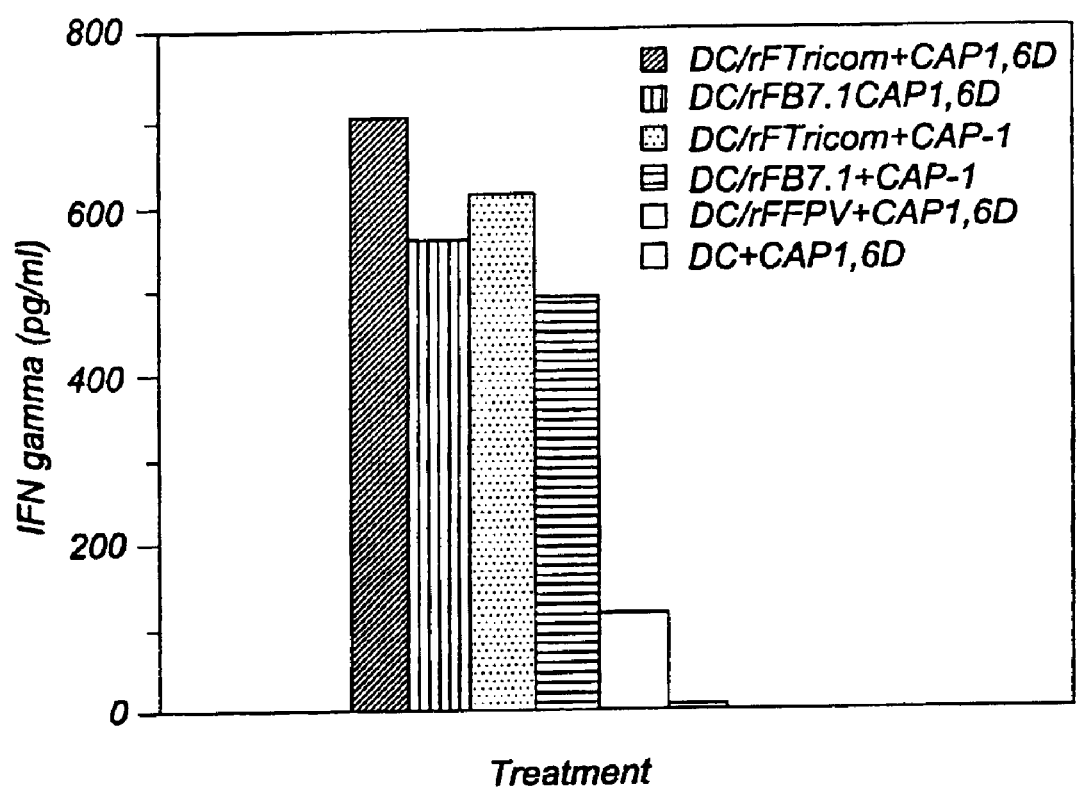
FIG. 47. Shows production of IFN-γ by human T cells isolated from peripheral blood mononuclear cells (PBMC) using rF-TRICOM-infected human dendritic cells pulsed with CEA peptides, CAP-I or CAP1, 6D.
Figure 48:
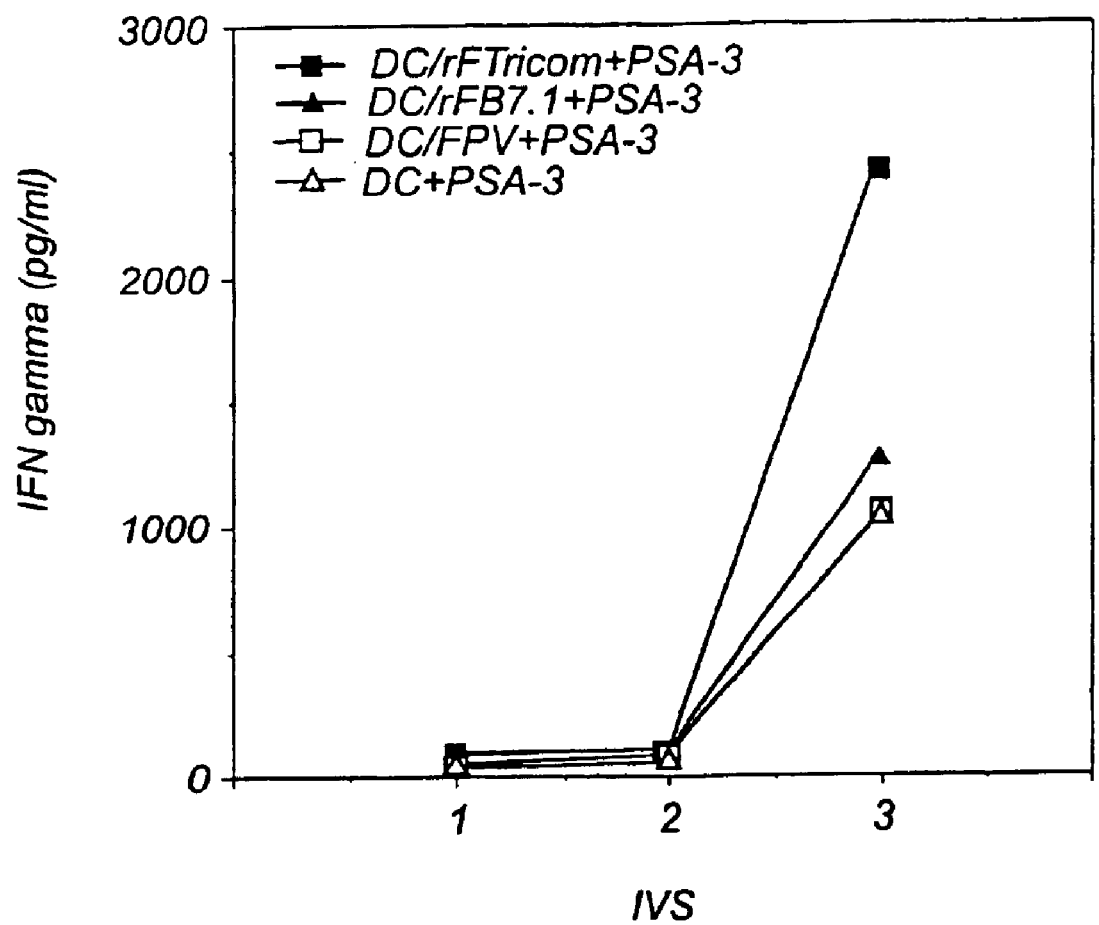
FIG. 48. Shows production of IFN-γ by human T cells using rF-TRICOM-infected human dendritic cells pulsed with PSA peptide, PSA-3.
Figure 49:
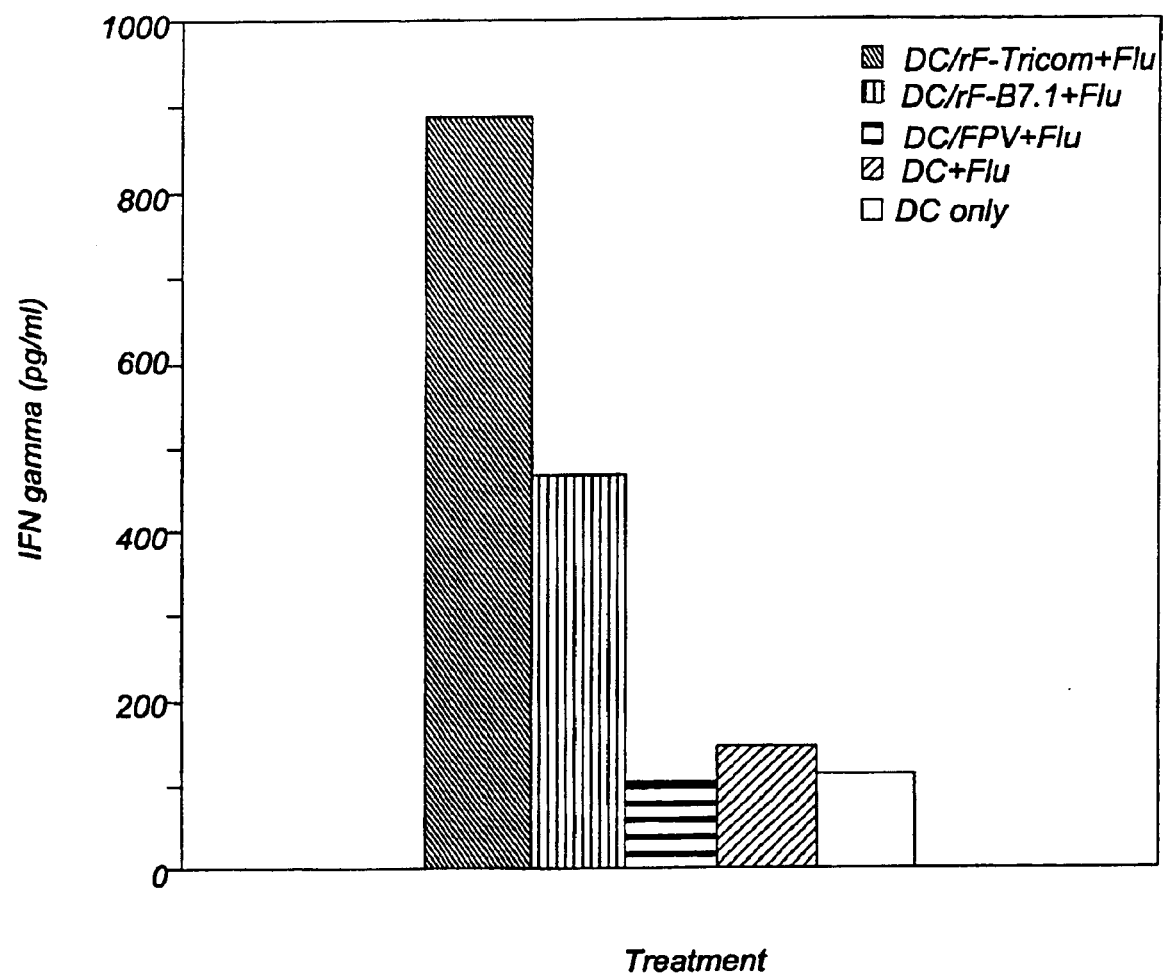
FIG. 49. Shows production of IFN-γ by human T cells isolated from PBMC using rF-TRICOM-infected human dendritic cells pulsed with Flu peptide 58–66.
Figure 50:
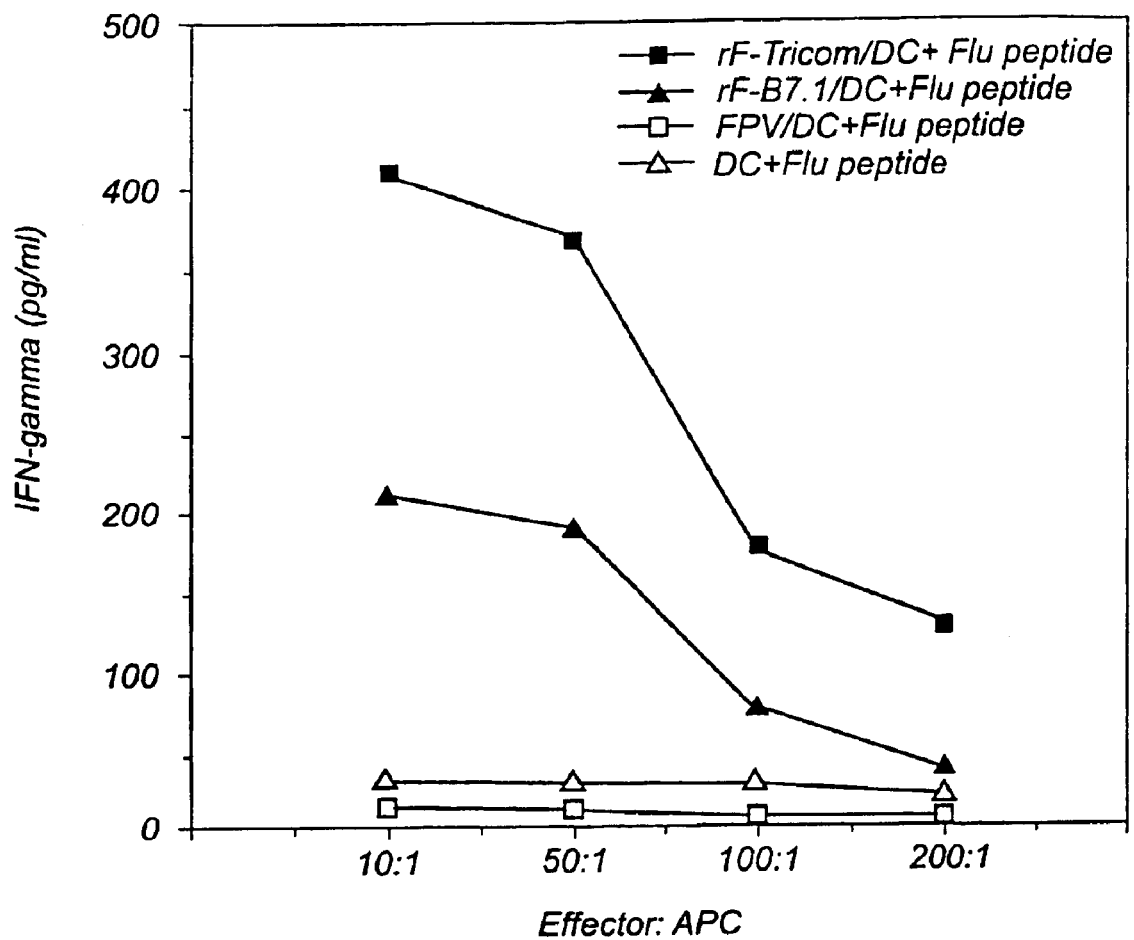
FIG. 50. Shows production of IFN-γ by human T cells isolated from PBMC using rF-TRICOM-or rF-B7.1-infected human dendritic cells pulsed with Flu peptide 58–66 at various effector: APC ratios.
Figure 51:
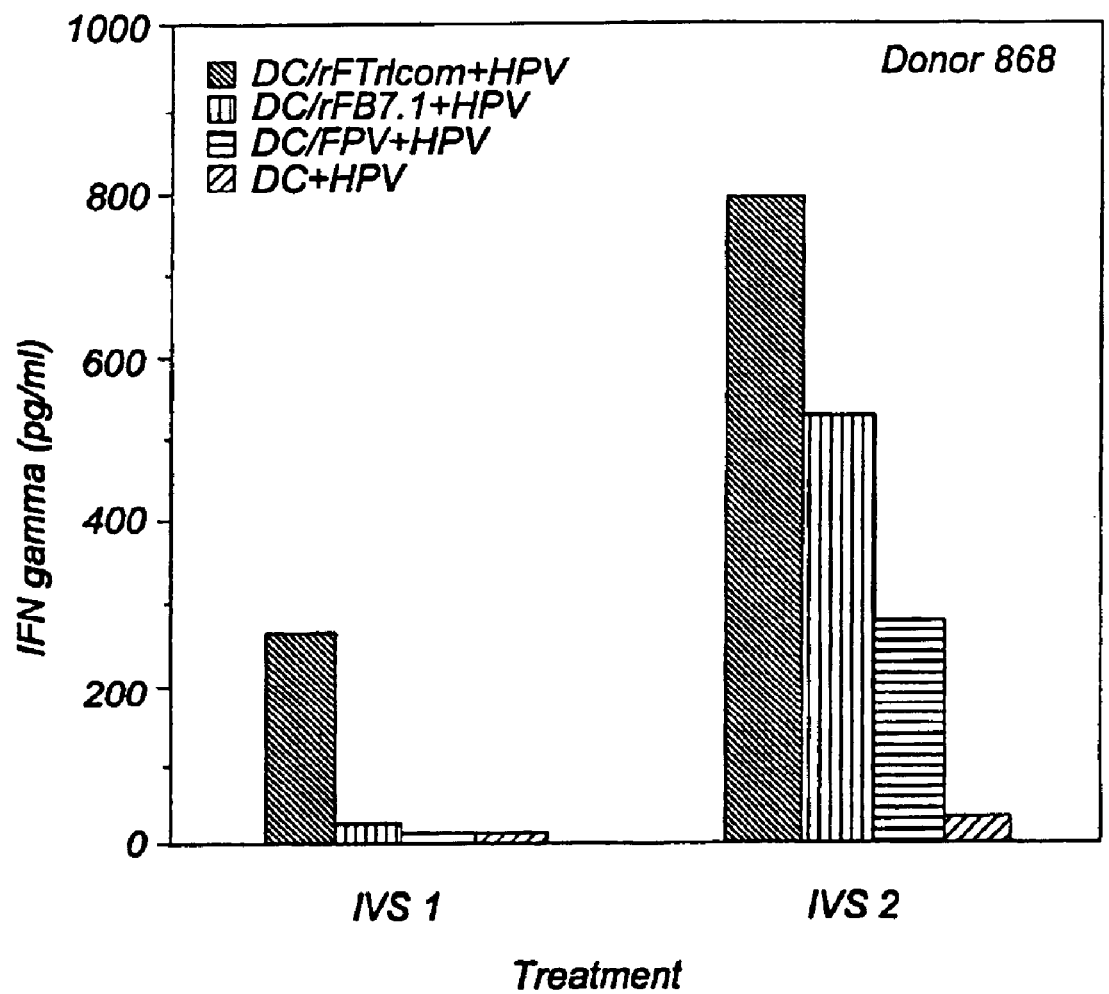
FIG. 51. Shows production of IFN-γ by human T cells from donor 868 using rF-TRICOM-infected human dendritic cells pulsed with HPV peptide (11–20) after one or two in vitro stimulation (IVS).
Figure 52:
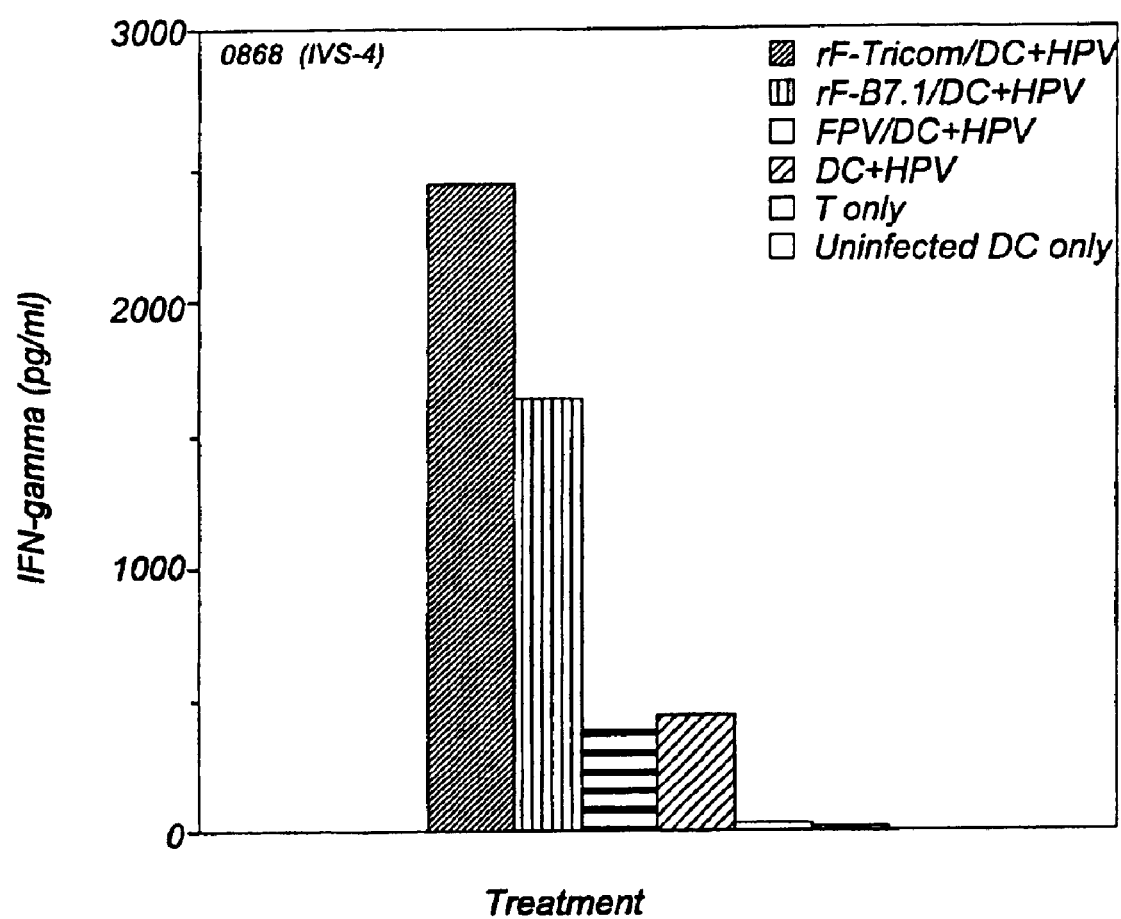
FIG. 52. Shows production of IFN-γ by human T cell line using rF-TRICOM-or rF-B7.1-infected human dendritic cells pulsed with HPV peptide (11–20).
Figure 53:
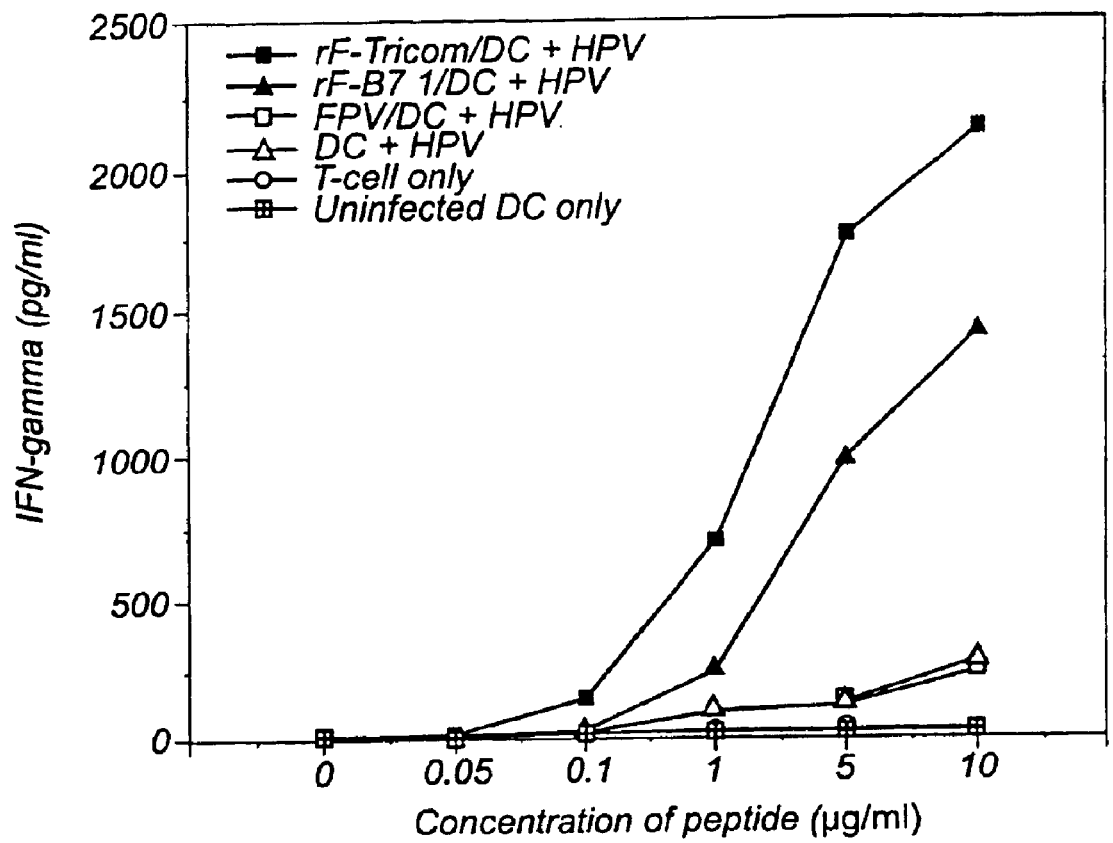
FIG. 53. Shows production of IFN-γ by a human T cell line using rF-TRICOM-or rF-B7.1-infected human dendritic cells pulsed with various concentrations of HPV peptide (11–20).
Figure 54:
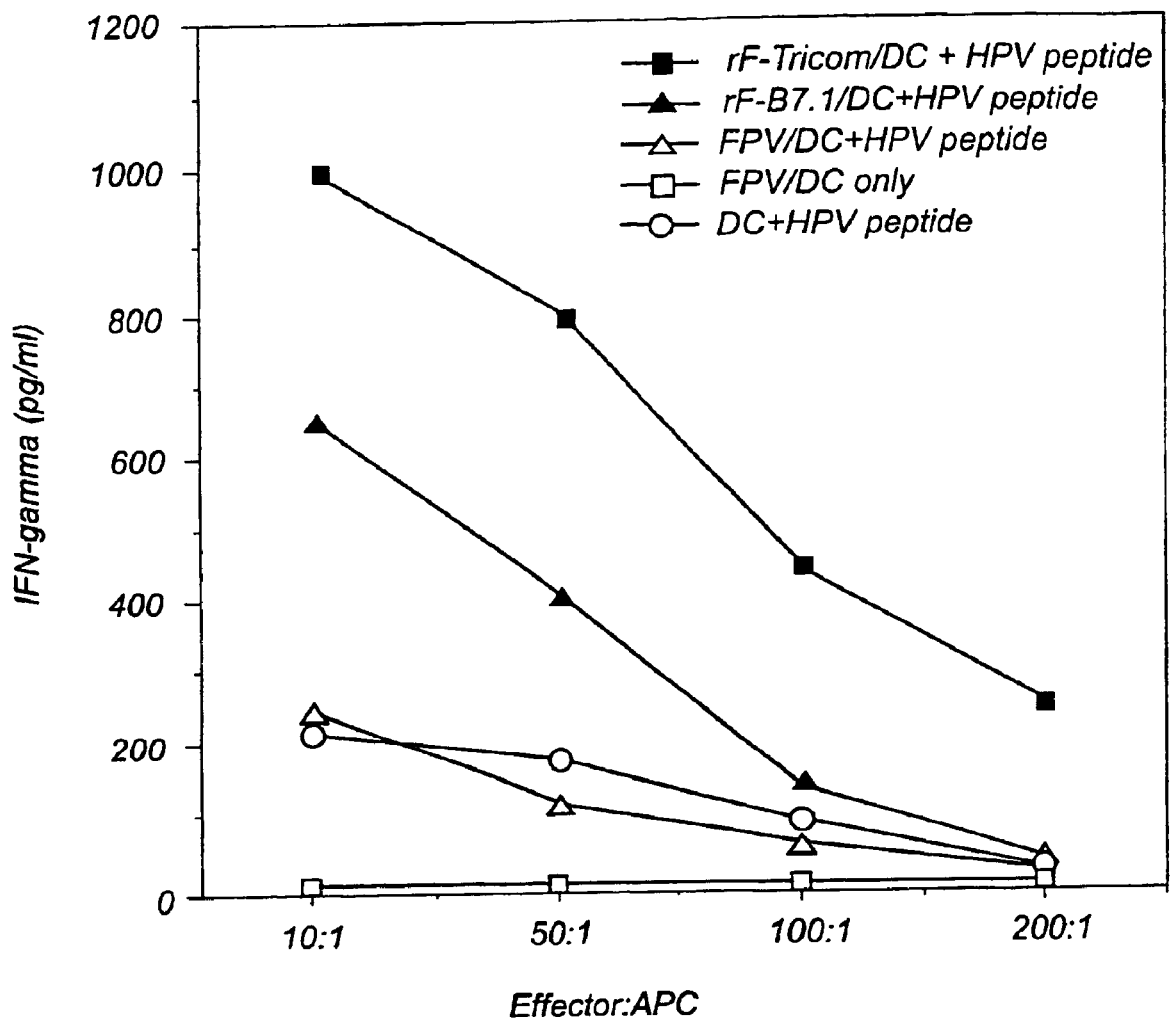
FIG. 54. Shows production of IFN-γ by human T cells using rF-TRICOM or rF-B7.1-infected human dendritic cells pulsed with HPV E7 peptide 11–20 at various effector: APC ratios.

It is generally believed that the generation of anti-vaccinia antibodies can prevent the repeated use of vaccinia virus as immunogens. However, little is known about the repeated use of vaccinia-infected cells as immunogen. To address this issue, an immunization scheme was carried out in which CAP-M8 peptide-pulsed DC immunogens were administered one, two, or three times, at 7-day intervals. As before, splenocytes were harvested 14 days following the final immunization, restimulated in vitro for 6 days, and assessed for their peptide-specific lytic ability against CAP-M8pulsed EL-4 cells. As seen in FIG. 41A, peptide-pulsed DC/rV-

TABLE 5

Effect of Pretreatment of DC with TNF-α or CD40 mAb Prior to rV-TRICOM Infection

| | | DC Panel [% positive cells (MFI)] | | | | | | | | |
|---|---|---|---|---|---|---|---|---|---|---|
| Infection | Pretreatment | I-A$^b$ | H-2K$^b$/D$^b$ | CD11b | CD11c | B7-2 | CD40 | B7-1 | ICAM-1 | LFA-3 |
| DC (Uninfected) | None | 90 (924) | 93 (225) | 90 (835) | 26 (174) | 65 (340) | 62 (182) | 93 (389) | 96 (415) | 90 (253) |
| DC (Uninfected) | TNF-α | 95 (1189) | 91 (195) | 84 (729) | 20 (149) | 71 (412) | 65 (159) | 85 (320) | 97 (421) | 87 (249) |
| DC (Uninfected) | CD40 mAb | 91 (990) | 89 (183) | 87 (788) | 22 (154) | 68 (374) | 69 (198) | 90 (297) | 95 (690) | 86 (216) |
| DC/rV-TRICOM | None | 87 (756) | 89 (214) | 85 (684) | 24 (98) | 69 (301) | 66 (103) | 95 (1989) | 98 (1487) | 93 (413) |
| DC/rV-TRICOM | TNF-α | 92 (991) | 90 (230) | 79 (558) | 21 (62) | 72 (398) | 68 (81) | 96 (1442) | 94 (1998) | 90 (394) |
| DC/rV-TRICOM | CD40 mAb | 91 (905) | 90 (216) | 81 (614) | 23 (69) | 65 (387) | 71 (120) | 94 (1382) | 97 (1444) | 89 (310) |

DC were treated with TNF-α (100 ng/ml) or CD40 mAb (1 μg/ml) during the final 24h of culture.
DC or treated DC were then infected with 25 MOI of rV-TRICOM for 5h.
After 18h incubation, cells were phenotyped by 3-color flow cytometric analysis.

DC Infected with W-TRICOM Are More Efficient at Priming CTL Responses In Vivo

Experiments were conducted to determine if the enhanced stimulatory capacity of DC/rV-TRICOM noted in vitro using Con A (FIG. 36E-F), mixed-lymphocyte reactions (FIG. 37) and two effector T-cell models (FIG. 38) would translate to enhanced efficacy in priming naïve T-cell responses in vivo. To that end, DC, DC/V-WT, and DC/rV- TRICOM induced higher levels of CTL activity when compared with peptide-pulsed DC. These data are similar to those seen in FIG. 40E-H. This single administration of DC/V-WT or DC/rV-TRICOM induced significant anti-vaccinia IgG antibody titers, with values ranging from 1:4,000 to 1:9,000 as determined by qualitative ELISA. These titers, however, had no effect on the capacity of these immunogens to boost CTL activity upon subsequent immunizations (FIGS. 41B and 41C). While anti-vaccinia virus titers after the second vaccination ranged from 1:12,000 to 1:50,000, a boost in the induction of peptide-specific CTL was seen in all groups. Again, the CTL activity observed employing DC/rV-TRICOM-pulsed cells was greater than that observed with peptide-pulsed DC.

EXAMPLE 32

Splenocytes or Bone Marrow Progenitor Cells Infected With TRICOM Vectors Induce T-cell Activation Comparable to Dendritic Cells Materials and Methods
Generation of Bone Marrow Progenitor Cells and Dendritic Cell Cultures.

The procedure used for generation of bone marrow-derived DC was that described by Inaba et al. with minor modifications. Briefly, the femurs were taken from 6–8 week old female C57BL/6 mice (Taconic Farms, Germantown, N.Y.) and the bone marrow was flushed and passed over a Ficoll-Hypaque gradient. Bone marrow cells were depleted of lymphocytes and Ia+ cells using a cocktail of magnetic beads specific for CD4, CD8, and MHC Class II (MiniMACS, Miltenyi Biotec, Auburn, Calif.). Designated as dendritic cell progenitors, these depleted bone marrow cells were then prepared for infection, or for dendritic cell cultures depleted bone marrow cells were plated in six-well culture plates ($10^6$ cells/ml, 5 ml/well) in CM supplemented with 10 ng/ml GM-CSF and 10 ng/ml IL-4 (R & D Systems, Minneapolis, Minn.). DC cultures were replated in fresh cytokine-supplemented CM on days 2 and 4, and split to new plates on day 4. At day 7 of culture, cells were harvested for analysis, in vitro assays, and in vivo immunizations.
Generation of Splenocyte Stimulator Cells.

Spleens were harvested from naïve female C57BL/6 mice, crushed into a single-cell suspension, and passed over a Ficoll-Hypaque gradient. Splenocytes were depleted of lymphocytes and Ia+ cells using a cocktail of magnetic beads specific for CD90, and MHC Class II. Purified splenocytes were then washed twice with Opti-Mem (Gibco-BRL) and prepared for infection with the recombinant poxviruses.
Infection of Stimulator Cells.

Bone marrow-derived dendritic cell progenitor and splenocyte cells were washed twice with Opti-Mem and mock infected or infected with either 25 MOI V-WT, rV-B7-1, rV-TRICOM, or 50 MOI FP-WT, rF-B7-1 or rF-TRICOM at 25 MOI (multiplicity of infection, PFU/cell) in 1 ml final volume of Opti-Mem for 5 hours. After infection, warm (37 degree) CM was added and the cells were incubated at 37° C. overnight. After infection the cells were harvested for immunostaining, in vitro costimulation analysis, and in vivo administration.

Costimulation Analysis

Rested CAP-M8 Tells (responders) were added at $5\times10^4$/well in a 96-well flat-bottomed plates (Costar, Cambridge, Mass.). Stimulator cells consisted of BMDC, splenocytes, or bone marrow progenitors, either uninfected, mock infected, or infected with either V-WT, rV-B7-1, rV-TRICOM, FP-WT, or rF-TRICOM and irradiated (20 Gy). Cells in wells were cultured in a total volume of 200 ml of CM. The costimulation assay was carried out using two sets of conditions: a) fixed ratio of responder stimulator cell of 2.5:1 for non-BMDC stimulators, and 10:1 for BMDC, cultured in the presence of several concentrations of Con-A as signal one, specific peptide, or appropriate control peptide, or b) a fixed concentration of Con-A as signal one, specific peptide, or control peptide, cultured at various responder: stimulator cell ratios. Cells were cultured for 48 or 72 hours for Con-A and peptide-specific assays, respectively, and labeled for the final 12–18 hours of the incubation with 1 $\mu$Ci/well 3H-Thymidine, harvested, and analyzed as described above.

Table 6 shows splenocyte and bone marrow (BM) cell surface expression of costimulatory molecules after infection with recombinant vectors. Purified murine splenocytes or bone marrow cells were infected for 5 hours with 25 MOI of vaccinia vectors or 50 MOI of fowlpox vectors. Cell phenotype was compared with that of DC. All cells were immunostained with costimulatory molecule-specific mAbs labeled with fluorescein isothiocyanate, phycoerythrin, or biotin/streptavidin-cychrome. Isotype control were negative (data no shown). Numbers indicate percent positive cells and mean fluorescence intensity in parentheses.

TABLE 6

Infection of BMDC, Splenocytes, and BMDC Progenitors with either rV-Tricom or rF-TRICOM increases the level of expression of B7-1, ICAM-1, and LFA-3[1]

|  |  | I-A[b] | H-2K[b]/D[b] | CD11b | CD11c | CD40 | B7-2 | B7-1 | ICAM-1 | LFA-3 | CD19 |
|---|---|---|---|---|---|---|---|---|---|---|---|
| DC[2] | Uninfected | 88 | 89 | 93 | 20 | 68 | 91 | 91 | 96 | 88 | 2 |
|  |  | (1124) | (125) | (935) | (74) | (82) | (329) | (329) | (595) | (153) | (26) |
| Splenocytes[3] | Uninfected | 92 | 96 | 3 | 1 | 87 | 49 | 46 | 85 | 77 | 42 |
|  |  | (102) | (389) | (136) | (54) | (494) | (61) | (540) | (258) | (40) | (25) |
|  | V-WT | 91 | 94 | 3 | 0.7 | 75 | 63 | 55 | 76 | 47 | 25 |
|  |  | (114) | (400) | (182) | (82) | (408) | (92) | (490) | (257) | (32) | (24) |
|  | rV-B7 | 91 | 95 | 3 | 1 | 81 | 61 | 87 | 85 | 45 | 33 |
|  |  | (123) | (402) | (89) | (159) | (369) | (89) | (1134) | (315) | (29) | (27) |
|  | rV-Tricom | 93 | 98 | 3 | 3 | 81 | 49 | 87 | 92 | 97 | 27 |
|  |  | (188) | (433) | (41) | (83) | (327) | (69) | (1104) | (788) | (192) | (33) |
|  | FP-WT | 90 | 90 | 2 | 0.9 | 79 | 60 | 55 | 70 | 49 | 53 |
|  |  | (104) | (410) | (162) | (92) | (418) | (72) | (460) | (157) | (32) | (29) |
|  | rF-B7-1 | 91 | 86 | 1 | 1 | 85 | 55 | 83 | 83 | 51 | 52 |
|  |  | (133) | (422) | (81) | (149) | (399) | (96) | (830) | (215) | (29) | (31) |
|  | rF-Tricom | 89 | 96 | 3 | 2 | 86 | 51 | 86 | 92 | 99 | 48 |
|  |  | (238) | (399) | (91) | (80) | (387) | (99) | (1001) | (588) | (292) | (33) |

TABLE 6-continued

Infection of BMDC, Splenocytes, and BMDC Progenitors with either rV-Tricom or rF-TRICOM increases the level of expression of B7-1, ICAM-1, and LFA-3[1]

|  |  | I-A$^b$ | H-2K$^b$/D$^b$ | CD11b | CD11c | CD40 | B7-2 | B7-1 | ICAM-1 | LFA-3 | CD19 |
|---|---|---|---|---|---|---|---|---|---|---|---|
| BM[4] | Uninfected | 9 | 99 | 80 | 1 | 26 | 28 | 79 | 68 | 37 | 1 |
|  |  | (289) | (389) | (114) | (909) | (136) | (72) | (115) | (144) | (89) | (147) |
|  | V-WT | 8 | 98 | 66 | 1 | 19 | 19 | 75 | 63 | 33 | 5 |
|  |  | (218) | (236) | (144) | (1131) | (161) | (98) | (131) | (151) | (64) | (50) |
|  | rV-B7 | 8 | 97 | 71 | 2 | 25 | 22 | 89 | 56 | 31 | 2 |
|  |  | (192) | (159) | (144) | (394) | (233) | (125) | (1117) | (204) | (65) | (106) |
|  | rV-Tricom | 7 | 92 | 70 | 1 | 16 | 16 | 92 | 80 | 38 | 3 |
|  |  | (242) | (183) | (129) | (875) | (171) | (91) | (880) | (490) | (112) | (62) |
|  | FP-WT | 8 | 98 | 64 | 1 | 23 | 22 | 74 | 60 | 35 | 2 |
|  |  | (318) | (298) | (133) | (1101) | (175) | (88) | (121) | (112) | (69) | (30) |
|  | rF-B7-1 | 7 | 99 | 75 | 2 | 26 | 26 | 91 | 50 | 34 | 1 |
|  |  | (292) | (259) | (129) | (1001) | (245) | (101) | (652) | (104) | (72) | (86) |
|  | rF-Tricom | 8 | 96 | 72 | 1 | 25 | 13 | 96 | 79 | 39 | 1 |
|  |  | (233) | (213) | (118) | (984) | (111) | (99) | (1880) | (310) | (109) | (52) |

[1]Cells were uninfected, or infected with 25 MOI of V-WT, rV-B7-1, rV-Tricom or 50 MOI FP-WT, rF-B7-1, or rF-TRICOM for five hours. After an eighteen hour incubation period, cells were phenotyped by 3-color flow cytometric analysis. Values are given as [G-positive cells (Mean Fluorescence Intensity)]. Bold numbers indicate a >2-fold change in cell surface expression (MFI).
[2]BMDC: day 6 bone marrow derived dendritic cells (cultured in 10 ng/ml GM-CSF/IL-4).
[3]Splenocytes depleted of T-cells via α-CD90 (Thy 1.2) magnetic beads.
[4]BMDC Progenitors: bone marrow cells were depleted of T-cells and MHCH cells via α-CD4, α-CD8, α-MHCH magnetic beads.

FIGS. 42A through 46 demonstrate that TRICOM-infected splenocytes are comparable to TRICOM infected bone marrow cells in stimulating T cell responses.

EXAMPLE 33

Human T cell Stimulation Using Allogeneic rF-TRICOM Infected Human Dendritic Cells Pulsed with Peptides Human dendritic cells were isolated for a normal, healthy individual by leucophoresis. The human dendritic cells were cultured in the presence of GM-CSF and IL-4 for 6–9 days, followed by the addition of rF-TRICOM or rF-Controls for infection of the dendritic cells. The rF-TRICOM-infected dendritic cells were pulsed with a CEA peptide (CAP-1 or CAP I, 6D) (FIG. 47); a PSA peptide (PSA-3) in. (FIG. 48); an influenza peptide (Flu peptide 5866) (FIGS. 49 and 50); or an HPV peptide (11–20) (FIGS. 51–45) for 1 hour. Human T cells isolated from peripheral blood mononuclear cells (PBMC) were cultured in the presence of the peptide-pulsed rF-TRICOM-infected dendritic cells and production of IFN by the T cells determined. FIGS. 47–54 show that peptide-pulsed rF-TRICOM infected human dendritic cells stimulated T cells to a greater extent than the controls. FIGS. 47–54, as well as Table 7 demonstrate that allogeneic human dendritic cells infected with rF-TRICOM can efficiently present any antigenic peptide to T cells for enhancement of an immune response.

TABLE 7

CTL activity of T cell lines by using DC pulsed with HPV E7(11–20) peptide

| | T cell lines established by using | | | |
|---|---|---|---|---|
| Target | A rF-Tricom + P | rF-B7.1 + P | rF-FPV + P | B DC + P |
| CIR-A2 + HPV | 39.6 (3.1) | 24.7 (0.4) | 19.9 (2.9) | 7.3 (0.4) |
| CIR-A2 | 5.1 (2.0) | 6.9 (4.0) | 7.6 (2.0) | 8.0 (0.2) |

E:T ratio = 25:1
An 6 hour 111-In release assay was performed. CIR-A2 cells were pulsed with HPV E7 peptide (11–20) YMDLQPETT at a concentration of 10 μg/ml.

The results presented in Table 7 demonstrate that DC infected with rF-TRICOM (A), are better as APC to generate CTL than are standard DC (B) when both are pulsed with peptide.

EXAMPLE 34

Human Clinical Trials of a rV-huTRICOM, rV-CEA huTRICOM Vaccine and rF-CEA TRICOM The objective of the human clinical trial is to determine the optimum tolerated dose (OTD) of the recombinant rV-huTRICOM and rV-CEA-huTRICOM vaccine that elicits a host anti-tumor immune response and is associated with acceptable toxicity in patients with advanced CEA-expressing adenocarcinomas.

The rV-huTRICOM and rV-CEA-huTRICOM vaccines are produced under conditions suitable for Phase I and Phase II human clinical trial.

In an initial trial, escalating doses of recombinant rV or rF CEA-huTRICOM live virus vaccine or rV-huTRICOM plus rV-CEA vaccine is provided at an initial dose of $10^6$ pfu virus, I.M., followed by a dose of $10^7$ pfu virus, I.M., which is followed later by of $10^8$ pfu virus, or $10^9$ S.C. or by scarification.

The anti-tumor response to each recombinant vaccine is determined using clinical, laboratory and radiologic evidence of tumor size, extent and growth using accepted standard criteria for measuring response of tumors to new forms of therapy as are known in the art.

The patient's immune response to the recombinant vaccine is assessed using a variety of immunological assays including anti-CEA antibody assay, anti-poxvirus antibody assay, immune complex assay, CEA-specific lymphoproliferative assay, CEA-specific cytotoxic T-lymphocyte assays, precursor frequency of CEA-reactive T cells in gamma-interferon release T-cell assay, a ELISPOT, Fast Immune, Tetramere assays for T-cell responses (Scheibenhogen et al *Int. J. Cancer* 71:932–936, 1997), HLA assays and the like. A comparison of pre-treatment and post-treatment samples are made to document development of humoral and cellular immune responses directed against the CEA tumor antigen.

EXAMPLE 35

Human Clinical Trials of an Recombinant Fowlpox-CEA-huTRICOM

In an initial trail, escalating doses of recombinant fowlpox-CEA huTRICOM vaccine of $10^6$ pfu virus, $10^7$ pfu virus and $10^8$ pfu virus is injected directly into a tumor mass of a patient with advanced CEA-expressing adeno carcinomas.

The specific anti-tumor and immune response to the recombinant vaccine is determined as described in Example 34.

EXAMPLE 36

Human Clinical Trial of T Lymphocytes Activated by Multiple Costimulatory Molecule-Overexpressing Dendritic Cells Peripheral blood lymphocytes and dendritic cells are obtained from a patient with advanced prostate cancer. The peripheral blood lymphocytes are enriched for CD8+ lymphocytes. The dendritic cells are infected with rV-PSA epitope QVHPQKVTK (residues 22–30 of SEQ ID NO: 32)/B7.1/ICAM-1/LFA-3 for a period of time sufficient to allow expression of the PSA epitope and overexpression of the multiple costimulatory molecules. PSA epitope-specific $CD8^+$ lymphocytes are activated and expanded in the presence of these treated dendritic cells. The activated PSA epitope-specific $CD8^+$ autologous T lymphocytes are injected into the patient alone and in combination with the PSA epitope. The specific anti-tumor and PSA-specific immune response to the treatment is determined by methods comparable to those described in Example 34.

Similar human clinical trials may be conducted for treatment of patients with other TAA-expressing cancers, by replacement of the gene encoding CEA with a gene encoding another TAA into the recombinant vector of the present invention.

EXAMPLE 37

Screen for Immunogenic Peptides and/or Human T Cells Immunoreactive with a Specific Peptide Using DC Infected with rF-TRICOM The present invention encompasses anticancer therapies using ex vivo engineering of DC with viral vectors carrying a tumor associated antigen gene to activate tumor-specific CTL. DC infected with rF-CEA in combination with TRICOM costimulatory molecules are used to augment CEA-specific immune responses. The CTL induction capacity of DC infected with rF-CEA/TRICOM and rF-TRICOM are evaluated. Tetrameric MHC class I CAP-I complex are used to visualize CAP-I specific CTL. This protocol is not limited to the tumor associate antigen, CEA, but may be modified to elicit antigen-specific immune responses for any antigenic peptide or immunogenic epitope thereof for immunotherapy against cancer, pathogenic bacteria, virus, protozoans, yeast and the like. Moreover, the method may be modified to screen for and identify immunogenic peptides from a source such as a natural protein, recombinant protein, synthetic protein, or fragments from each, combinatorial libraries, and the like.

Materials and Methods
Cell Cultures
Colorectal carcinoma cell lines SW1463 (HLA-A1,2), LS174T (HLA-A2,-), were purchased from American Type Culture Collection (Manassas, Md.). The cultures were free of mycoplasma and were maintained in complete medium [DMEM (Life Technologies, Inc., Grand Island, N.Y.) supplemented with 10% fetal bovine serum, 2 mM glutamine, 100 units/ml penicillin, and 100 µg/ml streptomycin (Life Technologies, Inc.)]. The C1R cell line is a human plasma leukemia cell line that does not express endogenous HLA-A or B antigens (Storkus, W. J. et al, *J. Immunol.* 138(6):1657–1659, 1987). C1R-A2 cells are C1R cells that express a transfected genomic clone of HLA-A2.1 (Hogan, K. T. et al, *J. Exp. Med.* 168(2):725–736, 1988).

These cells were obtained from Dr. William E. Biddison (National Institute of Neurological Disorders and Stroke, NIH, Bethesda, Md.). C1R-A2 culture was mycoplasma free and was maintained in RPMI 1640 complete medium (Life Technologies, Inc.). The V8T cell line, a CTL line directed against the CAP-1 epitope, was established from a patient with metastatic colon carcinoma who was enrolled in a Phase I trial using rV-CEA (Tsang, K. Y. et al., *Clin. Cancer Res.* 3(12):2439–2449, 1997). V8T cells were cultured in RPMI 1640 complete medium containing 10% human AB serum and IL-2 (provided by the National Cancer Institute, Surgery Branch, 20 units/ml). V8T cells were restimulated with CAP-1 peptide (25 µg/ml) on day 16 after prior restimulation at an effector cell-to-APC ratio of 1:3. Irradiated (23,000 rads) autologous EBV transformed B cells were used as APC.

Culture of DC from Peripheral Blood Mononuclear Cells

Peripheral blood mononuclear cells (PBMC) were obtained from heparinized blood from a patient (#15) with metastatic pelvic carcinoma who was enrolled in a Phase I trial using a combination of rV-CEA and ALVAC-CEA. All experiments involving patient materials were conducted according to NIH guidelines, and written, informed consent was obtained from all individuals. PBMC were separated using lymphocyte separation medium gradient (Organon Teknika, Durham, N.C.) as described previously (Boyum, A. *Scand J Cin Lab Invest Suppl.* 97:51–76, 1968). DC were prepared using a modification of the procedure described by Sallusto et al. (Sallusto, F. et al, *J. Exp. Med.* 179(4): 1109–1118, 1994). PBMC (1.5×10') were resuspended in AIM-V medium containing 2 mM glutamine, 50 µg/ml streptomycin, 10 µg/ml gentamycin (Life Technologies, Inc.) and allowed to adhere to a T-150 flask (Corning Costar Corp., Cambridge, Mass.). After 2 hours at 37° C., the non-adherent cells were removed with a gentle rinse. The adherent cells were cultured for 6–7 days in AIM-V medium containing 50 ng/ml of recombinant human GM-CSF (rhGM-CSF) and 0.5 ng/ml of recombinant human IL-4 (rhIL-4). The culture medium was replenished every three days.

Recombinant Virus and Infection of DC with Avipox Virus Containing CEA, CEA/TRICOM and TRICOM A 2109 bp DNA fragment encoding the entire open reading frame of CEA was obtained as described by Kaufman et al (Kaufman, F. et al. *Int. J. Cancer* 48(6):900–907, 1991). The recombinant CEA avipox virus (fowlpox CEA; vCP248) was supplied by Therion Corp using methods described by Taylor et al (Taylor, J. et al, *Virology* 187(1): 321–328, 1992), Cox et al (Cox, W. I. et al, *Virology* 187(1):321–328, 1992) and Perkus et al (Perkus, M. E. et al, *J. Virol.* 63(9):3829–3836). The recombinant avipox virus encoding CEA and human Tricom gene (designated rF-CEA-Tricom) and the recombinant human fowlpox-TRICOM (rF-Tricom) were made as disclosed herein. Wild type fowlpox (FP-WT) was used as a negative control in selected experiments. DC ($1×10^6$) were incubated in 1 ml of Optim-MEM medium (Life Technologies, Inc.) at 37° C. with rF TRICOM, rF-CEA, rF-CEA/TRICOM, FP-WT. Titration experiments indicated that 2×10' plaque-forming units/ml, equal to a multiplicity of infection (MOI) of 40:1 for 2 hours, were able to consistently induce expression of CEA in approximately 75% of the infected DC. The infected DC were suspended in 10 ml of fresh, warm RPMI-640 complete medium containing 50 ng/ml of rhGM-CSF and 0.5 ng/ml rhIL-4 cultured for 24 hours, and then subsequently used as stimulators.

Peptide

CAP-1 (Tsang, K. Y. et al, *J. Natl Cancer Inst.* 87(13): 982–990,1995), CEA amino acid position 571–579 YLSGANLNL (SEQ ID NO: 23), CAP1-6D (Zaremba, S. et al, *Cancer Res.* 57(20):4570–4577, 1997) YLSGADLNL (SEQ ID NO: 24) and Flu peptide, influenza matrix protein peptide 5866 GILGFVFTL (SEQ ID NO: 42) greater than 96% pure, were made by Multiple Peptide System (San Diego, Calif.).

Generation of T-cell lines

Modification of the protocol described by Tsang et al (Tsang, K. Y. et al, *J. Natl Cancer Inst.* 87(13):982–990, 1995) was used to generate CEA-specific CTL.

Uninfected DC and DC infected with rF-TRICOM, rF-CEA, or rF-CEA/TRICOM were used as APC. CAP-1 peptide was added to the uninfected or rF-TRICOM infected DC at a final concentration of 25 μg/ml. Autologous non adherent cells were then added to APC at an APC-to-effector ratio of 1:10. Cultures were then incubated for 3 days at 37° C. in a humidified atmosphere containing 5% $CO_2$. After removal of the peptide-containing medium, the cultures were then supplemented with recombinant human IL-2 at a concentration of 20 units/ml for 7 days, with IL-2 containing medium was replenished every 3 days. The 3-day incubation with peptide and 7 day IL-2 supplement constituted one IVS cycle. Primary cultures were restimulated with CAP-1 peptide (25 μg/ml) on day 11 to begin the next IVS cycle. Irradiated (23,000 rads) autologous EBV-transformed B cells were used as APC. A similar procedure was employed for CTL generation when DC infected with rF-CEA or rF-TRICOM were used as APC, with the exception that no CAP-I peptide was in the stimulation.

Construction of Peptide MHC Tetramers

Peptide-MHC complexes were synthesized as described by Altman et al (Altman, J. D. et al *Science* 274(5284):9495, 1996). In brief, the $\beta_2$ microglobulin ($\beta_2$M) clone was obtained from Dr. Garboczi (Harvard University, Cambridge, Mass.) (Garboczi, D. N. et al, *Proc Natl Acad Sci USA* 89(8):3429–3433, 1992) and the HLA-A2 construct was obtained from Immunotech (Beckrman-Coulter, Marseille, France). The soluble HLA-A2 molecules containing the 15 amino acid substrate peptide for BirA-dependent biotinylation to the COOH-terminus of the HLA-A2 heavy chain and $\beta_2$M were grown separately in *E. coli* and isolated as inclusion bodies. HLA-A2 and $\beta_2$M were solubilized and renatured in the presence of CAP-I or Flu-MI 58–66 peptide. The complex was purified by FPLC on Superdex 200 (Pharmacia, Piscataway, N.J.). Purified peptide-MHC complex was biotinylated using the BirA enzyme (Avidity, Denver, Colo.). Tetramers were produced by mixing the biotinylated peptide-MHC complex with phycoerythrin-labeled UltraAvidin (Leinco Technologies, Inc. Ballwin, Mo.) at a molar ratio of 4:1.

Flow Cytometry

Staining and sorting of T-cells: CAP-1-MHC tetramer-PE was used for flow cytometric analysis and sorting of T-cells. Similar procedure as described above was used for tetramer staining. CAP-1-MHC tetramer-PE was used at a concentration of 0.33 μg/2×10⁵ cells. Cells were stained with CAP-1 MHC tetramer-PE for 1 hour at 4° C. and then stained with anti-CD8 FITC for an additional hour. Cells were washed and analyzed on a Vantage Cell sorter (Becton Dickinson) or a FACScan (Becton Dickinson) using CellQuest software (Becton Dickinson). Sorter cells were cultured and expanded as described previously. Cells stained with UltrAvidin-PE and Flu-MHC tetramer were used as negative controls.

Cytotoxic Assay

Target cells were labeled with 50 μCi of $^{111}$Indium-labeled oxyquinoline (Medi-Physics Inc., Arlington, Ill.) for 15 min at room temperature. Target cells (0.3×10⁴) in 100 μl of RPMI-1640 complete medium were added to each of 96 wells in flat-bottomed assay plates (Corning Costar, Corp.). The labeled target cells were incubated with peptides for 60 min at 37° C. in 5% $CO_2$ before adding effector cells. No peptide was used when carcinoma cell lines were used as targets. Effector cells were suspended in 100 μl of RPMI-1640 complete medium supplemented with 10% pooled human AB serum and added to the target cells. The plates were then incubated at 37° C. in 5% $CO_2$ for 4 or 16 hours. Supernatant was harvested for gamma counting with the use of harvester frames (Skatron, Inc., Sterling, Va.). Determinations were carried out in triplicate, and standard deviations were calculated. Specific lysis was calculated with the use of the following formula (all values in cpm):

$$\% \text{ lysis} = \frac{\text{Observed release} - \text{Spontaneous release} \times 100}{\text{Total release} - \text{Spontaneous release}}$$

Spontaneous release was determined from wells to which 100 μl of RPMI-1640 complete medium was added. Total releasable radioactivity was obtained after treatment of targets with 2.5% Triton x-100.

HLA Typing

The HLA phenotyping was performed by the Blood Bank of the National Institutes of Health using a standard antibody-dependent microcytotoxicity assay and a defined panel of anti-HLA antisera The class I phenotypes of V8T cell line and patient #15 were HLA-A2,-; B18 (W6), 44 (12, W4) and HLA-A2, 28; B13 (BW4), B51 (BW4); CW6, respectively.

Detection of Cytokine

Supernatant of T cells exposed for 24 hours to DC infected with rF-CEA, rF-CEA/TRICOM or to peptide pulsed uninfected DC and rF-TRICOM-infected DC in IL-2-free medium at various responder stimulator ratio were screened for secretion of IFNγ using an ELISA kit (R&D Systems, Minneapolis, Minn.). The results were expressed in μg/ml.

ELISPOT Assay

A modification of the method described by Scheibenbogen et al (Scheibenbogen, C. et al, *Clin Cancer Res* 3(2): 221–226, 1997) was used to measure IFN-γ production to determine CAP-1 specific T cells. Briefly, 96-well Milliliter HA plates (Millipore Corporation, Bedford, Mass.) were coated with 100 μl of capture antibody against human IFNγ at a concentration of 10 μg/ml. After 24 hours incubation at room temperature, plates were blocked for 30 min with RPMI-1640 containing 10% human pool AB serum. 1×10⁵ cells to be assayed were added to each well. CAP-1-6D-pulsed C1R-A2 cells were added into each well as APC at an effector: APC ratio of 1:3. Unpulsed C1R-A2 cells were used as negative control. HLA-A2 binding Flu Matrix peptide 58–66 (GILGFVFTL) (SEQ ID NO: 42) were also used as control. The responding cells were determined by the use of a Domino Image Analyzer (Otpomax, Hollis, N.H.).

Statistical Analysis

Statistical analysis of differences between means was done using a two-tailed t test.

Discussion

When a naïve T cell encounters antigen, several distinct outcomes are possible including proliferation, cytokine secretion, and differentiation into effector cells, as well as inactivation, death, and unresponsiveness (anergy). The predominant outcome under physiologic conditions may be determined by whether appropriate costimulatory signals are delivered to the responding T cell (26). At least three distinct molecules normally found on the surface of professional APC have been thought to be capable of providing the signals critical for T-cell activation: B7-l, ICAM-1, and LFA-3. Here, the role of costimulatory molecules in naïve T-cell activation was examined by utilizing vectors engineered to express either B7-1, ICAM-1, LFA-3, or a combination of all three molecules.

Several groups have investigated the cooperation of two of these molecules in T-cell costimulation. Dubey et al. have reported that costimulation by both B7-1 and ICAM-1 is a prerequisite for naïve T-cell activation (26), while Cavallo et al. determined that B7-1 and ICAM-1 must by coexpressed by tumor cells to establish an antitumor memory response (27). In addition, costimulation by B7-1 and LFA-3 has been shown to act additively both upon T-cell proliferation and cytokine production (6, 23, 24). These previous studies were carried out using two costimulatory molecules and retroviral vectors. One gene was transduced into the target cell line, drug selected, and then transduced again with a second recombinant retroviral construct followed by selection with a different agent. This process often requires weeks or months. Utilizing recombinant poxvirus vectors, one is able to achieve the coexpression of three costimulatory molecules 5 hours post-infection. In vitro MC38 cells infected with either rV-B7-1/ICAM-1/LFA-3 or rF-CEA/B7-1/ICAM-1/LFA-3 were shown to enhance proliferation of T cells to a much greater extent than MC38 cells infected with vectors containing the gene for any single costimulatory molecule. In addition, the relative strength of the second signal delivered to the T cell by the combination of costimulatory molecules appeared to be several-fold (>6) greater than that delivered by MC38 cells expressing any single costimulatory molecule. Dubey et al. have demonstrated that at low stimulator to T-cell ratios, moderate to strong synergy was noted with B7-1 and ICAM-[(26). Our studies confirm these findings. However, at very low stimulator cell to T-cell ratios or weak signal-I (0.625 µg/ml Con A), the two-gene construct (rV-B7-1/ICAM-1) had little if any effect on proliferation; in contrast, stimulation via the triad construct (rV-B7-1/ICAM-1/LFA-3) had a substantial and statistically significant effect on proliferation. The predominant effect of stimulation via the multi-gene construct (rV-B7-1, ICAM-1, LFA-3) was IL-2 elaboration from CD4$^+$ cells and IFN-γ elaboration from CD8$^+$ T cells, while few, if any, type 2 cytokines were produced. Cytokine expression analysis by RNAse protection provided a profile compatible with the in vitro cytokine assay, manifested by significantly higher expression of IL-2 and IFN-γ in both CD4$^+$ and CD8$^+$ T cells stimulated with all three costimulatory molecules, as compared to stimulation by any single costimulatory molecule. These data are in accordance with previous studies which demonstrated that in the context of low CD28 costimulation, T cells produced low levels of IL-1, whereas strong CD28 costimulation supported production of IL-2, IFN-γ and IL-13 (28). Furthermore, it has been reported that IL-13 synergizes with IL-2 in regulating IFN-γ synthesis in T cells (29). Interestingly, our results further support this observation in that stimulation of CD4$^+$ T cells with MC38/B 7-1/CAM-1/LFA-3 results in a high level of IL-2 and IFN-γ expression, with some increased expression of IL-13. Moreover, it was noted that IL-9 expression was further enhanced in CD4$^+$ T cells upon stimulation with MC38/B7-1/ICAM-1/LFA-3. The increased expression of IL-9 in conjunction with upregulation of IL-2 noted in our studies is in agreement with previous studies which demonstrated that optimal production of IL-9 is regulated by IL-2 (30). Taken together, these studies suggest that optimal naïve T-cell responses require a higher level of costimulation than was previously thought, and that this could be provided by the combined action of three costimulatory molecules.

Perhaps the most studied T-cell costimulatory molecule is B7-1. This molecule's ability to enhance T-cell activation using retroviral vectors, anti-CTLA-4 antibodies, and poxvirus vectors is well established. The studies reported here rank the order of T-cell stimulation by a single costimulatory molecule as B7-1>ICAM-1>LFA-3. However, the employment of three costimulatory molecules was far superior to B7-1 alone or in B7 in combination with a second costimulatory molecule in both T-cell proliferation and cytokine production.

While not being bound by theory, there are several possible mechanisms for efficient cooperation between B7-1, ICAM-1 and LFA-3. The ICAM-1/LFA-3 interaction reportedly costimulates the TCR-mediated activation of T cells by sustaining the increase in the same intracellular second messengers as generated by TCR engagement. This observation suggests that the ligation of LFA-1 by ICAM-1 costimulates T cells by enhancing the signal delivered via the CD3/TCR complex (6). The ICAM-1/LFA-1 interaction is necessary to upregulate expression of the IL-2R-alpha chain and CD28 on T cells, which is required to render them competent to respond to IL-2 and B7-1 costimulation. On the other hand, the B7-1/CD28 interaction delivers a TCR-independent costimulatory signal that increases both transcriptionally and post-transcriptionally the expression of IL-2 and other immunoregulatory lymphokines. The LFA-3/CD2 interaction induces tyrosine phosphorylation of several intracellular second messengers, $Ca^{2+}$ mobilization, and cAMP production, resulting in elaboration of a variety of cytokines, notably IL-2 and IFN-γ (6). Thus, it appears that the three costimulatory molecules could be cooperating by enhancing the antigen-dependent activation of T cells, as well as their production of and response to autocrine and paracrine growth factors.

In conclusion, this invention demonstrates for the first time the ability of vectors to introduce three or more costimulatory molecules into a cell, and to rapidly and efficiently activate both CD4$^+$ and CD8$^+$ T-cell populations to levels far greater than those achieved when one or two of these costimulatory molecules is used. This new threshold of T-cell activation has broad implications in vaccine design and development.

The effect of the triad of costimulatory molecules on DCs was completely unexpected. DCs are known by those skilled in the art as the most potent APC. The data presented in this invention demonstrates that when DCs are infected with the "Tricom" vector, their ability to activate T-cells increases dramatically. These studies demonstrate for the first time that a DC is not the most potent APC.

REFERENCES

1. Hellstrom, K. E., Chen, L. & Hellstrom, I. (1996) *Cancer Chemother Pharmacol* 38, S40-1.
2. Damle, N. K, Klussman, K., Linsley, P. S. & Aruffo, A. (1992) *J Immunol* 148, 1985–92.
3. Green, J. M., Zheng, X. G., Shimizu, Y., Thompson, C. B. & Turka, L. A. (1994) *Eur J Immunol* 24, 265–72.
4. Guinan, E. C., Gribben, J. G., Boussiotis, V. A., Freeman, G. J. & Nadler, L. M. (1994) *Blood* 84, 3261–82.
5. Hodge, J. W., McLaughlin, 1. P., Abrams, S. I., Shupert, W. L., Schlom, J. & Kantor, J. A. (1995) *Cancer Res* 55, 3598–603.
6. Wingren, A. G., Parra, E., Varga, M., Kalland, T., Sjogren, H. O., Hedlund, G. & Dohlsten, M. (1995) *Crit Rev Immunol* 15, 235–53.
7. Parra, E., Wingren, A. G., Hedlund, G., Sjogren, H. O., Kalland, T., Sansom, D. & Dohlsten, M. (1993) *Scand J Immunol* 38, 508–14.
8. Harding, F. A. & Allison, J. P. (1993) *J Exp Med* 177, 1791–6.
9. Hellstrom, K E., Hellstrom, I., Linsley, P. & Chen, L. (1993) *Ann N Y Acad Sci* 690,225-30.
10. Hodge, J. W., Abrams, S., Schlom, J. & Kantor, J. A. (1994) *Cancer Res* 54, 5552–5.
11. Uzendoski, K, Kantor, J. A., Abrams, S. I., Schlom, J. & Hodge, J. W. (1997) *Hum Gene Ther* 8, 851–60.
12. Lorenz, M. G. O., Kantor, J. A., Schlom, J. & Hodge, J. W. (1998) *Human Gene Therapy In Press.*
13. Gritz, L., Destree, A., Cormier, N., Day, E., Stallard, V., Caiazzo, T., Mazzara, G. & Panicali, D. (1990) *J Virol* 64, 5948–57.
14. Mazzara, G. P., Destree, A. & Mahr, A. (1993) *Methods Enzymol* 217, 557–81.
15. Jenkins, S., Gritz, L., Fedor, C. H., O'Neill, E. M., Cohen, L. K. & Panicali, D. L. (1991) *AIDS Res Hum Retroviruses* 7, 991–8.
16. Chakrabarti, S., Sisler, J. R. & Moss, B. (1997) *BioTechniques* 23, 1094–7.
17. Perkus, M. E., Piccini, A., Lipinskas, B. R. & Paoletti, E. (1985) *Science* 229, 9814.
18. Schmitt, J. F. & Stunnenberg, H. G. (1988) *J Virol* 62, 1889–97.
19. Venkatesan, S., Baroudy, B. M. & Moss, B. (1981) *Cell* 25, 805–13.
20. Fox, B. A., Spiess, P. J., Kasid, A., Puri, R., Mule, J. J., Weber, J. S. & Rosenberg, S. A. (1990) *J Biol Response Mod* 9, 499–511.
21. Abrams, S. I., Dobrzanski, M. J., Wells, D. T., Stanziale, S. F., Zaremba, S., Masuelli, L., Kantor, J. A., Schlom, J. & Masuelle, L. (1995) *Eur J Immunol* 25,2588-97.
22. Sabzevari, H., Propp, S., Kono, D. H. & Theofilopoulos, A. N. (1997) *Eur J Immunol* 27, 1901–10.
23. Parra, E., Wingren, A. G., Hedlund, G., Bjorklund, M., Sjogren, H. O., Kalland, T., Sansom, D. & Dohlsten, M. (1994) *J Immunol* 153, 2479–87.
24. Parra, E., Wingren, A. G., Hedlund, G., Kalland, T. & Dohlsten, M. (1997) *J Immunol* 158, 637–42.
25. Sperling, A. I., Auger, J. A., Ehst, B. D., Rulifson, I. C., Thompson, C. B. & Bluestone, J. A. (1996) *J Immunol* 157, 3909–17.
26. Dubey, C., Croft, M. & Swain, S. L. (1995) *J Immunol* 155, 45–57.
27. Cavallo, F., Martin-Fontecha, A., Bellone, M., Heltai, S., Gatti, E., Tornaghi, P., Freschi, M., Formi, G., Dellabona, P. & Casorati, G. (1995) *Eur J Immunol* 25, 1154–62.
28. Delespesse, G., Yang, L. P., Ohshima, Y., Demeure, C., Shu, U., Byun, D. G. & Sarfati, M. (1998) *Vaccine* 16, 1415–9.
29. Minty, A., Chalon, P., Deroeq, J. M., Dumont, X., Guillemot, J. C., Kaghad, M., Labit, C., Leplatois, P., Liauzun, P., Miloux, B. & et al. (1993) *Nature* 362, 248–50.
30. Schmitt, E., Germann, T., Goedert, S., Hoehn, P., Huels, C., Koelsch, S., Kuhn, R., Muller, W., Palm, N. & Rude, E. (1994) *J Immunol* 153, 3989–96.
31. Chakrabarti, S., Brechling, K. and Moss, B (1985) *Mol. Cell. Biol.* 5:3403–3409.
32. Chakrabarti, S., Sisler, J. R, and Moss, B. (1997) *BioTechniques* 23:1094–1097.
33. Gillard, S., Spehner, D., Drillien, R., and Kim, A. (1986) *Proc. Natl. Acad. Sci USA* 83:5573–5577.
34. Morgan, J. R, and Roberts, B. E. (1994) *J. Virol* 51:283–297.
35. Panicali, D., Grzelecki, A., and Huang, C. (1986) *Gene* 47:193–199.
36. Sambrook, J., Fritsch, E. F., and Maniatis, T., eds. *Molecular Cloning,* Cold Spring Harbor Laboratory, 1989.
37. Schmitt, J. F. C. and Stunnenberg, H. G. 1988) *J. Virol.* 62:1889–1897.
38. Smith, K, Stallard, V., Ross, J., Hart, C., Cormier, N., Cohen, L., Roberts, B., and Payne, L. (1993) *Vaccine* 11:43–53.
39. Venkatesan, S., Baroudy, B. M., and Moss, B. (1981) *Cell* 125:805–813. 40. Bacchetti, S. and Graham, F. L. *Proc. Nat'l. Acad. Sci. USA* 74:1590–1594, 1977.
41. Inaba, K., Inaba, M., Romani, N., Aya, H., Deguchi, M., Ikehara, S., Muramatsu, S. & Steinman, R. M. (1992) *J. Exp. Med.* 176, 1693–702.
42. Sallusto, F. & Lanzavecchia, A. (1994) *J. Ex. Med.* 179, 1109–8.
43. Fields, R. C., Osterholzer, J. J., Fuller, J. A., Thomas, E. K, Geraghty, P. J. & Mule, J. J. (1998) *J. Immunother.* 21, 323–39.
44. Zaremba et al *Cancer Res.* 57:4570–4577, 1997.
45. Gong, J. et al *Proc. Natl. Acad. Sci. USA* 95:6279–6283, 1998.
46. Correale, P. et a] 1998, *J. Immunol.* 161(6):3186–94.

We claim:

1. A host cell infected, transfected or induced with a recombinant vector that comprises at least ons nucleic acid sequences encoding a combination of B7, ICAM-1 and LFA-3, wherein expression of the nucleic acid sequences occurs in the host cell.

2. The host cell according to claim 1, wherein the host cell comprises nucleic acid sequences encoding a target antigen.

3. The host cell according to claim 2, wherein target antigen is selected from the, group consisting of a tumor specific antigen, tumor associated antigen, tissue-specific antigen, bacterial antigen, viral antigen, yeast antigen, fungal antigen, protozoan antigen, a parasite antigen and a mitogen.

4. The host cell according to claim 3, wherein the antigen is a bacterial antigen derived from a bacterium selected from the group consisting of *Chlamydia, Mycobacteria, Legionella, Meningiococcus*, Group A *Streptococcus, Hemophilus influenzae, Salmonella*, and *Listeria*.

5. The host cell according to claim 3, wherein the antigen is a viral antigen derived from a virus selected from the group consisting of Lentivirus, Herpes virus, Hepatitis virus, Orthomyxovirus and Papillomavirus.

6. The host cell according to claim 5, wherein the viral antigen is a Lentiviral antigen.

7. The host cell according to claim 6, wherein the Lentiviral antigen is a HIV-1 antigen or an HIV-2 antigen.

8. The host cell according to claim 5, wherein the viral antigen is a Herpes virus antigen.

9. The host cell according to claim 8, wherein the Herpes viral antigen is an HSV antigen or a CMV antigen.

10. The host cell according to claim 5, wherein the viral antigen is a Hepatitis antigen.

11. The host cell according to claim 10, wherein the Hepatitis antigen is selected from the group consisting of a Hepatitis A antigen, Hepatitis B antigen, Hepatitis C antigen, Hepatitis D antigen and a Hepatitis E antigen.

12. The host cell according to claim 5, wherein the viral antigen is an orthomyxovirus antigen.

13. The host cell according to claim 12, wherein the orthomyxovirus antigen is an influenza antigen.

14. The host cell according to claim 3, wherein the antigen is a tumor associated antigen, a tumor specific antigen or a tissue-specific antigen.

15. The host cell according to claim 14, wherein the antigen is selected from the group consisting of CEA, MART-1, MAGE-1, MAGE-3, GP-100, MUC-1, MUC-2, pointed mutated ras oncogene, normal or point mutated p53, overexpressed p53, CA-125, PSA, C-erb/B2, BRCA I, BRCA II, PSMA, tyrosinase, TRP-1, TRP-2, NY-ESO-1, TAG72, KSA, HER-2/neu, bcr-abl, pax3-fkhr, ews-fli-1, modified TAAs, splice variants of TAAs, functional epitopes and epitope agonists thereof.

16. The host cell according to claim 15, wherein the antigen is CEA (6D) having aspartic acid at amino acid position 576.

17. The host cell according to claim 15, wherein the antigen is a is PSA and PSMA.

18. The host cell according to claim 15, wherein the antigen is MUC-1 encoded by a truncated MUC-1 gene having of a signal sequence, ten copies of a tandem repeat sequence, and a 3' coding sequence.

19. The host cell according to claim 3, wherein the antigen is a is a yeast or fungal antigen derived from a yeast or fungus selected from the group consisting of *Aspergillus, Nocardia, Histoplasmosis, Candida*, and *Cryptosporidia*.

20. The host cell according to claim 3, wherein the antigen is a parasitic antigen derived from a *Plasmodium* species, *Toxoplasma gondii, Pneumocystis carinii, Trypasosoma* species, or *Leishmania* species.

21. The host cell according to claim 1, wherein the vector further comprises a selectable marker.

22. The host cell according to claim 21, wherein the selectable marker is selected from the group consisting of lacZ gene, thymidine kinase, gpt, GUS, and a vaccinia K1L host range gene.

23. The host cell according to claim 1, wherein the vector further comprises at least one nucleic acid sequence encoding one or more of a cytokine, chemokine or flt-31.

24. A method of enhancing an immune response in an individual comprising:
   (a) activating a T lymphocyte by exposing the T lymphocyte in vitro to a host cell infected, transfected or induced with a recombinant vector that comprises nucleic acid sequences encoding a combination of B7, ICAM-1 and LFA-3, wherein expression of the nucleic acid sequences occurs in the host cell;
   (b) administering the activated T lymphocyte to an individual in an amount sufficient to enhance an immune response.

25. The method according to claim 24, wherein the T lymphocytes are autologous with the individual.

26. The method according to claim 24, wherein during the activating the T-lymphocyte is exposed to a cytokine, chemokine or fit 31.

27. The method according to claim 24, wherein the immune response is against the target antigen selected from the group consisting of a tumor specific antigen, tumor associated antigen, tissue-specific antigen, bacterial antigen, viral antigen, yeast antigen, fungal antigen, protozoan antigen, and parasite antigen.

28. The method according to claim 24, wherein the recombinant vector produces an enhanced immune response or treats a disease caused by a cell or organism selected from the group consisting of viruses, bacteria, protozoans, and parasites.

29. The method according to claim 24, wherein the host cell further comprises at least one nucleic acid sequence encoding a target antigen.

30. The method according to claim 24, wherein during the activating the T-lymphocyte is exposed to a target antigen.

31. The method according to claim 24, wherein the host cell further comprises at least one nucleic acid sequence encoding one or more of a cytokine, chemokine or fit-31.

32. The method according to claim 24, wherein the recombinant vector produces an enhanced immune response or treats a disease caused by premalignant cells or tumor cells.

* * * * *

UNITED STATES PATENT AND TRADEMARK OFFICE
CERTIFICATE OF CORRECTION

PATENT NO. : 6,969,609 B1 Page 1 of 1
APPLICATION NO. : 09/856988
DATED : November 29, 2005
INVENTOR(S) : Jeffrey Schlom et al.

It is certified that error appears in the above-identified patent and that said Letters Patent is hereby corrected as shown below:

On the Title Page of the Patent under (60) Related U.S. Application Data, add:

-- This application is a 371 of PCT/US99/26866, filed November 12, 1999. This application claims priority to U.S. Provisional Application Serial No. 60/111,582, filed December 9, 1998. --.

Signed and Sealed this

Twenty-seventh Day of February, 2007

JON W. DUDAS
*Director of the United States Patent and Trademark Office*

SEQUENCE LISTING

<160> NUMBER OF SEQ ID NOS: 42

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Lys Thr Trp Gly Gln Tyr Trp Glx Tyr
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Thr Asp Gln Val Pro Pro Ser Val
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Leu Glu Pro Gly Pro Val Thr Ala
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Leu Asp Gly Thr Ala Thr Leu Arg Leu
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Leu Tyr Arg Tyr Gly Ser Phe Ser Val
 1               5                  10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Gly Ile GLY ILE LEU Thr Val
 1               5

<210> SEQ ID NO 7
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Leu Thr Val Ile Leu Gly Val Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ser Leu Gln Arg Gln Phe Leu Arg
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Leu Leu Ala Val Leu Tyr Cys Leu
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Met Asn Gly Thr Met Ser Gln Val
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Glu Ile Trp Arg Asp Ile Asp Phe
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Phe Leu Pro Trp His Arg Leu Phe
```

-continued

```
<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Asn Ile Leu Leu Ser Asn Ala Pro Leu Gly Pro Gln Phe Pro
  1               5                  10                  15

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Tyr Leu Gln Asp Ser Asp Pro Asp Ser Phe Gln Asp
  1               5                  10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ala Asp Pro Thr Gly His Ser Tyr
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ala Tyr Gly Glu Pro Arg Lys Leu
  1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Val Asp Pro Ile Gly His Leu Tyr
  1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
            peptide

<400> SEQUENCE: 18

Phe Leu Trp Gly Pro Arg Ala Leu Val
  1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Arg Ala Val Phe Leu Ala Leu
  1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Arg Pro Arg Pro Arg Arg Tyr
  1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Pro Asp Val Phe Ile Arg Cys
  1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Tyr Gly Leu Asp Phe Tyr Ile Leu
  1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Leu Ser Gly Ala Asn Leu Asn Leu
  1               5

<210> SEQ ID NO 24
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Leu Ser Gly Ala Asp Leu Asn Leu
  1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Tyr Leu Asp Ser Gly Ile His Phe
  1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Glu Lys Leu Ile Val Val Leu Phe
  1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Cys Asp Pro His Ser Gly His Phe Val
  1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Ile Ser Ala Val Val Gly Ile Leu
  1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

```
Lys Ile Phe Gly Ser Leu Ala Phe Leu
  1               5
```

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Tyr Met Leu Asp Leu Gln Pro Glu Thr Thr
  1               5                  10
```

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Pro Asp Thr Arg Pro Ala Pro Gly Ser Thr Ala Pro Pro Ala His Gly
  1               5                  10                  15

Val Thr Ser Ala
             20
```

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Phe Leu Thr Pro Lys Lys Leu Gln Cys Val Asp Leu His Val Ile Ser
  1               5                  10                  15

Asn Asp Val Cys Ala Gln Val His Pro Gln Lys Val Thr Lys
             20                  25                  30
```

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Phe Leu Thr Pro Lys Lys Leu Gln Cys Val
  1               5                  10
```

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Lys Leu Gln Cys Val Asp Leu His Val
  1               5
```

```
<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Ile Ser Asn Asp Val Cys Ala Gln Val
 1               5                  10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Val His Pro Gln Lys Val Thr Lys
 1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Ala Gln Asn Thr Thr Tyr Leu
 1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ile Ile Asn Phe Glu Lys Leu
 1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Gly Tyr Val Tyr Gln Gly Leu
 1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 40

Ala Ser Asn Glu Asn Met Asp Ala Met
 1               5

<210> SEQ ID NO 41
<211> LENGTH: 2297
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 41
atgaccatga ttacgccaag cgcgcaatta accctcacta aagggaacaa aagctgggta      60
ccgggccccc cctcgaggtc gacggtatcg ataagcttga tatcgaattt cgaggtcgac     120
atgacaccgg gcacccagtc tcctttcttc ctgctgctgc tcctcacagt gcttacagct     180
accacagccc ctaaacccgc aacagttgtt acgggttctg gtcatgcaag ctctacccca     240
ggtggagaaa aggagacttc ggctacccag agaagttcag tgcccagctc tactgagaag     300
aatgctgtga gtatgacaag cttgatatcg aattccggtg tcggggctc caccgccccc     360 ccagcccacg gtgtcaccct ggccccggac accaggccgg ccccgggcag tactgcacca     420
ccggcacatg gcgtaacatc agcacctgat acaagacctg cacctggatc caccgcgccg     480
cctgcgcacg gagtgacgtc ggcgcccgac acgcgccccg ctcccgggtc aacagctcct     540
cccgctcatg gggttacttc tgctccagat actcgcccag ctccaggttc gacggccccc     600
cctgctcacg gtgtaacatc cgccccggat accagaccgg cccctggcag caccgcaccg     660
cccgcccatg gagttacaag tgcacccgat accggccgg cacccggaag taccgctcca     720
cctgcacacg gggtcacaag cgcgccagac actcgacctg cgccagggtc gactgcccct     780
ccggcgcatg tgtgacctc agctcctgac acaaggccag ccccaggttc aacggcacct     840
ccagcacacg gagtcacgtc tgcacccgac accgtccag ctccgggtag tacagcgcca     900
cccgcacatg gcgtcacgag cgctccggat acgagaccgg cgcctgctag cactctggtg     960
cacaacggca cctctgccag ggctaccaca accccagcca gcaagagcac tccattctca    1020
attcccagcc accactctga tactcctacc acccttgcca gccatagcac caagactgat    1080
gccagtagca ctcaccatag cacggtacct cctctcacct cctccaatca cagcacttct    1140
ccccagttgt ctactggggt ctctttcttt ttcctgtctt ttcacatttc aaacctccag    1200
tttaattcct ctctggaaga tcccagcacc gactactacc aagagctgca gagagacatt    1260
tctgaaatgt ttttgcagat ttataaacaa gggggttttc tgggcctctc caatattaag    1320
ttcaggccag gatctgtggt ggtacaattg actctgcct tccagaaagg taccatcaat    1380
gtccacgacg tggagacaca gttcaatcag tataaaacgg aagcagcctc tcgatataac    1440
ctgacgatcc cagacgtcag cgtgagtgat gtgccatttc ctttctctgc ccagtctggg    1500
gctggggtgc aggctgggg catcgcgctg ctggtgctgg tctgtgttct ggttgcgctg    1560
gccattgtct atctcattgc cttggctgtc tgtcagtgcc gccgaaagaa ctacgggcag    1620
ctggacatct ttccagcccg ggatacctac catcctatga gcgagtaccc cacctaccac    1680
acccatgggc gctatgtgcc cctagcagt accgatcgta gccccatga aaggttttct    1740 gcaggtaatg gtggcagcag cctctcttac acaaacccag cagtggcagc cacttctgcc    1800
aacttgtagg ggcacgtcgc ccgctgagct gagtggccag ccagtgccat tccactccac    1860
tcaggttctt cagggccaga cccctgcacc ctgtttgggc tggtgagctg ggagttcagg    1920
```

```
tgggctgctc acagcctcct tcagaggccc caccaatttc tcggacactt ctcagtgtgt    1980
ggaagctcat gtgggcccct gagggctcat gcctgggaag tgttgtggtg ggggctccca    2040
agaggactgg cccagagagc cctgagatag cggggatcca ctagttctag agcggcgcca    2100
ccgcggtgga gctccaattc gcctaatagt gagtcgtatt acgcgcgctc actggccgtc    2160
gttttacaac gtcgtgactg ggaaaacctg gcgttaccaa cttaatcgct tgcaacacat    2220
cccctttcgc agctggcgta atacgaagag gccgcacgat cgcccttcca acagttgcgc    2280
acctgaatgg caatgga                                                  2297
```

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Gly Ile Leu Gly Phe Val Phe Thr Leu
 1               5